US009926369B2

(12) United States Patent
Lowy et al.

(10) Patent No.: US 9,926,369 B2
(45) Date of Patent: *Mar. 27, 2018

(54) METHODS FOR TREATING HEPATOCELLULAR CANCER BY ADMINISTERING AN ANTI-ANG-2 ANTIBODY

(71) Applicant: Regeneron Pharmaceuticals, Inc., Tarrytown, NY (US)

(72) Inventors: Israel Lowy, Dobbs Ferry, NY (US); Gavin Thurston, White Plains, NY (US); Christopher Daly, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/616,534

(22) Filed: Feb. 6, 2015

(65) Prior Publication Data

US 2015/0147342 A1 May 28, 2015

Related U.S. Application Data

(63) Continuation of application No. 13/747,728, filed on Jan. 23, 2013, now Pat. No. 8,980,268, which is a (Continued)

(51) Int. Cl.
*C07K 16/22* (2006.01)
*A61K 39/395* (2006.01)
(Continued)

(52) U.S. Cl.
CPC ............ *C07K 16/22* (2013.01); *A61K 31/513* (2013.01); *A61K 38/1866* (2013.01); (Continued)

(58) Field of Classification Search
None
See application file for complete search history.

(56) References Cited

U.S. PATENT DOCUMENTS

| 5,521,073 A | 5/1996 | Davis et al. |
| 5,643,755 A | 7/1997 | Davis et al. |

(Continued)

FOREIGN PATENT DOCUMENTS

| WO | WO 06/068953 A2 | 6/2006 |
| WO | WO 06/045049 A1 | 8/2009 |

(Continued)

OTHER PUBLICATIONS

Dechkum et al., "Monocyte cheomattractant protein 1 (MCP-1) gene polymorphism is not associated with severe cerbral malaria in Thailand," Jpn. J. Infect. Dis., 59:239-244, (2006).
(Continued)

*Primary Examiner* — Claire Kaufman
(74) *Attorney, Agent, or Firm* — Schwabe, Williamson & Wyatt PC; Aparna G. Patankar; Thomas Triolo

(57) ABSTRACT

The present invention provides antibodies that bind to angiopoietin-2 (Ang-2) and methods of using same. According to certain embodiments of the invention, the antibodies are fully human antibodies that bind to human Ang-2. The antibodies of the invention are useful, inter alia, for the treatment of diseases and disorders associated with one or more Ang-2 biological activities including angiogenesis.

10 Claims, 3 Drawing Sheets

Related U.S. Application Data continuation-in-part of application No. 12/843,905, filed on Jul. 27, 2010, now Pat. No. 8,987,420.

(60) Provisional application No. 61/295,194, filed on Jan. 15, 2010, provisional application No. 61/229,418, filed on Jul. 29, 2009.

(51) Int. Cl.

| | | |
|---|---|---|
| *A61K 38/18* | (2006.01) | |
| *A61K 45/06* | (2006.01) | |
| *A61K 31/513* | (2006.01) | |
| *A61K 39/00* | (2006.01) | |

(52) U.S. Cl.
CPC .... *A61K 39/3955* (2013.01); *A61K 39/39558* (2013.01); *A61K 45/06* (2013.01); *A61K 2039/505* (2013.01); *A61K 2039/545* (2013.01); *C07K 2317/21* (2013.01); *C07K 2317/33* (2013.01); *C07K 2317/34* (2013.01); *C07K 2317/565* (2013.01); *C07K 2317/73* (2013.01); *C07K 2317/76* (2013.01); *C07K 2317/92* (2013.01)

(56) References Cited

U.S. PATENT DOCUMENTS

| | | | |
|---|---|---|---|
| 6,166,185 | A | 12/2000 | Davis et al. |
| 7,138,370 | B2 | 11/2006 | Oliner et al. |
| 7,205,275 | B2 | 4/2007 | Oliner et al. |
| 7,309,483 | B2 | 12/2007 | Wiegand et al. |
| 7,354,578 | B2 | 4/2008 | Kandel et al. |
| 7,521,053 | B2 | 4/2009 | Oliner et al. |
| 7,521,425 | B2 | 4/2009 | Bradshaw et al. |
| 7,658,924 | B2 | 2/2010 | Oliner et al. |
| 7,666,831 | B2 | 2/2010 | Oliner et al. |
| 7,666,832 | B2 | 2/2010 | Oliner et al. |
| 7,666,839 | B2 | 2/2010 | Oliner et al. |
| 7,723,499 | B2 | 5/2010 | Oliner et al. |
| 7,973,140 | B2 | 7/2011 | Green et al. |
| 8,980,268 | B2 * | 3/2015 | Lowy |
| 8,987,420 | B2 | 3/2015 | Thurston et al. |
| 2006/0018909 | A1 | 1/2006 | Oliner et al. |
| 2006/0246071 | A1 | 11/2006 | Green et al. |
| 2007/0154482 | A1 | 7/2007 | Sukhatme et al. |
| 2007/0225221 | A1 | 9/2007 | Oliner et al. |
| 2008/0267971 | A1 | 10/2008 | Green et al. |
| 2009/0054323 | A1 | 2/2009 | Oliner et al. |
| 2009/0123474 | A1 | 5/2009 | Blakey et al. |
| 2009/0191212 | A1 | 7/2009 | Oliner et al. |
| 2009/0304694 | A1 | 12/2009 | Oliner et al. |
| 2010/0159587 | A1 | 6/2010 | Brinkmann et al. |
| 2012/0189635 | A1 | 7/2012 | Thurston et al. |
| 2013/0129722 | A1 | 5/2013 | Lowy et al. |
| 2014/0112930 | A1 | 4/2014 | Thurston et al. |
| 2015/0152177 | A1 | 6/2015 | Thurston et al. |

FOREIGN PATENT DOCUMENTS

| | | |
|---|---|---|
| WO | WO 09/097325 A1 | 8/2009 |
| WO | WO 10/069532 A1 | 6/2010 |
| WO | WO 11/014469 A1 | 2/2011 |

OTHER PUBLICATIONS

GenBank: Accession No. AAB76728, "Sequence 4 from U.S. Pat. No. 5,648,077," Oct. 8, 1997. [Retrieved from the Internet Jun. 14, 2016: <URL: http://www.ncbi.nlm.nih.gov/protein/AAB76728>].
GenBank: Accession No. AAF37208, "Immunoglobulin heavy chain variable region, partial [*Homo sapiens*]," Dec. 4, 2000. [Retrieved from the Internet Jun. 14, 2016: <URL: http://www.ncbi.nlm.nih.gov/protein/AAG3720>].

GenBank: Accession No. AAQ22123, "immunoglobulin kappa chain variable region, partial [*Homo sapiens*]," Aug. 16, 2003. [Retrieved from the Internet Jun. 14, 2016: <URL: http://www.ncbi.nlm.nih.gov/protein/AAQ22123>].
GenBank: Accession No. AAR38512, "immunoglobulin heavy chain variable region, partial [*Homo sapiens*]," Nov. 23, 2005. [Retrieved from the Internet Aug. 14, 2016: <URL: http://www.ncbi.nlm.nih.gov/protein/AAR38512>].
GenBank: Accession No. AAS30574, "Sequence 44 from U.S. Pat. No. 6,680,209," Feb, 20, 2004. [Retrieved from the Internet Jun. 14, 2016: <URL: http://www.ncbi.nlm.nih.gov/protein/AAS30574>].
GenBank: Accession No. AAT12206, "immunoglobulin heavy chain variable region, partial [*Homo sapiens*]," Nov. 23, 2005. [Retrieved from the Internet Jun. 14, 2016: <URL: http://www.ncbi.nlm.nih.gov/protein/AAT12206>].
GenBank: Accession No. AAU84887, "immunoglobulin kappa chain variable region, partial [*Homo sapiens*]," Sep. 29, 2004. [Retrieved from the Internet Jun. 14, 2016: <URL: http://www.ncbi.nlm.nih.gov/protein/AAU84887>].
GenBank: Accession No. AAY12034, "Seqience 18 from U.S. Pat. No. 6,881,557," Apr. 20, 2005. [Retrieved from the Internet Jun. 14, 2016: <URL: http://www.ncbi.nlm.nih.gov/protein/AAY12034>].
GenBank: Accession No. AAZ08743, "immunoglobulin heavy chain variable region, partial [*Homo sapiens*]," Nov. 7, 2005. [Retrieved from the Internet Jun. 14, 2016: <URL: http://www.ncbi.nlm.nih.gov/protein/AAZ08743>].
GenBank: Accession No. ABC16500, "Sequence 1 from U.S. Pat. No. 6,972,324," Dec. 8, 2005. [Retrieved from the Internet Jun. 14, 2016: <URL: http://www.ncbi.nlm.nih.gov/protein/AB16500>].
GenBank: Accession No. ABL47907, "Sequence 240 from U.S. Pat. No. 7,135,558," Dec. 6, 2006. [Retrieved from the Internet Jun. 14, 2016: <URL: http://www.ncbi.nlm.nih.gov/protein/ABL47907>].
GenBank: Accession No. ABT81190, "Sequence 168660 from U.S. Pat. No. 7,214,786," Aug. 10, 2007. [Retrieved from the Internet Jun. 14, 2016: <URL: http://www.ncbi.nlm.nih.gov/protein/ABT81190>].
GenBank: Accession No. ABY17021, "Sequence 126 from U.S. Pat. No. 7,488,806," Feb. 13, 2009. [Retrieved from the Internet Jun. 14, 2016: <URL: http://www.ncbi.nlm.nih.gov/protein/ABY17021>].
GenBank: Accession No. ABY17023, "Sequence 88 from U.S. Pat. No. 7,288,251," Dec. 14, 2007. [Retrieved from the Internet Jun. 14, 2016: <URL: http://www.ncbi.nlm.nih.gov/protein/ABY17023>].
GenBank: Accession No. ACC02438, "Sequence 937 from U.S. Pat. No. 7,329,737," Apr. 14, 2008. [Retrieved from the Internet Jun. 14, 2016: <URL: http://www.ncbi.nlm.nih.gov/protein/ACC0243>].
GenBank: Accession No. ACH10871, "Sequence 13 from U.S. Pat. No. 7,396,914," Aug. 18, 2008. [Retrieved from the Internet Jun. 14, 2016: <URL: http://www.ncbi.nlm.nih.gov/protein/ACH10871>].
GenBank: Accession No. ACH10873, "Sequence 17 from U.S. Pat. No. 7,396,914," Aug. 18, 2008. [Retrieved from the Internet Jun. 14, 2016: <URL: http://www.ncbi.nlm.nih.gov/protein/ACH10873>].
GenBank: Accession No. ACH10879, "Sequence 149 from U.S. Pat. No. 7,396,914," Aug. 18, 2008. [Retrieved from the Internet Jun. 14, 2016: <URL: http://www.ncbi.nlm.nih.gov/protein/ACH10879>].
GenBank: Accession No. ACN04872, "Sequence 296 from U.S. Pat. No. 7,485,297," Feb. 13, 2009. [Retrieved from the Internet Jun. 14, 2016: <URL: http://www.ncbi.nlm.nih.gov/protein/ACN04872>].
GenBank: Accession No. ACQ23265, "Sequence 134 from U.S. Pat. No. 7,514,534," Apr. 29, 2009. [Retrieved from the Internet Jun. 14, 2016: <URL: http://www.ncbi.nlm.nih.gov/protein/ACQ23265>].
GenBank: Accession No. ADA49503, "Sequence 78 from U.S. Pat. No. 7,625,559," Dec. 14, 2009. [Retrieved from the Internet Jun. 14, 2016: <URL: http://www.ncbi.nlm.nih.gov/protein/ADA49503>].
GenBank: Accession No. CAC24888, "unnamed protein product, partial [synthetic construct]," Jan. 22, 2001. [Retrieved from the Internet Jun. 14, 2016: <URL: http://www.ncbi.nlm.nih.gov/protein/CAC24888>].

(56) References Cited

OTHER PUBLICATIONS

GenBank: Accession No. CAC24892, "unnamed protein product, partial [*Mus musculus*]," Jan. 22, 2001. [Retrieved from the Internet Jun. 14, 2016: <URL http://www.ncbi.nlm.nih.gov/protein/CAC24892>].
GenBank: Accession No. CAC27674, "immunoglobulin kappa chain variable region, partial [*Homo sapiens*]," Aug. 1, 2001. [Retrieved from the Internet Jun. 14, 2016: <URL: http://www.ncbi.nlm.nih.gov/protein/CAC27674>].
GenBank: Accession No. CAC43215, "immunoglobulin heavy chain variable region, partial [*Homo sapiens*]," Jul. 1, 2001. [Retrieved from the Internet Jun. 14, 2016: <URL: http://www.ncbi.nlm.nih.gov/protein/CAC43215>].
GenBank: Accession No. CAC60032, "unnamed protein product, partial [*Micromonospora carbonacea*]," Aug. 28, 2001. [Retrieved from the Internet Jun. 14, 2016: <URL: http://www.ncbi.nlm.nih.gov/protein/CAC60032>].
GenBank: Accession No. ABY17021, "Sequence 84 from U.S. Pat. No. 7,288,251," Dec. 14, 2007. [Retrieved from the Internet Jun. 14, 2016: <URL: http://www.ncbi.nlm.nih.gov/protein/ABY17021>].
GenBank: Accession No. CAB87468, "immunoglobulin heavy chain variable region, partial [*Homo sapiens*]," Oct. 27, 2000. [Retrieved from the Internet Jun. 14, 2016: <URL: http://www.ncbi.nlm.nih.gov/protein/CAB87468X>].
U.S. Appl. No. 14/134,880, Final Office Action dated Dec. 11, 2015.
U.S. Appl. No. 14/134,880, Non-Final Office Action dated Jul. 15, 2015.
U.S. Appl. No. 14/134,880, Notice of Allowance dated Feb. 24, 2016.
Barton et al., "Crystal structures of the Tie2 receptor ectodomain and the angiopoietin-2-Tie2 complex," Nat. Struct. Mol. Biol., 13:524-532, (2006).
Barton et al., "Structure of the angiopoietin-2 receptor binding domain and identification of surfaces involved in Tie2 recognition," Structure, 13:825-832, (2005).
Brown et al., "A Human Monoclonal Anti-ANG2 Antibody Leads to Broad Antitumor Activity in Combination . . . ," Mol. Cancer Ther., 9:145-56, (2010).
Cai et al., "Single chain Fv antibody angainst angiopoietin-2 inhibits VEGF-induced endotheli . . . ," Biochem. Biophys. Res. Commun., 309:946-51, (2003).
Conroy et al.,., "Endothelium-based biomarkers are associated with cerebral malaria in Malawian children: a retrospective case-control study," PLos One, 5(12):e15291, (2010).
Conroy et al., "Whole blood angiopoietin-1 and-2 levels discriminate cerebral and severe (non-cerebral) malaria from uncomplicated malaria," Malaria Journal, 8:295, (2009).
Coxon et al., "Combined treatment of angiopoietin and VEGF pathway antagonists enhances antitumor activity in preclinical models of colon carcinoma," Am Assoc Cancer Res, Ann Mtg, Abstract 1113, 49:262-263, (2006).
Falcon et al., "Complementary and opposing effects of angiopoietin-1 and angiopoietin-2 inhibitors on tumor blood vessels and normalization," Proceedings of the American Association for Cancer Research Annual Meeting, Abstract #1996, 50:483-483, (2009).
Holash et al., "Vessel Cooption, Regression, and Growth in Tumors Mediated by Angiopoietins and VEGF," Science, 284:1994-1998, (1999).
Hu et al., "Angiopoietin-2: Development of inhibitors for cancer therapy," Current Oncology Reports, 11:111-116, (2009).
Imanishi et al., "Angiopoietin-2 Stimulates Breast Cancer Metastasis through the alpha5beta1 Integrin . . . ," Cancer Res., 67:4254-63, (2007).
Jendreyko et al., Simultaneous, phenotypic knockout of VEGF-R2 and Tie-2 with an intradiabody enhances antiangiogenic effects in vivo, Klintsche Paediatrie, 218(3):143-151, (2006).
Ladner, "Mapping the epitopes of antibodies," Biotechnol. Genet. Eng. Rev., 24:1-30, (2007).
Leow et al., "MED13617, a fully human anti-angiopoietin 2 monoclonal antibody . . . ," Am Assoc Cancer Res, Ann Mtg, Denver CO, Abstract 2793, (2009).
Leow et al., "MEDI3617, a human anti-Angiopoietin 2-monoclonal antibody, inhibits angiognesis and turmor growth in human tumor xenograft model," Int J Oncol, 40(5):1321-1330, (2012).
Lovegrove et al., "Serum angiopeoietin-1 and -2 levels discriminate cerebral malaria from uncomplicated malaria and predict clinical outcome in African children," PLos One, 4(3):e4912, (2009).
Maisonpierre et al., "Angiopoietin-2, a Natural Antagonist for Tie2 That Disrupts in vivo Angiogenesis," Science, 277:55-60, (1997).
Nasarre et al., "Host-Derived Angiopoietin-2 Affects Early Stages of Tumor Development and Vessel Maturation but is Dispensable for Later Stages of Tumor Growth," Cancer Research, 69(4):1324-1333, (2009).
Neal et al., "AMG-386, a Selective Angiopoietin-1/-2-Neutralizing Peptibody for the Potential Treatment of Cancer," Curr. Opin. Mol. Therapeutics, 12:487-495, (2010).
Oliner et al., "Suppression of angiogenesis and tumor growth by selective inhibition of angiopietin-2," Cancer Cell, Cell Press, 6(5):507-516, (2004).
Oshima et al., "Different effects of angiopoietin-2 in different vascular beds in the eye . . . ," FASEB J., 19:963-965, (2005).
PCT International Preliminary Report on Patentatbility for application PCT/US2010/043295 dated Jul. 29, 2009.
PCT International Search Report for application PCT/US2010/043295 dated Nov. 2, 2010.
Penn et al., "Vascular endothelial growth factor in eye disease," Progress in Retinal Eye Research, 27:331-71, (2008).
Rudikoff et al., "Single amino acid substitution altering antigen-binding specificity," PNAS USA, Immunology, 79:1979-1983 (1982).
Seegar et al., "Tie1-Tie2 interactions mediate functional differences between angiopoietin ligands," Mol. Cell, 37:643-655, (2010).
Thurston et al., "Angiopietin-1 protects the adult vasculature against plasma leakage," Nature Medicine, 6:460-463. (2000).
Thurston et al., "Leakage-Resistant Blood Vessels in Mice Transgenically Overexpressing Angiopoietin-1," Science, 286:2511-2514, (1999).
U.S. Appl. No. 12/843,905, Final Office Action dated Jul. 25, 2012.
U.S. Appl. No. 12/843,905, Non-Final Office Action dated Mar. 5, 2012.
U.S. Appl. No. 12/843,905, Notice of Allowance dated Sep. 18, 2014.
U.S. Appl. No. 12/843,905, Notice of Allowance dated Nov. 13, 2014.
U.S. Appl. No. 12/843,905, Requirement for Restriction/Election dated Dec. 13, 2011.
U.S. Appl. No. 13/747,7208, Non-Final Office Action dated Jul. 7, 2014.
U.S. Appl. No. 13/747,728, Notice of Allowance dated Nov. 7, 2014.
U.S. Appl. No. 13/417,372, Non-Final Office Action dated Jun. 28, 2013.
Yeo at al., "Angiopoietin-2 is associated with decreased endothelial nitric oxide and poor clinical outcome in severe falciparum malaria" PNAS USA, 105(44):17097-17102, (2008).
U.S. Appl. No. 14/623,089, Requirement for Restriction/Election dated Aug. 5, 2016.

* cited by examiner

METHODS FOR TREATING HEPATOCELLULAR CANCER BY ADMINISTERING AN ANTI-ANG-2 ANTIBODY

CROSS-REFERENCE TO RELATED APPLICATIONS

This application is a continuation of U.S. non-provisional application Ser. No. 13/747,728, filed Jan. 23, 2013, which is a continuation-in-part of U.S. non-provisional application Ser. No. 12/843,905, filed on Jul. 27, 2010, which claims the benefit of priority under 35 U.S.C. § 119(e) of U.S. provisional application No. 61/229,418, filed on Jul. 29, 2009, and U.S. provisional application No. 61/295,194, filed on Jan. 15, 2010, the disclosures of which are herein incorporated by reference in their entireties.

FIELD OF THE INVENTION

The present invention relates to antibodies, and antigen-binding fragments thereof, which are specific for angiopoietin-2 (Ang-2).

SEQUENCE LISTING

This application includes an electronic sequence listing in a file named "457434-Sequence.txt", created on Feb. 6, 2015 and containing 304,998 bytes, which is hereby incorporated by reference in its entirety for all purposes.

BACKGROUND

Angiogenesis is the biological process whereby new blood vessels are formed. Aberrant angiogenesis is associated with several disease conditions including, e.g., proliferative retinopathies, rheumatoid arthritis and psoriasis. In addition, it is well established that angiogenesis is critical for tumor growth and maintenance. Angiopoietin-2 (Ang-2) is a ligand for the Tie-2 receptor (Tie-2) and has been shown to play a role in angiogenesis. Ang-2 is also referred to in the art as Tie-2 ligand. (U.S. Pat. No. 5,643,755; Yancopoulos et al., 2000, Nature 407:242-248).

Antibodies and other peptide inhibitors that bind to Ang-2 are mentioned in, e.g., U.S. Pat. Nos. 6,166,185; 7,521,053; 7,205,275; 2006/0018909 and 2006/0246071. There is a need in the art for novel Ang-2 modulating agents, including Ang-2 antibodies, which can be used to treat diseases and conditions caused by or exacerbated by angiogenesis.

BRIEF SUMMARY OF THE INVENTION

The present invention provides human antibodies that bind to human Ang-2. The present inventors, in view of various lines of evidence and investigation, have recognized a need for Ang-2 inhibitors which do not bind to or antagonize the related molecule Ang-1. For example, previous studies have demonstrated or suggested a beneficial role for Ang-1 in hemostasis (see, e.g., Li et al., 2001, *Thrombosis and Haemostasis* 85:191-374) and in protecting the adult vasculature against plasma leakage (see, e.g., Thurston et al., 2000, *Nature Medicine* 6:460-463; Thurston et al., 1999, *Science* 286:2511-2514). Thus, the present inventors recognized that, in certain anti-angiogenic therapeutic situations, it may be beneficial to preserve Ang-1 activity. Accordingly, the present invention provides antibodies which bind specifically to Ang-2 but do not substantially bind to Ang-1. The present invention also includes antibodies that block the interaction between Ang-2 and its receptor Tie-2 but do not substantially block the interaction between Ang-1 and Tie-2. The antibodies of the invention are useful, inter alia, for inhibiting the angiogenesis-promoting activities of Ang-2 and for treating diseases and disorders caused by or related to the process of angiogenesis. The invention also provides for methods of treating cancer, the methods comprising administering therapeutically effective amounts of anti-Ang-2 antibodies, as described herein.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions.

In one embodiment, the invention comprises an antibody or antigen-binding fragment of an antibody comprising a heavy chain variable region (HCVR) having an amino acid sequence selected from the group consisting of SEQ ID NO: 2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 474, 478, 482, 498, 502, 506, 514, and 516, or a substantially similar sequence thereof having at least 90%, at least 95%, at least 98% or at least 99% sequence identity. In one embodiment, the antibody or antigen-binding portion of an antibody comprises a HCVR having an amino acid sequence selected from the group consisting of SEQ ID NO: 18, 42, 66, 162, 210, 266, and 434.

In one embodiment, the invention comprises an antibody or antigen-binding fragment of an antibody comprising a light chain variable region (LCVR) having an amino acid sequence selected from the group consisting of SEQ ID NO: 10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452, 456, 466, 476, 480, 490, 500, and 504, or a substantially similar sequence thereof having at least 90%, at least 95%, at least 98% or at least 99% sequence identity. In one embodiment, the antibody or antigen-binding portion of an antibody comprises a LCVR having an amino acid sequence selected from the group consisting of SEQ ID NO: 20, 44, 68, 164, 212, 274, and 442.

In specific embodiments, the antibody or antigen-binding fragment thereof comprises a HCVR and LCVR (HCVR/LCVR) amino acid sequence pair selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, and 502/504. In one embodiment, the antibody or fragment thereof comprises a HCVR and LCVR selected from the amino acid sequence pairs of SEQ ID NO: 18/20, 42/44, 66/68, 162/164, 210/212, 266/274, and 434/442.

In a next aspect, the invention provides an antibody or antigen-binding fragment of an antibody comprising a heavy chain CDR3 (HCDR3) domain having an amino acid sequence selected from the group consisting of SEQ ID NO: 8, 32, 56, 80, 104, 128, 152, 176, 200, 224, 248, 272, 296, 320, 344, 368, 392, 416, 440, 464, 488, and 512, or a substantially similar sequence thereof having at least 90%, at least 95%, at least 98% or at least 99% sequence identity; and a light chain CDR3 (LCDR3) domain selected from the group consisting of SEQ ID NO: 16, 40, 64, 88, 112, 136, 160, 184, 208, 232, 256, 280, 304, 328, 352, 376, 400, 424, 448, 472, and 496, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 32/40, 56/64, 80/88, 104/112, 128/136, 152/160, 176/184, 200/208, 224/232, 248/256, 272/280, 296/304, 320/328, 344/352, 368/376, 392/400, 416/424, 440/448, 464/472, and 488/496. In one embodiment, the antibody or antigen-binding portion of an antibody comprises a HCDR3/LCDR3 amino acid sequence pair selected from the group consisting of SEQ ID NO: 8/16, 32/40, 56/64, 152/160, 200/208, 272/280, and 440/448. Non-limiting examples of anti-Ang-2 antibodies having these HCDR3/LCDR3 pairs are the antibodies designated H1H685, H1H690, H1H691, H1H696, H1H706, H1M724, and H2M744, respectively.

In a further embodiment, the invention comprises an antibody or fragment thereof further comprising a HCDR1 domain having an amino acid sequence selected from the group consisting of SEQ ID NO: 4, 28, 52, 76, 100, 124, 148, 172, 196, 220, 244, 268, 292, 316, 340, 364, 388, 412, 436, 460, 484, and 508, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 30, 54, 78, 102, 126, 150, 174, 198, 222, 246, 270, 294, 318, 342, 366, 390, 414, 438, 462, 486, and 510, or a substantially similar sequence thereof having at least 90%, at least 95%, at least 98% or at least 99% sequence identity; LCDR1 domain having an amino acid sequence selected from the group consisting of SEQ ID NO: 12, 36, 60, 84, 108, 132, 156, 180, 204, 228, 252, 276, 300, 324, 348, 372, 396, 420, 444, 468, and 492, or a substantially similar sequence thereof having at least 90%, at least 95%, at least 98% or at least 99% sequence identity; and a LCDR2 domain having an amino acid sequence selected from the group consisting of SEQ ID NO: 14, 38, 62, 86, 110, 134, 158, 182, 206, 230, 254, 278, 302, 326, 350, 374, 398, 422, 446, 470, and 494, or a substantially similar sequence thereof having at least 90%, at least 95%, at least 98% or at least 99% sequence identity.

Certain non-limiting, exemplary antibodies and antigen-binding fragments of the invention comprise HCDR1, HCDR2, HCDR3, LCDR1, LCDR2 and LCDR3 domains, respectively, selected from the group consisting of: (i) SEQ ID NO: 4, 6, 8, 12, 14 and 16 (e.g., H1H685); (ii) SEQ ID NO: 28, 30, 32, 36, 38 and 40 (e.g., H1H690); (iii) SEQ ID NO: 52, 54, 56, 60, 62 and 64 (e.g., H1H691); (iv) SEQ ID NO: 148, 150, 152, 156, 158 and 160 (e.g., H1H696); (v) SEQ ID NO: 196, 198, 200, 204, 206 and 208 (e.g., H1H706); (vi) SEQ ID NO: 268, 270, 272, 276, 278 and 280 (e.g., H1M724); and (vii) SEQ ID NO: 436, 438, 440, 444, 446 and 448 (e.g., H2M744).

In a related embodiment, the invention comprises an antibody or antigen-binding fragment of an antibody which specifically binds Ang-2, wherein the antibody or fragment comprises the heavy and light chain CDR domains (i.e., CDR1, CDR2 and CDR3) contained within heavy and light chain variable domain sequences selected from the group consisting of SEQ ID NO: 2/10, 18/20, 22/24, 26/34, 42/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/466, 474/476, 478/480, 482/490, 498/500, and 502/504. In one embodiment, the antibody or fragment thereof comprises the CDR sequences contained within HCVR and LCVR selected from the amino acid sequence pairs of SEQ ID NO: 18/20, 42/44, 66/68, 162/164, 210/212, 266/274, and 434/442.

In another aspect, the invention provides nucleic acid molecules encoding anti-Ang-2 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 473, 477, 481, 497, 501, 505, 513, and 515, or a substantially identical sequence having at least 90%, at least 95%, at least 98%, or at least 99% identity thereto. In one embodiment, the antibody or fragment thereof comprises a HCVR encoded by a nucleic acid sequence selected from the group consisting of SEQ ID NO: 17, 41, 65, 161, 209, 265, and 433.

In one embodiment, the invention provides an antibody or fragment thereof comprising a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451, 455, 465, 475, 479, 489, 499, and 503, or a substantially identical sequence having at least 90%, at least 95%, at least 98%, or at least 99% identity thereto. In one embodiment, the antibody or fragment thereof comprises a LCVR encoded by a nucleic acid sequence selected from the group consisting of SEQ ID NO: 19, 43, 67, 163, 211, 273, and 441.

In one embodiment, the invention provides an antibody or antigen-binding fragment of an antibody comprising a HCDR3 domain encoded by a nucleotide sequence selected from the group consisting of SEQ ID NO: 7, 31, 55, 79, 103, 127, 151, 175, 199, 223, 247, 271, 295, 319, 343, 367, 391, 415, 439, 463, 487, and 511, or a substantially identical sequence having at least 90%, at least 95%, at least 98%, or at least 99% identity thereto; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423, 447, 471, and 495, or a substantially identical sequence having at least 90%, at least 95%, at least 98%, or at least 99% identity thereto. In one embodiment, the antibody or fragment thereof comprises HCDR3 and LCDR3 sequences encoded by the nucleic acid sequence pairs selected from the group consisting of SEQ ID NO: 7/15, 31/39, 55/63, 151/159, 199/207, 271/279, and 439/447.

In a further embodiment, the antibody or fragment thereof further comprises: a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435, 459, 483, and 507, or a substantially identical sequence having at least 90%, at least 95%, at least 98%, or at least 99% identity thereto; a HCDR2 domain encoded by a nucleotide sequence selected from the group consisting of SEQ ID NO: 5, 29, 53, 77, 101, 125, 149, 173, 197, 221, 245, 269, 293, 317, 341, 365, 389, 413, 437, 461, 485, and 509, or a substantially identical sequence having at least 90%, at least 95%, at least 98%, or at least 99% identity thereto; a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419, 443, 467, and 491, or a substantially identical sequence having at least 90%, at least 95%, at least 98%, or at least 99% identity thereto; and a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421, 445, 469, and 493, or a substantially identical sequence having at least 90%, at least 95%, at least 98%, or at least 99% identity thereto.

In one embodiment, the antibody or fragment thereof comprises the heavy and light chain CDR sequences encoded by the nucleic acid sequences of SEQ ID NO: 17 and 19; SEQ ID NO: 41 and 43; SEQ ID NO: 65 and 67; SEQ ID NO: 161 and 163; SEQ ID NO: 209 and 211; SEQ ID NO: 265 and 273; or SEQ ID NO: 433 and 441.

The invention encompasses anti-Ang-2 antibodies having a modified glycosylation pattern. In some applications, modification to remove undesirable glycosylation sites may be useful. For example, the present invention encompasses modified versions of any antibody set forth herein wherein the modified version lacks a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds Ang-2 and a pharmaceutically acceptable carrier or diluent. In a related aspect, the invention features a composition which is a combination of an Ang-2 inhibitor and a second therapeutic agent. In one embodiment, the Ang-2 inhibitor is an antibody or fragment thereof. In one embodiment, the second therapeutic agent is any agent that is advantageously combined with an Ang-2 inhibitor. Exemplary agents that may be advantageously combined with an Ang-2 inhibitor include, without limitation, any agent that inhibits or reduces angiogenesis, other cancer therapeutic agents, anti-inflammatory agents, cytokine inhibitors, growth factor inhibitors, anti-hematopoietic factors, non-steroidal anti-inflammatory drugs (NSAIDs), antiviral agents, and antibiotics.

In another aspect, the invention provides methods for inhibiting Ang-2 activity using the anti-Ang-2 antibody or antigen-binding portion of the antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of Ang-2 activity. Preferably, the anti-Ang-2 antibody or antibody fragment of the invention is useful to treat any disease or condition caused by, associated with, or perpetuated by the process of angiogenesis. In certain embodiments of the invention, the anti-Ang-2 antibodies or antigen-binding portions thereof are useful for the treatment of cancer. In the context of cancer therapies, the anti-Ang-2 antibodies of the invention or antigen-binding portions thereof can be administered alone or in combination with other anti-cancer therapeutic antibodies, chemotherapeutic agents and/or radiation therapy. In other embodiments of the present invention, the anti-Ang-2 antibodies or antigen-binding fragments thereof are useful for the treatment of one or more eye disorders, e.g., age-related macular degeneration, diabetic retinopathy, etc., and/or one or more inflammatory or infectious diseases.

In yet another aspect, the invention provides methods for treating advanced cancer or solid tumor malignancies, wherein the methods comprise administering a therapeutically effective amount of an antibody or antigen binding fragment that specifically binds Ang-2 but does not substantially bind Ang-1. In certain embodiments, methods of the invention are used in treatment of advanced cancer that is resistant to conventional anti-cancer therapy. In some embodiments, the methods further comprise administering a second therapeutic agent. The second therapeutic agent may be another anti-angiogenic agent. An example of an anti-angiogenic agent that may be used in combination with the anti-Ang-2 antibodies in the methods of treatment of the present invention is aflibercept, a vascular endothelial growth factor (VEGF)-inhibiting fusion protein.

Other embodiments will become apparent from a review of the ensuing detailed description.

BRIEF DESCRIPTION OF THE FIGURES

FIG. 1 is an alignment of the last 88 C-terminal amino acids of human Ang-2 (residues 409 to 496 of SEQ ID NO:518) with the corresponding amino acid sequence of human Ang-1 (SEQ ID NO:531). Residues that differ between hAng-1 and hAng-2 are indicated by white text and black shading. Asterisks (*) indicate the amino acids of hAng-2 which were shown to interact with human Tie-2 by crystal structure analysis. See Barton et al., *Nat. Struct. Mol. Biol.* 13:524-532 (2006). Triangles (▲) indicate the Tie-2-interacting amino acid positions that differ between hAng-2 and hAng-1.

DETAILED DESCRIPTION

Figure 2:
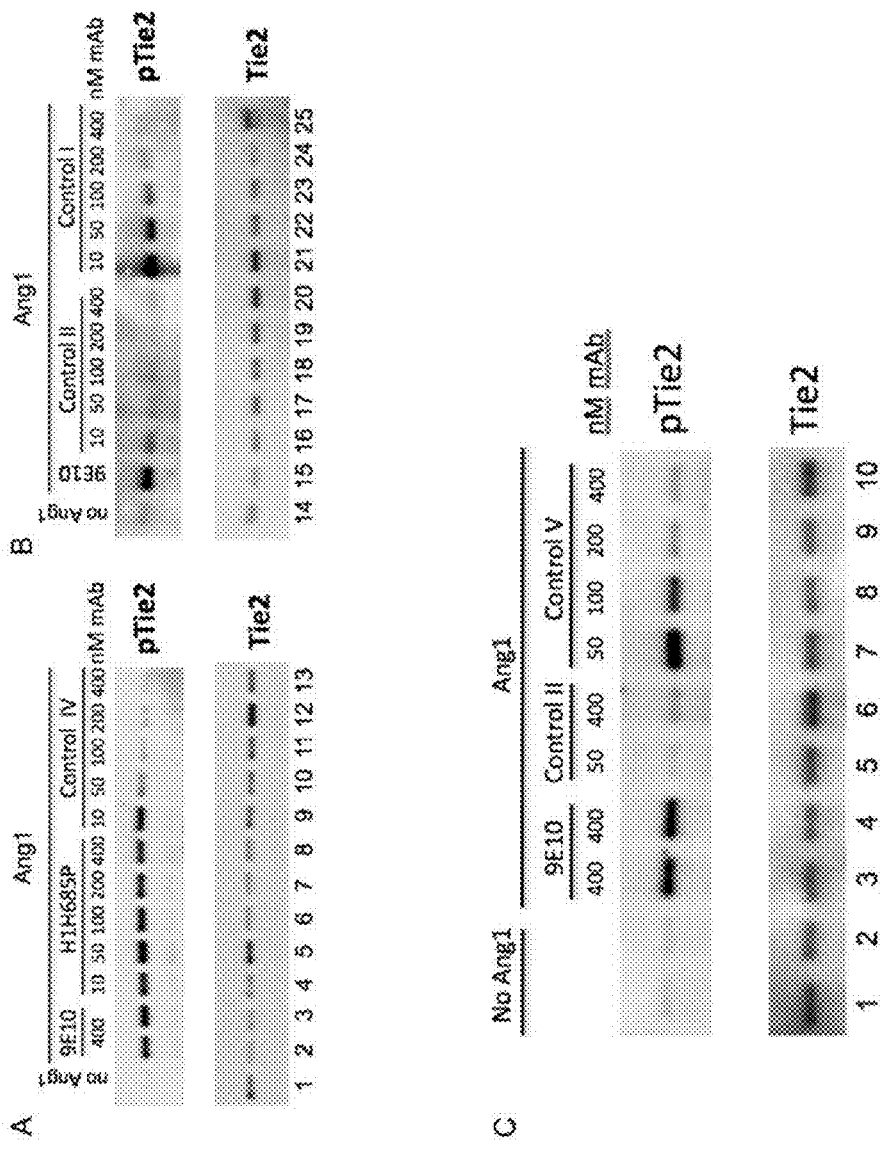
FIG. 2 (Panels A-C) depict the results of Western blots which illustrate the extent to which Ang-2 binding molecules inhibit, or fail to inhibit, Ang-1-induced Tie-2 phosphorylation.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

As used herein, the term "angiopoietin-2" or "Ang-2", unless specified as being from a non-human species (e.g., "mouse Ang-2," "monkey Ang-2," etc.), refers to human Ang-2 or a biologically active fragment thereof (e.g., a fragment of the Ang-2 protein which is capable of inducing angiogenesis in vitro or in vivo). Human Ang-2 is encoded by the nucleic acid sequence shown in SEQ ID NO:517 and has the amino acid sequence of SEQ ID NO:518. The amino acid sequences of mouse and monkey Ang-2 proteins are available from the NCBI protein sequence database under Accession Nos. NP_031452 and BAE89705.1, respectively.

The term "angiopoietin-1" or "Ang-1", unless specified as being from a non-human species (e.g., "mouse Ang-1," "monkey Ang-1," etc.), refers to human Ang-1 or a biologically active fragment thereof. Human Ang-1 has the amino acid sequence as set forth in the NCBI protein sequence database under Accession No. AAB50557. The term "Tie-2" (also referred to in the art as "TEK") unless specified as being from a non-human species (e.g., "mouse Tie-2," "monkey Tie-2," etc.), refers to human Tie-2 or a biologically active fragment thereof. Human Tie-2 has the amino acid sequence as set forth in the NCBI protein sequence database under Accession No. AAA61130.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody", as used herein, is intended to refer to an antibody that is substantially free of other antibodies having different antigenic specificities (e.g., an isolated antibody that specifically binds human Ang-2 or a human Ang-2 fragment is substantially free of antibodies that specifically bind antigens other than human Ang-2). The term "specifically binds," or the like, means that an antibody or antigen-binding fragment thereof forms a complex with an antigen that is relatively stable under physiologic conditions. Specific binding can be characterized by a $K_D$ of about $1\times10^{-8}$ M or less. Methods for determining whether two molecules specifically bind are well known in the art and include, for example, equilibrium dialysis, surface plasmon resonance, and the like. An isolated antibody that specifically binds human Ang-2 may, however, have cross-reactivity to other antigens, such as Ang-2 molecules from other species. Moreover, an isolated antibody may be substantially free of other cellular material and/or chemicals.

A "neutralizing" or "blocking" antibody, as used herein, is intended to refer to an antibody whose binding to Ang-2 blocks the interaction between Ang-2 and its receptor (Tie-2) and/or results in inhibition of at least one biological function of Ang-2. The inhibition caused by an Ang-2 neutralizing or blocking antibody need not be complete so long as it is detectable using an appropriate assay. Exemplary assays for detecting Ang-2 inhibition are described elsewhere herein.

The fully-human anti-Ang-2 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Ang-2 antibodies comprising variants of any of the HCVR, LCVR, and/or CDR amino acid sequences disclosed herein having one or more conservative substitutions. For example, the present invention includes anti-Ang-2 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. In one embodiment, the antibody comprises an HCVR having the amino acid sequence of SEQ ID NO:18 with 8 or fewer conservative amino acid substitutions. In another embodiment, the antibody comprises an HCVR having the amino acid sequence of SEQ ID NO:18 with 6 or fewer conservative amino acid substitutions. In another embodiment, the antibody comprises an HCVR having the amino acid sequence of SEQ ID NO:18 with 4 or fewer conservative amino acid substitutions. In another embodiment, the antibody comprises an HCVR having the amino acid sequence of SEQ ID NO:18 with 2 or fewer conservative amino acid substitutions. In one embodiment, the antibody comprises an LCVR having the amino acid sequence of SEQ ID NO: 20 with 8 or fewer conservative amino acid substitutions. In another embodiment, the antibody comprises an LCVR having the amino acid sequence of SEQ ID NO: 20 with 6 or fewer conservative amino acid substitutions. In another embodiment, the antibody comprises an LCVR having the amino acid sequence of SEQ ID NO:20 with 4 or fewer conservative amino acid substitutions. In another embodiment, the antibody comprises an LCVR having the amino acid sequence of SEQ ID NO:20 with 2 or fewer conservative amino acid substitutions.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.
Preparation of Human Antibodies Methods for generating monoclonal antibodies, including fully human monoclonal antibodies are known in the art. Any such known methods can be used in the context of the present invention to make human antibodies that specifically bind to human Ang-2 and which possess one or more of the antigen-binding and/or functional characteristics of any of the exemplary anti-Ang-2 antibodies disclosed herein.

Using VELOCIMMUNE™ technology or any other known method for generating monoclonal antibodies, high affinity chimeric antibodies to Ang-2 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-Ang-2 antibodies and antibody fragments of the present invention encompass proteins having amino acid sequences that vary from those of the described antibodies, but that retain the ability to bind human Ang-2. Such variant antibodies and antibody fragments comprise one or more additions, deletions, or substitutions of amino acids when compared to parent sequence, but exhibit biological activity that is essentially equivalent to that of the described antibodies. Likewise, the anti-Ang-2 antibody-encoding DNA sequences of the present invention encompass sequences that comprise one or more additions, deletions, or substitutions of nucleotides when compared to the disclosed sequence, but that encode an anti-Ang-2 antibody or antibody fragment that is essentially bioequivalent to an anti-Ang-2 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-Ang-2 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Biological and Therapeutic Characteristics of the Antibodies

In general, the antibodies of the instant invention bind to human Ang-2 with a $K_D$ of less than 100 pM, typically with a $K_D$ of less than 50 pM, and in certain embodiments, with a $K_D$ of less than 40 pM, when measured by binding to antigen either immobilized on solid phase or in solution phase.

In addition, certain exemplary anti-Ang-2 antibodies of the invention may exhibit one or more of the following characteristics: (1) ability to bind to human Ang-2 but not to mouse Ang-2; (2) ability to bind to human Ang-2 and to mouse Ang-2; (3) ability to bind to human Ang-2 but not to human Ang-1, -3 or -4; (4) ability to bind to human Ang-2 but not to mouse Ang-1, -3 or -4; (5) ability to bind to human Ang-2 and to human Ang-1, -3 or -4; (6) ability to bind to human Ang-2 and to mouse Ang-1, -3 or -4; (7) ability to block binding of human Ang-2 to human Tie-2; (8) ability to block binding of human Ang-2 to mouse Tie-2; (9) ability to block binding of mouse Ang-2 to human Tie-2; (10) ability to block binding of mouse Ang-2 to mouse Tie-2; (11) ability to block binding of human Ang-1 to human Tie-2; (12) ability to block binding of human Ang-1 to mouse Tie-2; (13) ability to block binding of mouse Ang-1 to human Tie-2; (14) ability to block binding of mouse Ang-1 to mouse Tie-2; (15) ability to inhibit human Ang-2-induced phosphorylation of human Tie-2; (16) ability to inhibit human Ang-2-induced phosphorylation of mouse Tie-2; (17) ability to inhibit mouse Ang-2-induced phosphorylation of human Tie-2; (18) ability to inhibit mouse Ang-2 induced phosphorylation of mouse Tie-2; (19) ability to inhibit human Ang-1-induced phosphorylation of human Tie-2; (20) ability to inhibit human Ang-1-induced phosphorylation of mouse Tie-2; (21) ability to inhibit mouse Ang-1-induced phosphorylation of human Tie-2; (22) ability to inhibit mouse-Ang-1-induced phosphorylation of mouse Tie-2; (23) ability to inhibit in vivo angiogenesis in an experimental model (e.g., angiogenesis induced by a Matrigel plug containing MCF-7 cells implanted subcutaneously into nude mice); and/or (24) ability to inhibit or decrease tumor volume in a mouse xenograft model.

The present invention also includes antibodies that bind with high affinity to a construct comprising the Ang-2 fibronectin-like domain but lacking the Ang-2 N-terminal coiled-coil domain (such constructs are referred to herein as "Ang-2FD"). Exemplary Ang-2FD constructs include human Ang-2FD (SEQ ID NO:519), mouse Ang-2FD (SEQ ID NO:520), and monkey Ang-2FD (SEQ ID NO:521). The human, mouse and monkey Ang-2FD constructs may be monomeric or dimeric. Ang-2FD constructs may also include other non-Ang-2 amino acid sequences such as a human or mouse Fc domain linked to the Ang-2FD molecules. Another exemplary Ang-2FD construct is referred to herein as "hBA2" (or human "bow-Ang2") which is a tetramer of human Ang-2 fibrinogen-like domains associated with one another via a human or mouse Fc domain to form a bow-tie-like configuration. Typically, hBA2 consists of two Ang-2 dimers, wherein each Ang-2 dimer contains two Ang-2 fibronectin-like domains connected to one another via an Fc domain. Exemplary hBA2 components include the polypeptides designated hBA2-hIgG1 (SEQ ID NO:522) and hBA2-mIgG2a (SEQ ID NO:523). Unexpectedly, certain anti-Ang-2 antibodies of the present invention were found to bind to Ang-2FD constructs with much higher affinities than an known Ang-2 control antibody (see Examples set forth herein).

High affinity binding, in the context of anti-Ang-2 antibody binding to a human or mouse dimeric Ang-2FD construct, means that the anti-Ang-2 antibody binds the human or mouse dimeric Ang-2FD with a $K_D$ of less than 300 pM. For example, anti-Ang-2 antibodies that bind with high affinity to human or mouse dimeric Ang-2FD include antibodies that bind to human or mouse dimeric Ang-2-FD with a $K_D$ of less than 300 pM, less than 250 pM, less than 200 pM, less than 190 pM, less than 180 pM, less than 170 pM, less than 160 pM, less than 150 pM, less than 140 pM, less than 130 pM, less than 120 pM, less than 110 pM, less than 100 pM, less than 90 pM, less than 80 pM, less than 70 pM, less than 60 pM or less than 50 pM, as measured at 25° C. in a surface Plasmon resonance assay.

High affinity binding, in the context of anti-Ang-2 antibody binding to a monkey dimeric Ang-2FD construct, means that the anti-Ang-2 antibody binds the monkey dimeric Ang-2FD with a $K_D$ of less than 500 pM. For example, anti-Ang-2 antibodies that bind with high affinity to monkey dimeric Ang-2FD include antibodies that bind to monkey Ang-2-FD with a $K_D$ of less than 500 pM, less than 450 pM, less than 400 pM, less than 350 pM, less than 300 pM, less than 250 pM, less than 200 pM, less than 190 pM, less than 180 pM, less than 170 pM, less than 160 pM, less than 150 pM, less than 140 pM, less than 130 pM, less than 120 pM, less than 110 pM, less than 100 pM, less than 90 pM, or less than 80 pM, as measured at 25° C. in a surface Plasmon resonance assay.

High affinity binding, in the context of anti-Ang-2 antibody binding to a human monomeric Ang-2FD construct, means that the anti-Ang-2 antibody binds the human monomeric Ang-2FD with a $K_D$ of less than 40 nM. For example, anti-Ang-2 antibodies that bind with high affinity to human monomeric Ang-2FD include antibodies that bind to human monomeric Ang-2-FD with a $K_D$ of less than 40 nM, less than 30 nM, less than 25 nM, less than 20 nM, less than 15 nM, less than 10 nM, less than 9 nM, less than 8 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, or less than 0.6 nM as measured at 25° C. in a surface Plasmon resonance assay.

High affinity binding, in the context of anti-Ang-2 antibody binding to a hBA2 construct, means that the anti-Ang-2 antibody binds the hBA2 with a $K_D$ of less than 80 pM. For example, anti-Ang-2 antibodies that bind with high affinity to hBA2 include antibodies that bind to hBA2 with a $K_D$ of less than 80 pM, less than 75 pM, less than 70 pM, less than 65 pM, less than 60 pM, less than 55 pM, less than 50 pM, less than 45 pM, less than 40 pM, less than 35 pM, less than 30 pM, less than 25 pM, less than 20 pM, less than 18 pM, less than 16 pM, less than 14 pM, or less than 12 pM, as measured at 25° C. in a surface Plasmon resonance assay.

The present invention includes antibodies that bind Ang-2 but do not substantially bind Ang-1. As used herein, an antibody "does not substantially bind Ang-1" if the antibody, when tested for binding to Ang-1 in a surface plasmon resonance assay in which the antibody is captured on a surface and full-length wild-type human Ang-1 at a concentration of about 25 nM is injected over the captured antibody surface at a flowrate of about 60 µl/min for about 3 minutes at 25° C., exhibits a $K_D$ of greater than about 1 nM, e.g., a $K_D$ of greater than about 5 nM, greater than about 10 nM, greater than about 50 nM, greater than about 100 nM, greater than about 150 nM, greater than about 200 nM, greater than about 250 nM, greater than about 300 nM, greater than about 350 nM, greater than about 400 nM, greater than about 450 nM, greater than about 500 nM, or more. (See, e.g., Example 4). In addition, an antibody "does not substantially bind Ang-1" if the antibody fails to exhibit any binding to Ang-1 when tested in such an assay or equivalent thereof.

The present invention also includes antibodies that block the binding of Ang-2 to Tie-2 but do not substantially block the binding of Ang-1 to Tie-2. As used herein, an antibody "does not substantially block the binding of Ang-1 to Tie-2" if, when the antibody is premixed with Ang-1 antigen at a ratio of about 100:1 (antibody:antigen) and allowed to incubate at 25° C. for about 60 minutes and then the equilibrated mixture is tested for binding to Tie-2 by surface plasmon resonance over a Tie-2-coated surface (5 µl/min for 5 min. at 25° C.), the amount of Ang-1 bound to Tie-2 is at least 50% the amount of Ang-1 bound to Tie-2 in the presence of an irrelevant control molecule. (See, e.g., Example 6). For example, if the amount of Ang-1 bound to Tie-2 following preincubation with an antibody is at least about 50%, at least about 55%, at least about 60%, at least about 65%, at least about 70%, at least about 75%, at least about 80%, at least about 85%, at least about 90%, at least about 95%, or about 100% the amount of Ang-1 that binds to Tie-2 following preincubation with an irrelevant control molecule under the above noted experimental conditions, then the antibody is deemed to "not substantially block the binding of Ang-1 to Tie-2."

Moreover, the present invention includes antibodies that block or substantially attenuate a biological activity of Ang-2 (e.g., Ang-2-mediated phosphorylation of Tie-2; Ang-2-induced angiogenesis; etc.) but do not block or substantially attenuate the corresponding biological activity of Ang-1 (e.g., Ang-1-mediated phosphorylation of Tie-2; Ang-1-induced angiogenesis; etc). Assays and tests useful for determining whether an antibody satisfies one or more of the characteristics listed above will be readily known and easily practiced by persons of ordinary skill in the art and/or can be fully ascertained from the present disclosure. For example, the experimental procedures detailed below can be used to determine whether a given antibody binds or does not bind to Ang-2 and/or Ang-1; blocks or does not block binding of Ang-2 and/or Ang-1 to Tie-2; inhibits or does not inhibit Ang-2- and/or Ang-1-mediated phosphorylation of Tie-2; etc.

Epitope Mapping and Related Technologies

To screen for antibodies that bind to a particular epitope (e.g., those which block binding of IgE to its high affinity receptor), a routine cross-blocking assay such as that described "Antibodies," Harlow and Lane (Cold Spring Harbor Press, Cold Spring Harb., N.Y.) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-Ang-2 antibodies of the invention into groups of antibodies binding different epitopes.

Anti-Ang-2 antibodies can bind to an epitope within the amino-terminal coiled-coil domain or within the carboxy-terminal fibrinogen-like domain ("FD"). In preferred embodiments of the present invention, the anti-Ang-2 antibodies and antigen binding fragments thereof bind to an epitope within the FD.

Figure 1:
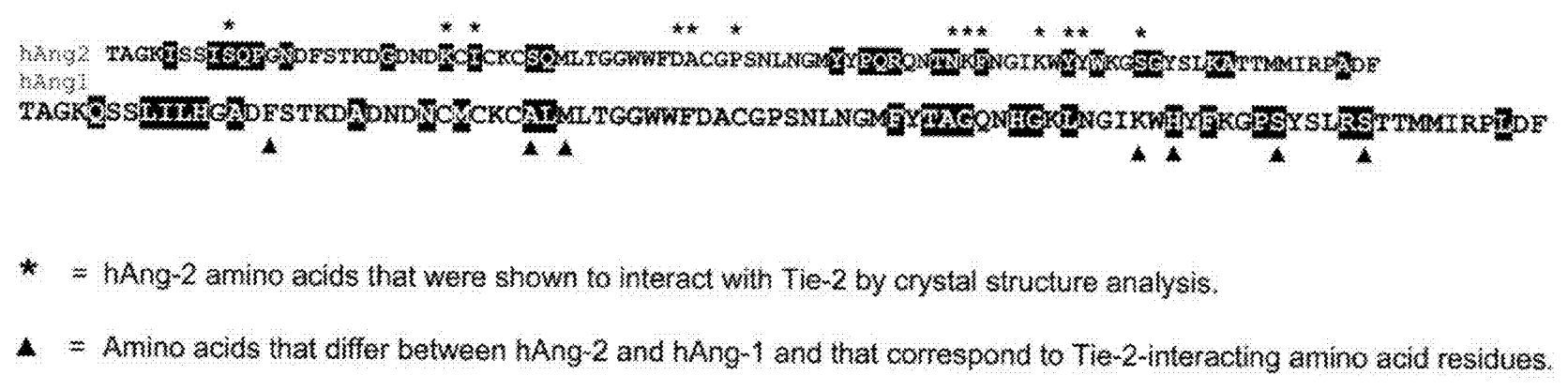

The amino acids within the FD of Ang-2 that interact with Tie-2 have been ascertained from crystal structure analysis. See Barton et al., Nat. Struct. Mol. Biol. 13:524-532 (May 2006). With regard to antibodies that block the binding of Ang-2 to Tie-2 but do not substantially block binding of Ang-1 to Tie-2 (e.g., H1H685P, see Examples 5 and 6 below), the epitope to which such antibodies bind may include one or more amino acids of Ang-2 that (a) interact with Tie-2 and (b) are non-identical to the corresponding amino acid in Ang-1. (See FIG. 1). Thus, the epitope to which such Ang-2 preferential antibodies bind may include one or more of the following amino acids of hAng-2 (SEQ ID NO:518): S-417; K-432; I-434; N-467; F-469; Y-475; or S-480. For example, the present inventors have discovered that antibodies which interact with amino acids F-469, Y-475, and S-480 of Ang-2 (SEQ ID NO:518) preferentially interact with Ang-2 over Ang-1, and this preferential binding may have therapeutic benefits. Thus, the present invention includes anti-Ang-2 antibodies which specifically bind human angiopoietin-2 (hAng-2) but do not substantially bind hAng-1, wherein the antibodies bind an epitope on hAng-2 (SEQ ID NO:518) comprising amino acids F-469, Y-475, and S-480. Similarly, the present invention includes anti-Ang-2 antibodies which block the binding of hAng-2 to hTie-2 but do not substantially block the binding of hAng-1 to hTie-2, wherein the antibodies bind an epitope on hAng-2 (SEQ ID NO:518) comprising amino acids F-469, Y-475, and S-480.

The present invention includes anti-Ang-2 antibodies that bind to the same epitope as any of the specific exemplary antibodies described herein (e.g., H1H685, H1H690, H1H691, H1H696, H1H706, H1M724 and/or H2M744). Likewise, the present invention also includes anti-Ang-2 antibodies that compete for binding to Ang-2 with any of the specific exemplary antibodies described herein (e.g., H1H685, H1H690, H1H691, H1H696, H1H706, H1M724 and/or H2M744).

One can easily determine whether an antibody binds to the same epitope as, or competes for binding with, a reference anti-Ang-2 antibody by using routine methods known in the art. For example, to determine if a test antibody binds to the same epitope as a reference anti-Ang-2 antibody of the invention, the reference antibody is allowed to bind to an Ang-2 protein or peptide under saturating conditions. Next, the ability of a test antibody to bind to the Ang-2 molecule is assessed. If the test antibody is able to bind to Ang-2 following saturation binding with the reference anti-Ang-2 antibody, it can be concluded that the test antibody binds to a different epitope than the reference anti-Ang-2 antibody. On the other hand, if the test antibody is not able to bind to the Ang-2 molecule following saturation binding with the reference anti-Ang-2 antibody, then the test antibody may bind to the same epitope as the epitope bound by the reference anti-Ang-2 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-Ang-2 antibody, the above-described binding methodology is performed in two orientations: In a first orientation, the reference antibody is allowed to bind to an Ang-2 molecule under saturating conditions followed by assessment of binding of the test antibody to the Ang-2 molecule. In a second orientation, the test antibody is allowed to bind to an Ang-2 molecule under saturating conditions followed by assessment of binding of the reference antibody to the Ang-2 molecule. If, in both orientations, only the first (saturating) antibody is capable of binding to the Ang-2 molecule, then it is concluded that the test antibody and the reference antibody compete for binding to Ang-2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Species Selectivity and Species Cross-Reactivity

According to certain embodiments of the invention, the anti-Ang-2 antibodies bind to human Ang-2 but not to Ang-2 from other species. Alternatively, the anti-Ang-2 antibodies of the invention, in certain embodiments, bind to human Ang-2 and to Ang-2 from one or more non-human species. For example, the Ang-2 antibodies of the invention may bind to human Ang-2 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee Ang-2.

Immunoconjugates

The invention encompasses anti-Ang-2 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, see for example, WO 05/103081).

Multispecific Antibodies

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The anti-Ang-2 antibodies of the present invention, or portions thereof, can be linked to or co-expressed with another functional molecule, e.g., another peptide or protein, to form a multispecific molecule. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Uses of the Antibodies

The antibodies of the invention are useful, inter alia, for the treatment, prevention and/or amelioration of any disease or disorder associated with Ang-2 activity, including diseases or disorders associated with angiogenesis. The antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, prostate cancer, malignant gliomas, osteosarcoma, colorectal cancer, malignant mesothelioma, multiple myeloma, ovarian cancer, small cell lung cancer, non-small cell lung cancer, synovial sarcoma, thyroid cancer, or melanoma.

For example, the present invention includes methods of treating advanced cancer, the methods comprising administering to a subject in need thereof an isolated antibody or antigen binding fragment thereof that binds specifically to Ang-2, but does not bind specifically to Ang-1, as described herein. Embodiments of the invention pertain to methods of treating advanced solid tumors such as advanced ovarian cancer, colorectal cancer or hepatocellular carcinoma. In some embodiments, the methods comprise administering a second therapeutic agent in combination with an anti-Ang-2 antibody. In one embodiment, the second therapeutic agent may be a VEGF antagonist (such as aflibercept, a recombinant fusion protein consisting of VEGF receptor extracellular domains fused to the Fc portion of human IgG1).

In certain embodiments, the present invention includes methods to inhibit angiogenesis, the methods comprising administering to a subject in need thereof an isolated antibody or antigen binding fragment thereof that binds specifically to Ang-2, but does not bind specifically to Ang-1. In some embodiments, the methods include administering a second angiogenesis inhibitor. The second angiogenesis inhibitor may be another antibody or a recombinant protein such as a VEGF antagonist (e.g., aflibercept).

The present invention includes methods to treat advanced cancer in patients who are refractory to standard or conventional anti-tumor therapy. For example, the present methods may be used in patients suffering from platinum-resistant ovarian cancer.

The antibodies and antigen-binding fragments of the present invention may also be useful for the treatment of one or more eye disorders. Exemplary eye disorders that can be treated with the antibodies and antigen-binding fragments of the invention include, e.g., age-related macular degeneration, diabetic retinopathy, and other eye disorders associated with choroidal neovascularization, vascular leak, retinal edema and inflammation. Additionally, the anti-Ang-2 antibodies of the invention may be administered as an adjuvant to glaucoma surgery to prevent early hem- and lymphangiogenesis and macrophage recruitment to the filtering bleb after glaucoma surgery, and improve clinical outcome.

In other embodiments of the present invention, the antibodies or antigen-binding fragments are used to treat hypertension, diabetes (including non-insulin dependent diabetes mellitus), psoriasis, arthritis (including rheumatoid arthritis), asthma, sepsis, kidney disease and edema associated with injury, stroke or tumor.

Ang-2 expression has been shown to correlate with the severity of various inflammatory and/or infectious diseases (see, e.g., Siner et al., 2009, Shock 31:348-353; Yeo et al., 2008, Proc. Natl. Acad. Sci. (USA):105:17097-17102).

Accordingly, the anti-Ang-2 antibodies of the present invention can be used to treat, prevent or ameliorate one or more inflammatory or infectious diseases. Exemplary infectious diseases that can be treated, prevented or ameliorated by administration of the anti-Ang-2 antibodies of the invention include, but are not limited to: malaria (*Plasmodium falciparum* infection), viral hemorrhagic fevers (e.g., dengue fever), rickettsial infection, toxic shock syndrome, sepsis, hepatitis C, *Bartonella bacilliformis* infection, leishmaniasis, mycobacterial infection, and Epstein-Barr virus infection Therapeutic Formulation and Administration The invention provides therapeutic compositions comprising the anti-Ang-2 antibodies or antigen-binding fragments thereof of the present invention. In certain embodiments, the invention provides for methods of treatment which comprise administering an anti-Ang-2 antibody to a patient, wherein the anti-Ang-2 antibody is contained within a pharmaceutical composition. The therapeutic compositions in of the present invention may further comprise one or more pharmaceutically acceptable carriers, excipients, and other agents that are incorporated into formulations to provide improved transfer, delivery, tolerance, and the like (herein collectively referred to as "pharmaceutically acceptable carriers or diluents"). A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, J Pharm Sci Technol 52:238-311.

The dose of antibody according to methods of the present invention may vary depending upon the age and the size of a subject to be administered, target disease, conditions, route of administration, and the like. The preferred dose is typically calculated according to body weight or body surface area. When an antibody of the present invention is used for treating a condition or disease associated with Ang-2 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering Ang-2 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered, e.g., subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

For the treatment of eye disorders, the antibodies and antigen-binding fragments of the invention may be administered, e.g., by eye drops, subconjunctival injection, subconjunctival implant, intravitreal injection, intravitreal implant, sub-Tenon's injection or sub-Tenon's implant.

The pharmaceutical composition can be also delivered in a vesicle, in particular a liposome (see Langer 1990 Science 249:1527-1533; Treat et al. (1989) in Liposomes in the Therapy of Infectious Disease and Cancer, Lopez-Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton 1987 CRC Crit. Ref. Biomed. Eng. 14:201). In another embodiment, polymeric materials can be used. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Dosage

The amount of anti-Ang-2 antibody administered to a subject according to the methods of the present invention is, generally, a therapeutically effective amount. As used herein, the phrase "therapeutically effective amount" means an amount of anti-Ang-2 antibody that results in one or more of: (a) regression of a tumor or inhibition of angiogenesis in a tumor; and/or (b) a detectable improvement in one or more symptoms or indicia of hepatic function or renal function or bone marrow function (as defined elsewhere herein). A "therapeutically effective amount" also includes an amount of anti-Ang-2 antibody that inhibits, prevents, lessens, or delays the progression of a tumor in a subject.

In the case of an anti-Ang-2 antibody, a therapeutically effective amount can be from about 0.1 mg to about 1500 mg, e.g., about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg, of the anti-Ang-2 antibody.

The amount of anti-Ang-2 antibody contained within the individual doses may be expressed in terms of milligrams of antibody per kilogram of patient body weight (i.e., mg/kg). For example, the anti-Ang-2 antibody may be administered to a patient at a dose of about 0.0001 to about 20 mg/kg of patient body weight. In certain embodiments, the anti-Ang-2 antibody may be administered at a dose of about 1, 3, 6, 12 or 20 mg/kg of patient body weight.

Combination Therapies

The methods of the present invention, according to certain embodiments, comprise administering to the subject one or more additional therapeutic agents in combination with an anti-Ang-2 antibody. As used herein, the expression "in combination with" means that the additional therapeutic agents are administered before, after, or concurrent with the pharmaceutical composition comprising the anti-Ang-2 antibody. The term "in combination with" also includes sequential or concomitant administration of anti-Ang-2 antibody and a second therapeutic agent.

For example, when administered "before" the pharmaceutical composition comprising the anti-Ang-2 antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-Ang-2 antibody. When administered "after" the pharmaceutical composition comprising the anti-Ang-2 antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-Ang-2 antibody. Administration "concurrent" or with the pharmaceutical composition comprising the anti-Ang-2 antibody means that the additional therapeutic agent is administered to the subject in a separate dosage form within less than 5 minutes (before, after, or at the same time) of administration of the pharmaceutical composition comprising the anti-Ang-2 antibody, or administered to the subject as a single combined dosage formulation comprising both the additional therapeutic agent and the anti-Ang-2 antibody.

Combination therapies may include an anti-Ang-2 antibody of the invention and, for example, another Ang-2 antagonist (e.g., an anti-Ang-2 antibody, peptibody, or CovX-body such as CVX-060 (see U.S. Pat. No. 7,521, 425)). Other exemplary additional therapeutic agents that may be combined with or administered in combination with an anti-Ang-2 antibody of the present invention include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., aflibercept, a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), a FOLH1 antagonist (e.g., an anti-FOLH1 antibody), a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), a monovalent CD20 antagonist (e.g., a monovalent anti-CD20 antibody such as rituximab), etc. Other agents that may be beneficially administered in combination with the anti-Ang-2 antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention also includes therapeutic combinations comprising any of the anti-Ang-2 antibodies mentioned herein and an inhibitor of one or more of VEGF, DLL4, EGFR, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The anti-Ang-2 antibodies of the invention may also be administered in combination with antivirals, antibiotics, analgesics, corticosteroids and/or NSAIDs. The anti-Ang-2 antibodies of the invention may also be administered as part of a treatment regimen that also includes radiation treatment and/or conventional chemotherapy. When combined with one or more additional agents, the anti-Ang-2 antibodies of the invention may be administered prior to, simultaneous with (e.g., in the same formulation or in separate formulations), or subsequent to the administration of the other agent(s).

The methods of the invention comprise administering an anti-Ang-2 antibody in combination with a second therapeutic agent for additive or synergistic activity to treat advanced solid tumor malignancy.

Administration Regimens

The present invention includes methods comprising administering to a subject a pharmaceutical composition comprising an anti-Ang-2 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-Ang-2 antibody, once in 2 weeks dosing at an amount of about 1, 3, 6 or 12 mg/kg of patient body weight, can be employed.

According to certain embodiments of the present invention, multiple doses of an anti-Ang-2 antibody may be administered to a subject over a defined time course. The methods according to this aspect of the invention comprise sequentially administering to a subject multiple doses of an anti-Ang-2 antibody. As used herein, "sequentially administering" means that each dose of anti-Ang-2 antibody is administered to the subject at a different point in time, e.g., on different days separated by a predetermined interval (e.g., hours, days, weeks or months). The present invention includes methods which comprise sequentially administering to the patient a single initial dose of an anti-Ang-2 antibody, followed by one or more secondary doses of the anti-Ang-2 antibody, and optionally followed by one or more tertiary doses of the anti-Ang-2 antibody.

The terms "initial dose," "secondary doses," and "tertiary doses," refer to the temporal sequence of administration of the anti-Ang-2 antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-Ang-2 antibody, but generally may differ from one another in terms of frequency of administration. In certain embodiments, however, the amount of anti-Ang-2 antibody contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an anti-Ang-2 antibody may be administered to a patient with advanced malignancy at a loading dose of about 600 mg or about 1200 mg followed by one or more maintenance doses of about 60 mg to about 360 mg.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of anti-Ang-2 antibody which is administered to a patient prior to the administration of the very next dose in the sequence with no intervening doses.

The methods according to this aspect of the invention may comprise administering to a patient any number of secondary and/or tertiary doses of an anti-Ang-2 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an anti-Ang-2 antibody and a second therapeutic agent, to a patient to treat advanced cancer. In some embodiments, the present methods comprise administering one or more doses of an anti-Ang-2 antibody followed by one or more doses of a second therapeutic agent. For example, one or more doses of about 1 mg/kg to about 12 mg/kg of patient body weight of anti-Ang-2 antibody may be administered after which one or more doses of a second therapeutic agent (e.g., aflibercept or any other therapeutic agent, as described elsewhere herein) may be administered to treat, alleviate, reduce or ameliorate one or more conditions associated with advanced cancer (e.g., angiogenesis inhibition). In some embodiments, the anti-Ang-2 antibody is administered at one or more doses resulting in an improvement in one or more bone marrow function- or hepatic function-associated parameters followed by the administration of a second therapeutic agent to prevent recurrence or have additive activity. Alternative embodiments of the invention pertain to concomitant administration of anti-Ang-2 antibody are administered and a second therapeutic agent is administered at a separate dosage at a similar or different frequency relative to the anti-Ang-2 antibody. In some embodiments, the second therapeutic agent is administered before, after or concurrently with the anti-Ang-2 antibody.

Treatment Populations

The present invention includes methods which comprise administering to a subject in need thereof a therapeutic composition comprising an isolated antibody or antigen-binding fragment thereof that binds specifically to Ang-2 but not specifically to Ang-1, as described herein. As used herein, the expression "a subject in need thereof" means a human or non-human animal that exhibits one or more symptoms or indicia of advanced solid tumor malignancy, and/or who has been diagnosed with advanced cancer. In certain embodiments, the methods of the present invention may be used to treat patients that show altered levels of one or more cancer-associated parameters or a diagnosis of advanced malignancy by histology, cytology or radiologic confirmation. For example, the methods of the present invention comprise administering an anti-Ang-2 antibody to patients with elevated levels of calculated creatinine clearance.

In the context of the present invention, "a subject in need thereof" may include, e.g., subjects who, prior to treatment, exhibit (or have exhibited) one or more biochemical parameters of bone marrow function (e.g, a high hemoglobin, absolute neutrophil count, platelet count), or hepatic function (e.g., total bilirubin, alkaline phosphatase) or renal function (e.g., serum creatinine, calculated creatinine clearance). In some embodiments, "a subject in need thereof" may include patients with confirmed diagnosis of adenocarcinoma by histology or cytology or by radiologic confirmation. In some embodiments, the methods may be used to treat a subject whose performance status as a cancer patient is assessed by one of the performance scores known in the art, e.g., the Eastern Cooperative Oncology Group (ECOG) performance score of 0 or 1. The ECOG performance status scores are given in the following table:

| Grade | Description |
| --- | --- |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of limited self-care, confined to bed or chair more than 50% of waking hours |
| 4 | Completely disabled. Cannot carry on any self-care. Totally confined to bed or chair |
| 5 | Dead |

The present invention includes methods to treat adult patients with advanced solid tumor malignancies. In some embodiments, the methods are used to treat patients with advanced ovarian cancer, advanced hepatocellular carcinoma or colorectal cancer. In some embodiments, the present methods are used for patients with confirmed diagnosis of adenocarcinoma of the ovary, fallopian tubes or primary peritoneal cancer, metastatic colorectal adenocarcinoma or advanced hepatocellular cancer.

The present invention includes methods to treat advanced cancer in patients resistant, non-responsive or inadequately responsive to standard or conventional anti-cancer therapy. The term "resistant, non-responsive or inadequately responsive to standard or conventional anti-cancer therapy", as used herein, refers to subjects or patients with cancer who have been treated with an anti-cancer agent known in the art and wherein said agent does not have a therapeutic effect. For example, the present methods may be used to treat patients with advanced platinum-resistant ovarian cancer. In some embodiments, the term refers to reduced patient compliance and/or toxicity and side effects and/or ineffectiveness of the administered anti-cancer agent to reduce or inhibit or delay tumor progression or kill tumor cells. In some embodiments, the term refers to patients suffering from advanced cancer who are refractory to treatment by an anti-cancer agent known in the art. In some embodiments, the term refers to patients suffering from cancer wherein there is tumor growth or disease progression while being treated with a conventional agent. In one embodiment, the methods of the present invention are used to treat platinum-resistant or refractory cancer disease wherein there is disease recurrence within 6 months of last dose of platinum- or disease progression while being treated with platinum-based regimen. In some embodiments, the patients who are "resistant, non-responsive or inadequately responsive to standard or conventional anti-cancer therapy" may show no improvement in one or more parameters of bone marrow function or hepatic function or renal function. Examples of such parameters are described elsewhere herein. For example, treatment with a conventional anti-cancer agent may result in no improvement in hepatic function as characterized by total bilirubin.

Diagnostic Uses of the Antibodies

The anti-Ang-2 antibodies of the present invention may also be used to detect and/or measure Ang-2 in a sample, e.g., for diagnostic purposes. For example, an anti-Ang-2 antibody, or fragment thereof, may be used to diagnose a condition or disease characterized by aberrant expression (e.g., over-expression, under-expression, lack of expression, etc.) of Ang-2. Exemplary diagnostic assays for Ang-2 may comprise, e.g., contacting a sample, obtained from a patient, with an anti-Ang-2 antibody of the invention, wherein the anti-Ang-2 antibody is labeled with a detectable label or reporter molecule. Alternatively, an unlabeled anti-Ang-2 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Ang-2 in a sample include enzyme-linked immunosorbent assay (ELISA), radioimmunoassay (RIA), and fluorescence-activated cell sorting (FACS).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for.

Unless indicated otherwise, parts are parts by weight, molecular weight is average molecular weight, temperature is in degrees Centigrade, and pressure is at or near atmospheric.

Example 1. Generation of Human Antibodies to Human Ang-2

Human Ang-2 antigen was administered directly, with an adjuvant to stimulate the immune response, to a VELOCIMMUNE® mouse comprising DNA encoding human Immunoglobulin heavy and kappa light chain variable regions. The antibody immune response was monitored by an Ang-2-specific immunoassay. When a desired immune response was achieved splenocytes were harvested and fused with mouse myeloma cells to preserve their viability and form hybridoma cell lines. The hybridoma cell lines were screened and selected to identify cell lines that produce Ang-2-specific antibodies. Using this technique several anti-Ang-2 chimeric antibodies (i.e., antibodies possessing human variable domains and mouse constant domains) were obtained; exemplary antibodies generated in this manner were designated as follows: H1M724, H1M727, H1M728, H2M730, H1M732, H1M737, H2M742, H2M743, H2M744, H1M749, H2M750 and H1M810.

Anti-Ang-2 antibodies were also isolated directly from antigen-positive B cells without fusion to myeloma cells, as described in U.S. 2007/0280945A1. Using this method, several fully human anti-Ang-2 antibodies (i.e., antibodies possessing human variable domains and human constant domains) were obtained; exemplary antibodies generated in this manner were designated as follows: H1H685, H1H690, H1H691, H1H693, H1H694, H1H695, H1H696, H1H704, H1H706 and H1H707.

The biological properties of the exemplary anti-Ang-2 antibodies generated in accordance with the methods of this Example are described in detail in the Examples set forth below. The exemplary anti-Ang-2 antibody used in Examples 14 and 15 below is the human anti-Ang-2 antibody designated in Table 2 as H1H685P (also referred to herein as "mAb1").

Example 2. Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each heavy chain variable region (HCVR) and light chain variable region (LCVR) (Table 1).

TABLE 1

| Antibody | HCVR | | | LCVR | | Antibody Identifier |
|---|---|---|---|---|---|---|
| | $V_H$ | $D_H$ | $J_H$ | $V_K$ | $J_K$ | HCVR/LCVR SEQ ID NOs |
| H1H685 | 3-13 | 3-16 | 4 | 3-20 | 1 | 2/10 |
| H1H690 | 3-23 | 4-4 | 3 | 3-11 | 4 | 26/34 |
| H1H691 | 3-9 | 4-17 | 6 | 3-20 | 4 | 50/58 |
| H1H693 | 3-23 | 4-4 | 3 | 1-12 | 1 | 74/82 |
| H1H694 | 3-15 | 6-6 | 4 | 1-5 | 1 | 98/106 |
| H1H695 | 3-33 | 5-12 | 6 | 3-15 | 5 | 122/130 |
| H1H696 | 3-11 | 4-17 | 4 | 1-16 | 4 | 146/154 |
| H1H704 | 3-33 | 6-6 | 4 | 1-16 | 5 | 170/178 |
| H1H706 | 3-33 | 3-3 | 3 | 1-16 | 1 | 194/202 |
| H1H707 | 3-33 | 3-3 | 3 | 3-20 | 4 | 218/226 |
| H1M724 | 3-33 | 3-3 | 5 | 1-17 | 4 | 266/274 |
| H1M727 | 1-18 | 3-3 | 6 | 2-28 | 2 | 338/346 |

TABLE 1-continued

| Antibody | HCVR | | | LCVR | | Antibody Identifier |
|---|---|---|---|---|---|---|
| | $V_H$ | $D_H$ | $J_H$ | $V_K$ | $J_K$ | HCVR/LCVR SEQ ID NOs |
| H1M728 | 3-7 | 6-19 | 4 | 1-5 | 1 | 290/298 |
| H2M730 | 3-7 | 6-13 | 4 | 1-5 | 1 | 362/370 |
| H1M732 | 3-15 | 1-7 | 4 | 1-17 | 3 | 242/250 |
| H2M742 | 3-23 | 5-5 | 5 | 2-28 | 4 | 386/394 |
| H2M743 | 3-23 | 2-8 | 4 | 1-12 | 4 | 410/418 |
| H2M744 | 1-18 | 4-4 | 5 | 1-12 | 4 | 434/442 |
| H1M749 | 3-33 | 5-5 | 4 | 3-15 | 1 | 314/322 |
| H2M750 | 3-33 | 6-6 | 4 | 1-16 | 4 | 458/466 |
| H1M810 | 3-23 | 3-3 | 3 | 1-12 | 1 | 482/490 |

Table 2 sets forth the heavy and light chain variable region amino acid sequence pairs of selected anti-Ang-2 antibodies and their corresponding antibody identifiers. The N, P and G designations refer to antibodies having heavy and light chains with identical CDR sequences but with sequence variations in regions that fall outside of the CDR sequences (i.e., in the framework regions). Thus, N, P and G variants of a particular antibody have identical CDR sequences within their heavy and light chain variable regions but contain modifications within the framework regions.

TABLE 2

| Name | HCVR/ LCVR SEQ ID NOs | Name | HCVR/ LCVR SEQ ID NOs | Name | HCVR/ LCVR SEQ ID NOs |
|---|---|---|---|---|---|
| H1H685N | 2/10 | H1H685P | 18/20 | H1H685G | 22/24 |
| H1H690N | 26/34 | H1H690P | 42/44 | H1H690G | 46/48 |
| H1H691N | 50/58 | H1H691P | 66/68 | H1H691G | 70/72 |
| H1H693N | 74/82 | H1H693P | 90/92 | H1H693G | 94/96 |
| H1H694N | 98/106 | H1H694P | 114/116 | H1H694G | 118/120 |
| H1H695N | 122/130 | H1H695P | 138/140 | H1H695G | 142/144 |
| H1H696N | 146/154 | H1H696P | 162/164 | H1H696G | 166/168 |
| H1H704N | 170/178 | H1H704P | 186/188 | H1H704G | 190/192 |
| H1H706N | 194/202 | H1H706P | 210/212 | H1H706G | 214/216 |
| H1H707N | 218/226 | H1H707P | 234/236 | H1H707G | 238/240 |
| H1M724N | 266/274 | H1M724P | 282/284 | H1M724G | 286/288 |
| H1M727N | 338/346 | H1M727P | 354/356 | H1M727G | 358/360 |
| H1M728N | 290/298 | H1M728P | 306/308 | H1M728G | 310/312 |
| H2M730N | 362/370 | H2M730P | 378/380 | H2M730G | 382/384 |
| H1M732N | 242/250 | H1M732P | 258/260 | H1M732G | 262/264 |
| H1M737N | 506/X* | H1M737P | 514/X* | H1M737G | 516/X* |
| H2M742N | 386/394 | H2M742P | 402/404 | H2M742G | 406/408 |
| H2M743N | 410/418 | H2M743P | 426/428 | H2M743G | 430/432 |
| H2M744N | 434/442 | H2M744P | 450/452 | H2M744G | 454/456 |
| H1M749N | 314/322 | H1M749P | 330/332 | H1M749G | 334/336 |
| H2M750N | 458/466 | H2M750P | 474/476 | H2M750G | 478/480 |
| H1M810N | 482/490 | H1M810P | 498/500 | H1M810G | 502/504 |

*The amino acid sequence of the LCVR of H1M737 is not shown.

Control Constructs Used in the Following Examples

Various control constructs (anti-Ang-2 antibodies and anti-Ang-2 peptibodies) were included in the following experiments for comparative purposes. The control constructs are designated as follows: Control I: a human anti-Ang-2 antibody with heavy and light chain variable domains having the amino acid sequences of the corresponding domains of "Ab536(THW)," as set forth in US 2006/0018909 (see also Oliner et al., 2004, Cancer Cell 6:507-516); Control II: a peptibody that binds human Ang-2 having the amino acid sequence of "2XCon4(C)," as set forth in U.S. Pat. No. 7,205,275, (see also Oliner et al., 2004, Cancer Cell 6:507-516); Control III: a peptibody that binds human Ang-2 having the amino acid sequence of "L1-7," as set forth in U.S. Pat. No. 7,138,370; Control IV: a human anti-Ang-2 antibody with heavy and light chain variable regions having the amino acid sequences of the corresponding domains of "3.19.3" as set forth in US 2006/0246071; and Control V: a human anti-Ang-2 antibody with heavy and light chain variable regions having the amino acid sequences of the corresponding domains of "MEDI1/5" as set forth in WO 2009/097325. (Not all control constructs were used in every Example). In the tables that follow, the notations "Ab" and "Pb" are included to identify antibody and peptibody controls, respectively (i.e., Control 1=Ab; Control II=Pb; Control III=Pb; Control IV=Ab; and Control V=Ab).

Example 3. Antigen Binding Affinity Determination

Equilibrium dissociation constants ($K_D$ values) for the binding of selected purified Ang-2 antibodies to dimeric fibrinogen-like domain of human (SEQ ID NO: 519), mouse (*Mus musculus*; SEQ ID NO: 520) and monkey (*Macca fascicularis*; SEQ ID NO: 521) Ang-2 (Ang-2FD) conjugated to human IgG1 (SEQ ID NO:528) were determined by surface kinetics using a real-time biosensor surface plasmon resonance assay. Antibody was captured on a goat anti-mouse IgG polyclonal antibody surface, a goat anti-human κ polyclonal antibody (Southern Biotech, Birmingham, Ala.) surface or a goat anti-human IgG polyclonal antibody (Jackson Immuno Research Lab, West Grove, Pa.) surface created through direct amine coupling to a BIACORE™ CM5 sensor chip to form a captured antibody surface. Varying concentrations (ranging from 50 nM to 6.25 nM) of protein were injected at 100 μl/min over captured antibody surface for 90 seconds. Antigen-antibody binding and dissociation were monitored in real time at room temperature. Kinetic analysis was performed to calculate $K_D$ and half-life of antigen/antibody complex dissociation. The results are summarized in Table 3 below.

TABLE 3

| Antibody | Dimeric Human Ang-2FD | | Dimeric Mouse Ang-2FD | | Dimeric Monkey Ang-2FD | |
|---|---|---|---|---|---|---|
| | $K_D$ (pM) | $T_{1/2}$ (min) | $K_D$ (pM) | $T_{1/2}$ (min) | $K_D$ (pM) | $T_{1/2}$ (min) |
| H1M724N | 179 | 42.7 | 694 | 16 | 730 | 25.7 |
| H1M728N | 137 | 58.4 | 5650 | 9.9 | 1580 | 69.5 |
| H2M730N | 210 | 47 | — | — | 842 | 36.6 |
| H1M732N | 484 | 35.5 | 1700 | 21.4 | 7330 | 24.1 |
| H1M737N | 251 | 34.5 | 1740 | 6.3 | 3810 | 16 |
| H2M742N | 295 | 38 | 610 | 30.8 | 6170 | 28.5 |
| H2M743N | 154 | 167 | 882 | 195.2 | 234 | 169.2 |
| H2M744N | 98.9 | 109.1 | 143 | 223.1 | 500 | 281.7 |
| H2M749N | 165 | 42.9 | 529 | 25.5 | 1500 | 40.9 |
| H2M750N | 362 | 32.2 | — | — | 1470 | 23 |

The above experiment was repeated using selected purified anti-Ang-2 antibodies cloned onto human IgG1. The results are summarized in Table 4 below.

TABLE 4

| Antibody | Dimeric Human Ang-2FD | | Dimeric Mouse Ang-2FD | | Dimeric Monkey Ang-2FD | |
|---|---|---|---|---|---|---|
| | $K_D$ (pM) | $T_{1/2}$ (min) | $K_D$ (pM) | $T_{1/2}$ (min) | $K_D$ (pM) | $T_{1/2}$ (min) |
| H1H685P | 71.4 | 229.4 | 148 | 128.7 | 99.4 | 177.1 |
| H1H690P | 79 | 126.1 | 91.3 | 105.2 | 55.6 | 195.2 |
| H1H691P | 220 | 38.5 | 220 | 43.8 | 290 | 41 |
| H1H693P | 500 | 37.1 | 446 | 63.7 | 1170 | 17.6 |
| H1H694P | 126 | 265.6 | 237 | 166.5 | 356 | 85.6 |
| H1H695P | 245 | 147 | 347 | 124.2 | 440 | 84.1 |
| H1H696P | 289 | 38.8 | 402 | 37.6 | 354 | 36.6 |
| H1H704P | 331 | 86.1 | 484 | 61.9 | 818 | 33.5 |
| H1H706P | 201 | 50.4 | 357 | 47 | 164 | 53.3 |
| H1H707P | 262 | 26.6 | 328 | 34.4 | 283 | 22.3 |
| H1H724N | 115 | 107 | 185 | 84 | 239 | 173 |
| H1H728N | 162 | 81 | 5760 | 20 | 2000 | 77 |
| H1H730N | 234 | 62 | 97.1 | 90 | 3400 | 87 |
| H1H732N | 386 | 57 | 529 | 51 | 439 | 118 |
| H1H742N | 186 | 65 | 276 | 58 | 683 | 93 |
| H1H743N | 88.2 | 254 | 124 | 233 | 96.5 | 780 |
| H1H744N | 114 | 127 | 158 | 115 | 346 | 164 |
| H1H749N | 118 | 109 | 177 | 96 | 407 | 143 |
| H1H750N | 164 | 127 | 218 | 121 | 199 | 244 |
| Control I (Ab) | 339 | 34.8 | 339 | 47.1 | 537 | 27.1 |

Additional binding experiments were conducted using selected anti-Ang-2 antibodies at two different temperatures to further assess cross-species affinity. Each selected antibody or control construct was captured at a flow rate of 40 μL/min for 1 minute on a goat anti-human kappa polyclonal antibody surface created through direct chemical coupling to a BIACORE™ chip to form a captured antibody surface. Human, monkey and mouse Ang-2FD-Fc at a concentration of 25 nM or 0.78 nM was injected over the captured antibody surface at a flowrate of 60 μL/min for 3 minutes, and antigen-antibody dissociation was monitored in real time for 20 minutes at either 25° C. or 37° C.

Results are summarized in Tables 5 (25° C. binding) and 6 (37° C. binding) below.

TABLE 5

Binding at 25° C.

| Antibody | Dimeric Human Ang-2FD-mFc | | Dimeric Mouse Ang-2FD-hFc | | Dimeric Monkey Ang-2FD-hFc | |
|---|---|---|---|---|---|---|
| | $K_D$ (Molar) | $T_{1/2}$ (min) | $K_D$ (Molar) | $T_{1/2}$ (min) | $K_D$ (Molar) | $T_{1/2}$ (min) |
| H1H685P | 1.17E−11 | 227 | 6.51E−11 | 208 | 2.20E−11 | 275 |
| H1H744N | 1.16E−10 | 23 | 3.85E−10 | 33 | 2.44E−10 | 24 |
| Control I (Ab) | 1.07E−09 | 15 | 1.07E−09 | 15 | 1.03E−09 | 4 |
| Control IV (Ab) | 1.27E−11 | 269 | 4.02E−11 | 289 | 1.55E−11 | 342 |

TABLE 6

Binding at 37° C.

| Antibody | Dimeric Human Ang-2FD-mFc | | Dimeric Mouse Ang-2FD-hFc | | Dimeric Monkey Ang-2FD-hFc | |
|---|---|---|---|---|---|---|
| | $K_D$ (Molar) | $T_{1/2}$ (min) | $K_D$ (Molar) | $T_{1/2}$ (min) | $K_D$ (Molar) | $T_{1/2}$ (min) |
| H1H685P | 2.70E−11 | 60 | 9.39E−11 | 64 | 7.21E−11 | 65 |
| H1H744N | 1.05E−10 | 18 | 2.15E−10 | 26 | 3.20E−10 | 11 |
| Control I (Ab) | — | — | 3.90E−10 | 12 | — | — |
| Control IV (Ab) | 9.91E−12 | 184 | 5.40E−11 | 119 | 4.74E−11 | 107 |

In another experiment, $K_D$ values for selected purified antibodies that bind to a human "bow-Ang-2" tetrameric construct ("hBA2") were determined (using the methods described above). hBA2 consists of two dimers, each dimer containing two Ang-2 fibronectin-like domains connected to one another by a human Fc domain. The amino acid sequence of the dimer constituents of hBA2 is represented by SEQ ID NO:522. The results are summarized in Table 7 below.

TABLE 7

| | hBA2 | |
|---|---|---|
| Antibody | $K_D$ (pM) | $T_{1/2}$ (min) |
| H1H685P | 11.9 | 587.2 |
| H1H690P | 17.9 | 299.3 |
| H1H691P | 106 | 50.6 |
| H1H693P | 299 | 28.7 |
| H1H694P | 68.4 | 111.3 |
| H1H695P | 40.1 | 254.3 |
| H1H696P | 111 | 51.5 |
| H1H704P | 93.9 | 117.7 |
| H1H706P | 79.1 | 63.9 |
| H1H707P | 75.2 | 51.4 |
| H1H724N | 23.3 | 323 |
| H1H728N | 41.8 | 185 |
| H1H730N | 55.9 | 152 |
| H1H732N | 132 | 73 |
| H1H742N | 72.1 | 87 |
| H1H743N | 9.71 | 1118 |
| H1H744N | 17.2 | 442 |
| H1H749N | 32.5 | 235 |
| H1H750N | 36.9 | 284 |
| Control I (Ab) | 83 | 57.5 |

In yet another experiment, $K_D$ values for selected purified antibodies that bind to wild-type human Ang-2 (hAng-2-WT; SEQ ID NO: 518) and the fibrinogen-like domain of human Ang2 (hAng-2FD) were determined (as described above). The results are summarized in Table 8 below.

TABLE 8

| | Monomeric hAng-2FD | | hAng-2-WT | |
|---|---|---|---|---|
| Antibody | $K_D$ (nM) | $T_{1/2}$ (min) | $K_D$ (pM) | $T_{1/2}$ (min) |
| H1M724N | 1.75 | 17.4 | 33.1 | 568 |
| H1M728N | 1.17 | 33.9 | 33.8 | 725 |
| H2M730N | 2.06 | 24.4 | 49.2 | 519 |
| H1M732N | 6.13 | 18.7 | 131 | 333 |
| H1M737N | 2.82 | 13.1 | 59.3 | 282 |
| H2M742N | 4.81 | 18.0 | 67.9 | 437 |
| H2M743N | 0.399 | 156.7 | 14.3 | 2366 |
| H2M744N | 0.475 | 89.3 | 28.9 | 846 |
| H2M749N | 1.38 | 27.9 | 49 | 479 |
| H2M750N | 4.42 | 21.5 | 40.8 | 991 |
| H1H685P | 0.578 | 55 | 47.6 | 1000 |
| H1H691P | 11 | 0.57 | 19.1 | 684.6 |
| H1H690P | 0.594 | 25.16 | 12.4 | 1568 |
| H1H693P | 44.8 | 0.61 | 425 | 100 |
| H1H694P | 7.89 | 9.85 | 158 | 209.7 |
| H1H695P | 1.12 | 50.59 | 31.1 | 1770.7 |
| H1H696P | 38.4 | 0.20 | 40.3 | 642.7 |
| H1H704P | 0.39 | 3.31 | 36.2 | 747.6 |
| H1H706P | 11 | 1.02 | 27.4 | 661.9 |
| H1H707P | 145 | — | 77.1 | 217.4 |
| H1H724N | 2.4 | 13.34 | 22.6 | 895 |
| H1H728N | 1.18 | 5.86 | 43 | 566 |
| H1H730N | 2.84 | 3.44 | 47.5 | 534 |
| H1H732N | 264 | 0.22 | 202 | 264 |
| H1H742N | 486 | 2.29 | 44.9 | 666 |
| H1H743N | 2.35 | 33.03 | 9.48 | 3927 |
| H1H744N | 1.02 | 42.14 | 30.8 | 837 |
| H1H749N | 1.13 | 33.48 | 12.5 | 1833 |
| H1H750N | 0.787 | 30.20 | 9.5 | 4442 |
| Control I (Ab) | 44.5 | 0.03 | 47.6 | 512 |
| Control II (Pb) | 90 | — | 44.7 | 334.8 |

Additional experiments were conducted to measure the binding properties of selected anti-Ang-2 antibodies to monomeric hAng-2FD at 25° C. and 37° C. Each selected antibody or control construct was captured at a flow rate of 40 μL/min for 1 minute on a goat anti-human IgG polyclonal antibody surface created through direct chemical coupling to a BIACORE™ chip to form a captured antibody surface. Human Ang-2FD at a concentration of 500 nM or 7.8 nM was injected over the captured antibody surface at a flowrate of 60 µL/min for 3 minutes, and antigen-antibody dissociation was monitored in real time for 20 minutes at either 25° C. or 37° C.

Results are summarized in Tables 9 (25° C.) and 10 (37° C.) below. N/D=not determined.

TABLE 9

Binding to monomeric hAng-2FD at 25° C.

| | ka (Ms$^{-1}$) | kd (s$^{-1}$) | $K_D$ (Molar) | T½ |
|---|---|---|---|---|
| H1H685P | 2.44E+05 | 7.96E−05 | 3.36E−10 | 145 minutes |
| H1H744N | 2.92E+05 | 1.24E−04 | 4.24E−10 | 93 minutes |
| Control I (Ab) | 4.00E+05 | 5.10E−02 | 1.28E−07 | 14 seconds |
| Control II (Pb) | steady-state | steady-state | 9.00E−08 | steady-state |
| Control III (Pb) | 5.40E+05 | 6.30E−02 | 1.17E−07 | 11 seconds |
| Control IV (Ab) | 2.84E+05 | 3.56E−02 | 1.25E−07 | 19 seconds |

TABLE 10

Binding to monomeric hAng-2FD at 37° C.

| | ka (Ms$^{-1}$) | kd (s$^{-1}$) | $K_D$ (Molar) | T½ |
|---|---|---|---|---|
| H1H685P | 4.06E+05 | 1.39E−04 | 3.42E−10 | 83 minutes |
| H1H744N | 3.86E+05 | 5.48E−04 | 1.42E−09 | 21 minutes |
| Control I (Ab) | steady-state | steady-state | 1.51E−07 | steady-state |
| Control II (Pb) | N/D | N/D | N/D | N/D |
| Control III (Pb) | steady-state | steady-state | 2.94E−07 | steady-state |
| Control IV (Ab) | steady-state | steady-state | 9.40E−08 | steady-state |

As shown in this Example, several of the anti-Ang-2 antibodies generated in accordance with the methods of Example 1 bound to Ang-2 constructs with equivalent or higher affinities than the controls. For example, antibodies H1H685, H1H690, H1H724 and H1H744 bound to dimeric human Ang-2-FD with $K_D$'s of 71.4, 79, 115, and 114 pM, respectively, whereas Control I antibody bound to dimeric human Ang-2-FD with a $K_D$ of 339 pM (see Table 4). Similarly, antibodies H1H685, H1H690, H1H724 and H1H744 bound to human BA2 (a tetrameric Ang-2 fibrinogen-like domain construct) with $K_D$'s of 11.9, 17.9, 23.3 and 17.2 pM, respectively, whereas Control I antibody bound to hBA2 with a $K_D$ of 83 pM (see Table 7). Thus, as compared to the control constructs, many of the antibodies of the invention exhibit enhanced binding to Ang-2. Antibody H1H685P showed especially robust binding properties to Ang-2 as compared to the control constructs.

Example 4. Preferential Binding to Ang-2 Over Ang-1

Binding experiments (plasmon resonance assays) were conducted to ascertain whether selected antibodies bound to both Ang-2 and Ang-1 or if they preferentially bound to Ang-2 only. Each selected antibody or control construct was captured at a flow rate of 40 µL/min for 1 minute on a goat anti-human IgG polyclonal antibody surface created through direct chemical coupling to a BIACORE™ chip to form a captured antibody surface. Full-length wild-type human Ang-1 or Ang-2 at a concentration of 25 nM or 0.78 nM were injected over the captured antibody surface at a flowrate of 60 µL/min for 3 minutes, and antigen-antibody dissociation was monitored in real time for 20 minutes at either 25° C. or 37° C.

The results of these experiments are summarized in Tables 11-14 below. N/D=not determined. "No binding" means that no detectable binding was observed under the particular experimental conditions used in these experiments.

TABLE 11a

Binding to hAng-2-WT at 25° C.

| | ka (Ms$^{-1}$) | kd (s$^{-1}$) | $K_D$ (Molar) | T½ (minutes) |
|---|---|---|---|---|
| H1H685P | 6.59E+05 | 1.60E−05 | 2.42E−11 | 722 |
| H1H744N | 7.65E+05 | 2.57E−05 | 3.35E−11 | 450 |
| Control I (Ab) | 4.74E+05 | 2.26E−05 | 4.76E−11 | 512 |
| Control II (Pb) | 7.73E+05 | 3.45E−05 | 4.47E−11 | 335 |
| Control III (Pb) | 3.29E+05 | 1.98E−05 | 6.01E−11 | 584 |
| Control IV (Ab) | 3.80E+06 | 2.74E−04 | 7.22E−11 | 42 |

TABLE 11b

Binding to hAng-2-WT at 25° C.

| | ka (Ms$^{-1}$) | kd (s$^{-1}$) | $K_D$ (Molar) | T½ (minutes) |
|---|---|---|---|---|
| H1H685P | 1.15E+05 | 8.50E−06 | 7.39E−11 | 1359 |
| Control II (Pb) | 8.30E+04 | 5.41E−05 | 6.52E−10 | 213 |
| Control V (Ab) | 1.12E+05 | 2.66E−05 | 2.73E−10 | 434 |

TABLE 12a

Binding to hAng-1-WT at 25° C.

| | ka (Ms$^{-1}$) | kd (s$^{-1}$) | $K_D$ (Molar) | T½ (minutes) |
|---|---|---|---|---|
| H1H685P | No binding | No binding | No binding | No binding |
| H1H744N | 4.10E+05 | 3.81E−05 | 9.30E−11 | 303 |
| Control I (Ab) | 4.55E+05 | 2.49E−05 | 5.47E−11 | 464 |
| Control II (Pb) | 4.53E+05 | 3.54E−05 | 7.82E−11 | 326 |
| Control III (Pb) | No binding | No binding | No binding | No binding |
| Control IV (Ab) | 6.60E+05 | 1.11E−04 | 1.68E−10 | 105 |

TABLE 12b

Binding to hAng-1-WT at 25° C.

| | ka (Ms$^{-1}$) | kd (s$^{-1}$) | $K_D$ (Molar) | T½ (minutes) |
|---|---|---|---|---|
| H1H685P | No binding | No binding | No binding | No binding |
| Control II (Pb) | 3.04E+05 | 2.51E−05 | 8.26E−11 | 460 |
| Control V (Ab) | 2.75E+05 | 6.68E−05 | 2.43E−10 | 173 |

TABLE 13a

Binding to hAng-2-WT at 37° C.

| | ka (Ms$^{-1}$) | kd (s$^{-1}$) | $K_D$ (Molar) | T½ (minutes) |
|---|---|---|---|---|
| H1H685P | 8.54E+05 | 3.76E−05 | 4.40E−11 | 707 |
| H1H744N | 7.01E+05 | 2.43E−04 | 3.47E−10 | 48 |

TABLE 13b

Binding to hAng-2-WT at 37° C.

| | ka (Ms⁻¹) | kd (s⁻¹) | $K_D$ (Molar) | $T^{1/2}$ (minutes) |
|---|---|---|---|---|
| H1H685P | 1.36E+05 | 2.16E−05 | 1.59E−10 | 535 |
| Control II (Pb) | 3.79E+04 | 1.17E−04 | 3.09E−09 | 99 |
| Control V (Ab) | 9.42E+04 | 7.92E−05 | 8.41E−10 | 146 |

TABLE 14a

Binding to hAng-1-WT at 37° C.

| | ka (Ms⁻¹) | kd (s⁻¹) | $K_D$ (Molar) | $T^{1/2}$ (minutes) |
|---|---|---|---|---|
| H1H685P | No binding | No binding | No binding | No binding |
| H1H744N | 1.47E+06 | 5.20E−05 | 3.12E−11 | 222 |
| Control III (Pb) | No binding | No binding | No binding | No binding |

TABLE 14b

Binding to hAng-1-WT at 37° C.

| | ka (Ms⁻¹) | kd (s⁻¹) | $K_D$ (Molar) | $T^{1/2}$ (minutes) |
|---|---|---|---|---|
| H1H685P | No binding | No binding | No binding | No binding |
| Control II (Pb) | 2.81E+05 | 4.35E−05 | 1.55E−10 | 266 |
| Control V (Ab) | 4.42E+05 | 5.47E−05 | 1.24E−10 | 211 |

These results show that H1H685P is unique among the antibodies tested in this experiment in that it binds with high affinity to Ang-2 but does not bind to Ang-1. The only other construct that exhibits binding to Ang-2 but not to Ang-1 is Control III. It should be emphasized, however, that Control III is a peptibody and that all of the other antibodies tested in this experiment bound to both Ang-2 and Ang-1. The selectivity for Ang-2 binding may confer therapeutic benefits on H1H685P that are not possessed by antibodies that bind to both Ang-2 and Ang-1.

Example 5. Inhibition of Ang-2 Binding to Human Tie-2

Tie-2 is a natural receptor for Ang-2. Anti-Ang-2 antibodies were tested for their ability to block Ang-2 binding to human Tie-2 (hTie-2). hTie-2-mFc (a chimeric construct consisting of human Tie-2 conjugated to mouse IgG; SEQ ID NO:525) was coated onto 96-well plates at a concentration of 2 µg/ml and incubated overnight followed by washing four times in wash buffer (PBS with 0.05% Tween-20). The plate was then blocked with PBS (Irvine Scientific, Santa Ana, Calif.) containing 0.5% BSA (Sigma-Aldrich Corp., St. Louis, Mo.) for one hour at room temperature. In a separate plate, purified anti-Ang-2 antibodies, at a starting concentration of 50 nM, were serially diluted by a factor of three across the plate. Human, mouse or monkey Ang-2FD protein conjugated to human IgG (Ang-2FD-hFc) were added to final concentrations of 2 nM, 8 nM, or 2 nM respectively and incubated for one hour at room temperature. The antibody/Ang-2FD-Fc mixture was then added to the plate containing hTie-2-mFc and incubated for one hour at room temperature. Detection of Ang-2FD-hFc bound to hTie-2-mFc protein was determined with Horse-Radish Peroxidase (HRP) conjugated to a-human IgG antibody (Jackson Immuno Research Lab, West Grove, Pa.) and developed by standard colorimetric response using tetramethylbenzidine (TMB) substrate (BD Biosciences, San Jose, Calif.). Absorbance was read at $OD_{450}$ for 0.1 sec. Percent blocking of Ang-2FD-hFc binding to hTie-2-mFc by 16.67 nM of selected anti-Ang-2 antibodies is shown in Table 15.

TABLE 15

Percent Blocking of Ang-2FD Binding to Tie-2

| Antibody | Human Ang-2FD-hFc | Mouse Ang-2FD-hFc | Monkey Ang-2FD-hFc |
|---|---|---|---|
| H1M724N | 99.5 | 96.6 | 95.2 |
| H1M728N | 98.5 | 83.9 | 97.1 |
| H2M730N | 98.9 | 55.0 | 97.3 |
| H1M732N | 97.7 | 90.9 | 95.8 |
| H1M737N | 99.1 | 95.4 | 90.5 |
| H2M742N | 99.6 | 98.6 | 94.1 |
| H2M743N | 99.6 | 98.4 | 95.1 |
| H2M744N | 99.5 | 98.4 | 95.5 |
| H2M749N | 99.5 | 97.3 | 97.4 |
| H2M750N | 99.4 | 53.7 | 97.4 |
| Control I (Ab) | 94.5 | 90.2 | 96.9 |

In a similar experiment, selected purified anti-Ang-2 antibodies cloned onto human IgG1 were tested for their ability to block Ang-2FD binding to hTie-2 (as described above). Percent blocking of Ang-2FD-hFc binding to hTie-2-mFc by 16.67 nM of selected anti-Ang-2 antibodies is shown in Table 16. NT: not tested.

TABLE 16

Percent Blocking of Ang-2FD Binding to Tie-2

| Antibody | Human Ang-2FD-hFc | Mouse Ang-2FD-hFc | Monkey Ang-2FD-hFc |
|---|---|---|---|
| H1H685P | 93.8 | 97.1 | 62.2 |
| H1H690P | 97.2 | 98.0 | 99.6 |
| H1H691P | 97.4 | 96.7 | 99.8 |
| H1H693P | 73.9 | 63.6 | NT |
| H1H694P | 79.8 | 36.0 | NT |
| H1H695P | 98.4 | 97.6 | NT |
| H1H696P | 98.2 | 94.9 | 99.2 |
| H1H704P | 97.0 | 41.8 | NT |
| H1H706P | 97.1 | 95.9 | 99.8 |
| H1H707P | 95.1 | 93.8 | NT |
| H1H724N | 96.6 | 97.1 | 96.6 |
| H1H744N | 97.9 | 97.6 | 96.2 |
| Control I (Ab) | 97.3 | 82.2 | 98.5 |

In another experiment, selected purified anti-Ang-2 antibodies were tested for their ability to block binding of 20 pM biotinylated hBA2 to hTie-2 (as described above). For this experiment, human Tie-2 conjugated to a histidine tag (hTie-2-His; SEQ ID NO:526) was used in a similar fashion to the hTie-2-mFc described above. Antibody concentrations from 5 nM were serially diluted three-fold. An $IC_{50}$ (Inhibitory Concentration) value was generated by calculating the amount of antibody required to block 50% of the signal from the binding of biotin-hBA2 to Tie-2. An average $IC_{50}$ value for each antibody was calculated based on two separate experiments. The results are summarized in Table 17. NB: no blocking observed at 5 nM concentration.

TABLE 17

| Antibody | Biotin - hBA2 Average $IC_{50}$ (pM) |
|---|---|
| H1M724N | 9.72 |
| H1M728N | 14.05 |

TABLE 17-continued

| Antibody | Biotin - hBA2 Average IC$_{50}$ (pM) |
|---|---|
| H2M730N | 14.60 |
| H1M732N | 82.17 |
| H1M737N | 13.01 |
| H2M742N | 9.65 |
| H2M743N | 11.01 |
| H2M744N | 11.43 |
| H2M749N | 6.43 |
| H2M750N | 8.83 |
| Control I (Ab) | 30.23 |
| Control II (Pb) | 7.75 |
| Control III (Pb) | 16.49 |

In a similar experiment, selected purified anti-Ang-2 antibodies cloned onto human IgG1 were tested for their ability to block binding of biotinylated hBA2 to hTie-2 (as described above). The results are shown in Table 18. NB: no blocking observed at 5 nM concentration.

TABLE 18

| Antibody | Biotin - hBA2 IC$_{50}$ (pM) |
|---|---|
| H1H685P | 20 |
| H1H690P | 17 |
| H1H691P | 13 |
| H1H693P | NB |
| H1H694P | NB |
| H1H695P | 59 |
| H1H696P | 22 |
| H1H704P | 56 |
| H1H706P | 8 |
| H1H707P | 22 |
| H1H724N | 4 |
| H1H744N | 25 |

This Example illustrates that several of the anti-Ang-2 antibodies generated in accordance with the methods of Example 1 blocked the interaction between the Ang-2 fibrinogen-like domain and its receptor (TIE-2) to an equivalent or greater extent than the control antibody. For example, antibodies H1H690, H1H691, H1H695, H1H696, H1H704, H1H706, H1H707, H1H724 and H1H744 each caused greater than 95% blocking of human, mouse and monkey Ang-2FD constructs to the TIE-2 receptor, similar to the results observed with the control constructs (see Table 16).

Example 6. Inhibition of Full-Length Ang-2 and Ang-1 Binding to Human Tie-2

Tie-2 is a receptor for Ang-1 as well as Ang-2. Therefore, in the present Example, the ability of certain anti-Ang-2 antibodies to block binding of Ang-2 or Ang-1 to human Tie-2 was measured and compared.

The ELISA experiments shown in this Example were conducted in a similar manner to the experiments of Example 5. Briefly, hTie-2-mFc (a chimeric construct consisting of human Tie-2 conjugated to mouse IgG; SEQ ID NO:525) was coated onto 96-well plates at a concentration of 2 µg/ml and incubated overnight followed by washing four times in wash buffer (PBS with 0.05% Tween-20). The plate was then blocked with PBS (Irvine Scientific, Santa Ana, Calif.) containing 0.5% BSA (Sigma-Aldrich Corp., St. Louis, Mo.) for one hour at room temperature. In a separate plate, purified anti-Ang-2 antibodies and control constructs, at a starting concentration of 300 nM, were serially diluted by a factor of three across the plate. Full-length human Ang-2 or Ang-1 protein conjugated to 6x histidine tag (R&D Systems, Minneapolis, Minn.) were added to a final concentration of 0.6 nM and incubated for one hour at room temperature. The antibody/antigen mixture was then added to the plate containing hTie-2-mFc and incubated for one hour at room temperature. Detection of Ang-2-His or Ang-1-His bound to hTie-2-mFc protein was determined with Horse-Radish Peroxidase (HRP) conjugated to a-Penta-His antibody (Qiagen, Valencia, Calif.) and developed by standard colorimetric response using tetramethylbenzidine (TMB) substrate (BD Biosciences, San Jose, Calif.). Absorbance was read at OD$_{450}$ for 0.1 sec. An IC$_{50}$ (Inhibitory Concentration) value was generated by calculating the amount of antibody required to block 50% of the signal from the binding of human Ang-2 or Ang-1 to Tie-2. The results, expressed in terms of IC$_{50}$ are shown in Table 19, columns (1) and (2). The extent to which the antibodies or control constructs block the hAng-2/Tie-2 interaction relative to the hAng-1/Tie-2 interaction is reflected in the fold difference in IC$_{50}$ shown in column (3); that is, a higher number in column (3) indicates a greater capacity to block the hAng-2/Tie-2 interaction than the hAng-1/Tie-2 interaction.

TABLE 19

| Antibody | (1) Blocking hAng-2 WT to Tie-2 IC$_{50}$ (M) | (2) Blocking hAng-1 WT to Tie-2 IC$_{50}$ (M) | (3) Fold Difference in hAng-1 Blocking IC$_{50}$ Compared to h-Ang-2 Blocking IC$_{50}$* |
|---|---|---|---|
| H1H685P | 1.294E-10 | >3.000E-07 | >2318 |
| H1H744N | 7.871E-11 | 1.872E-07 | 2378 |
| Control I (Ab) | 9.372E-11 | 6.171E-08 | 658 |
| Control II (Pb) | 3.096E-11 | 5.509E-11 | 1.8 |
| Control III (Pb) | 1.626E-10 | >1.000E-06 | >6150 |
| Control IV (Ab) | 1.476E-10 | 4.252E-09 | 28.8 |

*Calculated by dividing the hAng-1 blocking IC$_{50}$ (column 2) by the hAng-2 blocking IC$_{50}$ (column 1)

In an effort to further assess the ability of selected anti-hAng-2 antibodies to block the binding of Ang-1 to Tie-2, a biosensor surface plasmon resonance experiment was conducted. In this experiment, a human Tie-2 full-length extracellular domain construct (hTie-2-mFc-ecto) was amine-coupled on a BIACORE™ chip to create a receptor coated surface. Selected anti-hAng-2 antibodies and control constructs, at 1 µM (100-fold excess over antigen), were premixed with 10 nM of hAng-1-WT, followed by 60 minutes incubation at 25° C. to allow antibody-antigen binding to reach equilibrium to form equilibrated solutions. The equilibrated solutions were injected over the receptor surfaces at 5 µL/min for 5 minutes at 25° C. Changes in resonance units (RU) due to the binding of the hAng-1-WT to hTie-2-mFc were determined. An irrelevant peptibody construct with no binding to hAng-1 was included in this experiment to establish the 0% blocking baseline, and a human Tie-2-mFc construct was used as a positive control for blocking. The amount of Ang-1 bound to Tie-2 following antibody preincubation, expressed as a percentage of the amount of Ang-1 bound to Tie-2 following negative control preincubation, is shown in Table 20. (A greater amount of Ang-1 binding to Tie-2 signifies a lower degree of antibody blocking).

TABLE 20

| Antibody | RU (average) | Percent of Negative Control Binding |
|---|---|---|
| Negative Control (irrelevant peptibody) | 169 | 100 |
| hTie-2-mFc | 71 | 42 |
| H1H685P | 137 | 81 |
| H1H744N | 57 | 34 |
| H1H691P | 117 | 69 |
| H1H706P | 140 | 83 |
| H1H724N | 57 | 34 |
| Control I (Ab) | 48 | 28 |
| Control II (Pb) | 48 | 28 |
| Control III (Pb) | 160 | 95 |

The foregoing experiment was repeated using different amounts of Ang-2 blockers and controls. In particular, a human Tie-2 full-length extracellular domain construct (hTie-2-mFc-ecto) was amine-coupled on a BIACORE™ chip to create a receptor-coated surface. Selected anti-hAng-2 antibodies and control constructs (50 or 150 nM) were mixed with hAng-2-WT (25 nM) followed by 60 minutes incubation at 25° C. to allow antibody-antigen binding to reach equilibrium. The equilibrated solutions were injected over the receptor surfaces at 10 μL/min for 5 minutes at 25° C. To evaluate the ability of the selected anti-hAng-2 antibodies to block Ang-1-WT binding to hTie-2, a similar procedure was followed except the antibodies were tested at three concentrations (50, 100 or 1000 nM) and incubated with 10 nM of hAng-1-WT. Changes in resonance units (RU) due to the binding of the Ang-2-WT or hAng-1-WT to hTie-2-mFc were determined. An irrelevant antibody with no binding to either angiopoietin was included in these experiments to establish the 0% blocking baseline, and a human Tie-2-mFc construct was used as a positive control for blocking. Results are summarized in Tables 21 (hAng-1 applied to a hTie-2 surface) and 22 (hAng-2 applied to a hTie-2 surface).

TABLE 21

(hAng-1 WT)

| | Amount of Antibody or Control | | | | | |
|---|---|---|---|---|---|---|
| | 50 nM | | 100 nM | | 1000 nM | |
| Antibody | Specific Bound RU | Percent of Neg. Ctrl Binding | Specific Bound RU | Percent of Neg. Ctrl Binding | Specific Bound RU | Percent of Neg. Ctrl Binding |
| Negative Control (irrelevant antibody) | 316 | 100 | 307 | 100 | 276 | 100 |
| hTie-2-mFc | 70 | 22 | 39 | 13 | −47 | 0 |
| H1H685P | 299 | 95 | 291 | 95 | 289 | 105 |
| Control II (Pb) | 8 | 2.5 | 4 | 1.3 | −1 | 0 |
| Control V (Ab) | 150 | 48 | 114 | 37 | 29 | 11 |

TABLE 22

(hAng-2 WT)

| | Amount of Antibody or Control | | | |
|---|---|---|---|---|
| | 50 nM | | 150 nM | |
| Antibody | Specific Bound RU | Percent of Neg. Ctrl Binding | Specific Bound RU | Percent of Neg. Ctrl Binding |
| Negative Control (irrelevant antibody) | 281 | 100 | 278 | 100 |
| hTie-2-mFc | 97 | 35 | 82 | 30 |
| H1H685P | 12 | 4.3 | 12 | 4.3 |
| Control II (Pb) | 10 | 3.6 | 10 | 3.6 |
| Control V (Ab) | 12 | 4.3 | 12 | 4.3 |

The results obtained from these experiments are in agreement with previous results which showed that H1H685P preferentially binds to Ang-2 over Ang-1 (see Example 4). In particular, the results from this Example show that several anti-Ang-2 antibodies (e.g., H1H685P and H1H706P) do not significantly block the binding of human Ang-1 to human Tie-2, even though, in other experiments, it was demonstrated that these antibodies potently blocked the interaction between Ang-2 and Tie-2 (see Example 5, Table 16). Moreover, in these experiments none of the control constructs, except for the Control III peptibody, exhibited the same degree of preferential binding/blocking of Ang-2 over Ang-1 as the exemplary anti-Ang-2 antibodies of the present invention, such as H1H685P.

Example 7. Inhibition of Ang-2-Mediated Tie-2 Phosphorylation by Anti-Ang-2 Antibodies The inventors of the present invention have demonstrated that Ang-2 expression can be induced in human umbilical vein endothelial cells (HUVECs) by the transcription factor FOXO1 (Daly et al. 2006 PNAS 103:15491). Further, the inventors have shown that infection of HUVECs with an adenovirus encoding FOXO1 results in expression and secretion of Ang-2, followed by activation of Tie-2 phosphorylation (Daly et al. 2006 PNAS 103:15491).

Anti-Ang-2 antibodies were tested for their ability to inhibit Tie-2 phosphorylation. Briefly, $7 \times 10^5$ HUVECs (Vec Technologies, Rensselaer, N.Y.) were plated in 6 cm cell culture dishes in 3.5 ml of MCDB131 Complete medium (Vec Technologies, Rensselaer, N.Y.). The following day, the cells were washed with Opti-MEM (Invitrogen Corp., Carlsbad, Calif.) and fed with 2 ml of Opti-MEM. Recombinant adenoviruses encoding either green fluorescent protein (GFP; control) or human FOXO1 (Daly et al. 2004 Genes Dev. 18:1060) were added to the cells at a concentration of 10 pfu/cell and incubated for four hours. Cells were then washed with MCDB131 and fed with 2 ml of MCDB131 containing anti-Ang-2 antibodies at a concentration of 0.5 µg/ml. At twenty hours post infection, cells were lysed and subjected to Tie-2 immunoprecipitation as described by Daly et al., *Proc. Natl. Acad. Sci. USA* 103:15491-15496 (2006). Immunoglobulin was collected on protein A/G beads (Santa Cruz Biotechnology, Santa Cruz, Calif.) for one hour. Beads were washed with cold lysis buffer and resuspended in SDS sample buffer for analysis by western blot with antibodies specific for phosphotyrosine (Millipore, Billerica, Mass.) or Tie-2. Signals were detected using HRP-conjugated secondary antibodies and ECL reagents (GE Healthcare, Piscataway, N.J.). X-Ray films were scanned and the phospho-Tie-2 and Tie-2 signals were quantified using ImageJ software. The phospho-Tie-2/Tie-2 ratios were used to determine the % inhibition for each anti-Ang-2 antibody (i.e. Percent inhibition=Reduction in phospho-Tie-2/Tie-2 as compared to control). For example, a reduction in Tie-2 phosphorylation to the level observed in the control sample is considered to be 100% inhibition. Relative inhibition (+, ++, +++) for each anti-Ang-2 antibody tested according to the percent inhibition observed (25-50%, 50-75%, 75-100%, respectively) is shown in Table 23.

TABLE 23

| Antibody | Inhibition of Tie-2 phosphorylation |
|---|---|
| H1H685P | +++ |
| H1H690P | +++ |
| H1H691P | +++ |
| H1H693P | +++ |
| H1H694P | ++ |
| H1H695P | +++ |
| H1H696P | +++ |
| H1H704P | +++ |
| H1H706P | +++ |
| H1H707P | +++ |
| H1M724N | +++ |
| H1M728N | ++ |
| H1M732N | ++ |
| H1M742N | ++ |
| H1M743N | +++ |
| H1M744N | +++ |
| H1M749N | ++ |
| H1M750N | +++ |
| Control I (Ab) | + |
| Control II (Pb) | +++ |

As demonstrated in this Example, the anti-Ang-2 antibodies generated in accordance with the methods of Example 1 inhibited Tie-2 phosphorylation to a greater extent than the Control I antibody. Especially robust inhibition was observed with antibodies H1H685, H1H690, H1H691, H1H693, H1H695, H1H696, H1H704, H1H706, H1H707, H1M724, H1M744 and H1M750.

Example 8. Inhibition of Ang-1-Mediated Tie-2 Phosphorylation

As shown in the previous Example, Ang-2 can mediate the phosphorylation of Tie-2. Ang-1 is also capable of promoting Tie-2 phosphorylation. In the present Example, the ability of selected anti-Ang-2 antibodies to block Ang-1-mediated phosphorylation of Tie-2 was assessed.

EA.hy926 cells (Edgell et al., *Proc. Natl. Acad. Sci. USA* 80:3734-3737 (1983)) were plated at $5 \times 10^6$ cells per 10 cm dish in 10 ml DMEM with 10% FBS, HAT, L-glutamine and penicillin/streptomycin. After 24 hours, cells were serum-starved for 1 hour in 10 ml DMEM+1 mg/ml BSA. Cells were then stimulated for 10 minutes with 500 ng/ml of recombinant human Ang-1 (R&D Systems) in the presence of either an irrelevant isotype control antibody ("9E10") at 400 nM or the anti-Ang-2 antibody H1H685P, or control agents (Control I, Control II, Control IV, or Control V) at concentrations ranging from 10 to 400 nM.

Following incubation, cells were lysed and Tie-2 was immunoprecipitated as described by Daly et al., *Proc. Natl. Acad. Sci. USA* 103:15491-15496 (2006). Immune complexes were collected by incubation with protein A/G beads (Santa Cruz Biotechnology, Santa Cruz, Calif.) for 60 min. Beads were washed with cold lysis buffer and bound proteins were eluted by heating in SDS sample buffer. Samples were then subjected to Western blot analysis with monoclonal antibodies against Tie-2 or phosphotyrosine (clone 4G10, Millipore, Billerica, Mass.). Results are shown in FIG. 2.

Signals were detected using HRP-conjugated secondary antibodies and ECL reagents (GE Healthcare, Piscataway, N.J.). X-ray films were scanned and the phospho-Tie-2 and Tie-2 signals were quantified using ImageJ software. The phospho-Tie-2/Tie-2 ratios were used to determine the % inhibition for each antibody or peptibody. Percent inhibition=reduction in phospho-Tie-2/Tie-2 as compared to the control sample (400 nM isotype control antibody).

In the presence of the control antibody 9E10, Ang-1 strongly activated Tie-2 phosphorylation (FIG. 2, panel A—compare lanes 2 and 3 vs lane 1). All of the control agents that were tested significantly inhibited Tie-2 phosphorylation, with complete inhibition occurring at 50 nM for Control II (FIG. 2, panel B—lane 17), 100 nM for Control IV (FIG. 2, panel A—lane 11) and 200 nM for Control I (FIG. 2, panel B—lane 24) and Control V (FIG. 2, panel C—lane 9). By contrast, H1H685P had no significant inhibitory effect even at 400 nM (FIG. 2, panel A—lanes 4-8). These results provide additional confirmation of the specificity of H1H685P for Ang-2 over Ang-1.

Example 9. Inhibition of Tumor Growth by Anti-Ang-2 Antibodies

The effect of selected purified anti-Ang-2 antibodies on tumor growth was determined using two tumor cell lines.

PC3 (Human Prostate Cancer Cell Line)

Briefly, $5 \times 10^6$ PC3 cells in 100 µl of growth factor-reduced Matrigel (BD Biosciences) were injected subcutaneously into the flanks of 6-8 week old male NCr nude mice (Taconic, Hudson, N.Y.). After tumor volumes reached an average of about 200 mm³, mice were randomized into groups for treatment. Mice in each treatment group were administered an anti-Ang-2 antibody, Fc protein, or control construct, at a concentration of 10 mg/kg via intraperitoneal injection twice per week for approximately three weeks (Table 24) or at concentrations of 2.5, 12.5, or 25 mg/kg via subcutaneous injection twice per week for approximately three weeks (Table 25). Tumor volumes were measured twice per week over the course of the experiment and tumor weights were measured upon excision of tumors at the conclusion of the experiment. Averages (mean+/−standard deviation) of tumor weight and growth were calculated for each treatment group. Percent decrease of tumor weight and growth were calculated from comparison to Fc protein measurements. Results are summarized in Tables 24 and 25.

TABLE 24

| Antibody | Avg Tumor Weight (g) | % Decrease in Tumor Weight | Avg Tumor Growth (mm$^3$) | % Decrease in Tumor Growth |
| --- | --- | --- | --- | --- |
| Fc protein | 0.66 ± 0.26 | — | 509 ± 213 | — |
| Control I (Ab) | 0.47 ± 0.23 | 29 | 300 ± 242 | 41 |
| H1H724N | 0.55 ± 0.07 | 17 | 392 ± 169 | 23 |
| H1H744N | 0.43 ± 0.20 | 35 | 259 ± 212 | 49 |
| H1H685P | 0.44 ± 0.12 | 33 | 305 ± 143 | 40 |
| H1H691P | 0.59 ± 0.07 | 11 | 485 ± 141 | 5 |
| H1H706P | 0.52 ± 0.14 | 21 | 329 ± 125 | 35 |

TABLE 25

| Antibody | Avg Tumor Growth (mm$^3$) | % Decrease in Tumor Growth |
| --- | --- | --- |
| Fc protein | 1031 ± 485 | — |
| Control II (Pb) (2.5 mg/kg) | 356 ± 196 | 65 |
| Control II (Pb) (12.5 mg/kg) | 360 ± 162 | 65 |
| Control II (Pb) (25 mg/kg) | 527 ± 218 | 49 |
| H1H685P (2.5 mg/kg) | 308 ± 274 | 70 |
| H1H685P (12.5 mg/kg) | 550 ± 150 | 47 |
| H1H685P (25 mg/kg) | 413 ± 208 | 60 |

As shown above, antibodies H1H744N and H1H685P demonstrated especially marked anti-tumor activity in the PC3 mouse tumor model as compared to the control constructs.

The results of similar experiments using the PC3 mouse tumor model and different experimental antibodies (dosed at 2 mg/kg, twice per week) are shown in Tables 26 and 27.

TABLE 26

| Antibody | Avg Tumor Weight (g) | % Decrease in Tumor Weight | Avg Tumor Growth (mm$^3$) | % Decrease in Tumor Growth |
| --- | --- | --- | --- | --- |
| Fc protein | 0.626 ± 0.156 | — | 356 ± 93 | — |
| Control I (Ab) | 0.347 ± 0.093 | 45 | 250 ± 145 | 30 |
| H2M742N | 0.407 ± 0.076 | 35 | 220 ± 102 | 38 |
| H2M743N | 0.372 ± 0.122 | 41 | 179 ± 169 | 50 |

TABLE 27

| Antibody | Avg Tumor Weight (g) | % Decrease in Tumor Weight | Avg Tumor Growth (mm$^3$) | % Decrease in Tumor Growth |
| --- | --- | --- | --- | --- |
| Fc protein | 0.552 ± 0.211 | — | 473 ± 202 | — |
| H1M749N | 0.383 ± 0.275 | 31 | 220 ± 261 | 54 |
| H1M750N | 0.348 ± 0.128 | 37 | 227 ± 195 | 52 |

COLO 205 (Human Colorectal Adenocarcinoma Cell Line)

Briefly, 2×10$^6$ COLO 205 cells in 100 μl of serum-free medium were injected subcutaneously into the flank of 6-8 week old male NCr nude mice (Taconic, Hudson, N.Y.). After tumor volumes reached an average of about 150 mm$^3$, mice were randomized into groups for treatment with antibody or Fc protein. Mice in each treatment group were administered an anti-Ang-2 antibody or Fc protein at a concentration of 4 mg/kg via intraperitoneal injection twice per week for approximately two weeks. Tumor volumes were measured twice per week over the course of the experiment and tumor weights were measured upon excision of tumors at the conclusion of the experiment. Averages (mean+/−standard deviation) of tumor weight and growth were calculated for each treatment group. "Avg. Tumor Growth" represents the average growth from the time of treatment initiation (when tumors were approximately 150 mm$^3$). Percent decrease of tumor weight and growth are calculated from comparison to Fc protein measurements. Results are summarized in Table 28.

TABLE 28

| Antibody | Avg Tumor Weight (g) | % Decrease in Tumor Weight | Avg Tumor Growth (mm$^3$) | % Decrease in Tumor Growth |
| --- | --- | --- | --- | --- |
| Fc protein | 0.847 ± 0.180 | — | 731 ± 249 | — |
| Control I (Ab) | 0.503 ± 0.090 | 41 | 367 ± 121 | 50 |
| Control II (Pb) | 0.608 ± 0.085 | 28 | 492 ± 82 | 33 |
| H1M724N | 0.531 ± 0.103 | 37 | 336 ± 125 | 54 |
| H2M742N | 0.576 ± 0.057 | 32 | 427 ± 92 | 42 |
| H2M744N | 0.491 ± 0.051 | 42 | 409 ± 162 | 44 |
| H1M749N | 0.603 ± 0.142 | 29 | 449 ± 169 | 39 |

A similar experiment was carried out to assess the effect of H1H685P, in particular, on COLO 205 tumor growth. Briefly, 2×10$^6$ COLO 205 cells in 100 μl of serum-free medium were implanted subcutaneously into the right hind flank of 9-11 week-old male SCID CB17 mice. When the tumors reached ~125 mm$^3$, mice were randomized into 5 groups (n=7-8 mice/group) and treated twice per week with Fc protein (15 mg/kg), H1H685P (5 or 25 mg/kg) or Control II (5 or 25 mg/kg) for a period of 19 days. Tumor volumes were measured twice per week over the course of the experiment and tumor weights were measured upon excision of tumors at the end of the experiment. Averages of tumor weight and growth from the beginning of treatment were calculated for each group. Percent decrease of tumor weight and growth are calculated from comparison to the Fc control group. The results are shown in Table 29.

TABLE 29

| Antibody | Antibody Concentration | Avg Tumor Weight (g) | % Decrease in Tumor Weight | Avg Tumor Growth (mm³) | % Decrease in Tumor Growth |
|---|---|---|---|---|---|
| Fc protein | 25 mg/kg | 0.800 ± 0.108 | — | 675 ± 93 | — |
| Control II (Pb) | 5 mg/kg | 0.481 ± 0.091 | 40 | 288 ± 85 | 57 |
| Control II (Pb) | 25 mg/kg | 0.393 ± 0.136 | 51 | 267 ± 155 | 60 |
| H1H685P | 5 mg/kg | 0.458 ± 0.125 | 43 | 370 ± 114 | 45 |
| H1H685P | 25 mg/kg | 0.430 ± 0.139 | 46 | 295 ± 160 | 56 |

As with the PC3 mouse tumor model, several of the antibodies of the invention, including H1H685P, exhibited substantial anti-tumor activities in the COLO 205 mouse model that were at least equivalent to the anti-tumor activities exhibited by the control molecules.

Example 10. Inhibition of Tumor Growth and Perfusion by a Combination of an Anti-Ang-2 Antibody and a VEGF Inhibitor To determine the effect of combining an anti-Ang-2 antibody with a VEGF inhibitor on the growth of COLO 205 xenografts, $2 \times 10^6$ cells were implanted subcutaneously into the right hind flank of 6-8 week-old female SCID mice. When the tumors reached an average volume of ~350 mm³, mice were randomized into 4 groups (n=6 mice/group) and treated with: human Fc protein (7.5 mg/kg), H1H685P (5 mg/kg), VEGF Trap (see U.S. Pat. No. 7,087,411) (2.5 mg/kg) or the combination of H1H685P+VEGF Trap. Mice were given a total of 3 doses over 10 days of treatment. Tumor volumes were measured twice per week over the course of the experiment. Averages of tumor growth from the start of treatment (mean+/−standard deviation) were calculated for each treatment group. Percent decrease of tumor growth was calculated from comparison to the Fc control group. The results are shown in Table 30. Note that in the VEGF Trap and in the H1H685P+VEGF Trap groups the average tumor size was smaller at the end of treatment than at the beginning, i.e., tumor regression was observed.

TABLE 30

| Antibody | Avg Tumor Growth (mm³) | % Decrease in Tumor Growth |
|---|---|---|
| Fc protein | 366 ± 65 | — |
| H1H685P | 74 ± 77 | 80 |
| VEGF Trap | −62 ± 44 | 117 |
| H1H685P + VEGF Trap | −221 ± 131 | 160 |

The results of this experiment demonstrate that the combination of H1H685P+VEGF Trap causes a decrease in tumor growth that is greater than the percent decrease in tumor growth caused by either component alone.

To provide additional evidence of combination efficacy, the effect of the H1H685P+VEGF Trap combination on the growth of MMT tumors was assessed. $0.5 \times 10^6$ MMT cells were implanted subcutaneously into the right hind flank of 6-8 week-old female SCID mice. When the tumors reached an average volume of ~400 mm³, mice were randomized into 4 groups (n=11 mice/group) and treated with: human Fc protein (17.5 mg/kg), H1H685P (12.5 mg/kg), VEGF Trap (5 mg/kg) or the combination of H1H685P+VEGF Trap. The Fc and H1H685P groups were given 3 doses over 9 days. The VEGF Trap and combination groups were given 4 doses over 12 days. Tumor volumes were measured twice per week over the course of the experiment and tumor weights were measured upon excision of tumors at the end of the experiment (due to their large size, tumors from the Fc and H1H685P groups were collected 3 days before tumors from the VEGF Trap and combination groups). Averages (mean+/−standard deviation) of tumor growth from the beginning of treatment and of tumor weight were calculated for each group. Percent decrease of tumor weight and growth are calculated from comparison to the Fc control group. The results are shown in Table 31.

TABLE 31

| Antibody | Avg Tumor Weight (g) | % Decrease in Tumor Weight | Avg Tumor Growth (mm³) | % Decrease in Tumor Growth |
|---|---|---|---|---|
| Fc protein | 1.591 ± 0.265 | — | 1337 ± 273 | — |
| H1H685P | 1.409 ± 0.314 | 11 | 1135 ± 306 | 15 |
| VEGF Trap | 0.889 ± 0.141 | 44 | 536 ± 179 | 60 |
| H1H685P + VEGF Trap | 0.599 ± 0.066 | 62 | 215 ± 92 | 84 |

These results confirm the enhanced tumor inhibiting effect of H1H685P+VEGF Trap relative to the single agent treatments.

To determine whether the combination of H1H685P+VEGF Trap has a greater effect on tumor vessel function than the single agents, a micro-ultrasound (VisualSonics' Vevo 770 imaging system) was used to assess changes in tumor perfusion. COLO 205 tumors were grown to ~125 mm³ and mice were then treated for 24 hrs with H1H685P, VEGF Trap or the combination of both agents. Following treatment, tumor vessel perfusion was determined based on contrast-enhanced micro-ultrasound 2D image acquisition and analysis of a "wash-in" curve, which represents the amount of contrast agent entering the tumor. Average (mean+/−standard deviation) tumor perfusion was calculated for each group. Percent decrease was calculated from comparison to the Fc control group. The results are shown in Table 32.

TABLE 32

| Antibody | Relative Tumor Perfusion | % Decrease in Tumor Perfusion |
|---|---|---|
| Fc protein | 8.09 ± 2.16 | — |
| H1H685P | 6.32 ± 2.81 | 22 |
| VEGF Trap | 6.99 ± 1.36 | 14 |
| H1H685P + VEGF Trap | 2.46 ± 0.34 | 70 |

Consistent with the enhanced effect of the combination treatment on perfusion, anti-CD31 staining of tumor sections demonstrated a more potent effect of the combination on tumor blood vessel density (data not shown). The increased effect of the H1H685P+VEGF Trap combination on the function of the tumor vasculature provides a potential explanation for the enhanced effects of the combination therapy on tumor growth.

Example 11. Inhibition of Tumor Growth by a Combination of an Anti-Ang-2 Antibody and a Chemotherapeutic Agent To test the effect of H1H685P in combination with a chemotherapeutic agent on tumor growth, $2.5 \times 10^6$ COLO 205 tumor cells were implanted subcutaneously into the right hind flank of 8-9 week-old male SCID mice. When the tumors reached an average volume of ~150 mm$^3$ (day 17 after implantation), mice were randomized into 4 groups (n=5 mice/group) and treated as follows: the first group was treated sc with 15 mg/kg hFc and intraperitoneally (ip) with 5-FU vehicle; the second group was treated sc with 15 mg/kg of H1H685P; the third group was treated ip with 75 mg/kg of 5-FU; the fourth group was treated with the combination of 15 mg/kg H1H685P sc plus 75 mg/kg 5-FU ip. Mice received a total of three treatments, administered every 3-4 days. Tumor volumes were measured twice per week over the course of the experiment. Average (mean+/− standard deviation) tumor growth from the beginning of treatment until day 38 was calculated for each group. Percent decrease of tumor growth was calculated from comparison to the control group. The results are shown in Table 33.

TABLE 33

| Treatment | Avg Tumor Growth (mm$^3$) | % Decrease in Tumor Growth |
| --- | --- | --- |
| Fc protein + 5-FU vehicle | 574 ± 110 | — |
| H1H685P | 405 ± 80 | 29 |
| 5-FU | 313 ± 60 | 45 |
| H1H685P + 5-FU | 175 ± 78 | 70 |

The results of this experiment show that the combination of H1H685P and 5-FU caused a greater decrease in tumor growth than either agent administered separately.

Example 12. Anti-Ang-2 Antibodies Attenuate Ocular Angiogenesis In Vivo

In this Example, the effects of selected anti-Ang-2 antibodies on retinal vascularization in a mouse model was assessed.

In one set of experiments wild-type mice were used. In another set, mice expressing a human Ang-2 in place of the wild-type mouse Ang-2 (designated "hu-Ang-2 mice") were used. The mice at two days of age (P2) were injected subcutaneously with either control Fc or with selected anti-Ang-2 antibodies at a dose of 12.5 mg/kg. Three days later (at P5), pups were euthanized, and eyeballs were enucleated and fixed in 4% PFA for 30 minutes. Retinas were dissected, stained with *Griffonia simplicifolia* lectin-1 for 3 hours or overnight at 4° C. to visualize the vasculature, and flat-mounted on microscope slides. Images were taken using a Nikon Eclipse 80i microscope camera and analyzed using Adobe Photoshop CS3, Fovea 4.0, and Scion 1.63 software.

Areas of the retina covered with superficial vasculature were measured and used as a readout of antibody activity. The reduction in the size of the vascular areas in mice treated with antibody compared to Fc-treated controls is presented in Table 34. The percent reduction in vascular area reflects the anti-angiogenic potency of the antibody. (N/D=not determined)

TABLE 34

| | % Reduction in Vascular Area Relative to Fc Control | |
| --- | --- | --- |
| Antibody | Wild-Type Mice | hAng-2 Mice |
| H1H685P | 39.7 | N/D |
| H1H690P | 30.7 | 41.5 |
| H1H691P | 30.4 | N/D |
| H1H696P | 31.1 | N/D |
| H1H724N | 32.2 | 33.2 |
| H1H744N | 35.8 | 50.5 |
| Control I (Ab) | 26.9 | 35.6 |

As shown in this Example, the selected anti-Ang-2 antibodies of the present invention substantially inhibited ocular angiogenesis in vivo, thus reflecting the likely anti-angiogenic potential of these antibodies in other therapeutic contexts.

Example 13. Amino Acids of Ang-2 Important for Antibody Binding

To further characterize binding between hAng2 and anti-hAng2 mAbs of the invention, seven variant hAng2-FD-mFc proteins were generated, each containing a single point mutation. Amino acids selected for mutation were based on the difference in sequence between hAng-2 and hAng-1 in the region that interacts with hTie-2 (FIG. 1). In particular, amino acids within the fibrinogen-like domain (FD) of Ang-2 which are believed to interact with Tie-2 based on crystal structure analysis, but which differ from the corresponding amino acid in Ang-1, were individually mutated to the corresponding hAng-1 residue. The results of this example indicate the amino acid residues of hAng-2 with which the Ang-2 preferential binding antibodies interact. That is, if a particular residue (or residues) of hAng-2 is/are changed to the corresponding residue of hAng-1, and the binding of an Ang-2 preferential binding antibody is substantially reduced, then it can be concluded that the antibody interacts with that particular residue(s) of hAng-2.

Figure 3:
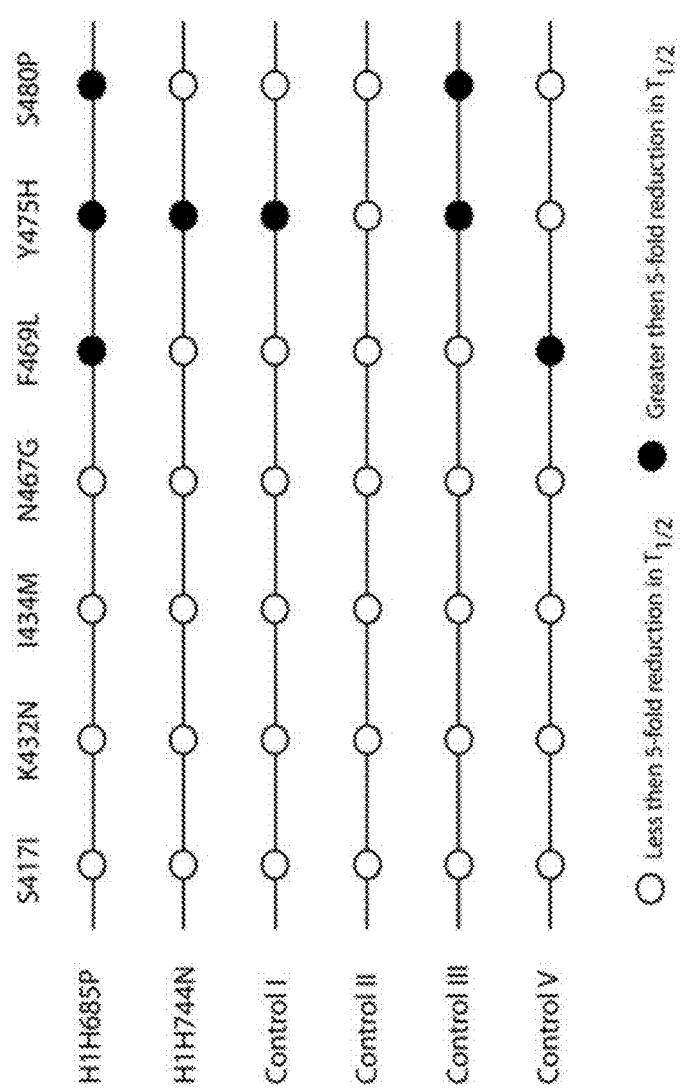
FIG. 3 is a summary of the Ang-2FD-mFc point mutant binding experiment of Example 13, showing the amino acid changes which resulted in greater than a five-fold reduction in T½ of dissociation (depicted by solid circles ●) relative to wild-type for the various antibodies and peptibodies tested.

In this experiment, each of the seven hAng-2FD-mFc mutant proteins were captured (~147-283 RU) on an anti-mouse-Fc surface created through direct chemical coupling to a BIACORE™ chip. Then each Ang-2 antibody (or peptibody, as the case may be) at 100 nM was injected over the captured mFc-tagged hAng-2FD protein surface at a flowrate of 50 µl/min for 180 sec, and the dissociation of variant hAng2-FD-mFc and antibody was monitored in real time for 20 min at 25° C. Results are summarized in Tables 35a-35d and FIG. 3.

TABLE 35a

| Mutated hAng-2 | H1H685P | | | H1H744N | | |
|---|---|---|---|---|---|---|
| Amino Acid(s)[1] | RU | $K_D$ (M) | T ½ (min) | RU | $K_D$ (M) | T ½ (min) |
| WT[2] | 210.70 | 2.23E−11 | 1988 | 213 | 3.98E−11 | 904 |
| S-417-I | 127.65 | 3.05E−11 | 1809 | 127 | 5.12E−11 | 1590 |
| K-432-N | 152.68 | 1.40E−11 | 4468 | 137 | 4.87E−11 | 1690 |
| I-434-M | 235.95 | 1.79E−11 | 3600 | 213 | 3.18E−11 | 2589 |
| N-467-G | 152.25 | 9.38E−12 | 6762 | 139 | 7.72E−11 | 1011 |
| F-469-L | 101.16 | 1.38E−08 | 4 | 180 | 1.95E−10 | 237 |
| Y-475-H | 181.53 | 1.96E−10 | 289 | 247 | 3.06E−10 | 136 |
| S-480-P | 161.13 | 2.05E−10 | 289 | 228 | 2.25E−11 | 2129 |

TABLE 35b

| Mutated hAng-2 | Control I (Ab) | | | Control II (Pb) | | |
|---|---|---|---|---|---|---|
| Amino Acid(s)[1] | RU | $K_D$ (M) | T ½ (min) | RU | $K_D$ (M) | T ½ (min) |
| WT[2] | 195.25 | 4.69E−10 | 54.33 | 67.44 | 4.29E−10 | 39.86 |
| S-417-I | 142.96 | 5.79E−10 | 32.81 | 49.99 | 1.88E−10 | 36.38 |
| K-432-N | 189.69 | 3.49E−10 | 51.75 | 63.21 | 1.39E−10 | 42.34 |
| I-434-M | 282.10 | 4.64E−10 | 48.80 | 89.15 | 1.36E−10 | 57.09 |
| N-467-G | 180.90 | 4.61E−10 | 44.66 | 60.94 | 1.54E−10 | 46.97 |
| F-469-L | 173.01 | 1.05E−09 | 25.13 | 46.73 | 2.40E−10 | 36.20 |
| Y-475-H | 170.05 | 1.15E−08 | 1.85 | 74.79 | 1.40E−10 | 54.12 |
| S-480-P | 181.32 | 2.98E−09 | 13.36 | 71.90 | 1.79E−10 | 45.45 |

TABLE 35c

| Mutated hAng-2 | Control III (Pb) | | | Control V (Ab) | | |
|---|---|---|---|---|---|---|
| Amino Acid(s)[1] | RU | $K_D$ (M) | T ½ (min) | RU | $K_D$ (M) | T ½ (min) |
| WT[2] | 80.33 | 2.07E−11 | 170.03 | 214.48 | 7.97E−10 | 48.43 |
| S-417-I | 57.13 | 5.31E−11 | 114.81 | 126.45 | 2.40E−09 | 29.17 |
| K-432-N | 79.22 | 2.88E−11 | 200.94 | 149.14 | 8.48E−10 | 75.59 |
| I-434-M | 116.22 | 2.15E−10 | 62.77 | 214.75 | 2.23E−09 | 31.76 |
| N-467-G | 74.64 | 8.90E−11 | 109.07 | 146.77 | 1.11E−09 | 55.66 |
| F-469-L | 72.66 | 2.74E−10 | 66.11 | 131.96 | 1.37E−08 | 1.46 |
| Y-475-H | 76.21 | 6.87E−09 | 4.11 | 260.93 | 2.66E−10 | 93.22 |
| S-480-P | 77.93 | 2.78E−09 | 11.69 | 177.10 | 3.47E−09 | 10.33 |

TABLE 35d

| Mutated hAng-2 | Negative Control (irrelevant antibody) | | |
|---|---|---|---|
| Amino Acid(s)[1] | RU | $K_D$ (M) | T ½ (min) |
| WT[2] | 0.81 | N/B | N/B |
| S-417-I | −1.21 | N/B | N/B |
| K-432-N | −0.38 | N/B | N/B |
| I-434-M | −1.31 | N/B | N/B |
| N-467-G | −1.09 | N/B | N/B |
| F-469-L | 0.32 | N/B | N/B |
| Y-475-H | −0.20 | N/B | N/B |
| S-480-P | −0.52 | N/B | N/B |

[1]Amino acid numbering is based on the amino acid numbering of SEQ ID NO: 518.
[2]WT = wild-type Ang-2FD-mFc construct.
N/B = no binding observed.

For purposes of the present invention, an anti-Ang-2 antibody is deemed to interact with a particular Ang-2 amino acid residue if, when the residue is mutated to the corresponding residue of Ang-1, the T½ of dissociation is at least 5-fold less than the T½ of dissociation observed for the wild-type construct under the experimental conditions used in this Example. In view of this definition, antibody H1H685P appears to be unique among the antibodies tested in that it interacts with F469, Y475 and S480. Since H1H685P is also unique because of its strong preferential binding to Ang-2 over Ang-1, it can be concluded that F469, Y475 and S480 comprise an epitope that enables the immunological distinction of Ang-2 from Ang-1. The other antibodies/peptibodies tested in this experiment appear to interact with at most one or two of these residues; i.e., H1H744N and Control I interact with Y475; Control III interacts with Y475 and S480; and Control V interacts with F469. Interestingly, Control II, which was shown to block both Ang-1 and Ang-2 binding to Tie-2 with equal potency, does not interact with any of the Ang-2-specific amino acids identified in this experiment.

Example 14. Ascending, Multiple-Dose Clinical Trial of Intravenously Administered Anti-Ang-2 Antibody (mAb1) in Patients with Advanced Cancer A. Study Design This study was an open-label, ascending, multiple-dose study of mAb1 administered as an intravenous (IV) infusion (30 minutes) at doses of 1, 3, 6, 12 or 20 mg/kg once every 2 weeks. The study was conducted in patients with advanced solid tumor malignancies who have failed conventional therapy. The purpose of the study was to explore the safety, recommended dose (RD), pharmacokinetics (PK), pharmacodynamics (PD) and anti-tumor activity of mAb1 (also known as "H1H685P").

Patients were screened to determine eligibility within 28 days prior to the first dose administration. Three patients were assigned to each of the five sequential cohorts (1, 3, 6, 12 or 20 mg/kg). Patients received mAb1 as a 30 minute IV infusion on Days 1 and 15 of each 4-week cycle (28 days). The dose of mAb1 was escalated until the recommended dose was determined, based on safety, tolerability, PK, PD testing and/or maximum tolerated dose (MTD). The MTD is defined as the highest dose at which less than 33% of patients experience dose-limiting toxicity (DLT) during the first cycle of therapy.

Dose Escalation

Six dose levels were planned for studying dose escalation. Starting at dose 1, a minimum of 3 patients was entered at each dose level. If none of the three patients exhibited a DLT during cycle 1, dose escalation proceeded to the next higher dose level. If one of 3 patients exhibited DLT during cycle 1, the cohort was expanded to 6 patients. If no further cycle 1 DLT was observed, dose escalation proceeded to the next dose level. If two or more patients experienced a cycle 1 DLT, dose escalation was stopped and the previous lower dose level was expanded to 6 patients. Once the RD was determined, up to 10 additional patients were enrolled to evaluate safety and other biological/clinical effects. A separate cohort was planned for patients with hepatocellular carcinoma (HCC) where up to 10 patients were enrolled based on the eligibility criteria (listed below).

A DLT is defined by any of the following treatment-related events occurring during the first cycle (28 days) of study treatment: (1) Hematologic toxicity as evidenced by (a) Grade 3 or 4 neutropenia complicated by fever 38.5° C. or infection; (b) Grade 4 neutropenia of at least 7 days duration; (c) Grade 3 thrombocytopenia complicated by hemorrhage; or (d) Grade 4 thrombocytopenia; and/or (2) Non-hematologic toxicity as evidenced by (a) any Grade 4 non-hematologic toxicity; or (b) Grade 3 non-hematologic toxicities except fatigue, anorexia, nausea, vomiting or diarrhea that can be controlled by medication. Grade 3 laboratory changes that reflected tumor burden were not considered as DLT.

The inclusion criteria for patients were: (1) Male of female of age ≥18 years; (2) histologically or cytologically confirmed diagnosis of malignancy; (3) failure of conventional therapy; (4) ECOG performance status 0-1; (5) resolution of toxicity from prior therapy to Grade ≤2; (6) albumin >35 g/L; (7) normal lactate dehydrogenase (LDH) level; (8) hepatic function as characterized by a) total bilirubin ≤1.5× upper limit of normal (ULN) (if liver metastases ≤3×ULN), and/or b) alanine aminotransferase (ALT) ≤2.5×ULN (or ≤5×ULN, if liver metastases); (9) renal function as characterized by calculated creatinine clearance >60 mL/min; (10) bone marrow function as characterized by a) hemoglobin >9.0 g/dL, b) absolute neutrophil count (ANC) >1.5×10$^9$/L, and/or c) platelet count >100×10$^9$/L; (11) International normalized ratio (INR)/partial thromboplastin time (PTT) ≤1.5×ULN; (12) for women of childbearing potential, a negative pregnancy test (serum or urine); (13) for men and women of childbearing potential, willingness to use adequate contraception during the course of the study; (14) signed informed consent form and ability to comply with scheduled visits, treatment plans, lab tests and other study procedures.

The exclusion criteria for the study were: (1) brain metastases, spinal cord compression, carcinomatous meningitis or other evidence of central nervous system CNS) involvement; (2) surgery ≤4 weeks prior to the initial administration of mAb1; (3) incomplete wound healing; (4) investigational treatment <4 half-lives prior to the initial administration of mAb1; (5) prior treatment with angiopoietin-1/2 or Tie-2 inhibitors; (6) bleeding diathesis or active bleeding; (7) diastolic BP >90 mmHg; (8) systolic BP >150 mmHg; (9) any of the following ≤6 months prior to the initial administration of mAb1: a) myocardial infarction, unstable angina pectoris, coronary/peripheral artery bypass graft, congestive heart failure (New York Heart Association (NYHA) class III or IV), or ventricular arrhythmia, b) cerebrovascular accident, transient ischemic attack, or Grade ≥2 peripheral neuropathy, and/or c) peptic ulcer disease, erosive esophagitis, or gastritis, infectious or inflammatory bowel disease, or diverticulitis; (10) history of deep vein thrombosis or pulmonary embolism; (11) breast-feeding or pregnancy; and (12) any acute or chronic medical or psychiatric condition or lab abnormality that, in the judgment of the investigator, made the patient inappropriate for entry into the study.

The inclusion criteria for the HCC cohort were: (1) Male or female aged >18 years; (2) Diagnosis of HCC by histopathology or radiologic confirmation of advanced HCC. Hepatocellular carcinoma can be diagnosed radiologically, without the need for biopsy if the typical imaging features are present per American Association for the Study of Liver Diseases (AASLD 2010); (3) ECOG performance status 0-1; (4) Resolution of toxicity from prior therapy (except alopecia) to grade <2; (5) Total bilirubin ≤3×ULN; (6) Albumin ≥3 g/dL; (7) ALT ≤5.0×ULN; (8) Aspartate aminotransferase (AST) ≤5.0×ULN; (9) Creatinine <1.5×ULN; (10) Spot urine protein <2+ (dipstick method) or proteinuria <1 g/24 hr; (11) Hemoglobin ≥9.0 g/dL; (12) Absolute neutrophil count (ANC) ≥1.5×10$^9$/L; (13) Platelet count ≥75×10$^9$/L; (14) Adequate coagulation function by INR ≤2; (15) At least 3 weeks must have elapsed since the last dose of chemotherapy, hormonal therapy (luteinizing hormone releasing hormone [LHRH] agonist is allowed for patients with castrate resistant prostate cancer), or radiotherapy (6 weeks for nitrosoureas, mitomycin C, or cytokine therapy) prior to the initial administration of mAb1 (Note: the 3-week waiting period for radiotherapy does not apply to localized radiation therapy for pain control); (16) For patients who have received prior local therapy (RFA or TACE), at least 4 weeks must have elapsed between receipt of the prior treatment and the first dose of mAb1; there must be evidence of tumor growth or untreated evaluable tumor; and toxicity related to the prior therapy must have returned to baseline, resolved, or be considered irreversible; (17) At least 6 weeks must have elapsed since the last dose of bevacizumab (Avastin™) prior to the initial administration of mAb1; (18) At least 3 weeks must have elapsed since the last dose of sorafenib prior to the initial administration of mAb1; (19) At least 4 weeks must have elapsed since the last surgery prior to the initial administration of mAb1; (20) At least 4 weeks must have elapsed since the last dose of investigational treatment prior to the initial administration of mAb1; (21) For women of childbearing potential, a negative pregnancy test (serum) within 72 hours prior to the initial administration of mAb1; (22) For women of childbearing potential and men whose sexual partners are of childbearing potential, willingness to use adequate contraception during the course of the study and for 30 days after last dose of mAb1; (23) Ability and willingness to comply with scheduled visits, treatment plans, laboratory tests, and other study procedures; and (24) Signed informed consent form (ICF).

The exclusion criteria for the HCC cohort were: (1) Brain metastases, spinal cord compression, carcinomatous meningitis, or other evidence of central nervous system involvement; (2) Decompensated cirrhosis with clinical, significant or intractable ascites and/or encephalopathy); (3) Serious non healing wound or acute ulcer; (4) Prior treatment with Ang2 or Tie-2 inhibitors; (5) Bleeding diathesis or active bleeding (bleeding from varices, treatment for bleeding from varices, or at risk for varices bleeding); (6) Anticoagulation therapy, except aspirin at doses of 325 mg or less per day or low-dose warfarin; (7) Abnormal 12-lead ECG of clinical significance; (8) Either systolic blood pressure >150 mm Hg or diastolic blood pressure >95 mm Hg on at least 2 repeated determinations on separate days within the screening period. Patients who were excluded by these criteria were rescreened after adequate control and stabilization of their blood pressure on repeat measurements; (9) Any of the following ≤6 months prior to the initial administration of mAb1: a) Myocardial infarction, unstable angina pectoris, coronary/peripheral artery bypass graft, congestive heart failure (NYHA class III or IV) or ventricular arrhythmia, and/or b) Cerebrovascular accident or transient ischemic attack; (10) Grade >2 peripheral neuropathy; (11) Deep vein thrombosis or pulmonary embolism within last 6 months prior to initial administration of mAb1. Asymptomatic portal vein thrombosis allowed; (12) Breast-feeding or pregnancy; (13) Any acute or chronic medical or psychiatric condition that, in the judgment of the investigator, made the patient inappropriate for entry into the study; and (14) Hypersensitivity to any compound in the tetracycline antibiotics group.

B. Study Objectives

The primary objectives of the study were: (1) to study the safety, tolerability and DLTs of IV administered mAb1; (2) to determine the RD of mAb1 administered IV every 2 weeks in patients with advanced solid malignancies; and (3) to assess the safety of mAb1 administered at the RD every 2 weeks to patients with advanced HCC or other advanced solid malignancies.

The secondary objectives of the study were: (1) to characterize the PK profile of mAb1; (2) to assess the immunogenicity of mAb1; (3) to study the preliminary anti-tumor activity of mAb1 administered to patients with HCC and other advanced solid malignancies; and (4) to evaluate correlative biomarkers of mAb1 activity.

C. Treatment

The study drug mAb1 was supplied as a liquid in sterile, single-use vials. Each vial contained a withdrawable volume of 10 mL of mAb1 at a concentration of 25 mg/mL. mAb1 was administered in an outpatient setting. Each patient's dose depended on individual body weight and assigned dosing cohort. The dose was adjusted each cycle for variations in body weight in kilograms if weight changed by ≥10%. mAb1 was administered once every 2 weeks as a 30-minute IV infusion. A cycle was defined as 28 days.

For IV administration, mAb1 was diluted into an IV bag of 0.9% sodium chloride injection US Pharmacopeia under aseptic conditions. Dilution of mAb1 into an IV bag of normal saline to concentrations below 1.0 mg/mL of mAb1 required the addition of diluent to stabilize the drug during delivery through the IV infusion apparatus. The infusion sets included a 0.2 μm polyethersulfone inline filter.

D. Statistical Analysis

The analysis of the study was descriptive and exploratory in nature. Results were summarized by cohort. A 3+3 dose escalation rule was used. Data was summarized using descriptive statistics only (number of patients, mean, median, standard deviation, minimum and maximum) for continuous variables and using frequency and percentages for discrete variables. Safety observations and measurements including drug exposure, adverse events, lab data, vital signs and ECOG performance status was summarized.

E. Safety Assessment

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

Safety assessments carried out at screening/baseline and during the study include physical examination (including complete neurological assessment at onset of symptoms or upon any brain MRI abnormal findings in any patient), laboratory tests, vital signs, brain MRI, pregnancy test, and tumor assessment.

The clinical laboratory data consists of hematology, blood chemistry and urinalysis. Blood samples for hematology testing were collected at every study visit; blood samples for serum chemistry testing and urine samples for urinalysis were collected to measure overall patient health at screening, day 1/baseline (pre-dose), day 8, day 15, and day 22 of the first cycle, and days 1, and 15 of subsequent cycles, or early termination if subject is discontinued from the study.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 8, 15, and 22 of the first cycle, and days 1, and 15 of subsequent cycles, or early termination. Vital signs were taken at 1 and 2 hours post-infusion following the study drug dose on days 1, and 15.

12-Lead ECG parameters include: Ventricular HR, PR interval, QRS interval, corrected QT interval (QTcF=QT/[RR$^{0.33}$] and QTcB=QT/[RR$^{0.5}$]) ECG status: normal, abnormal not clinical significant or abnormal clinical significant. A standard 12-lead ECG was performed at screening, and 30 days-post last dose (end of study) or early termination.

A thorough and complete physical examination was performed at screening, days 1 and 15 of each cycle, and 30 days-post last dose (end of study) or early termination.

A brain MRI was performed during screening (within 28 days prior to start of study drug administration). A brain MRI was also performed during even numbered cycles between days 15 and 28 and at the 30 day follow-up.

For tumor assessment, a CT or MRI was performed at the screening visit (within 28 days prior to infusion) and during every even-numbered cycle (eg cycles 2, 4, 6, 8) between days 15 and 28 and when disease progression was suspected.

Tumor assessment was performed according to Response Evaluation Criteria in Solid Tumors version 1.1 (RECIST version 1.1). RECIST criteria are developed to facilitate objective assessment of change in tumor burden such as tumor shrinkage and time to development of disease progression. RECIST guidelines are posted on the worldwide web at http://ctep(dot)cancer(dot)gov(slash)protocoldevelopment(slash)docs(slash)recist_guideline(dot)pdf. Tumor marker assessments were also collected, when available.

In addition, tumor and skin biopsies were obtained once before and once after treatment: at baseline and in cycle 1, on day 22.

Patients in the HCC cohort were additionally screened for hepatitis-B, hepatitis-C and for alpha-fetoprotein. Dynamic contrast-enhanced ultrasound imaging was performed before the tumor biopsy during screening and on day 22 of cycle 1.

F. Pharmacokinetic Studies

Blood samples were collected for RNA, serum cytokine testing, molecular profiling, anti-drug antibody (ADA) and serum mAb1 levels at screening and post-infusion on days 1, 2, 3, 8, 15 and 22 of cycle 1, and on day 1 of subsequent cycles. Tumor biopsies were obtained for immunohistochemistry studies for Ang-2. Results were scored as positive for Ang-2 in association with expression of endothelial cell CD31.

G. Preliminary Results 37 patients [17M/20F; median age 43.5 (range 22-82); ECOG PS 0(9)/1(28)] were enrolled. Twenty-three (23) patients were enrolled in the 1 (4), 3 (4), 6 (3), 12 (6) and 20 mg/kg (6) dose escalation cohorts. No DLTs were reported and a MTD was not reached. Fourteen (14) patients were enrolled in a 12 mg/kg expansion cohort; enrollment at 20 mg/kg expansion was started. Most common G½ treatment-related adverse events (TRAEs) were fatigue (19%), peripheral edema (17%), diarrhea (14%), abdominal distension (11%), and decreased appetite (11%). There were no ≥Grade 3 TRAEs. A confirmed sustained patient response (PR) (16 wks) was observed in 1 patient with adrenocortical cancer treated at 1 mg/kg. Stable disease (SD) (range 3.3-46.8 weeks) was reported for 17 of 32 (53%) patients evaluable for efficacy. A total of 16 patients received treatment >16 weeks. One patient with thyroid cancer had SD for 46 weeks. Across all dose levels, mAb1 pharmacokinetics (PK) appeared linear and dose-proportional. The PK profile is characterized by an initial distribution and a single monoexponential elimination phase. In 1 patient (3 mg/kg), positive ADA was detected. Total circulating serum Ang2 levels appeared saturated following treatment in all cohorts, indicating systemic target engagement at all doses tested.

H. Conclusions

Administration of mAb1 in patients with advanced cancer was generally well tolerated, with mainly mild and moderate TRAEs. Dose escalation was completed, and enrollment to the 20 mg/kg expansion continued. The safety profile supported combination with chemotherapy or other anti-angiogenic agents.

Example 15. Clinical Trial of Combined Administration of Anti-Angiogenesis Anti-Ang-2 Antibody and Aflibercept in Patients with Advanced Solid Tumor Malignancies A. Study Design The study consists of 2 phases. Phase 1b is an open-label, multi-centered, dose-escalation study of mAb1 (also known as "H1H685P") in combination with aflibercept (also known as "VEGF Trap"; see U.S. Pat. No. 7,087,411) administered in patients with advanced platinum-resistant ovarian cancer (OC), colorectal cancer (CRC) or HCC. Four dose levels of mAb1/aflibercept will be studied in a standard "3+3" design (up to 6 patients per cohort): mAb1 (3, 6 and 12 mg/kg) combined with a fixed dose of aflibercept (2 mg/kg). An additional cohort will then be enrolled using the highest tolerable dose combination of mAb1 in combination with 4 mg/kg of aflibercept. A total of 6 patients will be dosed at the highest dose combination of mAb1 and aflibercept prior to declaring the recommended dose (RD) for the second phase of the study.

Phase 2 is a double-blind, followed by an open-label, multi-centered, randomized study in patients with advanced platinum-resistant OC. Three arms (each with n=46) will be studied:

Arm 1: mAb1+aflibercept until PD (determined by RECIST 1.1)

Arm 2: mAb1 until PD (determined by RECIST 1.1), followed by mAb1+aflibercept until PD on the combination treatment (determined by RECIST 1.1, and using the measurements upon the switch as a new baseline)

Arm 3: Aflibercept until PD (determined by RECIST 1.1) followed by mAb1+aflibercept until PD on the combination treatment (determined by RECIST 1.1, and using the measurements upon the switch as a new baseline).

Patients will be screened to determine eligibility within 28 days prior to the initial administration of mAb1 and aflibercept. All patients will be observed for the occurrence of a dose-limiting toxicity (DLT) during cycle 1. The maximum tolerated dose (MTD) is defined as the highest dose level at which no more than 1 DLT out of 6 patients has been documented. The recommended Phase 2 dose (RP2D) will be determined based on a review of the safety (all cycles), PK, PD and efficacy observations documented during the dose escalation. The RP2D may be the same or lower than the MTD.

The study drug will be administered every 2 weeks. For Phase 1b, mAb1 will be administered as a 30-minute IV infusion, followed by aflibercept as a 60-minute IV infusion for a total infusion time of 90 minutes. The study drug will be administered on cycle days 1 and 15 of each 28-day cycle. Treatment will continue till disease progression, unacceptable toxicity or withdrawal of consent.

For Phase 2, the administration of the study drug for each of the three arms will be as follows:

Arm 1: Double blind administration of mAb1 as a 30-minute IV infusion, followed by aflibercept as a 60-minute IV infusion for a total infusion time of 90 minutes every 2 weeks until disease progression.

Arm 2: Double-blind administration of mAb1 as a 30-minute IV infusion, followed by normal saline as a 60-minute IV infusion for a total infusion time of 90 minutes every 2 weeks until disease progression. Then, open-label administration of mAb1 as a 30-minute IV infusion, followed by aflibercept as a 60-minute IV infusion for a total infusion time of 90 minutes every 2 weeks until disease progression.

Arm 3: Double blind administration of normal saline as a 30-minute IV infusion, followed by aflibercept as a 60-minute IV infusion for a total infusion time of 90 minutes every 2 weeks until disease progression. Then, open label administration of mAb1 as a 30-minute IV infusion, followed by aflibercept as a 60-minute IV infusion for a total infusion time of 90 minutes every two weeks until disease progression.

The study drug will be administered on cycle days 1 and 15 of each 28-day cycle. The dose is defined by the RP2D Phase 1b. Treatment will continue in each arm till disease progression, unacceptable toxicity or withdrawal of consent.

The patient inclusion criteria for Phase 1b are: (1) male or female of age ≥18 years; (2) confirmed diagnosis of one of the following—a) epithelial adenocarcinoma of the ovary (including fallopian tube or primary peritoneal cancer) by histology, b) unresectable or metastatic colorectal adenocarcinoma by histology or cytology, or c) advanced hepatocellular cancer by histopathology or radiologic confirmation. HCC can be diagnosed radiologically, without the need for biopsy if the typical imaging features are present per American Association for the Study of Liver Diseases (AASLD 2010); (3) no standard therapeutic options of proven benefit; (4) ECOG performance status 0 or 1; (5) bone marrow function as characterized by a) hemoglobin >9.0 g/dL, b) absolute neutrophil count (ANC) >1.5×10$^9$/L, and/or c) platelet count >75×10$^9$/L; (6) hepatic function as characterized by a) total bilirubin ≤1.5×ULN (≤3×ULN, if liver metastases or HCC), b) transaminases ≤2.5×ULN (or ≤5.0× ULN, if liver metastases or HCC), and/or c) alkaline phosphatase ≤2.5×ULN (or ≤5.0×ULN, if liver metastases or HCC); (7) renal function as characterized by a) serum creatinine ≤1.5 mg/dL, and/or b) spot urine protein <2+ (dipstick method) or proteinuria <1 g/24 hr; (8) calculated creatinine clearance >60 mL/min (Cockroft-Gault formula); (9) albumin >3.5 g/dL; (10) resolution of toxicity from prior therapy to Grade ≤1, including skin toxicity; (11) negative serum pregnancy test in women of child-bearing potential; (12) willingness to use adequate forms of contraception for males and females of child-bearing potential or avoidance of intercourse during the study; (13) patients capable of understanding and signing an informed consent form; and (14) ability to comply with scheduled visits, treatment plans, lab tests and other study procedures.

The exclusion criteria for Phase 1b are: (1) any active or previously treated brain metastases, spinal cord compression, carcinomatous meningitis, or other evidence of CNS involvement; (2) appearance in brain MRI at screening of any lesion that demonstrates contrast enhancement with T1 weighted imaging; (3) abnormal 12-lead ECG of clinical significance; (4) either systolic BP >150 mmHg or diastolic BP >95 mmHg on at least 2 repeated determinations on separate days within the screening period; (5) any of the following ≤6 months prior to the initial administration of mAb1/aflibercept—a) myocardial infarction, unstable angina pectoris, coronary/peripheral artery bypass graft, congestive heart failure or ventricular arrhythmia, b) cerebrovascular accident or transient ischemic attack, c) deep vein thrombosis or pulmonary embolism (including asymptomatic pulmonary embolism identified on imaging), d) serious non-healing wound or acute ulcer, and/or e) bleeding diathesis or active bleeding (bleeding from varices, treatment for bleeding from varices, or at risk for varices bleeding); (6) anticoagulation therapy, except aspirin at doses of 325 mg or less per day or low-dose warfarin or heparin; (7) major surgery <4 weeks prior to initial administration of mAb1/aflibercept; (8) IV port placement <7 days prior to initial administration of mAb1/aflibercept; (9) bleeding peptic ulcer disease, erosive gastritis, intestinal perforation or clinically significant GI hemorrhage within 6 months of enrollment; (10) transmural tumor bowel involvement; (11) history of abdominal or tracheal-esophageal fistula; (12) for HCC patients—decompensated cirrhosis with clinical, significant or intractable ascites and/or encephalopathy; (13) prior treatment with Ang2 or Tie-2 inhibitors; (14) prior treatment with aflibercept; (15) bevacizumab administration within 6 weeks of first study drug administration; (16) investigational treatment <5 half-lives prior to the initial administration of mAb1/aflibercept; (17) history of allergic reactions or acute hypersensitivity reaction attributable to antibiotics of the tetracycline class; (19) concurrent severe medical problems that would significantly limit patient compliance with the study requirements or interfere with the interpretation of study results; (20) breast-feeding or pregnancy; and (21) acute or chronic psychiatric problems that, under the evaluation of the investigator, make the patient ineligible for participation.

The inclusion criteria for Phase 2 are: (1) female of age ≥18 years; (2) confirmed diagnosis of epithelial adenocarcinoma of the ovary (including fallopian tube or primary peritoneal cancer) by histology; (3) platinum-resistant or refractory disease (disease recurrence within 6 months of last dose of platinum or disease progression while treated with platinum-based regimen); (4) measurable disease; (5) ECOG performance status 0 or 1; (6) at least 2 pretreatment samples minimum 2 weeks apart indicating CA125≥2× ULN; (7) bone marrow function as characterized by—a) hemoglobin >9.0 g/dL, b) ANC >1.5×10$^9$/L, and/or c) platelet count >75×10$^9$/L; (8) hepatic function as characterized by a) total bilirubin ≤1.5×ULN (≤3×ULN, if liver metastases or HCC), b) transaminases ≤2.5×ULN (or ≤5.0× ULN, if liver metastases or HCC), and/or c) alkaline phosphatase ≤2.5×ULN (or ≤5.0×ULN, if liver metastases or HCC); (9) renal function as characterized by a) serum creatinine ≤1.5 mg/dL, and/or b) spot urine protein <2+ (dipstick method) or proteinuria <1 g/24 hr; (10) calculated creatinine clearance >60 mL/min (Cockroft-Gault formula); (11) albumin >3.5 g/dL; (12) resolution of toxicity from prior therapy to Grade ≤1, including skin toxicity; (13) negative serum pregnancy test in women of child-bearing potential; (14) willingness to use adequate forms of contraception if patient is of child-bearing potential or avoidance of intercourse during the study; (15) patients capable of understanding and signing an informed consent form; and (16) ability to comply with scheduled visits, treatment plans, lab tests and other study procedures.

The exclusion criteria for Phase 2 are the same as given above for Phase 1b, with the addition of 2 more criteria: (1) more than 3 prior lines of platinum-based systemic therapies; and (2) more than 7 prior lines of systemic therapies.

B. Study Objectives

The primary objectives of the study for Phase 1b are: (1) to assess the safety profile of mAb1 administered in combination with aflibercept in patients with advanced platinum-resistant ovarian cancer (OC), colorectal cancer (CRC) or hepatocellular cancer (HCC); and (2) to determine the recommended phase 2 dose (RP2D) of the mAb1/aflibercept combination.

The secondary objectives of the study for Phase 1b are: (1) to characterize the pharmacokinetic (PK) profile of mAb1 when used in combination with aflibercept; (2) to characterize the PK profile of aflibercept when used in combination with mAb1; (3) to assess the immunogenicity of mAb1 when used in combination with aflibercept; (4) to assess the immunogenicity of aflibercept when used in combination with mAb1; (5) to describe the preliminary anti-tumor activity of mAb1/aflibercept combination in patients with advanced platinum-resistant OC, CRC or HCC; and (6) to explore the potential correlative (safety/efficacy) biomarkers of mAb1/aflibercept activity.

The primary objectives of the study for Phase 2 is to compare objective response rate determined by CA-125 based response criteria of mAb1 alone versus mAb1 combined with aflibercept in patients with advanced platinum-resistant OC.

The secondary objectives of the study for Phase 2 are: (1) to assess the safety profile of mAb1 followed by mAb1/aflibercept and aflibercept followed by mAb1/aflibercept; (2) to compare objective response rate determined by CA-125 of mAb1 alone versus aflibercept alone in patients with advanced platinum-resistant OC; (3) to compare objective response rate determined by CA-125 of mAb1 combined with aflibercept versus aflibercept alone in patients with advanced platinum-resistant OC; (4) to assess objective response rate and disease control rate determined by RECIST 1.1 of mAb1 alone, aflibercept alone and mAb1/aflibercept combination in patients with advanced platinum-resistant OC; (5) to assess disease control rate determined by CA-125 of mAb1 alone, aflibercept alone and mAb1/aflibercept combination in patients with advanced platinum-resistant OC; (6) to assess time to progression and progression-free survival determined by RECIST 1.1 of mAb1 alone, aflibercept alone and mAb1/aflibercept combination in patients with advanced platinum-resistant OC; (7) to assess time to progression and progression free survival determined by CA-125 of mAb1 alone, aflibercept alone and mAb1/aflibercept combination in patients with advanced platinum-resistant OC; (8) to assess landmark six month and one year OS rates of mAb1 alone, aflibercept alone and mAb1/aflibercept combination in patients with advanced platinum-resistant OC; (9) to assess safety and efficacy profile for patients who switched from mAb1 alone to combo mAb1/aflibercept and patients who switched from aflibercept alone to combo mAb1/aflibercept; (10) to characterize the PK profile of mAb1 when used in combination with aflibercept; (11) to characterize the PK profile of aflibercept when used in combination with mAb1; (12) to assess the immunogenicity of mAb1 when used in combination with aflibercept; (13) to assess the immunogenicity of aflibercept when used in combination with mAb1; and (14) to explore the potential correlative biomarkers (safety/efficacy) of mAb1/aflibercept activity.

C. Treatment mAb1 is administered in combination with aflibercept once every 2 weeks. mAb1 is administered as a 30-minute IV infusion followed by aflibercept as a 60-minute IV infusion, for a total infusion time of 90 minutes.

mAb1 is supplied in sterile single use vials at a withdrawable volume of 10 mL at a concentration of 25 mg/mL. For IV administration, mAb1 is diluted into an IV bag of 0.9% sodium chloride injection US Pharmacopeia under aseptic conditions. The infusion sets include a 0.2 μm polyethersulfone inline filter.

Aflibercept is supplied as a sterile, non-pyrogenic, colorless to pale-yellow-colored, 25 mg/mL solution, packaged in a type 1 clear glass vial stopped with an elastomeric closure and sealed with an aluminum seal. Prior to infusion, aflibercept is diluted directly into infusion bags of 0.9% injection US Pharmacopeia or 5% dextrose. The concentration of the diluted solution can range between 0.6 and 8 mg/mL. Dilution must be carried out under aseptic conditions as aflibercept does not contain any microbial preservative. The infusion sets include a 0.2 um polyethersulfone inline filter.

D. Statistical Analyses

The analyses for the initial phase will be descriptive and exploratory in nature. Results for the pre-specified endpoints will be summarized by cohort for each arm. Statistical considerations will be detailed in the statistical analysis plan (SAP).

For the Phase 2, stratification will be included for patients with prior bevacizumab. Based on assumption of a CA-125 response rate of 30% mAb1 alone and 60% response rate for mAb1/aflibercept, 42 patients per arm will have 80% power to detect treatment difference at two-sided 0.05 level by Chi-squared test. With the assumption of cycle 1 dropout rate of 10%, the total number of patients is 138 (46 per arm).

The primary endpoint will be analyzed using Pearson Chi-square test, the 2-sided 95% confidence interval for the difference of two treatment arms will be calculated using normal approximation. The other response type endpoints will be analyzed similarly with primary endpoint. The time-to-events data will be summarized by Kaplan-Meier methods and analyzed by log-rank test, if appropriate. There will be no multiplicity adjustment between the analysis of primary and secondary endpoints in the study.

E. Safety Assessment

Safety will be assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

Safety assessments carried out at screening/baseline and during the study include physical examination (including complete neurological assessment at onset of symptoms or upon any brain MRI abnormal findings in any patient), laboratory tests, vital signs, brain MRI, pregnancy test, and tumor assessment.

The clinical laboratory data consists of hematology, blood chemistry and urinalysis. Blood samples for hematology testing will be collected at every study visit; blood samples for serum chemistry testing and urine samples for urinalysis will be collected to measure overall patient health at screening, day 1/baseline (pre-dose), day 8, day 15, and day 22 of the first cycle, and days 1, and 15 of subsequent cycles, or early termination if subject is discontinued from the study. In addition, other laboratory tests including international normalized ratio/partial thromboplastin test, calculated creatinine clearance test, and hepatitis-B/C will be carried out.

Vital sign parameters include respiratory rate (bpm), pulse rate (bpm), systolic and diastolic blood pressure (mmHg) and body temperature (° C.). Vital signs were collected (pre-dose, on dosing days) at screening and day 1/baseline, and days 8, 15, and 22 of the first cycle, and days 1, and 15 of subsequent cycles, or early termination. Vital signs were taken at 1 and 2 hours post-infusion following the study drug dose on days 1, and 15.

12-Lead ECG parameters include: Ventricular HR, PR interval, QRS interval, corrected QT interval (QTcF=QT/[RR$^{0.33}$] and QTcB=QT/[RR$^{0.5}$]) ECG status: normal, abnormal not clinical significant or abnormal clinical significant. A standard 12-lead ECG will be performed at screening, and 30 days-post last dose (end of study) or early termination.

A thorough and complete physical examination will be performed at screening, days 1 and 15 of each cycle, and 30 days-post last dose (end of study) or early termination.

A brain MRI, with and without gadolinium contrast and with T1 and T2 weighted imaging sequences, will be performed during screening (within 28 days prior to start of study drug administration). A brain MRI will also be performed during even numbered cycles between days 15 and 28 and at the 30 day follow-up.

For tumor assessment, a CT or MRI is performed at the screening visit (within 28 days prior to infusion) and during every even-numbered cycle (eg cycles 2, 4, 6, 8) between days 15 and 28 and when disease progression is suspected. Tumor assessment is performed according to Response Evaluation Criteria in Solid Tumors version 1.1 (RECIST version 1.1). RECIST criteria are developed to facilitate objective assessment of change in tumor burden such as tumor shrinkage and time to development of disease progression. RECIST guidelines are posted on the worldwide web at http://ctep(dot)cancer(dot)gov(slash)protocoldevelopment(slash)docs(slash)recist_guideline(dot)pdf. Tumor marker assessments are also collected, when available.

In addition, tumor and skin biopsies will be obtained once before and once after treatment: at baseline and in cycle 1, on day 22.

F. Pharmacokinetic Studies

Blood samples will be collected for RNA, serum cytokine testing, CTAD (citrate, theophylline, adenosine and dipyridamole), molecular profiling, and serum mAb1 and aflibercept levels at screening and post-infusion on days 1, 2, 3, 8, 15 and 22 of cycle 1, on day 1 of subsequent cycles, and on day 30 post-last dose. Results will be used to study drug-related changes in expression of angiogenesis and inflammatory-related genes and proteins (eg, including but not limited to factors such as Ang-2, soluble Tie-2, VEGF, soluble VEGF receptor 2). Tumor biopsies will be obtained for immunohistochemistry studies for Ang-2 to assess the expression of angiogenesis-related factors including, but not limited to, Ang-1/2, VEGF-A/B/C/D, VEGF-R-1/2/3 and placental growth factor. In addition, tumor DNA/RNA will be extracted to determine the expression and potential genetic mutations and/or polymorphisms known to be associated with underlying disease characteristics, tumor progression and/or tumor angiogenesis.

The tumor burden of each patient with platinum-resistant ovarian cancer will be assessed by RECIST 1.1 every 2 cycles (8 weeks) and by serum CA-125 every dosing (2 weeks).

G. Status

The phase 1b study employs a standard 3+3 dose escalation design exploring 5 different combination treatment dose levels of mAb1 and aflibercept. Once the recommended phase 2 dose (RD) of the combination treatment is determined, additional patients will be enrolled in a safety expansion cohort, for a planned total enrollment of up to 40 patients. The primary study objectives are to evaluate the safety and determine the RD of the 2 drugs in combination both administered IV every 2 weeks in patients with advanced solid tumors. Secondary endpoints include characterization of the PK and potential immunogenicity of mAb1 and aflibercept when given in combination, evaluation of correlative PD biomarkers related to mAb1 and aflibercept in addition to exploring preliminary antitumor activity. Enrollment to cohorts 1 and 2 has been completed without DLT.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for treating advanced hepatocellular cancer, the method comprising:
   (a) selecting a patient with advanced hepatocellular carcinoma wherein the patient is resistant to conventional anti-tumor therapy; and
   (b) sequentially administering to the patient in need thereof one or more doses of an antibody or antigen-binding fragment thereof which specifically binds human angiopoietin-2 (hAng-2) but does not substantially bind hAng-1, wherein the antibody or antigen-binding fragment thereof comprises a heavy chain variable region (HCVR) comprising three heavy chain CDRs (HCDR1, HCDR2 and HCDR3) from SEQ ID NO: 18, and a light chain variable region (LCVR) comprising three light chain CDRs (LCDR1, LCDR2 and LCDR3) from SEQ ID NO: 20.

2. The method of claim 1, wherein:
   (a) the HCDR1 comprises SEQ ID NO: 4;
   (b) the HCDR2 comprises SEQ ID NO: 6;
   (c) the HCDR3 comprises SEQ ID NO: 8;
   (d) the LCDR1 comprises SEQ ID NO: 12;
   (e) the LCDR2 comprises SEQ ID NO: 14; and
   (f) the LCDR3 comprises SEQ ID NO: 16.

3. The method of claim 1, wherein the HCVR comprises SEQ ID NO: 18.

4. The method of claim 1, wherein the LCVR comprises SEQ ID NO: 20.

5. The method of claim 1, wherein the HCVR comprises SEQ ID NO: 18 and the LCVR comprises SEQ ID NO: 20.

6. The method of claim 1, wherein step (b) comprises administering an initial dose comprising the anti-Ang-2 antibody followed by one or more subsequent doses of the anti-Ang-2 antibody.

7. The method of claim 6, wherein each subsequent dose is administered 2 weeks after the immediately preceding dose.

8. The method of claim 1, wherein the one or more doses of the anti-Ang-2 antibody comprises 1-20 mg/kg of patient body weight.

9. The method of claim 1, wherein the antibody or antigen-binding fragment thereof is administered in combination with a vascular endothelial growth factor (VEGF) antagonist.

10. The method of claim 9, wherein the VEGF antagonist is selected from the group consisting of an anti-VEGF antibody, a small molecule kinase inhibitor of VEGF receptor and a VEGF-inhibiting fusion protein.

* * * * *

SEQUENCE LISTING

<160> NUMBER OF SEQ ID NOS: 531

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1

```
caggtgcagc tggtgcagtc tgggggaggc ttggtacagc cggggggtc cctgagactc      60 tcctgtgcag cctctggatt caccttcagt agctacgaca tacactgggt ccgtcaagct     120
acaggaaaag gtctggagtg ggtctcagct attggtcctg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag aggtttgatt     300
acgtttgggg ggcttatcgc cccgtttgac tactgggcc agggaaccct ggtcaccgtc     360
tcctca                                                                366
```

<210> SEQ ID NO 2
<211> LENGTH: 122
<212> TYPE: PRT
<213> ORGANISM: Artificial Sequence
<220> FEATURE:

<223> OTHER INFORMATION: synthetic

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtagcta cgac                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Asp
1               5

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
attggtcctg ctggtgacac a                                             21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Ile Gly Pro Ala Gly Asp Thr
1               5

```
<210> SEQ ID NO 7
<211> LENGTH: 48
<212> TYPE: DNA
<213> ORGANISM: Artificial Sequence
<220> FEATURE:
<223> OTHER INFORMATION: synthetic

<400> SEQUENCE: 7
gcaagaggtt tgattacgtt tggggggctt atcgccccgt ttgactac            48

<210> SEQ ID NO 8
<211> LENGTH: 16
<212> TYPE: PRT
<213> ORGANISM: Artificial Sequence
<220> FEATURE:
<223> OTHER INFORMATION: synthetic

<400> SEQUENCE: 8

Ala Arg Gly Leu Ile Thr Phe Gly Gly Leu Ile Ala Pro Phe Asp Tyr
 1               5                  10                  15

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccagt tgacccagtc tccaggcacc ctgtctttgt ctccagggga aagagccacc      60
ctctcctgca gggccagtca gagtgttagc agcacctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattatgata actcacaaac gttcggccaa     300
gggaccaagg tggaaatcaa acga                                            324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg
            100                 105

<210> SEQ ID NO 11
```

```
<211> LENGTH: 21
<212> TYPE: DNA
<213> ORGANISM: Artificial Sequence
<220> FEATURE:
<223> OTHER INFORMATION: synthetic

<400> SEQUENCE: 11
cagagtgtta gcagcaccta c                                             21

<210> SEQ ID NO 12
<211> LENGTH: 7
<212> TYPE: PRT
<213> ORGANISM: Artificial Sequence
<220> FEATURE:
<223> OTHER INFORMATION: synthetic

<400> SEQUENCE: 12

Gln Ser Val Ser Ser Thr Tyr
 1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 ggtgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Gly Ala Ser
 1

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
cagcattatg ataactcaca aacg                                          24

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Gln His Tyr Asp Asn Ser Gln Thr
 1               5

<210> SEQ ID NO 17
<211> LENGTH: 366
<212> TYPE: DNA
<213> ORGANISM: Artificial Sequence
<220> FEATURE:
```

<223> OTHER INFORMATION: synthetic

<400> SEQUENCE: 17

| | |
|---|---|
| gaggtgcagc tggtggagtc tgggggaggc ttggtacagc cggggggtc cctgagactc | 60 |
| tcctgtgcag cctctggatt caccttcagt agctacgaca tacactgggt ccgtcaagct | 120 |
| acaggaaaag gtctggagtg gtctcagct attggtcctg ctggtgacac atactatcca | 180 |
| ggctccgtga agggccgatt caccatctcc agagaaaatg ccaagaactc cttgtatctt | 240 |
| caaatgaaca gcctgagagc cggggacacg gctgtgtatt actgtgcaag aggtttgatt | 300 |
| acgtttgggg ggcttatcgc cccgtttgac tactggggcc agggaaccct ggtcaccgtc | 360 |
| tcctca | 366 |

<210> SEQ ID NO 18
<211> LENGTH: 122
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser
        115                 120

<210> SEQ ID NO 19
<211> LENGTH: 321
<212> TYPE: DNA
<213> ORGANISM: Artificial Sequence
<220> FEATURE:
<223> OTHER INFORMATION: synthetic

<400> SEQUENCE: 19

| | |
|---|---|
| gaaattgtgt tgacgcagtc tccaggcacc ctgtctttgt ctccagggga agagccacc | 60 |
| ctctcctgca gggccagtca gagtgttagc agcacctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cattatgata actcacaaac gttcggccaa | 300 |
| gggaccaagg tggaaatcaa a | 321 |

<210> SEQ ID NO 20
<211> LENGTH: 107
<212> TYPE: PRT
<213> ORGANISM: Artificial Sequence
<220> FEATURE:
<223> OTHER INFORMATION: synthetic

<400> SEQUENCE: 20

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asp Asn Ser Gln
                 85                  90                  95

Thr Phe Gly Gln Gly Thr Lys Val Glu Ile Lys
            100                 105

<210> SEQ ID NO 21
<211> LENGTH: 366
<212> TYPE: DNA
<213> ORGANISM: Artificial Sequence
<220> FEATURE:
<223> OTHER INFORMATION: synthetic

<400> SEQUENCE: 21
gaggtgcagc tggtggagtc tgggggaggc ttggtacagc ctgggggttc cctgagactc      60
tcctgtgcag cctctggatt caccttcagt agctacgaca tgcactgggt ccgccaagct     120
acaggaaaag gtctggagtg gtctcagct attggtcctg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag aggttttgatt    300 acgtttgggg ggcttatcgc cccgtttgac tactggggcc agggaaccct ggtcaccgtc     360
tcctca                                                                366

<210> SEQ ID NO 22
<211> LENGTH: 122
<212> TYPE: PRT
<213> ORGANISM: Artificial Sequence
<220> FEATURE:
<223> OTHER INFORMATION: synthetic

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Gly Pro Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Leu Ile Thr Phe Gly Gly Leu Ile Ala Pro Phe Asp Tyr Trp

```
                100                 105                 110
Gly Gln Gly Thr Leu Val Thr Val Ser Ser
        115                 120

<210> SEQ ID NO 23
<211> LENGTH: 322
<212> TYPE: DNA
<213> ORGANISM: Artificial Sequence
<220> FEATURE:
<223> OTHER INFORMATION: synthetic

<400> SEQUENCE: 23
gaaattgtgt tgacgcagtc tccaggcacc ctgtctttgt ctccagggga aagagccacc      60
ctctcctgca gggccagtca gagtgttagc agcacctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattatgata actcacaaac gttcggccaa     300
gggaccaagg tggaaatcaa ac                                              322

<210> SEQ ID NO 24
<211> LENGTH: 107
<212> TYPE: PRT
<213> ORGANISM: Artificial Sequence
<220> FEATURE:
<223> OTHER INFORMATION: synthetic

<400> SEQUENCE: 24

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Asp Asn Ser Gln
                 85                  90                  95

Thr Phe Gly Gln Gly Thr Lys Val Glu Ile Lys
            100                 105

<210> SEQ ID NO 25
<211> LENGTH: 366
<212> TYPE: DNA
<213> ORGANISM: Artificial Sequence
<220> FEATURE:
<223> OTHER INFORMATION: synthetic

<400> SEQUENCE: 25
gaggtgcagc tggtgcagtc tgggggaggc ttggttcagc ctggggagtc cctgagactc      60
tcctgtgcag cctctggatt cacctttagc agctatgcca tgagctgggt ccgccagggt     120
ccagggaagg gcctggagtg gtctcaagt attactggga gtggtgatac acatactac      180 gcagactccg tgaagggccg gttcaccatc tccagagaca attccaagaa cacgctgtat     240
ctgcacatga acagcctgag agccgaggac acggccgtat attactgtgc gaaagatttt     300
cttgactaca gtacctacct tgcttttgat ctctggggcc aagggacaat ggtcaccgtc     360
```

-continued tcttca                                                                                                366

<210> SEQ ID NO 26
<211> LENGTH: 122
<212> TYPE: PRT
<213> ORGANISM: Artificial Sequence
<220> FEATURE:
<223> OTHER INFORMATION: synthetic

<400> SEQUENCE: 26

Glu Val Gln Leu Val Gln Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Thr Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ggattcacct ttagcagcta tgcc                                                                            24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Ser Ser Tyr Ala
1               5

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
attactggga gtggtgatac caca                                                                            24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Ile Thr Gly Ser Gly Asp Thr Thr
1               5

<210> SEQ ID NO 31
<211> LENGTH: 45
<212> TYPE: DNA
<213> ORGANISM: Artificial Sequence
<220> FEATURE:
<223> OTHER INFORMATION: synthetic

<400> SEQUENCE: 31
gcgaaagatt tcttgactca cagtacctac cttgcttttg atctc            45

<210> SEQ ID NO 32
<211> LENGTH: 15
<212> TYPE: PRT
<213> ORGANISM: Artificial Sequence
<220> FEATURE:
<223> OTHER INFORMATION: synthetic

<400> SEQUENCE: 32

Ala Lys Asp Phe Leu Asp Tyr Ser Thr Tyr Leu Ala Phe Asp Leu
1               5                   10                  15

<210> SEQ ID NO 33
<211> LENGTH: 324
<212> TYPE: DNA
<213> ORGANISM: Artificial Sequence
<220> FEATURE:
<223> OTHER INFORMATION: synthetic

<400> SEQUENCE: 33
gacatccaga tgacccagtc tccagccacc ctgtctttgt ctccagggga aagagccacc     60
ctctcctgca gggccagtca gagtgttagc agctacttaa cctggtacca gcagaaacct    120
ggccaggctc ccaggctcct cagctatgat gcatctaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgctcac tttcggcgga    300
gggaccaagg tggaaatcaa acga                                           324

<210> SEQ ID NO 34
<211> LENGTH: 108
<212> TYPE: PRT
<213> ORGANISM: Artificial Sequence
<220> FEATURE:
<223> OTHER INFORMATION: synthetic

<400> SEQUENCE: 34

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Thr Trp Tyr Gln Gln Lys Pro Gly Gln Ala Pro Arg Leu Leu Ser
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
            85                  90                  95

Thr Phe Gly Gly Gly Thr Lys Val Glu Ile Lys Arg
            100                 105

<210> SEQ ID NO 35
<211> LENGTH: 18
<212> TYPE: DNA
<213> ORGANISM: Artificial Sequence
<220> FEATURE:
<223> OTHER INFORMATION: synthetic

<400> SEQUENCE: 35
cagagtgtta gcagctac                                                    18

<210> SEQ ID NO 36
<211> LENGTH: 6
<212> TYPE: PRT
<213> ORGANISM: Artificial Sequence
<220> FEATURE:
<223> OTHER INFORMATION: synthetic

<400> SEQUENCE: 36

Gln Ser Val Ser Ser Tyr
 1               5

<210> SEQ ID NO 37
<211> LENGTH: 9
<212> TYPE: DNA
<213> ORGANISM: Artificial Sequence
<220> FEATURE:
<223> OTHER INFORMATION: synthetic

<400> SEQUENCE: 37 gatgcatct                                                               9

<210> SEQ ID NO 38
<211> LENGTH: 3
<212> TYPE: PRT
<213> ORGANISM: Artificial Sequence
<220> FEATURE:
<223> OTHER INFORMATION: synthetic

<400> SEQUENCE: 38

Asp Ala Ser
 1

<210> SEQ ID NO 39
<211> LENGTH: 27
<212> TYPE: DNA
<213> ORGANISM: Artificial Sequence
<220> FEATURE:
<223> OTHER INFORMATION: synthetic

<400> SEQUENCE: 39
cagcagcgta gcaactggcc gctcact                                          27

<210> SEQ ID NO 40
<211> LENGTH: 9
<212> TYPE: PRT
<213> ORGANISM: Artificial Sequence
<220> FEATURE:
<223> OTHER INFORMATION: synthetic

<400> SEQUENCE: 40

Gln Gln Arg Ser Asn Trp Pro Leu Thr
 1               5

<210> SEQ ID NO 41
<211> LENGTH: 366
<212> TYPE: DNA
<213> ORGANISM: Artificial Sequence
<220> FEATURE:
<223> OTHER INFORMATION: synthetic

<400> SEQUENCE: 41

```
gaggtgcagc tggtggagtc tgggggaggc ttggttcagc ctggggagtc cctgagactc      60
tcctgtgcag cctctggatt cacctttagc agctatgcca tgagctgggt ccgccagggt     120
ccagggaagg gcctggagtg gtctcaagt attactggga gtggtgatac cacatactac     180
gcagactccg tgaagggccg gttcaccatc tccagagaca attccaagaa cacgctgtat     240
ctgcacatga acagcctgag agccgaggac acggccgtat attactgtgc gaaagatttt     300
cttgactaca gtacctacct tgctttt gat ctctggggcc aagggacaat ggtcaccgtc     360
tcttca                                                                  366
```

<210> SEQ ID NO 42
<211> LENGTH: 122
<212> TYPE: PRT
<213> ORGANISM: Artificial Sequence
<220> FEATURE:
<223> OTHER INFORMATION: synthetic

<400> SEQUENCE: 42

Glu Val Gln Leu Val Glu Ser Gly Gly Gly Leu Val Gln Pro Gly Glu
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Thr Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 43
<211> LENGTH: 321
<212> TYPE: DNA
<213> ORGANISM: Artificial Sequence
<220> FEATURE:
<223> OTHER INFORMATION: synthetic

<400> SEQUENCE: 43

```
gaaattgtgt tgacacagtc tccagccacc ctgtctttgt ctccagggga aagagccacc      60
ctctcctgca gggccagtca gagtgttagc agctacttaa cctggtacca gcagaaacct     120
ggccaggctc ccaggctcct cagctatgat gcatctaaca gggccactgg catcccagcc     180
aggttcagtg gcagtgggtc tgggacagac ttcactctca ccatcagcag cctagagcct     240
```

```
gaagatttg cagtttatta ctgtcagcag cgtagcaact ggccgctcac tttcggcgga    300
gggaccaagg tggagatcaa a                                             321
```

<210> SEQ ID NO 44
<211> LENGTH: 107
<212> TYPE: PRT
<213> ORGANISM: Artificial Sequence
<220> FEATURE:
<223> OTHER INFORMATION: synthetic

<400> SEQUENCE: 44

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Thr Trp Tyr Gln Gln Lys Pro Gly Gln Ala Pro Arg Leu Leu Ser
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 45
<211> LENGTH: 366
<212> TYPE: DNA
<213> ORGANISM: Artificial Sequence
<220> FEATURE:
<223> OTHER INFORMATION: synthetic

<400> SEQUENCE: 45

```
gaggtgcagc tggtggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct attactggga gtggtgatac cacatactac    180
gcagactccg tgaagggccg gttcaccatc tccagagaca attccaagaa cacgctgtat    240
ctgcaaatga acagcctgag agccgaggac acggccgtat attactgtgc gaaagatttt    300
cttgactaca gtacctacct tgcttttgat ctctggggcc aagggacaat ggtcaccgtc    360
tcttca                                                              366
```

<210> SEQ ID NO 46
<211> LENGTH: 122
<212> TYPE: PRT
<213> ORGANISM: Artificial Sequence
<220> FEATURE:
<223> OTHER INFORMATION: synthetic

<400> SEQUENCE: 46

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Thr Gly Ser Gly Asp Thr Thr Tyr Tyr Ala Asp Ser Val
```

```
                     50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 47
<211> LENGTH: 322
<212> TYPE: DNA
<213> ORGANISM: Artificial Sequence
<220> FEATURE:
<223> OTHER INFORMATION: synthetic

<400> SEQUENCE: 47
gaaattgtgt tgacacagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatctaaca gggccactgg catcccagcc    180
aggttcagtg gcagtgggtc tgggagagac ttcactctca ccatcagcag cctagagcct    240
gaagattttg cagtttatta ctgtcagcag cgtagcaact ggccgctcac tttcggcgga    300
gggaccaagg tggagatcaa ac                                             322

<210> SEQ ID NO 48
<211> LENGTH: 107
<212> TYPE: PRT
<213> ORGANISM: Artificial Sequence
<220> FEATURE:
<223> OTHER INFORMATION: synthetic

<400> SEQUENCE: 48

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Arg Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc ttggtgcagc ctggcaggtc cctgagactc      60
```

```
tcctgtgcag cctctggatt cacctttgat gattatgcca tgcactgggt ccggcaagct    120
ccagggaagg gcctggagtg ggtctcaggt attagttgga atagtggtga cataggctat    180
gcggactctg tgaagggccg attcaccatc tccagagaca acgccaagaa ctccctgtat    240
ctgcaaatga acagtctgag agctcaggac acggccttgt attactgtgc aaaagcttac    300
ggtgactact actacttta cggtatggac gtctggggcc aagggaccac ggtcaccgtc    360
tcctca                                                               366
```

<210> SEQ ID NO 50
<211> LENGTH: 122
<212> TYPE: PRT
<213> ORGANISM: Artificial Sequence
<220> FEATURE:
<223> OTHER INFORMATION: synthetic

<400> SEQUENCE: 50

```
Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gln Asp Thr Ala Leu Tyr Tyr Cys
                85                  90                  95

Ala Lys Ala Tyr Gly Asp Tyr Tyr Tyr Phe Tyr Gly Met Asp Val Trp
           100                 105                 110

Gly Gln Gly Thr Thr Val Thr Val Ser Ser
       115                 120
```

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51

```
ggattcacct ttgatgatta tgcc                                            24
```

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

```
Gly Phe Thr Phe Asp Asp Tyr Ala
 1               5
```

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
attagttgga atagtggtga cata                                                24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Ser Trp Asn Ser Gly Asp Ile
1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcaaaagctt acggtgacta ctactacttt tacggtatgg acgtc             45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Lys Ala Tyr Gly Asp Tyr Tyr Tyr Phe Tyr Gly Met Asp Val
1               5                   10                  15

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57
gacatcgtga tgacccagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatcttt agtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgata actcactcac tttcggcgga     300
gggaccaaag tggatatcaa acga                                            324

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Phe Ser Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Leu
                85                  90                  95

Thr Phe Gly Gly Gly Thr Lys Val Asp Ile Lys Arg
            100                 105

```
<210> SEQ ID NO 59
<211> LENGTH: 21
<212> TYPE: DNA
<213> ORGANISM: Artificial Sequence
<220> FEATURE:
<223> OTHER INFORMATION: synthetic

<400> SEQUENCE: 59
cagagtgtta gcagcagcta c                                         21

<210> SEQ ID NO 60
<211> LENGTH: 7
<212> TYPE: PRT
<213> ORGANISM: Artificial Sequence
<220> FEATURE:
<223> OTHER INFORMATION: synthetic

<400> SEQUENCE: 60
```

Gln Ser Val Ser Ser Ser Tyr
1               5

```
<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 agtgcatcc                                                        9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62
```

Ser Ala Ser
1

```
<210> SEQ ID NO 63
<211> LENGTH: 24
<212> TYPE: DNA
<213> ORGANISM: Artificial Sequence
<220> FEATURE:
<223> OTHER INFORMATION: synthetic

<400> SEQUENCE: 63
cagcagtatg ataactcact cact                                      24
```

<210> SEQ ID NO 64
<211> LENGTH: 8
<212> TYPE: PRT
<213> ORGANISM: Artificial Sequence
<220> FEATURE:
<223> OTHER INFORMATION: synthetic

<400> SEQUENCE: 64

Gln Gln Tyr Asp Asn Ser Leu Thr
1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65

```
gaagtgcagc tggtggagtc tgggggaggc ttggtgcagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtga cataggctat   180
gcggactctg tgaagggccg attcaccatc tccagagaca cgccaagaa ctccctgtat   240 ctgcaaatga acagtctgag agctcaggac acggccttgt attactgtgc aaaagcttac   300
ggtgactact actactttta cggtatggac gtctggggcc aagggaccac ggtcaccgtc   360
tcc                                                                 363
```

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asp Ile Gly Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Gln Asp Thr Ala Leu Tyr Tyr Cys
                85                  90                  95

Ala Lys Ala Tyr Gly Asp Tyr Tyr Tyr Phe Tyr Gly Met Asp Val Trp
            100                 105                 110

Gly Gln Gly Thr Thr Val Thr Val Ser
        115                 120

<210> SEQ ID NO 67
<211> LENGTH: 321
<212> TYPE: DNA
<213> ORGANISM: Artificial Sequence
<220> FEATURE:
<223> OTHER INFORMATION: synthetic

<400> SEQUENCE: 67

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatcttt agtgcatcca gcagggccac tggcatccca   180
gacaggttca gtggcagtgg gtctgggaca gacttcactc tcaccatcag cagactggag   240
cctgaagatt ttgcagtgta ttactgtcag cagtatgata actcactcac tttcggcgga   300
gggaccaagg tggagatcaa a                                             321
```

<210> SEQ ID NO 68
<211> LENGTH: 107
<212> TYPE: PRT
<213> ORGANISM: Artificial Sequence
<220> FEATURE:
<223> OTHER INFORMATION: synthetic

<400> SEQUENCE: 68

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Ser Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Leu
                85                  90                  95

Thr Phe Gly Gly Gly Thr Lys Val Glu Ile Lys
            100                 105
```

<210> SEQ ID NO 69
<211> LENGTH: 364
<212> TYPE: DNA
<213> ORGANISM: Artificial Sequence
<220> FEATURE:
<223> OTHER INFORMATION: synthetic

<400> SEQUENCE: 69

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtga cataggctat   180
gcggactctg tgaagggccg attcaccatc tccagagaca acgccaagaa ctccctgtat   240
ctgcaaatga acagtctgag agctgaggac acggccttgt attactgtgc aaaagcttac   300
ggtgactact actactttta cggtatggac gtctggggcc aagggaccac ggtcaccgtc   360
tcct                                                                364
```

<210> SEQ ID NO 70
<211> LENGTH: 121
<212> TYPE: PRT
<213> ORGANISM: Artificial Sequence
<220> FEATURE:
<223> OTHER INFORMATION: synthetic

<400> SEQUENCE: 70

Glu Val Gln Leu Val Glu Ser Gly Gly Gly Leu Val Gln Pro Gly Arg

```
                1               5                  10                 15
              Ser Leu Arg Leu Ser Cys Ala Ala Ser Gly Phe Thr Phe Asp Asp Tyr
                          20                  25                  30

Ala Met His Trp Val Arg Gln Ala Pro Gly Lys Gly Leu Glu Trp Val
                          35                  40                  45

Ser Gly Ile Ser Trp Asn Ser Gly Asp Ile Gly Tyr Ala Asp Ser Val
                          50                  55                  60

Lys Gly Arg Phe Thr Ile Ser Arg Asp Asn Ala Lys Asn Ser Leu Tyr
               65                  70                  75                  80

Leu Gln Met Asn Ser Leu Arg Ala Glu Asp Thr Ala Leu Tyr Tyr Cys
                          85                  90                  95

Ala Lys Ala Tyr Gly Asp Tyr Tyr Phe Tyr Gly Met Asp Val Trp
                          100                 105                 110

Gly Gln Gly Thr Thr Val Thr Val Ser
                          115                 120
```

<210> SEQ ID NO 71
<211> LENGTH: 322
<212> TYPE: DNA
<213> ORGANISM: Artificial Sequence
<220> FEATURE:
<223> OTHER INFORMATION: synthetic

<400> SEQUENCE: 71

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat agtgcatcca gcagggccac tggcatccca   180
gacaggttca gtggcagtgg gtctgggaca gacttcactc tcaccatcag cagactggag   240
cctgaagatt ttgcagtgta ttactgtcag cagtatgata actcactcac tttcggcgga   300
gggaccaagg tggagatcaa ac                                           322
```

<210> SEQ ID NO 72
<211> LENGTH: 107
<212> TYPE: PRT
<213> ORGANISM: Artificial Sequence
<220> FEATURE:
<223> OTHER INFORMATION: synthetic

<400> SEQUENCE: 72

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Ser Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Asn Ser Leu
            85                  90                  95

Thr Phe Gly Gly Gly Thr Lys Val Glu Ile Lys
            100                 105
```

<210> SEQ ID NO 73
<211> LENGTH: 366

<212> TYPE: DNA
<213> ORGANISM: Artificial Sequence
<220> FEATURE:
<223> OTHER INFORMATION: synthetic

<400> SEQUENCE: 73

```
caggtgcagc tggtggagtc tgggggaggc ttggttcagc ctggggagtc cctgagactc    60
tcctgtgcag cctctggatt cacctttagc agctatgcca tgagctgggt ccgccagggt   120
ccagggaagg gcctggagtg gtctcaagt attagtggga gtggtggtac cacttactac   180
gcagactccg tggagggccg gttcaccatc tccagagaca attccaagaa cacgctgtat   240
ctgcacatga acagcctgag agccgaggac acggccgtat attactgtgc gaaagatttt   300
cttgactaca gtacctacct tgcttttgat ctctggggcc aagggacaat ggtcaccgtc   360
tcttca                                                              366
```

<210> SEQ ID NO 74
<211> LENGTH: 122
<212> TYPE: PRT
<213> ORGANISM: Artificial Sequence
<220> FEATURE:
<223> OTHER INFORMATION: synthetic

<400> SEQUENCE: 74

Gln Val Gln Leu Val Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75

```
ggattcacct ttagcagcta tgcc                                          24
```

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Phe Thr Phe Ser Ser Tyr Ala
1               5

<210> SEQ ID NO 77
<211> LENGTH: 24
<212> TYPE: DNA
<213> ORGANISM: Artificial Sequence
<220> FEATURE:
<223> OTHER INFORMATION: synthetic

<400> SEQUENCE: 77
attagtggga gtggtggtac cact                                          24

<210> SEQ ID NO 78
<211> LENGTH: 8
<212> TYPE: PRT
<213> ORGANISM: Artificial Sequence
<220> FEATURE:
<223> OTHER INFORMATION: synthetic

<400> SEQUENCE: 78

Ile Ser Gly Ser Gly Gly Thr Thr
 1               5

<210> SEQ ID NO 79
<211> LENGTH: 45
<212> TYPE: DNA
<213> ORGANISM: Artificial Sequence
<220> FEATURE:
<223> OTHER INFORMATION: synthetic

<400> SEQUENCE: 79
gcgaaagatt tcttgacta cagtacctac cttgcttttg atctc                    45

<210> SEQ ID NO 80
<211> LENGTH: 15
<212> TYPE: PRT
<213> ORGANISM: Artificial Sequence
<220> FEATURE:
<223> OTHER INFORMATION: synthetic

<400> SEQUENCE: 80

Ala Lys Asp Phe Leu Asp Tyr Ser Thr Tyr Leu Ala Phe Asp Leu
 1               5                   10                  15

<210> SEQ ID NO 81
<211> LENGTH: 324
<212> TYPE: DNA
<213> ORGANISM: Artificial Sequence
<220> FEATURE:
<223> OTHER INFORMATION: synthetic

<400> SEQUENCE: 81
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat tcactctca ccatcagcag cctgcagcct    240
gaagattttg caacttacta ttgtcaacag gctaacagtt ccctcggac gttcggccaa    300 gggaccaagg tggagatcaa acga                                          324

<210> SEQ ID NO 82
<211> LENGTH: 108
<212> TYPE: PRT
<213> ORGANISM: Artificial Sequence
<220> FEATURE:

<223> OTHER INFORMATION: synthetic

<400> SEQUENCE: 82

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys Arg
            100                 105

<210> SEQ ID NO 83
<211> LENGTH: 18
<212> TYPE: DNA
<213> ORGANISM: Artificial Sequence
<220> FEATURE:
<223> OTHER INFORMATION: synthetic

<400> SEQUENCE: 83
cagggtatta gcagctgg                                                        18

<210> SEQ ID NO 84
<211> LENGTH: 6
<212> TYPE: PRT
<213> ORGANISM: Artificial Sequence
<220> FEATURE:
<223> OTHER INFORMATION: synthetic

<400> SEQUENCE: 84

Gln Gly Ile Ser Ser Trp
 1               5

<210> SEQ ID NO 85
<211> LENGTH: 9
<212> TYPE: DNA
<213> ORGANISM: Artificial Sequence
<220> FEATURE:
<223> OTHER INFORMATION: synthetic

<400> SEQUENCE: 85 gctgcatcc                                                                   9

<210> SEQ ID NO 86
<211> LENGTH: 3
<212> TYPE: PRT
<213> ORGANISM: Artificial Sequence
<220> FEATURE:
<223> OTHER INFORMATION: synthetic

<400> SEQUENCE: 86

Ala Ala Ser
 1

<210> SEQ ID NO 87
<211> LENGTH: 27
<212> TYPE: DNA

<213> ORGANISM: Artificial Sequence
<220> FEATURE:
<223> OTHER INFORMATION: synthetic

<400> SEQUENCE: 87
caacaggcta acagtttccc tcggacg         27

<210> SEQ ID NO 88
<211> LENGTH: 9
<212> TYPE: PRT
<213> ORGANISM: Artificial Sequence
<220> FEATURE:
<223> OTHER INFORMATION: synthetic

<400> SEQUENCE: 88

Gln Gln Ala Asn Ser Phe Pro Arg Thr
 1               5

<210> SEQ ID NO 89
<211> LENGTH: 366
<212> TYPE: DNA
<213> ORGANISM: Artificial Sequence
<220> FEATURE:
<223> OTHER INFORMATION: synthetic

<400> SEQUENCE: 89
gaggtgcagc tggtggagtc tggggggaggc ttggttcagc ctggggagtc cctgagactc      60
tcctgtgcag cctctggatt cacctttagc agctatgcca tgagctgggt ccgccagggt     120
ccagggaagg gcctggagtg gtctcaagt attagtggga gtggtggtac cacttactac     180
gcagactccg tggagggccg gttcaccatc tccagagaca attccaagaa cacgctgtat     240
ctgcacatga acagcctgag agccgaggac acggccgtat attactgtgc gaaagatttt     300
cttgactaca gtacctacct tgcttttgat ctctggggcc aagggacaat ggtcaccgtc     360
tcttca                                                                366

<210> SEQ ID NO 90
<211> LENGTH: 122
<212> TYPE: PRT
<213> ORGANISM: Artificial Sequence
<220> FEATURE:
<223> OTHER INFORMATION: synthetic

<400> SEQUENCE: 90

Glu Val Gln Leu Val Glu Ser Gly Gly Gly Leu Val Gln Pro Gly Glu
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Gly Pro Gly Lys Gly Leu Glu Trp Val
        35                  40                  45

Ser Ser Ile Ser Gly Ser Gly Gly Thr Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Phe Leu Asp Tyr Ser Thr Tyr Leu Ala Phe Asp Leu Trp
            100                 105                 110

Gly Gln Gly Thr Met Val Thr Val Ser Ser
        115                 120

<210> SEQ ID NO 91
<211> LENGTH: 321
<212> TYPE: DNA
<213> ORGANISM: Artificial Sequence
<220> FEATURE:
<223> OTHER INFORMATION: synthetic

<400> SEQUENCE: 91

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctcggac gttcggccaa   300
gggaccaagg tggaaatcaa a                                             321
```

<210> SEQ ID NO 92
<211> LENGTH: 107
<212> TYPE: PRT
<213> ORGANISM: Artificial Sequence
<220> FEATURE:
<223> OTHER INFORMATION: synthetic

<400> SEQUENCE: 92

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105
```

<210> SEQ ID NO 93
<211> LENGTH: 366
<212> TYPE: DNA
<213> ORGANISM: Artificial Sequence
<220> FEATURE:
<223> OTHER INFORMATION: synthetic

<400> SEQUENCE: 93

```
gaggtgcagc tggtggagtc tgggggaggc ttggtacagc ctgggggtc cctgagactc     60
tcctgtgcag cctctggatt cacctttagc agctatgcca tgagctgggt ccgccaggct   120
ccagggaagg gctggagtg gtctcagct attagtggga gtggtggtac cacttactac    180
gcagactccg tgaagggccg gttcaccatc tccagagaca attccaagaa cacgctgtat   240
ctgcaaatga acagcctgag agccgaggac acggccgtat attactgtgc gaaagatttt   300
cttgactaca gtacctacct tgcttttgat ctctggggcc aagggacaat ggtcaccgtc   360
tcttca                                                              366
```

<210> SEQ ID NO 94

<211> LENGTH: 122
<212> TYPE: PRT
<213> ORGANISM: Artificial Sequence
<220> FEATURE:
<223> OTHER INFORMATION: synthetic

<400> SEQUENCE: 94

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Phe Leu Asp Tyr Ser Thr Tyr Leu Ala Phe Asp Leu Trp
            100                 105                 110
Gly Gln Gly Thr Met Val Thr Val Ser Ser
        115                 120

<210> SEQ ID NO 95
<211> LENGTH: 322
<212> TYPE: DNA
<213> ORGANISM: Artificial Sequence
<220> FEATURE:
<223> OTHER INFORMATION: synthetic

<400> SEQUENCE: 95
gacatccaga tgacccagtc tccatcttct gtgtctgcat ctgtaggaga cagagtcacc        60
atcacttgtc gggcgagtca gggtattagc agctggttag cctggtatca gcagaaacca       120
gggaaagccc ctaagctcct gatctatgct gcatccagtt tgcaaagtgg ggtcccatca       180
aggttcagcg gcagtggatc tgggacagat ttcactctca ctatcagcag cctgcagcct       240
gaagattttg caacttacta ttgtcaacag gctaacagtt tccctcggac gttcggccaa       300
gggaccaagg tggaaatcaa ac                                                322

<210> SEQ ID NO 96
<211> LENGTH: 107
<212> TYPE: PRT
<213> ORGANISM: Artificial Sequence
<220> FEATURE:
<223> OTHER INFORMATION: synthetic

<400> SEQUENCE: 96

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 97
<211> LENGTH: 363
<212> TYPE: DNA
<213> ORGANISM: Artificial Sequence
<220> FEATURE:
<223> OTHER INFORMATION: synthetic

<400> SEQUENCE: 97
caggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg tggacaaca    180 gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatggcgtag cagctcgtta ctttgactac tggggccagg gaaccctggt caccgtctcc    360
tca                                                                  363

<210> SEQ ID NO 98
<211> LENGTH: 121
<212> TYPE: PRT
<213> ORGANISM: Artificial Sequence
<220> FEATURE:
<223> OTHER INFORMATION: synthetic

<400> SEQUENCE: 98

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Val Ala Ala Arg Tyr Phe Asp Tyr Trp Gly
            100                 105                 110

Gln Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggattcactt tcagtaacgc ctgg                                            24

<210> SEQ ID NO 100
<211> LENGTH: 8

```
<212> TYPE: PRT
<213> ORGANISM: Artificial Sequence
<220> FEATURE:
<223> OTHER INFORMATION: synthetic

<400> SEQUENCE: 100

Gly Phe Thr Phe Ser Asn Ala Trp
 1               5

<210> SEQ ID NO 101
<211> LENGTH: 30
<212> TYPE: DNA
<213> ORGANISM: Artificial Sequence
<220> FEATURE:
<223> OTHER INFORMATION: synthetic

<400> SEQUENCE: 101
attaaaagca aaactgatgg tgggacaaca                                    30

<210> SEQ ID NO 102
<211> LENGTH: 10
<212> TYPE: PRT
<213> ORGANISM: Artificial Sequence
<220> FEATURE:
<223> OTHER INFORMATION: synthetic

<400> SEQUENCE: 102

Ile Lys Ser Lys Thr Asp Gly Gly Thr Thr
 1               5                  10

<210> SEQ ID NO 103
<211> LENGTH: 36
<212> TYPE: DNA
<213> ORGANISM: Artificial Sequence
<220> FEATURE:
<223> OTHER INFORMATION: synthetic

<400> SEQUENCE: 103
accacagatg gcgtagcagc tcgttacttt gactac                             36

<210> SEQ ID NO 104
<211> LENGTH: 12
<212> TYPE: PRT
<213> ORGANISM: Artificial Sequence
<220> FEATURE:
<223> OTHER INFORMATION: synthetic

<400> SEQUENCE: 104

Thr Thr Asp Gly Val Ala Ala Arg Tyr Phe Asp Tyr
 1               5                  10

<210> SEQ ID NO 105
<211> LENGTH: 324
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
```
gggaccaagg tggagatcaa acga                                                    324

<210> SEQ ID NO 106
<211> LENGTH: 108
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Arg
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagtatta gtagctgg                                                           18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 aaggcgtct                                                                      9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Lys Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacagtata atagttattc tcggacg                                          27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Asn Ser Tyr Ser Arg Thr
 1               5

<210> SEQ ID NO 113
<211> LENGTH: 363
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc tgggggaggc ttggtaaagc ctgggggggtc ccttagactc      60 tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
gatggcgtag cagctcgtta cttttgactac tggggccagg gaaccctggt caccgtctcc     360
tca                                                                  363

<210> SEQ ID NO 114
<211> LENGTH: 121
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Val Ala Ala Arg Tyr Phe Asp Tyr Trp Gly
            100                 105                 110

Gln Gly Thr Leu Val Thr Val Ser Ser
        115                 120

<210> SEQ ID NO 115
<211> LENGTH: 321
<212> TYPE: DNA
<213> ORGANISM: Artificial Sequence
<220> FEATURE:
<223> OTHER INFORMATION: synthetic

<400> SEQUENCE: 115
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa a                                             321

<210> SEQ ID NO 116
<211> LENGTH: 107
<212> TYPE: PRT
<213> ORGANISM: Artificial Sequence
<220> FEATURE:
<223> OTHER INFORMATION: synthetic

<400> SEQUENCE: 116

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 117
<211> LENGTH: 363
<212> TYPE: DNA
<213> ORGANISM: Artificial Sequence
<220> FEATURE:
<223> OTHER INFORMATION: synthetic

<400> SEQUENCE: 117
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggagtg ggttggccgt attaaaagca aaactgatgg tgggacaaca   180
gactacgctg cacccgtgaa aggcagattc accatctcaa gagatgattc aaaaaacacg   240

```
ctgtatctgc aaatgaacag cctgaaaacc gaggacacag ccgtgtatta ctgtaccaca      300
gatggcgtag cagctcgtta ctttgactac tggggccagg aaccctggt caccgtctcc      360 tca                                                                   363
```

<210> SEQ ID NO 118
<211> LENGTH: 121
<212> TYPE: PRT
<213> ORGANISM: Artificial Sequence
<220> FEATURE:
<223> OTHER INFORMATION: synthetic

<400> SEQUENCE: 118

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Val Ala Ala Arg Tyr Phe Asp Tyr Trp Gly
            100                 105                 110

Gln Gly Thr Leu Val Thr Val Ser Ser
        115                 120
```

<210> SEQ ID NO 119
<211> LENGTH: 322
<212> TYPE: DNA
<213> ORGANISM: Artificial Sequence
<220> FEATURE:
<223> OTHER INFORMATION: synthetic

<400> SEQUENCE: 119

```
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt attctcggac gttcggccaa      300
gggaccaagg tggaaatcaa ac                                               322
```

<210> SEQ ID NO 120
<211> LENGTH: 107
<212> TYPE: PRT
<213> ORGANISM: Artificial Sequence
<220> FEATURE:
<223> OTHER INFORMATION: synthetic

<400> SEQUENCE: 120

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
                100                 105
```

<210> SEQ ID NO 121
<211> LENGTH: 366
<212> TYPE: DNA
<213> ORGANISM: Artificial Sequence
<220> FEATURE:
<223> OTHER INFORMATION: synthetic

<400> SEQUENCE: 121

```
gaggtgcagc tggtgcagtc tggggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atgtggtatg atgaaactaa taaatactat   180
gcagactccg tgaagggccg attcaccatc tccagagaca attccaagaa cacgctgtat   240
ctgcaaatga acagcctgag agccgaggac acggctgtgt attactgtgc gagatatagt   300
ggctacgagg actactacca cggtatggac gtctggggcc aagggaccac ggtcaccgtc   360
tcctca                                                              366
```

<210> SEQ ID NO 122
<211> LENGTH: 122
<212> TYPE: PRT
<213> ORGANISM: Artificial Sequence
<220> FEATURE:
<223> OTHER INFORMATION: synthetic

<400> SEQUENCE: 122

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Met Trp Tyr Asp Glu Thr Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Ser Gly Tyr Glu Asp Tyr Tyr His Gly Met Asp Val Trp
                100                 105                 110

Gly Gln Gly Thr Thr Val Thr Val Ser Ser
        115                 120
```

<210> SEQ ID NO 123
<211> LENGTH: 24
<212> TYPE: DNA
<213> ORGANISM: Artificial Sequence
<220> FEATURE:

<223> OTHER INFORMATION: synthetic

<400> SEQUENCE: 123
ggattcacct tcagtagcta tggc    24

<210> SEQ ID NO 124
<211> LENGTH: 8
<212> TYPE: PRT
<213> ORGANISM: Artificial Sequence
<220> FEATURE:
<223> OTHER INFORMATION: synthetic

<400> SEQUENCE: 124

Gly Phe Thr Phe Ser Ser Tyr Gly
 1               5

<210> SEQ ID NO 125
<211> LENGTH: 24
<212> TYPE: DNA
<213> ORGANISM: Artificial Sequence
<220> FEATURE:
<223> OTHER INFORMATION: synthetic

<400> SEQUENCE: 125
atgtggtatg atgaaactaa taaa    24

<210> SEQ ID NO 126
<211> LENGTH: 8
<212> TYPE: PRT
<213> ORGANISM: Artificial Sequence
<220> FEATURE:
<223> OTHER INFORMATION: synthetic

<400> SEQUENCE: 126

Met Trp Tyr Asp Glu Thr Asn Lys
 1               5

<210> SEQ ID NO 127
<211> LENGTH: 45
<212> TYPE: DNA
<213> ORGANISM: Artificial Sequence
<220> FEATURE:
<223> OTHER INFORMATION: synthetic

<400> SEQUENCE: 127
gcgagatata gtggctacga ggactactac cacggtatgg acgtc    45

<210> SEQ ID NO 128
<211> LENGTH: 15
<212> TYPE: PRT
<213> ORGANISM: Artificial Sequence
<220> FEATURE:
<223> OTHER INFORMATION: synthetic

<400> SEQUENCE: 128

Ala Arg Tyr Ser Gly Tyr Glu Asp Tyr Tyr His Gly Met Asp Val
 1               5                  10                  15

<210> SEQ ID NO 129
<211> LENGTH: 321
<212> TYPE: DNA
<213> ORGANISM: Artificial Sequence
<220> FEATURE:
<223> OTHER INFORMATION: synthetic

<400> SEQUENCE: 129

```
gccatccaga tgacccagtc tccagccacc ccgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcac tataataact ggatcacctt cggccaaggg   300
acacgactgg agattaaacg a                                             321
```

<210> SEQ ID NO 130
<211> LENGTH: 107
<212> TYPE: PRT
<213> ORGANISM: Artificial Sequence
<220> FEATURE:
<223> OTHER INFORMATION: synthetic

<400> SEQUENCE: 130

```
Ala Ile Gln Met Thr Gln Ser Pro Ala Thr Pro Ser Val Ser Pro Gly
 1               5                  10                  15

Glu Arg Ala Thr Leu Ser Cys Arg Ala Ser Gln Ser Ile Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
 65              70                  75                  80

Glu Asp Phe Ala Val Tyr Tyr Cys Gln His Tyr Asn Asn Trp Ile Thr
                85                  90                  95

Phe Gly Gln Gly Thr Arg Leu Glu Ile Lys Arg
            100                 105
```

<210> SEQ ID NO 131
<211> LENGTH: 18
<212> TYPE: DNA
<213> ORGANISM: Artificial Sequence
<220> FEATURE:
<223> OTHER INFORMATION: synthetic

<400> SEQUENCE: 131

```
cagagtatta gcagcaac                                                  18
```

<210> SEQ ID NO 132
<211> LENGTH: 6
<212> TYPE: PRT
<213> ORGANISM: Artificial Sequence
<220> FEATURE:
<223> OTHER INFORMATION: synthetic

<400> SEQUENCE: 132

```
Gln Ser Ile Ser Ser Asn
 1               5
```

<210> SEQ ID NO 133
<211> LENGTH: 9
<212> TYPE: DNA
<213> ORGANISM: Artificial Sequence
<220> FEATURE:
<223> OTHER INFORMATION: synthetic

<400> SEQUENCE: 133

```
ggtgcatcc                                                             9
```

<210> SEQ ID NO 134
<211> LENGTH: 3
<212> TYPE: PRT
<213> ORGANISM: Artificial Sequence
<220> FEATURE:
<223> OTHER INFORMATION: synthetic

<400> SEQUENCE: 134

Gly Ala Ser
 1

<210> SEQ ID NO 135
<211> LENGTH: 24
<212> TYPE: DNA
<213> ORGANISM: Artificial Sequence
<220> FEATURE:
<223> OTHER INFORMATION: synthetic

<400> SEQUENCE: 135
cagcactata ataactggat cacc                                              24

<210> SEQ ID NO 136
<211> LENGTH: 8
<212> TYPE: PRT
<213> ORGANISM: Artificial Sequence
<220> FEATURE:
<223> OTHER INFORMATION: synthetic

<400> SEQUENCE: 136

Gln His Tyr Asn Asn Trp Ile Thr
 1               5

<210> SEQ ID NO 137
<211> LENGTH: 363
<212> TYPE: DNA
<213> ORGANISM: Artificial Sequence
<220> FEATURE:
<223> OTHER INFORMATION: synthetic

<400> SEQUENCE: 137
caggtgcagc tggtggagtc tgggggaggc gtggtccagc ctggggaggtc cctgagactc        60 tcctgtgcag cgtctggatt caccttcagt agctatggca tgcactgggt ccgccaggct       120
ccaggcaagg ggctggagtg ggtggcagtt atgtggtatg atgaaactaa taatactat        180 gcagactccg tgaagggccg attcaccatc tccagagaca attccaagaa cacgctgtat       240
ctgcaaatga acagcctgag agccgaggac acggctgtgt attactgtgc gagatatagt       300
ggctacgagg actactacca cggtatggac gtctggggcc aagggaccac ggtcaccgtc       360
tcc                                                                     363

<210> SEQ ID NO 138
<211> LENGTH: 121
<212> TYPE: PRT
<213> ORGANISM: Artificial Sequence
<220> FEATURE:
<223> OTHER INFORMATION: synthetic

<400> SEQUENCE: 138

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
        35                  40                  45

Ala Val Met Trp Tyr Asp Glu Thr Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ser Gly Tyr Glu Asp Tyr Tyr His Gly Met Asp Val Trp
            100                 105                 110

Gly Gln Gly Thr Thr Val Thr Val Ser
            115                 120

<210> SEQ ID NO 139
<211> LENGTH: 318
<212> TYPE: DNA
<213> ORGANISM: Artificial Sequence
<220> FEATURE:
<223> OTHER INFORMATION: synthetic

<400> SEQUENCE: 139
gaaatagtga tgacgcagtc tccagccacc ccgtctgtgt ctccagggga aagagccacc      60
ctctcctgca gggccagtca gagtattagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcac tataataact ggatcacctt cggccaaggg     300
acacgactgg agattaaa                                                   318

<210> SEQ ID NO 140
<211> LENGTH: 106
<212> TYPE: PRT
<213> ORGANISM: Artificial Sequence
<220> FEATURE:
<223> OTHER INFORMATION: synthetic

<400> SEQUENCE: 140

Glu Ile Val Met Thr Gln Ser Pro Ala Thr Pro Ser Val Ser Pro Gly
 1               5                  10                  15

Glu Arg Ala Thr Leu Ser Cys Arg Ala Ser Gln Ser Ile Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Tyr Asn Asn Trp Ile Thr
                 85                  90                  95

Phe Gly Gln Gly Thr Arg Leu Glu Ile Lys
            100                 105

<210> SEQ ID NO 141
<211> LENGTH: 364
<212> TYPE: DNA
<213> ORGANISM: Artificial Sequence
<220> FEATURE:
<223> OTHER INFORMATION: synthetic
```

<400> SEQUENCE: 141

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt atgtggtatg atgaaactaa taaatactat      180
gcagactccg tgaagggccg attcaccatc tccagagaca actccaagaa cacgctgtat     240
ctgcaaatga acagcctgag agccgaggac acggctgtgt attactgtgc gagatatagt     300
ggctacgagg actactacca cggtatggac gtctggggcc aagggaccac ggtcaccgtc     360
tcct                                                                  364
```

<210> SEQ ID NO 142
<211> LENGTH: 121
<212> TYPE: PRT
<213> ORGANISM: Artificial Sequence
<220> FEATURE:
<223> OTHER INFORMATION: synthetic

<400> SEQUENCE: 142

```
Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Met Trp Tyr Asp Glu Thr Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Tyr Ser Gly Tyr Glu Asp Tyr Tyr His Gly Met Asp Val Trp
            100                 105                 110
Gly Gln Gly Thr Thr Val Thr Val Ser
        115                 120
```

<210> SEQ ID NO 143
<211> LENGTH: 319
<212> TYPE: DNA
<213> ORGANISM: Artificial Sequence
<220> FEATURE:
<223> OTHER INFORMATION: synthetic

<400> SEQUENCE: 143

```
gaaatagtga tgacgcagtc tccagccacc ctgtctgtgt ctccagggga aagagccacc      60
ctctcctgca gggccagtca gagtattagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcac tataataact ggatcacctt cggccaaggg     300
acacgactgg agattaaac                                                  319
```

<210> SEQ ID NO 144
<211> LENGTH: 106
<212> TYPE: PRT
<213> ORGANISM: Artificial Sequence
<220> FEATURE:
<223> OTHER INFORMATION: synthetic

<400> SEQUENCE: 144

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asn Trp Ile Thr
                85                  90                  95

Phe Gly Gln Gly Thr Arg Leu Glu Ile Lys
            100                 105

<210> SEQ ID NO 145
<211> LENGTH: 357
<212> TYPE: DNA
<213> ORGANISM: Artificial Sequence
<220> FEATURE:
<223> OTHER INFORMATION: synthetic

<400> SEQUENCE: 145
caggtgcagc tggtgcagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagttata ctggtaggac catatactac       180
gcggactctg tgaagggccg attcaccatc tccaggaca acgccaagaa ctcactgtat      240
ctgcaaatga acagcctgag agccgaggac acggccgtgt attactgtgc gagagatacg     300
gactacggtg acttctttga ctactggggc cagggaaccc tggtcaccgt ctcctca       357

<210> SEQ ID NO 146
<211> LENGTH: 119
<212> TYPE: PRT
<213> ORGANISM: Artificial Sequence
<220> FEATURE:
<223> OTHER INFORMATION: synthetic

<400> SEQUENCE: 146

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Tyr Thr Gly Arg Thr Ile Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Tyr Gly Asp Phe Phe Asp Tyr Trp Gly Gln Gly
            100                 105                 110

Thr Leu Val Thr Val Ser Ser
            115

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggattcacct tcagtgacta ctac                                          24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Phe Thr Phe Ser Asp Tyr Tyr
 1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
attagttata ctggtaggac cata                                          24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ser Tyr Thr Gly Arg Thr Ile
 1               5

<210> SEQ ID NO 151
<211> LENGTH: 36
<212> TYPE: DNA
<213> ORGANISM: Artificial Sequence
<220> FEATURE:
<223> OTHER INFORMATION: synthetic

<400> SEQUENCE: 151
gcgagagata cggactacgg tgacttcttt gactac                             36

<210> SEQ ID NO 152
<211> LENGTH: 12
<212> TYPE: PRT
<213> ORGANISM: Artificial Sequence
<220> FEATURE:
<223> OTHER INFORMATION: synthetic

<400> SEQUENCE: 152

Ala Arg Asp Thr Asp Tyr Gly Asp Phe Phe Asp Tyr
 1               5                  10

<210> SEQ ID NO 153
<211> LENGTH: 324

<212> TYPE: DNA
<213> ORGANISM: Artificial Sequence
<220> FEATURE:
<223> OTHER INFORMATION: synthetic

<400> SEQUENCE: 153

```
gccatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt acccgctcac tttcggcgga   300
gggaccaagg tggagatcaa acga                                          324
```

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

```
Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Ser Asn Tyr
            20                  25                  30
Leu Ala Trp Phe Gln Gln Lys Pro Gly Lys Ala Pro Lys Ser Leu Ile
        35                  40                  45
Tyr Ala Ala Ser Ser Leu Gln Ser Gly Val Pro Ser Lys Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys Arg
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155

```
cagggcatta gcaattat                                                  18
```

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

```
Gln Gly Ile Ser Asn Tyr
 1               5
```

<210> SEQ ID NO 157
<211> LENGTH: 9
<212> TYPE: DNA

```
<213> ORGANISM: Artificial Sequence
<220> FEATURE:
<223> OTHER INFORMATION: synthetic

<400> SEQUENCE: 157 gctgcatcc                                                                  9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagtata atagttaccc gctcact                                              27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Tyr Asn Ser Tyr Pro Leu Thr
 1               5

<210> SEQ ID NO 161
<211> LENGTH: 357
<212> TYPE: DNA
<213> ORGANISM: Artificial Sequence
<220> FEATURE:
<223> OTHER INFORMATION: synthetic

<400> SEQUENCE: 161
caggtgcagc tggtggagtc tgggggaggc ttggtcaagc ctggagggtc cctgagactc          60
tcctgtgcag cctctggatt caccttcagt gactactaca tgagctggat ccgccaggct         120
ccagggaagg ggctggagtg ggtttcatac attagttata ctggtaggac catatactac         180
gcggactctg tgaagggccg attcaccatc tccagggaca cgccaagaa ctcactgtat          240 ctgcaaatga acagcctgag agccgaggac acggccgtgt attactgtgc gagagatacg         300
gactacggtg acttctttga ctactggggc cagggaaccc tggtcaccgt ctcctca           357

<210> SEQ ID NO 162
<211> LENGTH: 119
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Leu Val Lys Pro Gly Gly
```

```
                1               5                  10                 15
Ser Leu Arg Leu Ser Cys Ala Ala Ser Gly Phe Thr Phe Ser Asp Tyr
                20                  25                 30

Tyr Met Ser Trp Ile Arg Gln Ala Pro Gly Lys Gly Leu Glu Trp Val
        35                  40                  45

Ser Tyr Ile Ser Tyr Thr Gly Arg Thr Ile Tyr Tyr Ala Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Val Tyr Tyr Cys
                85                  90                  95

Ala Arg Asp Thr Asp Tyr Gly Asp Phe Phe Asp Tyr Trp Gly Gln Gly
                100                 105                 110

Thr Leu Val Thr Val Ser Ser
            115
```

<210> SEQ ID NO 163
<211> LENGTH: 321
<212> TYPE: DNA
<213> ORGANISM: Artificial Sequence
<220> FEATURE:
<223> OTHER INFORMATION: synthetic

<400> SEQUENCE: 163

```
gacatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt acccgctcac tttcggcgga   300
gggaccaagg tggagatcaa a                                             321
```

<210> SEQ ID NO 164
<211> LENGTH: 107
<212> TYPE: PRT
<213> ORGANISM: Artificial Sequence
<220> FEATURE:
<223> OTHER INFORMATION: synthetic

<400> SEQUENCE: 164

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 165
<211> LENGTH: 357

<212> TYPE: DNA
<213> ORGANISM: Artificial Sequence
<220> FEATURE:
<223> OTHER INFORMATION: synthetic

<400> SEQUENCE: 165

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagttata ctggtaggac catatactac     180
gcagactctg tgaagggccg attcaccatc tccagggaca acgccaagaa ctcactgtat     240
ctgcaaatga acagcctgag agccgaggac acggccgtgt attactgtgc gagagatacg     300
gactacggtg acttctttga ctactggggc cagggaaccc tggtcaccgt ctcctca        357
```

<210> SEQ ID NO 166
<211> LENGTH: 119
<212> TYPE: PRT
<213> ORGANISM: Artificial Sequence
<220> FEATURE:
<223> OTHER INFORMATION: synthetic

<400> SEQUENCE: 166

```
Gln Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Asp Tyr
             20                  25                  30
Tyr Met Ser Trp Ile Arg Gln Ala Pro Gly Lys Gly Leu Glu Trp Val
         35                  40                  45
Ser Tyr Ile Ser Tyr Thr Gly Arg Thr Ile Tyr Tyr Ala Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Thr Asp Tyr Gly Asp Phe Phe Asp Tyr Trp Gly Gln Gly
            100                 105                 110
Thr Leu Val Thr Val Ser Ser
        115
```

<210> SEQ ID NO 167
<211> LENGTH: 322
<212> TYPE: DNA
<213> ORGANISM: Artificial Sequence
<220> FEATURE:
<223> OTHER INFORMATION: synthetic

<400> SEQUENCE: 167

```
gacatccaga tgacccagtc tccatcctca ctgtctgcat ctgtaggaga cagagtcacc      60
atcacttgtc gggcgagtca gggcattagc aattatttag cctggtttca gcagaaacca     120
gggaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgctcac tttcggcgga     300
gggaccaagg tggagatcaa ac                                              322
```

<210> SEQ ID NO 168
<211> LENGTH: 107
<212> TYPE: PRT

```
<213> ORGANISM: Artificial Sequence
<220> FEATURE:
<223> OTHER INFORMATION: synthetic

<400> SEQUENCE: 168

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 169
<211> LENGTH: 360
<212> TYPE: DNA
<213> ORGANISM: Artificial Sequence
<220> FEATURE:
<223> OTHER INFORMATION: synthetic

<400> SEQUENCE: 169
caggtgcagc tggtgcagtc ggggggagac gtggtccagc ctgggaggtc cctgagactc      60
tcctgtgcag cgtctggatt caccttcagt agttatggca tgcactgggt ccgccaggct     120
ccaggcaagg gactggagtg ggtggcaatt atatggtatg atggaagtaa taaatattat     180
gcagactccg tgaagggccg attcaccatc tccagagaca attccaagaa cacgctttat     240
ctccaaatga acagcctgag agtcgaggac acggctgtgt actcctgtgc gagagatttt     300
agtatatcat ctcgccactt tgactattgg ggccagggaa ccctggtcac cgtctcctca     360

<210> SEQ ID NO 170
<211> LENGTH: 120
<212> TYPE: PRT
<213> ORGANISM: Artificial Sequence
<220> FEATURE:
<223> OTHER INFORMATION: synthetic

<400> SEQUENCE: 170

Gln Val Gln Leu Val Gln Ser Gly Gly Asp Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Ser Cys
                85                  90                  95

Ala Arg Asp Phe Ser Ile Ser Ser Arg His Phe Asp Tyr Trp Gly Gln
            100                 105                 110
```

Gly Thr Leu Val Thr Val Ser Ser
        115                 120

<210> SEQ ID NO 171
<211> LENGTH: 24
<212> TYPE: DNA
<213> ORGANISM: Artificial Sequence
<220> FEATURE:
<223> OTHER INFORMATION: synthetic

<400> SEQUENCE: 171
ggattcacct tcagtagtta tggc                                          24

<210> SEQ ID NO 172
<211> LENGTH: 8
<212> TYPE: PRT
<213> ORGANISM: Artificial Sequence
<220> FEATURE:
<223> OTHER INFORMATION: synthetic

<400> SEQUENCE: 172

Gly Phe Thr Phe Ser Ser Tyr Gly
1               5

<210> SEQ ID NO 173
<211> LENGTH: 24
<212> TYPE: DNA
<213> ORGANISM: Artificial Sequence
<220> FEATURE:
<223> OTHER INFORMATION: synthetic

<400> SEQUENCE: 173
atatggtatg atggaagtaa taaa                                          24

<210> SEQ ID NO 174
<211> LENGTH: 8
<212> TYPE: PRT
<213> ORGANISM: Artificial Sequence
<220> FEATURE:
<223> OTHER INFORMATION: synthetic

<400> SEQUENCE: 174

Ile Trp Tyr Asp Gly Ser Asn Lys
1               5

<210> SEQ ID NO 175
<211> LENGTH: 39
<212> TYPE: DNA
<213> ORGANISM: Artificial Sequence
<220> FEATURE:
<223> OTHER INFORMATION: synthetic

<400> SEQUENCE: 175
gcgagagatt ttagtatatc atctcgccac tttgactat                          39

<210> SEQ ID NO 176
<211> LENGTH: 13
<212> TYPE: PRT
<213> ORGANISM: Artificial Sequence
<220> FEATURE:
<223> OTHER INFORMATION: synthetic

<400> SEQUENCE: 176

Ala Arg Asp Phe Ser Ile Ser Ser Arg His Phe Asp Tyr
1               5                   10

<210> SEQ ID NO 177
<211> LENGTH: 324
<212> TYPE: DNA
<213> ORGANISM: Artificial Sequence
<220> FEATURE:
<223> OTHER INFORMATION: synthetic

<400> SEQUENCE: 177

```
gacatccaga tgacccagtc tccatcctct ctgtctgcat ctgtaggaga cagagtcacc      60
atcacttgtc gggcgagtca ggccattaac aattatttag cctggtttca gcagaaacca    120
gggaaagccc ctaagtccct gatctatgct acatccaatt tgcaaagtgg ggtcccttca    180
cagttcagcg gcagtggatc tgggacagat tacactctca ccatcagcag cctgcagcct    240
gaagattttg caacttatta ctgccaacag tattatattt acccgatcac cttcggccaa    300
gggacacgac tggagattaa acga                                           324
```

<210> SEQ ID NO 178
<211> LENGTH: 108
<212> TYPE: PRT
<213> ORGANISM: Artificial Sequence
<220> FEATURE:
<223> OTHER INFORMATION: synthetic

<400> SEQUENCE: 178

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ala Ile Asn Asn Tyr
            20                  25                  30
Leu Ala Trp Phe Gln Gln Lys Pro Gly Lys Ala Pro Lys Ser Leu Ile
        35                  40                  45
Tyr Ala Thr Ser Asn Leu Gln Ser Gly Val Pro Ser Gln Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Ile
                85                  90                  95
Thr Phe Gly Gln Gly Thr Arg Leu Glu Ile Lys Arg
            100                 105

<210> SEQ ID NO 179
<211> LENGTH: 18
<212> TYPE: DNA
<213> ORGANISM: Artificial Sequence
<220> FEATURE:
<223> OTHER INFORMATION: synthetic

<400> SEQUENCE: 179

```
caggccatta acaattat                                                   18
```

<210> SEQ ID NO 180
<211> LENGTH: 6
<212> TYPE: PRT
<213> ORGANISM: Artificial Sequence
<220> FEATURE:
<223> OTHER INFORMATION: synthetic

<400> SEQUENCE: 180

Gln Ala Ile Asn Asn Tyr
1               5

<210> SEQ ID NO 181
<211> LENGTH: 9
<212> TYPE: DNA
<213> ORGANISM: Artificial Sequence
<220> FEATURE:
<223> OTHER INFORMATION: synthetic

<400> SEQUENCE: 181 gctacatcc                                                                  9

<210> SEQ ID NO 182
<211> LENGTH: 3
<212> TYPE: PRT
<213> ORGANISM: Artificial Sequence
<220> FEATURE:
<223> OTHER INFORMATION: synthetic

<400> SEQUENCE: 182

Ala Thr Ser
 1

<210> SEQ ID NO 183
<211> LENGTH: 27
<212> TYPE: DNA
<213> ORGANISM: Artificial Sequence
<220> FEATURE:
<223> OTHER INFORMATION: synthetic

<400> SEQUENCE: 183
caacagtatt atatttaccc gatcacc                                             27

<210> SEQ ID NO 184
<211> LENGTH: 9
<212> TYPE: PRT
<213> ORGANISM: Artificial Sequence
<220> FEATURE:
<223> OTHER INFORMATION: synthetic

<400> SEQUENCE: 184

Gln Gln Tyr Tyr Ile Tyr Pro Ile Thr
 1               5

<210> SEQ ID NO 185
<211> LENGTH: 360
<212> TYPE: DNA
<213> ORGANISM: Artificial Sequence
<220> FEATURE:
<223> OTHER INFORMATION: synthetic

<400> SEQUENCE: 185
caggtgcagc tggtggagtc tgggggagac gtggtccagc ctggggaggtc cctgagactc          60 tcctgtgcag cgtctggatt caccttcagt agttatggca tgcactgggt ccgccaggct         120
ccaggcaagg gactggagtg ggtggcaatt atatggtatg atggaagtaa taaatattat         180
gcagactccg tgaagggccg attcaccatc tccagagaca attccaagaa cacgctttat         240
ctccaaatga acagcctgag agtcgaggac acggctgtgt actcctgtgc gagagatttt         300
agtatatcat ctcgccactt tgactattgg ggccagggaa ccctggtcac cgtctcctca         360

<210> SEQ ID NO 186
<211> LENGTH: 120
<212> TYPE: PRT
<213> ORGANISM: Artificial Sequence
<220> FEATURE:
<223> OTHER INFORMATION: synthetic

<400> SEQUENCE: 186

Gln Val Gln Leu Val Glu Ser Gly Gly Asp Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Val Glu Asp Thr Ala Val Tyr Ser Cys
                85                  90                  95
Ala Arg Asp Phe Ser Ile Ser Ser Arg His Phe Asp Tyr Trp Gly Gln
            100                 105                 110
Gly Thr Leu Val Thr Val Ser Ser
        115                 120

<210> SEQ ID NO 187
<211> LENGTH: 321
<212> TYPE: DNA
<213> ORGANISM: Artificial Sequence
<220> FEATURE:
<223> OTHER INFORMATION: synthetic

<400> SEQUENCE: 187
gacatccaga tgacccagtc tccatcctct ctgtctgcat ctgtaggaga cagagtcacc      60
atcacttgtc gggcgagtca ggccattaac aattatttag cctggtttca gcagaaacca     120
gggaaagccc ctaagtccct gatctatgct acatccaatt tgcaaagtgg ggtcccttca     180
cagttcagcg gcagtggatc tgggacagat tacactctca ccatcagcag cctgcagcct     240
gaagattttg caacttatta ctgccaacag tattatattt acccgatcac cttcggccaa     300
gggacacgac tggagattaa a                                              321

<210> SEQ ID NO 188
<211> LENGTH: 107
<212> TYPE: PRT
<213> ORGANISM: Artificial Sequence
<220> FEATURE:
<223> OTHER INFORMATION: synthetic

<400> SEQUENCE: 188

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ala Ile Asn Asn Tyr
            20                  25                  30
Leu Ala Trp Phe Gln Gln Lys Pro Gly Lys Ala Pro Lys Ser Leu Ile
        35                  40                  45
Tyr Ala Thr Ser Asn Leu Gln Ser Gly Val Pro Ser Gln Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Ile
                85                  90                  95
Thr Phe Gly Gln Gly Thr Arg Leu Glu Ile Lys
            100                 105

<210> SEQ ID NO 189
<211> LENGTH: 360
<212> TYPE: DNA
<213> ORGANISM: Artificial Sequence
<220> FEATURE:
<223> OTHER INFORMATION: synthetic

<400> SEQUENCE: 189

```
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg gctagagtg gtggcagtt atatggtatg atggaagtaa taaatactat      180
gcagactccg tgaagggccg attcaccatc tccagagaca attccaagaa cacgctgtat     240
ctgcaaatga acagcctgag agccgaggac acggctgtgt attactgtgc gagagatttt     300
agtatatcat ctcgccactt tgactattgg ggccaggaa cccctggtcac cgtctcctca     360
```

<210> SEQ ID NO 190
<211> LENGTH: 120
<212> TYPE: PRT
<213> ORGANISM: Artificial Sequence
<220> FEATURE:
<223> OTHER INFORMATION: synthetic

<400> SEQUENCE: 190

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Ile Ser Ser Arg His Phe Asp Tyr Trp Gly Gln
            100                 105                 110

Gly Thr Leu Val Thr Val Ser Ser
        115                 120

<210> SEQ ID NO 191
<211> LENGTH: 322
<212> TYPE: DNA
<213> ORGANISM: Artificial Sequence
<220> FEATURE:
<223> OTHER INFORMATION: synthetic

<400> SEQUENCE: 191

```
gacatccaga tgacccagtc tccatcctca ctgtctgcat ctgtaggaga cagagtcacc      60
atcacttgtc gggcgagtca ggccattaac aattatttag cctggtttca gcagaaacca     120
gggaaagccc ctaagtccct gatctatgct acatccagtt tgcaaagtgg ggtcccatca     180
aggttcagcg gcagtggatc tgggacagat ttcactctca ccatcagcag cctgcagcct     240
gaagattttg caacttatta ctgccaacag tattatattt acccgatcac cttcggccaa     300
gggacacgac tggagattaa ac                                              322
```

```
<210> SEQ ID NO 192
<211> LENGTH: 107
<212> TYPE: PRT
<213> ORGANISM: Artificial Sequence
<220> FEATURE:
<223> OTHER INFORMATION: synthetic

<400> SEQUENCE: 192
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asn Asn Tyr
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ile
                85                  90                  95

Thr Phe Gly Gln Gly Thr Arg Leu Glu Ile Lys
            100                 105

```
<210> SEQ ID NO 193
<211> LENGTH: 372
<212> TYPE: DNA
<213> ORGANISM: Artificial Sequence
<220> FEATURE:
<223> OTHER INFORMATION: synthetic

<400> SEQUENCE: 193
```
gaggtgcagc tggtggagtc tgggggaggc gtggtccagc ctggggaggtc cctgagactc      60 tcctgtgcag cgtctggatt caccttcagt agctatggca tgcactgggt ccgccaggct     120
ccagacaagg ggctggagtg ggtggcagtt aaatgggatg atggaagtaa taaatattat     180
gcagactccg tgaagggccg attcaccatc tccagagaca attccaagaa cacgctgtat     240
ctgcaaatga acagcctgag agccgaggac acggctgtgt attactgtgc gagagaaggc     300
ccttacgatt tttacagtgg ttatggagct tttgatatct ggggccaagg gacaatggtc     360
accgtctctt ca                                                         372

```
<210> SEQ ID NO 194
<211> LENGTH: 124
<212> TYPE: PRT
<213> ORGANISM: Artificial Sequence
<220> FEATURE:
<223> OTHER INFORMATION: synthetic

<400> SEQUENCE: 194
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Asp Lys Gly Leu Glu Trp Val
        35                  40                  45

Ala Val Lys Trp Asp Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195
ggattcacct tcagtagcta tggc                                         24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

Gly Phe Thr Phe Ser Ser Tyr Gly
 1               5

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197
aaatgggatg atggaagtaa taaa                                         24

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Lys Trp Asp Asp Gly Ser Asn Lys
 1               5

<210> SEQ ID NO 199
<211> LENGTH: 51
<212> TYPE: DNA
<213> ORGANISM: Artificial Sequence
<220> FEATURE:
<223> OTHER INFORMATION: synthetic

<400> SEQUENCE: 199
gcgagagaag gcccttacga ttttacagt ggttatggag cttttgatat c             51

<210> SEQ ID NO 200
<211> LENGTH: 17
<212> TYPE: PRT
<213> ORGANISM: Artificial Sequence
<220> FEATURE:
<223> OTHER INFORMATION: synthetic -continued

<400> SEQUENCE: 200

Ala Arg Glu Gly Pro Tyr Asp Phe Tyr Ser Gly Tyr Gly Ala Phe Asp
1               5                   10                  15

Ile

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcctca ctgtctgcat ctgtaggaga cagagtcacc      60
atcacttgtc gggcgagtca gggcattagc aattatttag cctggtttca gcagaaacca     120
gggaaagccc ctaagtccct gatctatgct gcatccagtt tgcaaagtgg ggtcccatca     180 agttcagcg gcagtggatc tgggacagat tcactctca ccatcagcag cctgcagcct      240
gaagattttg caacttatta ctgccaacag tataatagtt accctcggac gttcggccaa     300
gggaccaagg tggagatcaa acga                                            324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys Arg
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggcatta gcaattat                                                   18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Gly Ile Ser Asn Tyr
  1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                                9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
  1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
caacagtata atagttaccc tcggacg                                            27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Tyr Asn Ser Tyr Pro Arg Thr
  1               5

<210> SEQ ID NO 209
<211> LENGTH: 372
<212> TYPE: DNA
<213> ORGANISM: Artificial Sequence
<220> FEATURE:
<223> OTHER INFORMATION: synthetic

<400> SEQUENCE: 209
caggtgcagc tggtggagtc tgggggaggc gtggtccagc ctgggaggtc cctgagactc        60
tcctgtgcag cgtctggatt caccttcagt agctatggca tgcactgggt ccgccaggct       120
ccagacaagg ggctggagtg ggtggcagtt aaatgggatg atggaagtaa taaatattat       180
gcagactccg tgaagggccg attcaccatc tccagagaca attccaagaa cacgctgtat       240
ctgcaaatga acagcctgag agccgaggac acggctgtgt attactgtgc gagagaaggc       300
ccttacgatt ttacagtggg ttatggagct tttgatatct ggggccaagg gacaatggtc       360
accgtctctt ca                                                          372

<210> SEQ ID NO 210
<211> LENGTH: 124
<212> TYPE: PRT
<213> ORGANISM: Artificial Sequence
<220> FEATURE:
<223> OTHER INFORMATION: synthetic

<400> SEQUENCE: 210

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Val Arg Gln Ala Pro Asp Lys Gly Leu Glu Trp Val
        35                  40                  45

Ala Val Lys Trp Asp Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120
```

<210> SEQ ID NO 211
<211> LENGTH: 321
<212> TYPE: DNA
<213> ORGANISM: Artificial Sequence
<220> FEATURE:
<223> OTHER INFORMATION: synthetic

<400> SEQUENCE: 211

```
gacatccaga tgacccagtc tccatcctca ctgtctgcat ctgtaggaga cagagtcacc     60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa a                                              321
```

<210> SEQ ID NO 212
<211> LENGTH: 107
<212> TYPE: PRT
<213> ORGANISM: Artificial Sequence
<220> FEATURE:
<223> OTHER INFORMATION: synthetic

<400> SEQUENCE: 212

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 213
<211> LENGTH: 372
<212> TYPE: DNA
<213> ORGANISM: Artificial Sequence
<220> FEATURE:
<223> OTHER INFORMATION: synthetic

<400> SEQUENCE: 213
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctagagtg ggtggcagtt aaatgggatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagaaggc   300
ccttacgatt tttacagtgg ttatggagct tttgatatct ggggccaagg gacaatggtc   360
accgtctctt ca                                                       372

<210> SEQ ID NO 214
<211> LENGTH: 124
<212> TYPE: PRT
<213> ORGANISM: Artificial Sequence
<220> FEATURE:
<223> OTHER INFORMATION: synthetic

<400> SEQUENCE: 214

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Lys Trp Asp Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120

<210> SEQ ID NO 215
<211> LENGTH: 322
<212> TYPE: DNA
<213> ORGANISM: Artificial Sequence
<220> FEATURE:
<223> OTHER INFORMATION: synthetic

<400> SEQUENCE: 215
gacatccaga tgacccagtc tccatcctca ctgtctgcat ctgtaggaga cagagtcacc    60

```
atcacttgtc gggcgagtca gggcattagc aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa ac                                             322
```

<210> SEQ ID NO 216
<211> LENGTH: 107
<212> TYPE: PRT
<213> ORGANISM: Artificial Sequence
<220> FEATURE:
<223> OTHER INFORMATION: synthetic

<400> SEQUENCE: 216

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105
```

<210> SEQ ID NO 217
<211> LENGTH: 372
<212> TYPE: DNA
<213> ORGANISM: Artificial Sequence
<220> FEATURE:
<223> OTHER INFORMATION: synthetic

<400> SEQUENCE: 217

```
gaggtgcagc tggtgcagtc tgggggaggc gtggtccagc ctgggaggtc cctgagactc    60
tcctgtgcag cgtctggatt caccttcagt agctatggca tgcactgggt ccgccaggct    120
ccagacaagg gctggagtg gtggcagtt aaatgggatg atggaagtaa taaatattat    180
gcagactccg tgaagggccg attcaccatc tccagagaca attccaagaa cacgctgtat    240
ctgcaaatga acagcctgag agccgaggac acggctgtgt attactgtgc gagagaaggc    300
ccttacgatt tttacagtgg ttatggagct tttgatatct ggggccaagg gacaatggtc    360
accgtctctt ca                                                        372
```

<210> SEQ ID NO 218
<211> LENGTH: 124
<212> TYPE: PRT
<213> ORGANISM: Artificial Sequence
<220> FEATURE:
<223> OTHER INFORMATION: synthetic

<400> SEQUENCE: 218

```
Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
```

```
                    20                  25                  30
Gly Met His Trp Val Arg Gln Ala Pro Asp Lys Gly Leu Glu Trp Val
             35                  40                  45

Ala Val Lys Trp Asp Asp Gly Ser Asn Lys Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Pro Tyr Asp Phe Tyr Ser Gly Tyr Gly Ala Phe Asp
                100                 105                 110

Ile Trp Gly Gln Gly Thr Met Val Thr Val Ser Ser
            115                 120
```

<210> SEQ ID NO 219
<211> LENGTH: 24
<212> TYPE: DNA
<213> ORGANISM: Artificial Sequence
<220> FEATURE:
<223> OTHER INFORMATION: synthetic

<400> SEQUENCE: 219
ggattcacct tcagtagcta tggc                                        24

<210> SEQ ID NO 220
<211> LENGTH: 8
<212> TYPE: PRT
<213> ORGANISM: Artificial Sequence
<220> FEATURE:
<223> OTHER INFORMATION: synthetic

<400> SEQUENCE: 220

```
Gly Phe Thr Phe Ser Ser Tyr Gly
 1               5
```

<210> SEQ ID NO 221
<211> LENGTH: 24
<212> TYPE: DNA
<213> ORGANISM: Artificial Sequence
<220> FEATURE:
<223> OTHER INFORMATION: synthetic

<400> SEQUENCE: 221
aaatgggatg atggaagtaa taaa                                        24

<210> SEQ ID NO 222
<211> LENGTH: 8
<212> TYPE: PRT
<213> ORGANISM: Artificial Sequence
<220> FEATURE:
<223> OTHER INFORMATION: synthetic

<400> SEQUENCE: 222

```
Lys Trp Asp Asp Gly Ser Asn Lys
 1               5
```

<210> SEQ ID NO 223
<211> LENGTH: 51
<212> TYPE: DNA
<213> ORGANISM: Artificial Sequence
<220> FEATURE:
<223> OTHER INFORMATION: synthetic

<400> SEQUENCE: 223
gcgagagaag gcccttacga tttttacagt ggttatggag cttttgatat c    51

<210> SEQ ID NO 224
<211> LENGTH: 17
<212> TYPE: PRT
<213> ORGANISM: Artificial Sequence
<220> FEATURE:
<223> OTHER INFORMATION: synthetic

<400> SEQUENCE: 224

Ala Arg Glu Gly Pro Tyr Asp Phe Tyr Ser Gly Tyr Gly Ala Phe Asp
 1               5                  10                  15

Ile

<210> SEQ ID NO 225
<211> LENGTH: 324
<212> TYPE: DNA
<213> ORGANISM: Artificial Sequence
<220> FEATURE:
<223> OTHER INFORMATION: synthetic

<400> SEQUENCE: 225
gacatccagt tgacccagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcactcac tttcggcgga   300
gggaccaagc tggagatcaa acga                                          324

<210> SEQ ID NO 226
<211> LENGTH: 108
<212> TYPE: PRT
<213> ORGANISM: Artificial Sequence
<220> FEATURE:
<223> OTHER INFORMATION: synthetic

<400> SEQUENCE: 226

Asp Ile Gln Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Leu Glu Ile Lys Arg
            100                 105

<210> SEQ ID NO 227
<211> LENGTH: 21
<212> TYPE: DNA
<213> ORGANISM: Artificial Sequence
<220> FEATURE:
<223> OTHER INFORMATION: synthetic

<400> SEQUENCE: 227
cagagtgtta gcagcagcta c                                            21

<210> SEQ ID NO 228
<211> LENGTH: 7
<212> TYPE: PRT
<213> ORGANISM: Artificial Sequence
<220> FEATURE:
<223> OTHER INFORMATION: synthetic

<400> SEQUENCE: 228

Gln Ser Val Ser Ser Ser Tyr
 1               5

<210> SEQ ID NO 229
<211> LENGTH: 9
<212> TYPE: DNA
<213> ORGANISM: Artificial Sequence
<220> FEATURE:
<223> OTHER INFORMATION: synthetic

<400> SEQUENCE: 229 ggtgcatcc                                                           9

<210> SEQ ID NO 230
<211> LENGTH: 3
<212> TYPE: PRT
<213> ORGANISM: Artificial Sequence
<220> FEATURE:
<223> OTHER INFORMATION: synthetic

<400> SEQUENCE: 230

Gly Ala Ser
 1

<210> SEQ ID NO 231
<211> LENGTH: 24
<212> TYPE: DNA
<213> ORGANISM: Artificial Sequence
<220> FEATURE:
<223> OTHER INFORMATION: synthetic

<400> SEQUENCE: 231
cagcagtatg gtagctcact cact                                         24

<210> SEQ ID NO 232
<211> LENGTH: 8
<212> TYPE: PRT
<213> ORGANISM: Artificial Sequence
<220> FEATURE:
<223> OTHER INFORMATION: synthetic

<400> SEQUENCE: 232

Gln Gln Tyr Gly Ser Ser Leu Thr
 1               5

<210> SEQ ID NO 233
<211> LENGTH: 372
<212> TYPE: DNA
<213> ORGANISM: Artificial Sequence
<220> FEATURE:
<223> OTHER INFORMATION: synthetic

<400> SEQUENCE: 233
caggtgcagc tggtggagtc tgggggaggc gtggtccagc ctggggaggtc cctgagactc    60

```
tcctgtgcag cgtctggatt caccttcagt agctatggca tgcactgggt ccgccaggct    120
ccagacaagg ggctggagtg ggtggcagtt aaatgggatg atggaagtaa taaatattat    180
gcagactccg tgaagggccg attcaccatc tccagagaca attccaagaa cacgctgtat    240
ctgcaaatga acagcctgag agccgaggac acggctgtgt attactgtgc gagagaaggc    300
ccttacgatt tttacagtgg ttatggagct tttgatatct ggggccaagg gacaatggtc    360
accgtctctt ca                                                        372
```

<210> SEQ ID NO 234
<211> LENGTH: 124
<212> TYPE: PRT
<213> ORGANISM: Artificial Sequence
<220> FEATURE:
<223> OTHER INFORMATION: synthetic

<400> SEQUENCE: 234

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Asp Lys Gly Leu Glu Trp Val
         35                  40                  45

Ala Val Lys Trp Asp Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Pro Tyr Asp Phe Tyr Ser Gly Tyr Gly Ala Phe Asp
            100                 105                 110

Ile Trp Gly Gln Gly Thr Met Val Thr Val Ser Ser
        115                 120
```

<210> SEQ ID NO 235
<211> LENGTH: 321
<212> TYPE: DNA
<213> ORGANISM: Artificial Sequence
<220> FEATURE:
<223> OTHER INFORMATION: synthetic

<400> SEQUENCE: 235

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcactcac tttcggcgga    300
gggaccaagg tggagatcaa a                                              321
```

<210> SEQ ID NO 236
<211> LENGTH: 107
<212> TYPE: PRT
<213> ORGANISM: Artificial Sequence
<220> FEATURE:
<223> OTHER INFORMATION: synthetic

<400> SEQUENCE: 236

```
Glu Ile Val Leu Thr Gln Ser Pro Gly Thr Leu Ser Leu Ser Pro Gly
```

```
  1               5                  10                 15
Glu Arg Ala Thr Leu Ser Cys Arg Ala Ser Gln Ser Val Ser Ser
                20                 25                 30

Tyr Leu Ala Trp Tyr Gln Gln Lys Pro Gly Gln Ala Pro Arg Leu Leu
        35                 40                 45

Ile Tyr Gly Ala Ser Ser Arg Ala Thr Gly Ile Pro Asp Arg Phe Ser
        50                 55                 60

Gly Ser Gly Ser Gly Thr Asp Phe Thr Leu Thr Ile Ser Arg Leu Glu
65                  70                 75                 80

Pro Glu Asp Phe Ala Val Tyr Tyr Cys Gln Gln Tyr Gly Ser Ser Leu
                85                 90                 95

Thr Phe Gly Gly Gly Thr Lys Val Glu Ile Lys
                100                105

<210> SEQ ID NO 237
<211> LENGTH: 372
<212> TYPE: DNA
<213> ORGANISM: Artificial Sequence
<220> FEATURE:
<223> OTHER INFORMATION: synthetic

<400> SEQUENCE: 237
caggtgcagc tggtggagtc tgggggaggc gtggtccagc ctggaggtc cctgagactc      60 tcctgtgcag cgtctggatt caccttcagt agctatggca tgcactgggt ccgccaggct    120
ccaggcaagg ggctagagtg ggtggcagtt aaatgggatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagaaggc    300
ccttacgatt tttacagtgg ttatggagct tttgatatct ggggccaagg gacaatggtc    360
accgtctctt ca                                                        372

<210> SEQ ID NO 238
<211> LENGTH: 124
<212> TYPE: PRT
<213> ORGANISM: Artificial Sequence
<220> FEATURE:
<223> OTHER INFORMATION: synthetic

<400> SEQUENCE: 238

Gln Val Gln Leu Val Glu Ser Gly Gly Gly Val Val Gln Pro Gly Arg
1               5                  10                 15

Ser Leu Arg Leu Ser Cys Ala Ala Ser Gly Phe Thr Phe Ser Ser Tyr
                20                 25                 30

Gly Met His Trp Val Arg Gln Ala Pro Gly Lys Gly Leu Glu Trp Val
        35                 40                 45

Ala Val Lys Trp Asp Asp Gly Ser Asn Lys Tyr Tyr Ala Asp Ser Val
        50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Thr Ala Val Tyr Tyr Cys
                85                 90                 95

Ala Arg Glu Gly Pro Tyr Asp Phe Tyr Ser Gly Tyr Gly Ala Phe Asp
                100                105                110

Ile Trp Gly Gln Gly Thr Met Val Thr Val Ser Ser
        115                120
```

<210> SEQ ID NO 239
<211> LENGTH: 322
<212> TYPE: DNA
<213> ORGANISM: Artificial Sequence
<220> FEATURE:
<223> OTHER INFORMATION: synthetic

<400> SEQUENCE: 239

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcactcac tttcggcgga     300
gggaccaagg tggagatcaa ac                                              322
```

<210> SEQ ID NO 240
<211> LENGTH: 107
<212> TYPE: PRT
<213> ORGANISM: Artificial Sequence
<220> FEATURE:
<223> OTHER INFORMATION: synthetic

<400> SEQUENCE: 240

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Leu
                 85                  90                  95

Thr Phe Gly Gly Gly Thr Lys Val Glu Ile Lys
            100                 105
```

<210> SEQ ID NO 241
<211> LENGTH: 360
<212> TYPE: DNA
<213> ORGANISM: Artificial Sequence
<220> FEATURE:
<223> OTHER INFORMATION: synthetic

<400> SEQUENCE: 241

```
gaggtgcaat tggtggagtc ggggggaggc ttggtaaggc cggggggtc ccttagactc       60
tcctgtgcag cctctggatt cactttcact aacgcctgga tgagctgggt ccgccaggct     120
ccagggaagg ggctggagtg gattggccag attaaaagca aaactgatgg tgggacaata     180
gactacgctg cacccgtgaa aggcagattc accgtctcaa gagatgattc agaaaatacg     240
ctgtttctgc aaatgaacag cctgaaaacc gaggacacag ccgtgtatta ctgtgcgggg     300
aactggaact acgtggactt tgactactgg ggccagggaa ccctggtcac cgtctcctca     360
```

<210> SEQ ID NO 242
<211> LENGTH: 120
<212> TYPE: PRT
<213> ORGANISM: Artificial Sequence

```
<220> FEATURE:
<223> OTHER INFORMATION: synthetic

<400> SEQUENCE: 242

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Ile
        35                  40                  45

Gly Gln Ile Lys Ser Lys Thr Asp Gly Gly Thr Ile Asp Tyr Ala Ala
    50                  55                  60

Pro Val Lys Gly Arg Phe Thr Val Ser Arg Asp Asp Ser Glu Asn Thr
65                  70                  75                  80

Leu Phe Leu Gln Met Asn Ser Leu Lys Thr Glu Asp Thr Ala Val Tyr
                85                  90                  95

Tyr Cys Ala Gly Asn Trp Asn Tyr Val Asp Phe Asp Tyr Trp Gly Gln
            100                 105                 110

Gly Thr Leu Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcactt tcactaacgc ctgg                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Thr Asn Ala Trp
1               5

<210> SEQ ID NO 245
<211> LENGTH: 30
<212> TYPE: DNA
<213> ORGANISM: Artificial Sequence
<220> FEATURE:
<223> OTHER INFORMATION: synthetic

<400> SEQUENCE: 245
attaaaagca aaactgatgg tgggacaata                                    30

<210> SEQ ID NO 246
<211> LENGTH: 10
<212> TYPE: PRT
<213> ORGANISM: Artificial Sequence
<220> FEATURE:
<223> OTHER INFORMATION: synthetic

<400> SEQUENCE: 246

Ile Lys Ser Lys Thr Asp Gly Gly Thr Ile
1               5                   10
```

<210> SEQ ID NO 247
<211> LENGTH: 33
<212> TYPE: DNA
<213> ORGANISM: Artificial Sequence
<220> FEATURE:
<223> OTHER INFORMATION: synthetic

<400> SEQUENCE: 247
gcggggaact ggaactacgt ggactttgac tac                                    33

<210> SEQ ID NO 248
<211> LENGTH: 11
<212> TYPE: PRT
<213> ORGANISM: Artificial Sequence
<220> FEATURE:
<223> OTHER INFORMATION: synthetic

<400> SEQUENCE: 248

Ala Gly Asn Trp Asn Tyr Val Asp Phe Asp Tyr
 1               5                  10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccatcctcc ctgtctgcat ctgtaggaga cagagtcacc        60
atcacttgcc gggcaagtca ggacattaga aatgatttag ctggtatca gcagaaacca       120 gggaaagccc ctaagcgcct gatctatgct gcatccagtt tgcaaggtgg ggtcccatca      180
aggttcagcg gcagtggatc tgggacagaa ttcactctca caatcagcag cctgcagcct     240
gaagattttg caacttatta ctgtctacag cataatagtt acccttcac tttcggccct     300 gggaccaaag tggatatcaa a                                                321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Gly Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Phe
                 85                  90                  95

Thr Phe Gly Pro Gly Thr Lys Val Asp Ile Lys
            100                 105

```
<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251
caggacatta gaaatgat                                                 18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Asp Ile Arg Asn Asp
 1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gctgcatcc                                                            9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Ala Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
ctacagcata atagttaccc tttcact                                        27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Leu Gln His Asn Ser Tyr Pro Phe Thr
 1               5

<210> SEQ ID NO 257
<211> LENGTH: 360
<212> TYPE: DNA
<213> ORGANISM: Artificial Sequence
```

<220> FEATURE:
<223> OTHER INFORMATION: synthetic

<400> SEQUENCE: 257

```
gaggtgcagc tggtggagtc tgggggaggc ttggtaaggc cggggggtc ccttagactc      60
tcctgtgcag cctctggatt cactttcact aacgcctgga tgagctgggt ccgccaggct    120
ccagggaagg gctggagtg gattggccag attaaaagca aaactgatgg tgggacaata    180
gactacgctg cacccgtgaa aggcagattc accgtctcaa gagatgattc agaaaatacg    240
ctgtttctgc aaatgaacag cctgaaaacc gaggacacag ccgtgtatta ctgtgcgggg    300
aactggaact acgtggactt tgactactgg ggccaggaa ccctggtcac cgtctcctca    360
```

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

```
Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Ile
        35                  40                  45

Gly Gln Ile Lys Ser Lys Thr Asp Gly Gly Thr Ile Asp Tyr Ala Ala
    50                  55                  60

Pro Val Lys Gly Arg Phe Thr Val Ser Arg Asp Asp Ser Glu Asn Thr
65                  70                  75                  80

Leu Phe Leu Gln Met Asn Ser Leu Lys Thr Glu Asp Thr Ala Val Tyr
                85                  90                  95

Tyr Cys Ala Gly Asn Trp Asn Tyr Val Asp Phe Asp Tyr Trp Gly Gln
            100                 105                 110

Gly Thr Leu Val Thr Val Ser Ser
        115                 120
```

<210> SEQ ID NO 259
<211> LENGTH: 321
<212> TYPE: DNA
<213> ORGANISM: Artificial Sequence
<220> FEATURE:
<223> OTHER INFORMATION: synthetic

<400> SEQUENCE: 259

```
gacatccaga tgacccagtc tccatcctcc ctgtctgcat ctgtaggaga cagagtcacc     60
atcacttgcc gggcaagtca ggacattaga aatgatttag ctggtatca gcagaaacca    120
gggaaagccc ctaagcgcct gatctatgct gcatccagtt tgcaaggtgg ggtcccatca    180
aggttcagcg gcagtggatc tgggacagaa ttcactctca caatcagcag cctgcagcct    240
gaagattttg caacttatta ctgtctacag cataatagtt accctttcac tttcggccct    300
gggaccaaag tggatatcaa a                                              321
```

<210> SEQ ID NO 260
<211> LENGTH: 107
<212> TYPE: PRT
<213> ORGANISM: Artificial Sequence
<220> FEATURE:

<223> OTHER INFORMATION: synthetic

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Gly Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
            100                 105

<210> SEQ ID NO 261
<211> LENGTH: 360
<212> TYPE: DNA
<213> ORGANISM: Artificial Sequence
<220> FEATURE:
<223> OTHER INFORMATION: synthetic

<400> SEQUENCE: 261
gaggtgcagc tggtggagtc tgggggaggc ttggtaaagc ctgggggggtc ccttagactc    60 tcctgtgcag cctctggatt cactttcact aacgcctgga tgagctgggt ccgccaggct   120
ccagggaagg ggctggagtg ggttggccgt attaaaagca aaactgatgg tgggacaata   180
gactacgctg cacccgtgaa aggcagattc accatctcaa gagatgattc aaaaaacacg   240
ctgtatctgc aaatgaacag cctgaaaacc gaggacacag ccgtgtatta ctgtgcgggg   300
aactggaact acgtggactt tgactactgg ggccaggaa ccctggtcac cgtctcctca   360

<210> SEQ ID NO 262
<211> LENGTH: 120
<212> TYPE: PRT
<213> ORGANISM: Artificial Sequence
<220> FEATURE:
<223> OTHER INFORMATION: synthetic

<400> SEQUENCE: 262

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Ile Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Gly Asn Trp Asn Tyr Val Asp Phe Asp Tyr Trp Gly Gln
            100                 105                 110

Gly Thr Leu Val Thr Val Ser Ser
        115                 120

<210> SEQ ID NO 263
<211> LENGTH: 322
<212> TYPE: DNA
<213> ORGANISM: Artificial Sequence
<220> FEATURE:
<223> OTHER INFORMATION: synthetic

<400> SEQUENCE: 263

```
gacatccaga tgacccagtc tccatcctcc ctgtctgcat ctgtaggaga cagagtcacc    60
atcacttgcc gggcaagtca ggacattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccttttcac tttcggccct   300
gggaccaaag tggatatcaa ac                                            322
```

<210> SEQ ID NO 264
<211> LENGTH: 107
<212> TYPE: PRT
<213> ORGANISM: Artificial Sequence
<220> FEATURE:
<223> OTHER INFORMATION: synthetic

<400> SEQUENCE: 264

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Phe
                85                  90                  95
Thr Phe Gly Pro Gly Thr Lys Val Asp Ile Lys
            100                 105

<210> SEQ ID NO 265
<211> LENGTH: 375
<212> TYPE: DNA
<213> ORGANISM: Artificial Sequence
<220> FEATURE:
<223> OTHER INFORMATION: synthetic

<400> SEQUENCE: 265

```
caggtgcagc tggtggagtc tggggaggc gtggtccagc ctggaggtc cctgagactc     60
tcctgtgcag cgtctggatt caccctcagt aactatggca tgcactgggt ccgccaggct   120
ccaggcaagg ggctggagtg ggtggcagtt atatggcatg atggaagtaa tacatactat   180
gcagactccg tgaagggccg attcaccatc tccagagaca attctaagaa cacgctgtat   240
ctgcaaatga acagcctgag agccgaagac acggctgtgt attactgtac gagagagggg   300
ctcgattttt ggagtggtta ttaccctaac tggttcgacc cctggggcca gggaaccctg   360
gtcaccgtct cctca                                                    375
```

```
<210> SEQ ID NO 266
<211> LENGTH: 125
<212> TYPE: PRT
<213> ORGANISM: Artificial Sequence
<220> FEATURE:
<223> OTHER INFORMATION: synthetic

<400> SEQUENCE: 266

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Leu Ser Asn Tyr
                20                  25                  30

Gly Met His Trp Val Arg Gln Ala Pro Gly Lys Gly Leu Glu Trp Val
            35                  40                  45

Ala Val Ile Trp His Asp Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Glu Gly Leu Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125

<210> SEQ ID NO 267
<211> LENGTH: 24
<212> TYPE: DNA
<213> ORGANISM: Artificial Sequence
<220> FEATURE:
<223> OTHER INFORMATION: synthetic

<400> SEQUENCE: 267
ggattcaccc tcagtaacta tggc                                         24

<210> SEQ ID NO 268
<211> LENGTH: 8
<212> TYPE: PRT
<213> ORGANISM: Artificial Sequence
<220> FEATURE:
<223> OTHER INFORMATION: synthetic

<400> SEQUENCE: 268

Gly Phe Thr Leu Ser Asn Tyr Gly
 1               5

<210> SEQ ID NO 269
<211> LENGTH: 24
<212> TYPE: DNA
<213> ORGANISM: Artificial Sequence
<220> FEATURE:
<223> OTHER INFORMATION: synthetic

<400> SEQUENCE: 269
atatggcatg atggaagtaa taca                                         24

<210> SEQ ID NO 270
<211> LENGTH: 8
<212> TYPE: PRT
<213> ORGANISM: Artificial Sequence
<220> FEATURE:
<223> OTHER INFORMATION: synthetic
```

<400> SEQUENCE: 270

Ile Trp His Asp Gly Ser Asn Thr
1               5

<210> SEQ ID NO 271
<211> LENGTH: 54
<212> TYPE: DNA
<213> ORGANISM: Artificial Sequence
<220> FEATURE:
<223> OTHER INFORMATION: synthetic

<400> SEQUENCE: 271
acgagagagg ggctcgattt ttggagtggt tattacccta actggttcga cccc        54

<210> SEQ ID NO 272
<211> LENGTH: 18
<212> TYPE: PRT
<213> ORGANISM: Artificial Sequence
<220> FEATURE:
<223> OTHER INFORMATION: synthetic

<400> SEQUENCE: 272

Thr Arg Glu Gly Leu Asp Phe Trp Ser Gly Tyr Tyr Pro Asn Trp Phe
1               5                   10                  15

Asp Pro

<210> SEQ ID NO 273
<211> LENGTH: 321
<212> TYPE: DNA
<213> ORGANISM: Artificial Sequence
<220> FEATURE:
<223> OTHER INFORMATION: synthetic

<400> SEQUENCE: 273
gacatccaga tgacccagtc tccatcctcc ctgtctgcat ctgtaggaga cagagtcacc   60
atcacttgcc gggcaagtca gggcattaga aatgatttag ctggtatca gcagaaacca  120
gggaaagccc ctaagcgcct gatctatgct gcatccaatt tgcaaggtgg ggtcccatca  180
aggttcagcg gcagtggatc tgggacagaa ttcactctca caatcagcag cctgcagcct  240
gaagattttg cagcttatta ctgtctacag cataatattt acccgctcac tttcggcgga  300
gggaccaagg tggagatcaa a                                            321

<210> SEQ ID NO 274
<211> LENGTH: 107
<212> TYPE: PRT
<213> ORGANISM: Artificial Sequence
<220> FEATURE:
<223> OTHER INFORMATION: synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Asn Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ala Tyr Tyr Cys Leu Gln His Asn Ile Tyr Pro Leu
            85                  90                  95

Thr Phe Gly Gly Gly Thr Lys Val Glu Ile Lys
            100                 105

<210> SEQ ID NO 275
<211> LENGTH: 18
<212> TYPE: DNA
<213> ORGANISM: Artificial Sequence
<220> FEATURE:
<223> OTHER INFORMATION: synthetic

<400> SEQUENCE: 275
cagggcatta gaaatgat                                                 18

<210> SEQ ID NO 276
<211> LENGTH: 6
<212> TYPE: PRT
<213> ORGANISM: Artificial Sequence
<220> FEATURE:
<223> OTHER INFORMATION: synthetic

<400> SEQUENCE: 276

Gln Gly Ile Arg Asn Asp
1               5

<210> SEQ ID NO 277
<211> LENGTH: 9
<212> TYPE: DNA
<213> ORGANISM: Artificial Sequence
<220> FEATURE:
<223> OTHER INFORMATION: synthetic

<400> SEQUENCE: 277 gctgcatcc                                                            9

<210> SEQ ID NO 278
<211> LENGTH: 3
<212> TYPE: PRT
<213> ORGANISM: Artificial Sequence
<220> FEATURE:
<223> OTHER INFORMATION: synthetic

<400> SEQUENCE: 278

Ala Ala Ser
1

<210> SEQ ID NO 279
<211> LENGTH: 27
<212> TYPE: DNA
<213> ORGANISM: Artificial Sequence
<220> FEATURE:
<223> OTHER INFORMATION: synthetic

<400> SEQUENCE: 279
ctacagcata atatttaccc gctcact                                       27

<210> SEQ ID NO 280
<211> LENGTH: 9
<212> TYPE: PRT
<213> ORGANISM: Artificial Sequence
<220> FEATURE:
<223> OTHER INFORMATION: synthetic

<400> SEQUENCE: 280

Leu Gln His Asn Ile Tyr Pro Leu Thr

<210> SEQ ID NO 281
<211> LENGTH: 375
<212> TYPE: DNA
<213> ORGANISM: Artificial Sequence
<220> FEATURE:
<223> OTHER INFORMATION: synthetic

<400> SEQUENCE: 281

```
caggtgcagc tggtggagtc tgggggaggc gtggtccagc ctggggaggtc cctgagactc    60
tcctgtgcag cgtctggatt caccctcagt aactatggca tgcactgggt ccgccaggct   120
ccaggcaagg ggctggagtg ggtggcagtt atatggcatg atggaagtaa tacatactat   180
gcagactccg tgaagggccg attcaccatc tccagagaca attctaagaa cacgctgtat   240
ctgcaaatga acagcctgag agccgaagac acggctgtgt attactgtac gagagagggg   300
ctcgattttt ggagtggtta ttaccctaac tggttcgacc cctggggcca gggaaccctg   360
gtcaccgtct cctca                                                    375
```

<210> SEQ ID NO 282
<211> LENGTH: 125
<212> TYPE: PRT
<213> ORGANISM: Artificial Sequence
<220> FEATURE:
<223> OTHER INFORMATION: synthetic

<400> SEQUENCE: 282

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Leu Ser Asn Tyr
            20                  25                  30
Gly Met His Trp Val Arg Gln Ala Pro Gly Lys Gly Leu Glu Trp Val
        35                  40                  45
Ala Val Ile Trp His Asp Gly Ser Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Arg Glu Gly Leu Asp Phe Trp Ser Gly Tyr Tyr Pro Asn Trp Phe
            100                 105                 110
Asp Pro Trp Gly Gln Gly Thr Leu Val Thr Val Ser Ser
        115                 120                 125
```

<210> SEQ ID NO 283
<211> LENGTH: 321
<212> TYPE: DNA
<213> ORGANISM: Artificial Sequence
<220> FEATURE:
<223> OTHER INFORMATION: synthetic

<400> SEQUENCE: 283

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccaatt tgcaaggtgg ggtcccatca   180
aggttcagcg gcagtggatc tgggacagaa ttcactctca caatcagcag cctgcagcct   240
gaagattttg cagcttatta ctgtctacag cataatattt acccgctcac tttcggcgga   300
```
gggaccaagg tggagatcaa a                                              321

<210> SEQ ID NO 284
<211> LENGTH: 107
<212> TYPE: PRT
<213> ORGANISM: Artificial Sequence
<220> FEATURE:
<223> OTHER INFORMATION: synthetic

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Asn Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ala Tyr Tyr Cys Leu Gln His Asn Ile Tyr Pro Leu
                85                  90                  95

Thr Phe Gly Gly Gly Thr Lys Val Glu Ile Lys
            100                 105

<210> SEQ ID NO 285
<211> LENGTH: 375
<212> TYPE: DNA
<213> ORGANISM: Artificial Sequence
<220> FEATURE:
<223> OTHER INFORMATION: synthetic

<400> SEQUENCE: 285
caggtgcagc tggtggagtc tgggggaggc gtggtccagc ctgggaggtc cctgagactc      60
tcctgtgcag cgtctggatt caccctcagt aactatggca tgcactgggt ccgccaggct     120
ccaggcaagg gctagagtg gtggcagtt atatggcatg atggaagtaa tacatactat       180
gcagactccg tgaagggccg attcaccatc tccagagaca attccaagaa cacgctgtat     240
ctgcaaatga acagcctgag agccgaggac acggctgtgt attactgtac gagagagggg     300 ctcgatttt ggagtggtta ttaccctaac tggttcgacc cctggggcca gggaaccctg      360
gtcaccgtct cctca                                                      375

<210> SEQ ID NO 286
<211> LENGTH: 125
<212> TYPE: PRT
<213> ORGANISM: Artificial Sequence
<220> FEATURE:
<223> OTHER INFORMATION: synthetic

<400> SEQUENCE: 286

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Asn Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Glu Gly Leu Asp Phe Trp Ser Gly Tyr Tyr Pro Asn Trp Phe
            100                 105                 110

Asp Pro Trp Gly Gln Gly Thr Leu Val Thr Val Ser Ser
        115                 120                 125

<210> SEQ ID NO 287
<211> LENGTH: 322
<212> TYPE: DNA
<213> ORGANISM: Artificial Sequence
<220> FEATURE:
<223> OTHER INFORMATION: synthetic

<400> SEQUENCE: 287
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatattt acccgctcac tttcggcgga     300
gggaccaagg tggagatcaa ac                                              322

<210> SEQ ID NO 288
<211> LENGTH: 107
<212> TYPE: PRT
<213> ORGANISM: Artificial Sequence
<220> FEATURE:
<223> OTHER INFORMATION: synthetic

<400> SEQUENCE: 288

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ile Tyr Pro Leu
                 85                  90                  95

Thr Phe Gly Gly Gly Thr Lys Val Glu Ile Lys
            100                 105

<210> SEQ ID NO 289
<211> LENGTH: 363
<212> TYPE: DNA
<213> ORGANISM: Artificial Sequence
<220> FEATURE:
<223> OTHER INFORMATION: synthetic

<400> SEQUENCE: 289
gaggtgcagc tggtggagtc tggggggagac ttggtccagc ctggggggtc cctgagactc      60
tcctgtacag cctctggatt cacctttagt aaatattgga tgacctgggt ccgccaggct     120
```

```
ccagggaggg ggctggagtg ggtggccaac ataaaggaag atggaaatga aaaatacttt    180
ctggactctg tgaagggccg cttcaccatt tccagagaca cgccaagga tttattgttt    240 ctgcaaatga acagcctgag aggcgaggac acggctgtgt attactgtgt gagagatcga    300
ggtatagaag tggctggccc ctttgactac tggggccagg aaccctggt caccgtctcc    360 tca                                                                 363
```

```
<210> SEQ ID NO 290
<211> LENGTH: 121
<212> TYPE: PRT
<213> ORGANISM: Artificial Sequence
<220> FEATURE:
<223> OTHER INFORMATION: synthetic

<400> SEQUENCE: 290

Glu Val Gln Leu Val Glu Ser Gly Gly Asp Leu Val Gln Pro Gly Gly
  1               5                  10                  15

Ser Leu Arg Leu Ser Cys Thr Ala Ser Gly Phe Thr Phe Ser Lys Tyr
             20                  25                  30

Trp Met Thr Trp Val Arg Gln Ala Pro Gly Arg Gly Leu Glu Trp Val
         35                  40                  45

Ala Asn Ile Lys Glu Asp Gly Asn Glu Lys Tyr Phe Leu Asp Ser Val
     50                  55                  60

Lys Gly Arg Phe Thr Ile Ser Arg Asp Asn Ala Lys Asp Leu Leu Phe
 65                  70                  75                  80

Leu Gln Met Asn Ser Leu Arg Gly Glu Asp Thr Ala Val Tyr Tyr Cys
                 85                  90                  95

Val Arg Asp Arg Gly Ile Glu Val Ala Gly Pro Phe Asp Tyr Trp Gly
            100                 105                 110

Gln Gly Thr Leu Val Thr Val Ser Ser
        115                 120
```

```
<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct ttagtaaata ttgg                                           24
```

```
<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Ser Lys Tyr Trp
  1               5
```

```
<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
```

-continued ataaaggaag atggaaatga aaaa                                          24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Lys Glu Asp Gly Asn Glu Lys
1               5

<210> SEQ ID NO 295
<211> LENGTH: 42
<212> TYPE: DNA
<213> ORGANISM: Artificial Sequence
<220> FEATURE:
<223> OTHER INFORMATION: synthetic

<400> SEQUENCE: 295
gtgagagatc gaggtataga agtggctggc ccctttgact ac                      42

<210> SEQ ID NO 296
<211> LENGTH: 14
<212> TYPE: PRT
<213> ORGANISM: Artificial Sequence
<220> FEATURE:
<223> OTHER INFORMATION: synthetic

<400> SEQUENCE: 296

Val Arg Asp Arg Gly Ile Glu Val Ala Gly Pro Phe Asp Tyr
1               5                   10

<210> SEQ ID NO 297
<211> LENGTH: 318
<212> TYPE: DNA
<213> ORGANISM: Artificial Sequence
<220> FEATURE:
<223> OTHER INFORMATION: synthetic

<400> SEQUENCE: 297
gacatccaga tgacccagtc tccttccacc ctgtctgcat ctgttgggga cagagtcacc    60
gtcacttgcc gggccagtca gactattatt aattggttgg cctggtatca gcagaaacca   120
gggaaagccc ctaaactcct gatctctaag gcgtctagtt tagaaagtgg ggtcccatca   180
aggttcagcg gcagtggatc tgggacagaa ttcactctca ccattagcag cctgcagcct   240
gatgattttg caacttatta ctgccaacag tataataggt attggacgtt cggccaaggg   300
accatggtgg aaatcaaa                                                 318

<210> SEQ ID NO 298
<211> LENGTH: 106
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Thr Leu Ser Ala Ser Val Gly
1               5                   10                  15

Asp Arg Val Thr Val Thr Cys Arg Ala Ser Gln Thr Ile Ile Asn Trp
            20                  25                  30

Leu Ala Trp Tyr Gln Gln Lys Pro Gly Lys Ala Pro Lys Leu Leu Ile
            35                  40                  45

Ser Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Trp Thr
                 85                  90                  95

Phe Gly Gln Gly Thr Met Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299
cagactatta ttaattgg                                                   18

<210> SEQ ID NO 300
<211> LENGTH: 6
<212> TYPE: PRT
<213> ORGANISM: Artificial Sequence
<220> FEATURE:
<223> OTHER INFORMATION: synthetic

<400> SEQUENCE: 300

Gln Thr Ile Ile Asn Trp
 1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 aaggcgtct                                                              9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Lys Ala Ser
 1

<210> SEQ ID NO 303
<211> LENGTH: 24
<212> TYPE: DNA
<213> ORGANISM: Artificial Sequence
<220> FEATURE:
<223> OTHER INFORMATION: synthetic

<400> SEQUENCE: 303
caacagtata ataggtattg gacg                                            24

<210> SEQ ID NO 304

<211> LENGTH: 8
<212> TYPE: PRT
<213> ORGANISM: Artificial Sequence
<220> FEATURE:
<223> OTHER INFORMATION: synthetic

<400> SEQUENCE: 304

Gln Gln Tyr Asn Arg Tyr Trp Thr
1               5

<210> SEQ ID NO 305
<211> LENGTH: 363
<212> TYPE: DNA
<213> ORGANISM: Artificial Sequence
<220> FEATURE:
<223> OTHER INFORMATION: synthetic

<400> SEQUENCE: 305
gaggtgcagc tggtggagtc tgggggagac ttggtccagc ctgggggtc cctgagactc      60 tcctgtacag cctctggatt cacctttagt aaatattgga tgacctgggt ccgccaggct    120
ccagggaggg ggctggagtg ggtggccaac ataaaggaag atggaaatga aaaatacttt    180
ctggactctg tgaagggccg cttcaccatt tccagagaca acgccaagga tttattgttt    240
ctgcaaatga acagcctgag aggcgaggac acggctgtgt attactgtgt gagagatcga    300
ggtatagaag tggctggccc ctttgactac tggggccagg gaaccctggt caccgtctcc    360
tca                                                                  363

<210> SEQ ID NO 306
<211> LENGTH: 121
<212> TYPE: PRT
<213> ORGANISM: Artificial Sequence
<220> FEATURE:
<223> OTHER INFORMATION: synthetic

<400> SEQUENCE: 306

Glu Val Gln Leu Val Glu Ser Gly Gly Asp Leu Val Gln Pro Gly Gly
1               5                   10                  15

Ser Leu Arg Leu Ser Cys Thr Ala Ser Gly Phe Thr Phe Ser Lys Tyr
            20                  25                  30

Trp Met Thr Trp Val Arg Gln Ala Pro Gly Arg Gly Leu Glu Trp Val
        35                  40                  45

Ala Asn Ile Lys Glu Asp Gly Asn Glu Lys Tyr Phe Leu Asp Ser Val
    50                  55                  60

Lys Gly Arg Phe Thr Ile Ser Arg Asp Asn Ala Lys Asp Leu Leu Phe
65                  70                  75                  80

Leu Gln Met Asn Ser Leu Arg Gly Glu Asp Thr Ala Val Tyr Tyr Cys
                85                  90                  95

Val Arg Asp Arg Gly Ile Glu Val Ala Gly Pro Phe Asp Tyr Trp Gly
            100                 105                 110

Gln Gly Thr Leu Val Thr Val Ser Ser
        115                 120

<210> SEQ ID NO 307
<211> LENGTH: 318
<212> TYPE: DNA
<213> ORGANISM: Artificial Sequence
<220> FEATURE:
<223> OTHER INFORMATION: synthetic

<400> SEQUENCE: 307

```
gacatccaga tgacccagtc tccttccacc ctgtctgcat ctgttgggga cagagtcacc      60
gtcacttgcc gggccagtca gactattatt aattggttgg cctggtatca gcagaaacca     120
gggaaagccc ctaaactcct gatctctaag gcgtctagtt tagaaagtgg ggtcccatca     180
aggttcagcg gcagtggatc tgggacagaa ttcactctca ccattagcag cctgcagcct     240
gatgattttg caacttatta ctgccaacag tataataggt attggacgtt cggccaaggg     300
accaaggtgg aaatcaaa                                                   318

<210> SEQ ID NO 308
<211> LENGTH: 106
<212> TYPE: PRT
<213> ORGANISM: Artificial Sequence
<220> FEATURE:
<223> OTHER INFORMATION: synthetic

<400> SEQUENCE: 308

Asp Ile Gln Met Thr Gln Ser Pro Ser Thr Leu Ser Ala Ser Val Gly
 1               5                  10                  15

Asp Arg Val Thr Val Thr Cys Arg Ala Ser Gln Thr Ile Ile Asn Trp
             20                  25                  30

Leu Ala Trp Tyr Gln Gln Lys Pro Gly Lys Ala Pro Lys Leu Leu Ile
         35                  40                  45

Ser Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Trp Thr
                 85                  90                  95

Phe Gly Gln Gly Thr Lys Val Glu Ile Lys
            100                 105

<210> SEQ ID NO 309
<211> LENGTH: 363
<212> TYPE: DNA
<213> ORGANISM: Artificial Sequence
<220> FEATURE:
<223> OTHER INFORMATION: synthetic

<400> SEQUENCE: 309
gaggtgcagc tggtggagtc tgggggaggc ttggtccagc ctggggggtc cctgagactc      60
tcctgtgcag cctctggatt cacctttagt aaatattgga tgagctgggt ccgccaggct     120
ccagggaagg ggctggagtg ggtggccaac ataaaggaag atggaaatga aaaatactat     180
gtggactctg tgaagggccg attcaccatc tccagagaca acgccaagaa ctcactgtat     240
ctgcaaatga acagcctgag agccgaggac acggctgtgt attactgtgt gagagatcga     300
ggtatagaag tggctggccc ctttgactac tggggccagg gaaccctggt caccgtctcc     360
tca                                                                   363

<210> SEQ ID NO 310
<211> LENGTH: 121
<212> TYPE: PRT
<213> ORGANISM: Artificial Sequence
<220> FEATURE:
<223> OTHER INFORMATION: synthetic

<400> SEQUENCE: 310

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Phe Thr Phe Ser Lys Tyr
             20                  25                  30

Trp Met Ser Trp Val Arg Gln Ala Pro Gly Lys Gly Leu Glu Trp Val
         35                  40                  45

Ala Asn Ile Lys Glu Asp Gly Asn Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Asp Arg Gly Ile Glu Val Ala Gly Pro Phe Tyr Trp Gly
                100                 105                 110

Gln Gly Thr Leu Val Thr Val Ser Ser
        115                 120

<210> SEQ ID NO 311
<211> LENGTH: 319
<212> TYPE: DNA
<213> ORGANISM: Artificial Sequence
<220> FEATURE:
<223> OTHER INFORMATION: synthetic

<400> SEQUENCE: 311
gacatccaga tgacccagtc tccttccacc ctgtctgcat ctgtaggaga cagagtcacc    60
atcacttgcc gggccagtca gactattatt aattggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataataggt attggacgtt cggccaaggg   300
accaaggtgg aaatcaaac                                                319

<210> SEQ ID NO 312
<211> LENGTH: 106
<212> TYPE: PRT
<213> ORGANISM: Artificial Sequence
<220> FEATURE:
<223> OTHER INFORMATION: synthetic

<400> SEQUENCE: 312

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Thr Ile Ile Asn Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Trp Thr
                 85                  90                  95

Phe Gly Gln Gly Thr Lys Val Glu Ile Lys
                100                 105

<210> SEQ ID NO 313
<211> LENGTH: 363
<212> TYPE: DNA

<213> ORGANISM: Artificial Sequence
<220> FEATURE:
<223> OTHER INFORMATION: synthetic

<400> SEQUENCE: 313

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagtt atatggtatg atgaatttaa taaatactat       180
gcagactccg tgaagggccg attcaccatc tccagagaca attccaagaa cacgctgtat     240
ctgcaaatga acagcctgag agccgaggac acggctgtgt attactgtgc gagagagaga     300
gagagtggat acagttatgg ttttgactac tggggccagg gaaccctggt caccgtctcc     360
tca                                                                   363
```

<210> SEQ ID NO 314
<211> LENGTH: 121
<212> TYPE: PRT
<213> ORGANISM: Artificial Sequence
<220> FEATURE:
<223> OTHER INFORMATION: synthetic

<400> SEQUENCE: 314

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Ile Trp Tyr Asp Glu Phe Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Glu Arg Glu Ser Gly Tyr Ser Tyr Gly Phe Asp Tyr Trp Gly
            100                 105                 110
Gln Gly Thr Leu Val Thr Val Ser Ser
        115                 120
```

<210> SEQ ID NO 315
<211> LENGTH: 24
<212> TYPE: DNA
<213> ORGANISM: Artificial Sequence
<220> FEATURE:
<223> OTHER INFORMATION: synthetic

<400> SEQUENCE: 315

```
ggattcacct tcagtagcta tggc                                             24
```

<210> SEQ ID NO 316
<211> LENGTH: 8
<212> TYPE: PRT
<213> ORGANISM: Artificial Sequence
<220> FEATURE:
<223> OTHER INFORMATION: synthetic

<400> SEQUENCE: 316

```
Gly Phe Thr Phe Ser Ser Tyr Gly
 1               5
```

<210> SEQ ID NO 317
<211> LENGTH: 24
<212> TYPE: DNA
<213> ORGANISM: Artificial Sequence
<220> FEATURE:
<223> OTHER INFORMATION: synthetic

<400> SEQUENCE: 317
atatggtatg atgaatttaa taaa         24

<210> SEQ ID NO 318
<211> LENGTH: 8
<212> TYPE: PRT
<213> ORGANISM: Artificial Sequence
<220> FEATURE:
<223> OTHER INFORMATION: synthetic

<400> SEQUENCE: 318

Ile Trp Tyr Asp Glu Phe Asn Lys
1               5

<210> SEQ ID NO 319
<211> LENGTH: 42
<212> TYPE: DNA
<213> ORGANISM: Artificial Sequence
<220> FEATURE:
<223> OTHER INFORMATION: synthetic

<400> SEQUENCE: 319
gcgagagaga gagagagtgg atacagttat ggttttgact ac         42

<210> SEQ ID NO 320
<211> LENGTH: 14
<212> TYPE: PRT
<213> ORGANISM: Artificial Sequence
<220> FEATURE:
<223> OTHER INFORMATION: synthetic

<400> SEQUENCE: 320

Ala Arg Glu Arg Glu Ser Gly Tyr Ser Tyr Gly Phe Asp Tyr
1               5                   10

<210> SEQ ID NO 321
<211> LENGTH: 318
<212> TYPE: DNA
<213> ORGANISM: Artificial Sequence
<220> FEATURE:
<223> OTHER INFORMATION: synthetic

<400> SEQUENCE: 321
gaaatagtga tgacgcagtc tccagccacc ctgtctgtgt ctccagggga aagagccacc     60
ctctcctgca gggccggtca gagtgttagc agcaacttag cctggtacca gcaaaaacct    120
ggccaggctc ccaggctcct catctatggt gcgtccacca gggccactgg tatcccagcc    180
aggttcagtg gcagtgggtc tgggacagag ttcactctca ccatcagcag cctgcagtct    240
gaagattttg cagtttatta ctgtcagcag tataataact ggtggacgtt cggccaaggg    300
accaaggtgg aaatcaaa                                                  318

<210> SEQ ID NO 322
<211> LENGTH: 106
<212> TYPE: PRT
<213> ORGANISM: Artificial Sequence
<220> FEATURE:
<223> OTHER INFORMATION: synthetic

<400> SEQUENCE: 322

Glu Ile Val Met Thr Gln Ser Pro Ala Thr Leu Ser Val Ser Pro Gly
 1               5                  10                  15

Glu Arg Ala Thr Leu Ser Cys Arg Ala Gly Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 323
<211> LENGTH: 18
<212> TYPE: DNA
<213> ORGANISM: Artificial Sequence
<220> FEATURE:
<223> OTHER INFORMATION: synthetic

<400> SEQUENCE: 323
cagagtgtta gcagcaac                                           18

<210> SEQ ID NO 324
<211> LENGTH: 6
<212> TYPE: PRT
<213> ORGANISM: Artificial Sequence
<220> FEATURE:
<223> OTHER INFORMATION: synthetic

<400> SEQUENCE: 324

Gln Ser Val Ser Ser Asn
 1               5

<210> SEQ ID NO 325
<211> LENGTH: 9
<212> TYPE: DNA
<213> ORGANISM: Artificial Sequence
<220> FEATURE:
<223> OTHER INFORMATION: synthetic

<400> SEQUENCE: 325 ggtgcgtcc                                                      9

<210> SEQ ID NO 326
<211> LENGTH: 3
<212> TYPE: PRT
<213> ORGANISM: Artificial Sequence
<220> FEATURE:
<223> OTHER INFORMATION: synthetic

<400> SEQUENCE: 326

Gly Ala Ser
 1

<210> SEQ ID NO 327
<211> LENGTH: 24
<212> TYPE: DNA
<213> ORGANISM: Artificial Sequence
<220> FEATURE:
<223> OTHER INFORMATION: synthetic

<400> SEQUENCE: 327
cagcagtata ataactggtg gacg                                              24

<210> SEQ ID NO 328
<211> LENGTH: 8
<212> TYPE: PRT
<213> ORGANISM: Artificial Sequence
<220> FEATURE:
<223> OTHER INFORMATION: synthetic

<400> SEQUENCE: 328

Gln Gln Tyr Asn Asn Trp Trp Thr
1               5

<210> SEQ ID NO 329
<211> LENGTH: 363
<212> TYPE: DNA
<213> ORGANISM: Artificial Sequence
<220> FEATURE:
<223> OTHER INFORMATION: synthetic

<400> SEQUENCE: 329
caggtgcagc tggtggagtc tgggggaggc gtggtccagc ctggaggtc cctgagactc         60 tcctgtgcag cgtctggatt caccttcagt agctatggca tgcactgggt ccgccaggct        120
ccaggcaagg ggctggagtg ggtggcagtt atatggtatg atgaatttaa taaatactat        180
gcagactccg tgaagggccg attcaccatc tccagagaca attccaagaa cacgctgtat        240
ctgcaaatga acagcctgag agccgaggac acggctgtgt attactgtgc gagagagaga        300
gagagtggat acagttatgg ttttgactac tggggccagg gaaccctggt caccgtctcc        360
tca                                                                    363

<210> SEQ ID NO 330
<211> LENGTH: 121
<212> TYPE: PRT
<213> ORGANISM: Artificial Sequence
<220> FEATURE:
<223> OTHER INFORMATION: synthetic

<400> SEQUENCE: 330

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Phe Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Glu Ser Gly Tyr Ser Tyr Gly Phe Asp Tyr Trp Gly
            100                 105                 110

Gln Gly Thr Leu Val Thr Val Ser Ser
        115                 120

<210> SEQ ID NO 331
<211> LENGTH: 318
<212> TYPE: DNA
<213> ORGANISM: Artificial Sequence
<220> FEATURE:
<223> OTHER INFORMATION: synthetic

<400> SEQUENCE: 331

```
gaaatagtga tgacgcagtc tccagccacc ctgtctgtgt ctccagggga aagagccacc      60
ctctcctgca gggccggtca gagtgttagc agcaacttag cctggtacca gcaaaaacct     120
ggccaggctc ccaggctcct catctatggt gcgtccacca gggccactgg tatcccagcc     180
aggttcagtg gcagtgggtc tgggacagag ttcactctca ccatcagcag cctgcagtct     240
gaagattttg cagtttatta ctgtcagcag tataataact ggtggacgtt cggccaaggg     300
accaaggtgg aaatcaaa                                                   318
```

<210> SEQ ID NO 332
<211> LENGTH: 106
<212> TYPE: PRT
<213> ORGANISM: Artificial Sequence
<220> FEATURE:
<223> OTHER INFORMATION: synthetic

<400> SEQUENCE: 332

Glu Ile Val Met Thr Gln Ser Pro Ala Thr Leu Ser Val Ser Pro Gly
1               5                   10                  15

Glu Arg Ala Thr Leu Ser Cys Arg Ala Gly Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr
                85                  90                  95

Phe Gly Gln Gly Thr Lys Val Glu Ile Lys
            100                 105

<210> SEQ ID NO 333
<211> LENGTH: 363
<212> TYPE: DNA
<213> ORGANISM: Artificial Sequence
<220> FEATURE:
<223> OTHER INFORMATION: synthetic

<400> SEQUENCE: 333

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atgaatttaa taatactat     180
gcagactccg tgaagggccg attcaccatc tccagagaca actccaagaa cacgctgtat     240
ctgcaaatga acagcctgag agccgaggac acggctgtgt attactgtgc gagagagaga     300
gagagtggat acagttatgg ttttgactac tggggccagg gaaccctggt caccgtctcc     360
tca                                                                  363
```

<210> SEQ ID NO 334
<211> LENGTH: 121

<212> TYPE: PRT
<213> ORGANISM: Artificial Sequence
<220> FEATURE:
<223> OTHER INFORMATION: synthetic

<400> SEQUENCE: 334

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Phe Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Glu Ser Gly Tyr Ser Tyr Gly Phe Asp Tyr Trp Gly
            100                 105                 110

Gln Gly Thr Leu Val Thr Val Ser Ser
        115                 120

<210> SEQ ID NO 335
<211> LENGTH: 319
<212> TYPE: DNA
<213> ORGANISM: Artificial Sequence
<220> FEATURE:
<223> OTHER INFORMATION: synthetic

<400> SEQUENCE: 335
gaaatagtga tgacgcagtc tccagccacc ctgtctgtgt ctccagggga agagccacc      60 ctctcctgca gggccagtca gagtgttagc agcaacttag cctggtacca gcagaaacct     120
ggccaggctc ccaggctcct catctatggt gcgtccacca gggccactgg tatcccagcc     180
aggttcagtg gcagtgggtc tgggacagag ttcactctca ccatcagcag cctgcagtct     240
gaagattttg cagtttatta ctgtcagcag tataataact ggtggacgtt cggccaaggg     300
accaaggtgg aaatcaaac                                                  319

<210> SEQ ID NO 336
<211> LENGTH: 106
<212> TYPE: PRT
<213> ORGANISM: Artificial Sequence
<220> FEATURE:
<223> OTHER INFORMATION: synthetic

<400> SEQUENCE: 336

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Trp Thr

```
                          85                  90                  95
Phe Gly Gln Gly Thr Lys Val Glu Ile Lys
            100                 105

<210> SEQ ID NO 337
<211> LENGTH: 375
<212> TYPE: DNA
<213> ORGANISM: Artificial Sequence
<220> FEATURE:
<223> OTHER INFORMATION: synthetic

<400> SEQUENCE: 337
caggttcagc tggtgcagtc tggacctgag gtgaaggagc ctggggcctc agtgaaggtc     60
tcctgcaagg cttctggtta cacctttacc acctatagta tcacctgggt gcgacaggcc    120
cctggacaag gcttgagtg gatgggatgg atcagcgctt acaattatga cacaaattat     180
gcacagaaga tccagggcag agtcaccatg accacagaca catccacgaa cacagcctac    240
atggaactga ggagcctgag atctgacgac acggccgtgt attactgtgc gagaggcgat    300
ttctggatta attattccta ctactactac ggtgtggacg tctggggcca agggaccacg    360
gtcaccgtct cctca                                                    375

<210> SEQ ID NO 338
<211> LENGTH: 125
<212> TYPE: PRT
<213> ORGANISM: Artificial Sequence
<220> FEATURE:
<223> OTHER INFORMATION: synthetic

<400> SEQUENCE: 338

Gln Val Gln Leu Val Gln Ser Gly Pro Glu Val Lys Glu Pro Gly Ala
1               5                   10                  15

Ser Val Lys Val Ser Cys Lys Ala Ser Gly Tyr Thr Phe Thr Thr Tyr
            20                  25                  30

Ser Ile Thr Trp Val Arg Gln Ala Pro Gly Gln Gly Leu Glu Trp Met
        35                  40                  45

Gly Trp Ile Ser Ala Tyr Asn Tyr Asp Thr Asn Tyr Ala Gln Lys Ile
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
            100                 105                 110

Asp Val Trp Gly Gln Gly Thr Thr Val Thr Val Ser Ser
        115                 120                 125

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggttacacct ttaccaccta tagt                                           24

<210> SEQ ID NO 340
<211> LENGTH: 8
<212> TYPE: PRT
```

```
<213> ORGANISM: Artificial Sequence
<220> FEATURE:
<223> OTHER INFORMATION: synthetic

<400> SEQUENCE: 340

Gly Tyr Thr Phe Thr Thr Tyr Ser
 1               5

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atcagcgctt acaattatga caca                                            24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

Ile Ser Ala Tyr Asn Tyr Asp Thr
 1               5

<210> SEQ ID NO 343
<211> LENGTH: 54
<212> TYPE: DNA
<213> ORGANISM: Artificial Sequence
<220> FEATURE:
<223> OTHER INFORMATION: synthetic

<400> SEQUENCE: 343
gcgagaggcg atttctggat taattattcc tactactact acggtgtgga cgtc           54

<210> SEQ ID NO 344
<211> LENGTH: 18
<212> TYPE: PRT
<213> ORGANISM: Artificial Sequence
<220> FEATURE:
<223> OTHER INFORMATION: synthetic

<400> SEQUENCE: 344

Ala Arg Gly Asp Phe Trp Ile Asn Tyr Ser Tyr Tyr Tyr Gly Val
 1               5                  10                  15

Asp Val

<210> SEQ ID NO 345
<211> LENGTH: 339
<212> TYPE: DNA
<213> ORGANISM: Artificial Sequence
<220> FEATURE:
<223> OTHER INFORMATION: synthetic

<400> SEQUENCE: 345
gacattgtga tgacgcagtc tccactctcc ctgcccgtca tccctggaga gccggcctcc     60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
```

```
agcagagtgg aggctgagga tgttggggtt tattactgca tgcaagctct acaaactccc    300
atgtacactt ttggccaggg gaccaagctg gagatcaaa                          339
```

<210> SEQ ID NO 346
<211> LENGTH: 113
<212> TYPE: PRT
<213> ORGANISM: Artificial Sequence
<220> FEATURE:
<223> OTHER INFORMATION: synthetic

<400> SEQUENCE: 346

```
Asp Ile Val Met Thr Gln Ser Pro Leu Ser Leu Pro Val Ile Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Met Tyr Thr Phe Gly Gln Gly Thr Lys Leu Glu Ile
            100                 105                 110

Lys
```

<210> SEQ ID NO 347
<211> LENGTH: 33
<212> TYPE: DNA
<213> ORGANISM: Artificial Sequence
<220> FEATURE:
<223> OTHER INFORMATION: synthetic

<400> SEQUENCE: 347

```
cagagcctcc tgcatagtaa tggatacaac tat                                 33
```

<210> SEQ ID NO 348
<211> LENGTH: 11
<212> TYPE: PRT
<213> ORGANISM: Artificial Sequence
<220> FEATURE:
<223> OTHER INFORMATION: synthetic

<400> SEQUENCE: 348

```
Gln Ser Leu Leu His Ser Asn Gly Tyr Asn Tyr
 1               5                  10
```

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349

```
ttgggttct                                                             9
```

<210> SEQ ID NO 350
<211> LENGTH: 3
<212> TYPE: PRT
<213> ORGANISM: Artificial Sequence

```
<220> FEATURE:
<223> OTHER INFORMATION: synthetic

<400> SEQUENCE: 350

Leu Gly Ser
  1

<210> SEQ ID NO 351
<211> LENGTH: 30
<212> TYPE: DNA
<213> ORGANISM: Artificial Sequence
<220> FEATURE:
<223> OTHER INFORMATION: synthetic

<400> SEQUENCE: 351
atgcaagctc tacaaactcc catgtacact                                          30

<210> SEQ ID NO 352
<211> LENGTH: 10
<212> TYPE: PRT
<213> ORGANISM: Artificial Sequence
<220> FEATURE:
<223> OTHER INFORMATION: synthetic

<400> SEQUENCE: 352

Met Gln Ala Leu Gln Thr Pro Met Tyr Thr
  1               5                  10

<210> SEQ ID NO 353
<211> LENGTH: 372
<212> TYPE: DNA
<213> ORGANISM: Artificial Sequence
<220> FEATURE:
<223> OTHER INFORMATION: synthetic

<400> SEQUENCE: 353
caggttcagc tggtgcagtc tggacctgag gtgaaggagc ctggggcctc agtgaaggtc          60
tcctgcaagg cttctggtta cacctttacc acctatagta tcacctgggt gcgacaggcc        120
cctggacaag ggcttgagtg gatgggatgg atcagcgctt acaattatga cacaaattat        180
gcacagaaga tccagggcag agtcaccatg accacagaca tccacgaa acagcctac           240 atggaactga ggagcctgag atctgacgac acggccgtgt attactgtgc gagaggcgat        300
ttctggatta ttattccta ctactactac ggtgtggacg tctggggcca agggaccacg        360
gtcaccgtct cc                                                           372

<210> SEQ ID NO 354
<211> LENGTH: 124
<212> TYPE: PRT
<213> ORGANISM: Artificial Sequence
<220> FEATURE:
<223> OTHER INFORMATION: synthetic

<400> SEQUENCE: 354

Gln Val Gln Leu Val Gln Ser Gly Pro Glu Val Lys Glu Pro Gly Ala
  1               5                  10                  15

Ser Val Lys Val Ser Cys Lys Ala Ser Gly Tyr Thr Phe Thr Thr Tyr
                 20                  25                  30

Ser Ile Thr Trp Val Arg Gln Ala Pro Gly Gln Gly Leu Glu Trp Met
             35                  40                  45

Gly Trp Ile Ser Ala Tyr Asn Tyr Asp Thr Asn Tyr Ala Gln Lys Ile
         50                  55                  60
```

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
            100                 105                 110

Asp Val Trp Gly Gln Gly Thr Thr Val Thr Val Ser
        115                 120

<210> SEQ ID NO 355
<211> LENGTH: 339
<212> TYPE: DNA
<213> ORGANISM: Artificial Sequence
<220> FEATURE:
<223> OTHER INFORMATION: synthetic

<400> SEQUENCE: 355
gatattgtga tgactcagtc tccactctcc ctgcccgtca tccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
atgtacactt ttggccaggg gaccaagctg gagatcaaa                           339

<210> SEQ ID NO 356
<211> LENGTH: 113
<212> TYPE: PRT
<213> ORGANISM: Artificial Sequence
<220> FEATURE:
<223> OTHER INFORMATION: synthetic

<400> SEQUENCE: 356

Asp Ile Val Met Thr Gln Ser Pro Leu Ser Leu Pro Val Ile Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Met Tyr Thr Phe Gly Gln Gly Thr Lys Leu Glu Ile
            100                 105                 110

Lys

<210> SEQ ID NO 357
<211> LENGTH: 373
<212> TYPE: DNA
<213> ORGANISM: Artificial Sequence
<220> FEATURE:
<223> OTHER INFORMATION: synthetic

<400> SEQUENCE: 357
caggttcagc tggtgcagtc tggagctgag gtgaagaagc ctggggcctc agtgaaggtc      60

```
tcctgcaagg cttctggtta cacctttacc acctatagta tcagctgggt gcgacaggcc    120
cctggacaag ggcttgagtg gatgggatgg atcagcgctt acaattatga cacaaactat    180
gcacagaagc tccagggcag agtcaccatg accacagaca catccacgag cacagcctac    240
atggagctga ggagcctgag atctgacgac acggccgtgt attactgtgc gagaggcgat    300
ttctggatta attattccta ctactactac ggtgtggacg tctggggcca agggaccacg    360
gtcaccgtct cct                                                       373
```

```
<210> SEQ ID NO 358
<211> LENGTH: 124
<212> TYPE: PRT
<213> ORGANISM: Artificial Sequence
<220> FEATURE:
<223> OTHER INFORMATION: synthetic

<400> SEQUENCE: 358

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Ser Ile Ser Trp Val Arg Gln Ala Pro Gly Gln Gly Leu Glu Trp Met
        35                  40                  45

Gly Trp Ile Ser Ala Tyr Asn Tyr Asp Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Phe Trp Ile Asn Tyr Ser Tyr Tyr Tyr Gly Val
            100                 105                 110

Asp Val Trp Gly Gln Gly Thr Thr Val Thr Val Ser
        115                 120
```

```
<210> SEQ ID NO 359
<211> LENGTH: 340
<212> TYPE: DNA
<213> ORGANISM: Artificial Sequence
<220> FEATURE:
<223> OTHER INFORMATION: synthetic

<400> SEQUENCE: 359
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactccc    300
atgtacactt ttggccaggg gaccaagctg gagatcaaac                          340
```

```
<210> SEQ ID NO 360
<211> LENGTH: 113
<212> TYPE: PRT
<213> ORGANISM: Artificial Sequence
<220> FEATURE:
<223> OTHER INFORMATION: synthetic

<400> SEQUENCE: 360

Asp Ile Val Met Thr Gln Ser Pro Leu Ser Leu Pro Val Thr Pro Gly
```

```
              1               5                  10                 15
         Glu Pro Ala Ser Ile Ser Cys Arg Ser Ser Gln Ser Leu Leu His Ser
                         20                 25                 30

Asn Gly Tyr Asn Tyr Leu Asp Trp Tyr Leu Gln Lys Pro Gly Gln Ser
                     35                 40                 45

Pro Gln Leu Leu Ile Tyr Leu Gly Ser Asn Arg Ala Ser Gly Val Pro
              50                 55                 60

Asp Arg Phe Ser Gly Ser Gly Ser Gly Thr Asp Phe Thr Leu Lys Ile
         65                 70                 75                 80

Ser Arg Val Glu Ala Glu Asp Val Gly Val Tyr Tyr Cys Met Gln Ala
                             85                 90                 95

Leu Gln Thr Pro Met Tyr Thr Phe Gly Gln Gly Thr Lys Leu Glu Ile
                         100                105                110

Lys
```

<210> SEQ ID NO 361
<211> LENGTH: 363
<212> TYPE: DNA
<213> ORGANISM: Artificial Sequence
<220> FEATURE:
<223> OTHER INFORMATION: synthetic

<400> SEQUENCE: 361

```
gaggtgcagc tggtggagtc tgggggaggc ttggtccagc ctggggggtc cctgagactc    60
tcctgtgcag cctctggatt cgcctttaga agttattgga tgacctgggt ccgccaggct   120
ccagggaagg ggctggagtg ggtggccaac atacagcaag atggaaatga taaatactat   180
gtggactctg tgaagggccg attcaccatc tccagagaca cgccaagaa ctcactgtat    240 ctgcaaatga acagcctgag agccgaggac acggctgtgt attactgtgc gagagatacc   300
ggtatagcag aagctggtcc ttttgactac tggggccagg gaaccctggt caccgtctcc   360
tca                                                                  363
```

<210> SEQ ID NO 362
<211> LENGTH: 121
<212> TYPE: PRT
<213> ORGANISM: Artificial Sequence
<220> FEATURE:
<223> OTHER INFORMATION: synthetic

<400> SEQUENCE: 362

```
         Glu Val Gln Leu Val Glu Ser Gly Gly Gly Leu Val Gln Pro Gly Gly
         1               5                  10                 15

Ser Leu Arg Leu Ser Cys Ala Ala Ser Gly Phe Ala Phe Arg Ser Tyr
                         20                 25                 30

Trp Met Thr Trp Val Arg Gln Ala Pro Gly Lys Gly Leu Glu Trp Val
                     35                 40                 45

Ala Asn Ile Gln Gln Asp Gly Asn Asp Lys Tyr Tyr Val Asp Ser Val
                 50                 55                 60

Lys Gly Arg Phe Thr Ile Ser Arg Asp Asn Ala Lys Asn Ser Leu Tyr
         65                 70                 75                 80

Leu Gln Met Asn Ser Leu Arg Ala Glu Asp Thr Ala Val Tyr Tyr Cys
                             85                 90                 95

Ala Arg Asp Thr Gly Ile Ala Glu Ala Gly Pro Phe Asp Tyr Trp Gly
                         100                105                110

Gln Gly Thr Leu Val Thr Val Ser Ser
                         115                120
```

<210> SEQ ID NO 363
<211> LENGTH: 24
<212> TYPE: DNA
<213> ORGANISM: Artificial Sequence
<220> FEATURE:
<223> OTHER INFORMATION: synthetic

<400> SEQUENCE: 363
ggattcgcct ttagaagtta ttgg                                             24

<210> SEQ ID NO 364
<211> LENGTH: 8
<212> TYPE: PRT
<213> ORGANISM: Artificial Sequence
<220> FEATURE:
<223> OTHER INFORMATION: synthetic

<400> SEQUENCE: 364

Gly Phe Ala Phe Arg Ser Tyr Trp
 1               5

<210> SEQ ID NO 365
<211> LENGTH: 24
<212> TYPE: DNA
<213> ORGANISM: Artificial Sequence
<220> FEATURE:
<223> OTHER INFORMATION: synthetic

<400> SEQUENCE: 365
atacagcaag atggaaatga taaa                                             24

<210> SEQ ID NO 366
<211> LENGTH: 8
<212> TYPE: PRT
<213> ORGANISM: Artificial Sequence
<220> FEATURE:
<223> OTHER INFORMATION: synthetic

<400> SEQUENCE: 366

Ile Gln Gln Asp Gly Asn Asp Lys
 1               5

<210> SEQ ID NO 367
<211> LENGTH: 42
<212> TYPE: DNA
<213> ORGANISM: Artificial Sequence
<220> FEATURE:
<223> OTHER INFORMATION: synthetic

<400> SEQUENCE: 367
gcgagagata ccggtatagc agaagctggt cctttttgact ac                        42

<210> SEQ ID NO 368
<211> LENGTH: 14
<212> TYPE: PRT
<213> ORGANISM: Artificial Sequence
<220> FEATURE:
<223> OTHER INFORMATION: synthetic

<400> SEQUENCE: 368

Ala Arg Asp Thr Gly Ile Ala Glu Ala Gly Pro Phe Asp Tyr
 1               5                  10

<210> SEQ ID NO 369
<211> LENGTH: 318

<212> TYPE: DNA
<213> ORGANISM: Artificial Sequence
<220> FEATURE:
<223> OTHER INFORMATION: synthetic

<400> SEQUENCE: 369

```
gacatccaga tgacccagtc tccttccacc ctgtctgcat ctgtaggaga cagagtctcc    60
atcacttgcc gggccagtca gactattatt agctggttgg cctggtatca gcagaaacca   120
gggaaagccc ctaggctcct gatctataag gcgtctagtt tagaaagtgg ggtcccatca   180
aggttcagcg gcagtggatc tgggacagaa ttcactctca ccatcaacag cctgcagcct   240
gatgattttg caacttatta ctgccaacag tataatcgtt attggacgtt cggccaaggg   300
accaaggtgg aaatcaaa                                                  318
```

<210> SEQ ID NO 370
<211> LENGTH: 106
<212> TYPE: PRT
<213> ORGANISM: Artificial Sequence
<220> FEATURE:
<223> OTHER INFORMATION: synthetic

<400> SEQUENCE: 370

```
Asp Ile Gln Met Thr Gln Ser Pro Ser Thr Leu Ser Ala Ser Val Gly
 1               5                  10                  15
Asp Arg Val Ser Ile Thr Cys Arg Ala Ser Gln Thr Ile Ile Ser Trp
            20                  25                  30
Leu Ala Trp Tyr Gln Gln Lys Pro Gly Lys Ala Pro Arg Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Asn Ser Leu Gln Pro
65                  70                  75                  80
Asp Asp Phe Ala Thr Tyr Tyr Cys Gln Gln Tyr Asn Arg Tyr Trp Thr
                85                  90                  95
Phe Gly Gln Gly Thr Lys Val Glu Ile Lys
            100                 105
```

<210> SEQ ID NO 371
<211> LENGTH: 18
<212> TYPE: DNA
<213> ORGANISM: Artificial Sequence
<220> FEATURE:
<223> OTHER INFORMATION: synthetic

<400> SEQUENCE: 371

```
cagactatta ttagctgg                                                   18
```

<210> SEQ ID NO 372
<211> LENGTH: 6
<212> TYPE: PRT
<213> ORGANISM: Artificial Sequence
<220> FEATURE:
<223> OTHER INFORMATION: synthetic

<400> SEQUENCE: 372

```
Gln Thr Ile Ile Ser Trp
 1               5
```

<210> SEQ ID NO 373
<211> LENGTH: 9
<212> TYPE: DNA

<210> SEQ ID NO 373
<211> LENGTH: 9
<212> TYPE: DNA
<213> ORGANISM: Artificial Sequence
<220> FEATURE:
<223> OTHER INFORMATION: synthetic

<400> SEQUENCE: 373 aaggcgtct                                                                 9

<210> SEQ ID NO 374
<211> LENGTH: 3
<212> TYPE: PRT
<213> ORGANISM: Artificial Sequence
<220> FEATURE:
<223> OTHER INFORMATION: synthetic

<400> SEQUENCE: 374

Lys Ala Ser
 1

<210> SEQ ID NO 375
<211> LENGTH: 24
<212> TYPE: DNA
<213> ORGANISM: Artificial Sequence
<220> FEATURE:
<223> OTHER INFORMATION: synthetic

<400> SEQUENCE: 375
caacagtata atcgttattg gacg                                               24

<210> SEQ ID NO 376
<211> LENGTH: 8
<212> TYPE: PRT
<213> ORGANISM: Artificial Sequence
<220> FEATURE:
<223> OTHER INFORMATION: synthetic

<400> SEQUENCE: 376

Gln Gln Tyr Asn Arg Tyr Trp Thr
 1               5

<210> SEQ ID NO 377
<211> LENGTH: 363
<212> TYPE: DNA
<213> ORGANISM: Artificial Sequence
<220> FEATURE:
<223> OTHER INFORMATION: synthetic

<400> SEQUENCE: 377
gaggtgcagc tggtggagtc tgggggaggc ttggtccagc ctgggggtc cctgagactc         60 tcctgtgcag cctctggatt cgcctttaga agttattgga tgacctgggt ccgccaggct       120
ccagggaagg ggctggagtg ggtggccaac atacagcaag atggaaatga taaatactat       180
gtggactctg tgaagggccg attcaccatc tccagagaca cgccaagaa ctcactgtat        240 ctgcaaatga acagcctgag agccgaggac acggctgtgt attactgtgc gagagatacc       300
ggtatagcag aagctggtcc ttttgactac tggggccagg gaaccctggt caccgtctcc       360
tca                                                                    363

<210> SEQ ID NO 378
<211> LENGTH: 121
<212> TYPE: PRT
<213> ORGANISM: Artificial Sequence
<220> FEATURE:
<223> OTHER INFORMATION: synthetic

<400> SEQUENCE: 378

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Arg Ser Tyr
            20                  25                  30

Trp Met Thr Trp Val Arg Gln Ala Pro Gly Lys Gly Leu Glu Trp Val
        35                  40                  45

Ala Asn Ile Gln Gln Asp Gly Asn Asp Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Ile Ala Glu Ala Gly Pro Phe Asp Tyr Trp Gly
                100                 105                 110

Gln Gly Thr Leu Val Thr Val Ser Ser
            115                 120

<210> SEQ ID NO 379
<211> LENGTH: 318
<212> TYPE: DNA
<213> ORGANISM: Artificial Sequence
<220> FEATURE:
<223> OTHER INFORMATION: synthetic

<400> SEQUENCE: 379
gacatccaga tgacccagtc tccttccacc ctgtctgcat ctgtaggaga cagagtctcc      60
atcacttgcc gggccagtca gactattatt agctggttgg cctggtatca gcagaaacca     120
gggaaagccc ctaggctcct gatctataag gcgtctagtt tagaaagtgg ggtcccatca     180
aggttcagcg gcagtggatc tgggacagaa ttcactctca ccatcaacag cctgcagcct     240
gatgattttg caacttatta ctgccaacag tataatcgtt attggacgtt cggccaaggg     300
accaaggtgg aaatcaaa                                                   318

<210> SEQ ID NO 380
<211> LENGTH: 106
<212> TYPE: PRT
<213> ORGANISM: Artificial Sequence
<220> FEATURE:
<223> OTHER INFORMATION: synthetic

<400> SEQUENCE: 380

Asp Ile Gln Met Thr Gln Ser Pro Ser Thr Leu Ser Ala Ser Val Gly
1               5                   10                  15

Asp Arg Val Ser Ile Thr Cys Arg Ala Ser Gln Thr Ile Ile Ser Trp
            20                  25                  30

Leu Ala Trp Tyr Gln Gln Lys Pro Gly Lys Ala Pro Arg Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Asn Arg Tyr Trp Thr
                85                  90                  95

Phe Gly Gln Gly Thr Lys Val Glu Ile Lys
            100                 105

-continued

<210> SEQ ID NO 381
<211> LENGTH: 363
<212> TYPE: DNA
<213> ORGANISM: Artificial Sequence
<220> FEATURE:
<223> OTHER INFORMATION: synthetic

<400> SEQUENCE: 381

```
gaggtgcagc tggtggagtc tgggggaggc ttggtccagc ctgggggtc cctgagactc      60
tcctgtgcag cctctggatt cgcctttaga agttattgga tgagctgggt ccgccaggct    120
ccagggaagg ggctggagtg ggtggccaac atacagcaag atggaaatga taaatactat    180
gtggactctg tgaagggccg attcaccatc tccagagaca acgccaagaa ctcactgtat    240
ctgcaaatga acagcctgag agccgaggac acggctgtgt attactgtgc gagagatacc    300
ggtatagcag aagctggtcc ttttgactac tggggccagg gaaccctggt caccgtctcc    360
tca                                                                  363
```

<210> SEQ ID NO 382
<211> LENGTH: 121
<212> TYPE: PRT
<213> ORGANISM: Artificial Sequence
<220> FEATURE:
<223> OTHER INFORMATION: synthetic

<400> SEQUENCE: 382

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ala Phe Arg Ser Tyr
            20                  25                  30
Trp Met Ser Trp Val Arg Gln Ala Pro Gly Lys Gly Leu Glu Trp Val
        35                  40                  45
Ala Asn Ile Gln Gln Asp Gly Asn Asp Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Thr Gly Ile Ala Glu Ala Gly Pro Phe Asp Tyr Trp Gly
            100                 105                 110
Gln Gly Thr Leu Val Thr Val Ser Ser
        115                 120
```

<210> SEQ ID NO 383
<211> LENGTH: 319
<212> TYPE: DNA
<213> ORGANISM: Artificial Sequence
<220> FEATURE:
<223> OTHER INFORMATION: synthetic

<400> SEQUENCE: 383

```
gacatccaga tgacccagtc tccttccacc ctgtctgcat ctgtaggaga cagagtcacc      60
atcacttgcc gggccagtca gactattatt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatcgtt attggacgtt cggccaaggg    300
accaaggtgg aaatcaaac                                                 319
```

<210> SEQ ID NO 384
<211> LENGTH: 106
<212> TYPE: PRT
<213> ORGANISM: Artificial Sequence
<220> FEATURE:
<223> OTHER INFORMATION: synthetic

<400> SEQUENCE: 384

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Thr Ile Ile Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Arg Tyr Trp Thr
             85                  90                  95

Phe Gly Gln Gly Thr Lys Val Glu Ile Lys
            100                 105
```

<210> SEQ ID NO 385
<211> LENGTH: 372
<212> TYPE: DNA
<213> ORGANISM: Artificial Sequence
<220> FEATURE:
<223> OTHER INFORMATION: synthetic

<400> SEQUENCE: 385

```
gacgtgcaac tgttggagtc tgggggagac ttggtacagc ctggggggtc cctgagactc      60
tcctgtgaag cctctggatt cacctttaga aactatgtca tgatctgggt ccgccaggct     120
ccagggaagg ggctggagtg ggtctcaggt attagtaata gtggtggtac tacacactac     180
acagactccg tgaagggccg gttcaccatt tccagagaca attccaaaaa cacgctgtat     240
ctgcaaatta caagtctgcg agccgaggat acggccgtct attactgtgc gaagggctac     300
ttagacacat ctctgattga ggggaactgg ttcgaccoct ggggccaggg aaccctggtc     360
accgtctcct ca                                                        372
```

<210> SEQ ID NO 386
<211> LENGTH: 124
<212> TYPE: PRT
<213> ORGANISM: Artificial Sequence
<220> FEATURE:
<223> OTHER INFORMATION: synthetic

<400> SEQUENCE: 386

```
Asp Val Gln Leu Leu Glu Ser Gly Gly Asp Leu Val Gln Pro Gly Gly
  1               5                  10                  15

Ser Leu Arg Leu Ser Cys Glu Ala Ser Gly Phe Thr Phe Arg Asn Tyr
             20                  25                  30

Val Met Ile Trp Val Arg Gln Ala Pro Gly Lys Gly Leu Glu Trp Val
         35                  40                  45

Ser Gly Ile Ser Asn Ser Gly Gly Thr Thr His Tyr Thr Asp Ser Val
 50                  55                  60

Lys Gly Arg Phe Thr Ile Ser Arg Asp Asn Ser Lys Asn Thr Leu Tyr
 65                  70                  75                  80
```

Leu Gln Ile Asn Ser Leu Arg Ala Glu Asp Thr Ala Val Tyr Tyr Cys
            85                  90                  95

Ala Lys Gly Tyr Leu Asp Thr Ser Leu Ile Glu Gly Asn Trp Phe Asp
        100                 105                 110

Pro Trp Gly Gln Gly Thr Leu Val Thr Val Ser Ser
        115                 120

<210> SEQ ID NO 387
<211> LENGTH: 24
<212> TYPE: DNA
<213> ORGANISM: Artificial Sequence
<220> FEATURE:
<223> OTHER INFORMATION: synthetic

<400> SEQUENCE: 387
ggattcacct ttagaaacta tgtc                                          24

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

Gly Phe Thr Phe Arg Asn Tyr Val
 1               5

<210> SEQ ID NO 389
<211> LENGTH: 24
<212> TYPE: DNA
<213> ORGANISM: Artificial Sequence
<220> FEATURE:
<223> OTHER INFORMATION: synthetic

<400> SEQUENCE: 389
attagtaata gtggtggtac taca                                          24

<210> SEQ ID NO 390
<211> LENGTH: 8
<212> TYPE: PRT
<213> ORGANISM: Artificial Sequence
<220> FEATURE:
<223> OTHER INFORMATION: synthetic

<400> SEQUENCE: 390

Ile Ser Asn Ser Gly Gly Thr Thr
 1               5

<210> SEQ ID NO 391
<211> LENGTH: 51
<212> TYPE: DNA
<213> ORGANISM: Artificial Sequence
<220> FEATURE:
<223> OTHER INFORMATION: synthetic

<400> SEQUENCE: 391
gcgaagggct acttagacac atctctgatt gagggggaact ggttcgaccc c           51

<210> SEQ ID NO 392
<211> LENGTH: 17
<212> TYPE: PRT
<213> ORGANISM: Artificial Sequence
<220> FEATURE:
<223> OTHER INFORMATION: synthetic

<400> SEQUENCE: 392

Ala Lys Gly Tyr Leu Asp Thr Ser Leu Ile Glu Gly Asn Trp Phe Asp
1               5                   10                  15

Pro

<210> SEQ ID NO 393
<211> LENGTH: 336
<212> TYPE: DNA
<213> ORGANISM: Artificial Sequence
<220> FEATURE:
<223> OTHER INFORMATION: synthetic

<400> SEQUENCE: 393
aatattgtga tgactcagtc tccactctcc ctgcccgtca cccctggaga gccggcctcc      60
atctcctgca ggtctagtca gagcctccta catagtaatg gattcaacta tttgaattgg     120
ttcctgcaga agccagggca gtctccacag ctcctgatct atttgggttc taatcgggcc     180
tccggggtcc ctgacaagtt cagtggcagt ggatcaggca cagattttac actgaacatc     240
aacagagtgg aggctgagga tgttggaatt tatttctgca tgcagactct acaaactccc     300
ctcactttcg gcggagggac caaggtggag atcaaa                               336

<210> SEQ ID NO 394
<211> LENGTH: 112
<212> TYPE: PRT
<213> ORGANISM: Artificial Sequence
<220> FEATURE:
<223> OTHER INFORMATION: synthetic

<400> SEQUENCE: 394

Asn Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asn Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Lys Phe Ser Gly Ser Gly Ser Gly Thr Asp Phe Thr Leu Asn Ile
65                  70                  75                  80

Asn Arg Val Glu Ala Glu Asp Val Gly Ile Tyr Phe Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 395
<211> LENGTH: 33
<212> TYPE: DNA
<213> ORGANISM: Artificial Sequence
<220> FEATURE:
<223> OTHER INFORMATION: synthetic

<400> SEQUENCE: 395
cagagcctcc tacatagtaa tggattcaac tat                                   33

<210> SEQ ID NO 396
<211> LENGTH: 11
<212> TYPE: PRT
<213> ORGANISM: Artificial Sequence
<220> FEATURE:

<223> OTHER INFORMATION: synthetic

<400> SEQUENCE: 396

Gln Ser Leu Leu His Ser Asn Gly Phe Asn Tyr
 1               5                   10

<210> SEQ ID NO 397
<211> LENGTH: 9
<212> TYPE: DNA
<213> ORGANISM: Artificial Sequence
<220> FEATURE:
<223> OTHER INFORMATION: synthetic

<400> SEQUENCE: 397 ttgggttct                                                              9

<210> SEQ ID NO 398
<211> LENGTH: 3
<212> TYPE: PRT
<213> ORGANISM: Artificial Sequence
<220> FEATURE:
<223> OTHER INFORMATION: synthetic

<400> SEQUENCE: 398

Leu Gly Ser
 1

<210> SEQ ID NO 399
<211> LENGTH: 27
<212> TYPE: DNA
<213> ORGANISM: Artificial Sequence
<220> FEATURE:
<223> OTHER INFORMATION: synthetic

<400> SEQUENCE: 399
atgcagactc tacaaactcc cctcact                                         27

<210> SEQ ID NO 400
<211> LENGTH: 9
<212> TYPE: PRT
<213> ORGANISM: Artificial Sequence
<220> FEATURE:
<223> OTHER INFORMATION: synthetic

<400> SEQUENCE: 400

Met Gln Thr Leu Gln Thr Pro Leu Thr
 1               5

<210> SEQ ID NO 401
<211> LENGTH: 372
<212> TYPE: DNA
<213> ORGANISM: Artificial Sequence
<220> FEATURE:
<223> OTHER INFORMATION: synthetic

<400> SEQUENCE: 401
gaggtgcagc tgttggagtc tgggggagac ttggtacagc ctggggggtc cctgagactc      60
tcctgtgaag cctctggatt cacctttaga aactatgtca tgatctgggt ccgccaggct     120
ccagggaagg ggctggagtg ggtctcaggt attagtaata gtggtggtac tacacactac     180
acagactccg tgaagggccg gttcaccatt tccagagaca attccaaaaa cacgctgtat     240
ctgcaaatta acagtctgcg agccgaggat acggccgtct attactgtgc gaagggctac     300
ttagacacat ctctgattga ggggaactgg ttcgaccccct ggggccaggg aaccctggtc     360
accgtctcct ca                                                          372

<210> SEQ ID NO 402
<211> LENGTH: 124
<212> TYPE: PRT
<213> ORGANISM: Artificial Sequence
<220> FEATURE:
<223> OTHER INFORMATION: synthetic

<400> SEQUENCE: 402

Glu Val Gln Leu Leu Glu Ser Gly Gly Asp Leu Val Gln Pro Gly Gly
1               5                   10                  15

Ser Leu Arg Leu Ser Cys Glu Ala Ser Gly Phe Thr Phe Arg Asn Tyr
            20                  25                  30

Val Met Ile Trp Val Arg Gln Ala Pro Gly Lys Gly Leu Glu Trp Val
        35                  40                  45

Ser Gly Ile Ser Asn Ser Gly Gly Thr Thr His Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Lys Gly Tyr Leu Asp Thr Ser Leu Ile Glu Gly Asn Trp Phe Asp
            100                 105                 110

Pro Trp Gly Gln Gly Thr Leu Val Thr Val Ser Ser
        115                 120

<210> SEQ ID NO 403
<211> LENGTH: 336
<212> TYPE: DNA
<213> ORGANISM: Artificial Sequence
<220> FEATURE:
<223> OTHER INFORMATION: synthetic

<400> SEQUENCE: 403
gatattgtga tgactcagtc tccactctcc ctgcccgtca cccctggaga gccggcctcc      60
atctcctgca ggtctagtca gagcctccta catagtaatg gattcaacta tttgaattgg     120
ttcctgcaga agccagggca gtctccacag ctcctgatct atttgggttc taatcgggcc     180
tccggggtcc ctgacaagtt cagtggcagt ggatcaggca cagattttac actgaacatc     240
aacagagtgg aggctgagga tgttggaatt tatttctgca tgcagactct acaaactccc     300
ctcactttcg gcggagggac caaggtggag atcaaa                              336

<210> SEQ ID NO 404
<211> LENGTH: 112
<212> TYPE: PRT
<213> ORGANISM: Artificial Sequence
<220> FEATURE:
<223> OTHER INFORMATION: synthetic

<400> SEQUENCE: 404

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asn Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Lys Phe Ser Gly Ser Gly Ser Gly Thr Asp Phe Thr Leu Asn Ile
 65                  70                  75                  80

Asn Arg Val Glu Ala Glu Asp Val Gly Ile Tyr Phe Cys Met Gln Thr
                 85                  90                  95

Leu Gln Thr Pro Leu Thr Phe Gly Gly Gly Thr Lys Val Glu Ile Lys
            100                 105                 110
```

<210> SEQ ID NO 405
<211> LENGTH: 372
<212> TYPE: DNA
<213> ORGANISM: Artificial Sequence
<220> FEATURE:
<223> OTHER INFORMATION: synthetic

<400> SEQUENCE: 405

```
gaggtgcagc tgttggagtc tgggggaggc ttggtacagc ctgggggtc cctgagactc      60 tcctgtgcag cctctggatt cacctttaga aactatgtca tgagctgggt ccgccaggct    120
ccagggaagg ggctggagtg ggtctcagct attagtaata gtggtggtac tacatactac    180
gcagactccg tgaagggccg gttcaccatc tccagagaca attccaagaa cacgctgtat    240
ctgcaaatga acagcctgag agccgaggac acggccgtat attactgtgc gaagggctac    300
ttagacacat ctctgattga ggggaactgg ttcgacccct ggggccaggg aaccctggtc    360
accgtctcct ca                                                        372
```

<210> SEQ ID NO 406
<211> LENGTH: 124
<212> TYPE: PRT
<213> ORGANISM: Artificial Sequence
<220> FEATURE:
<223> OTHER INFORMATION: synthetic

<400> SEQUENCE: 406

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Asn Tyr
                 20                  25                  30

Val Met Ser Trp Val Arg Gln Ala Pro Gly Lys Gly Leu Glu Trp Val
             35                  40                  45

Ser Ala Ile Ser Asn Ser Gly Gly Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Tyr Leu Asp Thr Ser Leu Ile Glu Gly Asn Trp Phe Asp
            100                 105                 110

Pro Trp Gly Gln Gly Thr Leu Val Thr Val Ser Ser
        115                 120
```

<210> SEQ ID NO 407
<211> LENGTH: 337
<212> TYPE: DNA
<213> ORGANISM: Artificial Sequence
<220> FEATURE:
<223> OTHER INFORMATION: synthetic

<400> SEQUENCE: 407

```
gatattgtga tgactcagtc tccactctcc ctgcccgtca cccctggaga gccggcctcc      60
```

```
atctcctgca ggtctagtca gagcctccta catagtaatg gattcaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcagactct acaaactccc    300
ctcactttcg gcggagggac caaggtggag atcaaac                              337
```

<210> SEQ ID NO 408
<211> LENGTH: 112
<212> TYPE: PRT
<213> ORGANISM: Artificial Sequence
<220> FEATURE:
<223> OTHER INFORMATION: synthetic

<400> SEQUENCE: 408

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Thr Phe Gly Gly Gly Thr Lys Val Glu Ile Lys
            100                 105                 110

<210> SEQ ID NO 409
<211> LENGTH: 366
<212> TYPE: DNA
<213> ORGANISM: Artificial Sequence
<220> FEATURE:
<223> OTHER INFORMATION: synthetic

<400> SEQUENCE: 409

```
gaggtgcagc tgttggagtc tgggggaggc ttggtacagc ctggggggtc cctgagactc     60
tcctgtgcag cctctggatt cacctttagg aagtatgcca tgagctgggt ccgccaggct    120
ccagggaagg gctggagtg gtctcagtt attagtgtta gtggtggtaa cacatactac     180
gcagactccg tgaagggccg gttcaccatc tccagagaca attccaagaa cacgctgtat    240
ctgcaactga acagcctgag agccgaggac acggccgtat attactgtgc gaaggatcta    300
acggatattg tacttatggt gtatgtcgac tactggggcc agggaaccct ggtcaccgtc    360
tcctca                                                                366
```

<210> SEQ ID NO 410
<211> LENGTH: 122
<212> TYPE: PRT
<213> ORGANISM: Artificial Sequence
<220> FEATURE:
<223> OTHER INFORMATION: synthetic

<400> SEQUENCE: 410

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Arg Lys Tyr
        20                  25                  30

Ala Met Ser Trp Val Arg Gln Ala Pro Gly Lys Gly Leu Glu Trp Val
            35                  40                  45

Ser Val Ile Ser Val Ser Gly Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Asp Leu Thr Asp Ile Val Leu Met Val Tyr Val Asp Tyr Trp
            100                 105                 110

Gly Gln Gly Thr Leu Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: synthetic

<400> SEQUENCE: 411
ggattcacct ttaggaagta tgcc                                          24

<210> SEQ ID NO 412
<211> LENGTH: 8
<212> TYPE: PRT
<213> ORGANISM: Artificial Sequence
<220> FEATURE:
<223> OTHER INFORMATION: synthetic

<400> SEQUENCE: 412

Gly Phe Thr Phe Arg Lys Tyr Ala
1               5

<210> SEQ ID NO 413
<211> LENGTH: 24
<212> TYPE: DNA
<213> ORGANISM: Artificial Sequence
<220> FEATURE:
<223> OTHER INFORMATION: synthetic

<400> SEQUENCE: 413
attagtgtta gtggtggtaa caca                                          24

<210> SEQ ID NO 414
<211> LENGTH: 8
<212> TYPE: PRT
<213> ORGANISM: Artificial Sequence
<220> FEATURE:
<223> OTHER INFORMATION: synthetic

<400> SEQUENCE: 414

Ile Ser Val Ser Gly Gly Asn Thr
1               5

<210> SEQ ID NO 415
<211> LENGTH: 45
<212> TYPE: DNA
<213> ORGANISM: Artificial Sequence
<220> FEATURE:
<223> OTHER INFORMATION: synthetic
```

<400> SEQUENCE: 415
gcgaaggatc taacggatat tgtacttatg gtgtatgtcg actac          45

<210> SEQ ID NO 416
<211> LENGTH: 15
<212> TYPE: PRT
<213> ORGANISM: Artificial Sequence
<220> FEATURE:
<223> OTHER INFORMATION: synthetic

<400> SEQUENCE: 416

Ala Lys Asp Leu Thr Asp Ile Val Leu Met Val Tyr Val Asp Tyr
1               5                   10                  15

<210> SEQ ID NO 417
<211> LENGTH: 321
<212> TYPE: DNA
<213> ORGANISM: Artificial Sequence
<220> FEATURE:
<223> OTHER INFORMATION: synthetic

<400> SEQUENCE: 417
gacatccaga tgacccagtc tccatcttcc gtgtctgcat ctgtaggaga cagagtcacc    60
atcacttgtc gggcgagtca ggatattgac aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcac cctgcagcct   240
gaagattttg caacttacta ttgtcaacag gctaacagtt tgccgttcac tttcggcgga   300
gggaccaagg tggagatcaa a                                             321

<210> SEQ ID NO 418
<211> LENGTH: 107
<212> TYPE: PRT
<213> ORGANISM: Artificial Sequence
<220> FEATURE:
<223> OTHER INFORMATION: synthetic

<400> SEQUENCE: 418

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Asp Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Gly Gly Thr Lys Val Glu Ile Lys
            100                 105

<210> SEQ ID NO 419
<211> LENGTH: 18
<212> TYPE: DNA
<213> ORGANISM: Artificial Sequence
<220> FEATURE:
<223> OTHER INFORMATION: synthetic

<400> SEQUENCE: 419

```
caggatattg acaggtgg                                                      18

<210> SEQ ID NO 420
<211> LENGTH: 6
<212> TYPE: PRT
<213> ORGANISM: Artificial Sequence
<220> FEATURE:
<223> OTHER INFORMATION: synthetic

<400> SEQUENCE: 420

Gln Asp Ile Asp Arg Trp
 1               5

<210> SEQ ID NO 421
<211> LENGTH: 9
<212> TYPE: DNA
<213> ORGANISM: Artificial Sequence
<220> FEATURE:
<223> OTHER INFORMATION: synthetic

<400> SEQUENCE: 421 gctgcatcc                                                                 9

<210> SEQ ID NO 422
<211> LENGTH: 3
<212> TYPE: PRT
<213> ORGANISM: Artificial Sequence
<220> FEATURE:
<223> OTHER INFORMATION: synthetic

<400> SEQUENCE: 422

Ala Ala Ser
 1

<210> SEQ ID NO 423
<211> LENGTH: 27
<212> TYPE: DNA
<213> ORGANISM: Artificial Sequence
<220> FEATURE:
<223> OTHER INFORMATION: synthetic

<400> SEQUENCE: 423
caacaggcta acagtttgcc gttcact                                            27

<210> SEQ ID NO 424
<211> LENGTH: 9
<212> TYPE: PRT
<213> ORGANISM: Artificial Sequence
<220> FEATURE:
<223> OTHER INFORMATION: synthetic

<400> SEQUENCE: 424

Gln Gln Ala Asn Ser Leu Pro Phe Thr
 1               5

<210> SEQ ID NO 425
<211> LENGTH: 366
<212> TYPE: DNA
<213> ORGANISM: Artificial Sequence
<220> FEATURE:
<223> OTHER INFORMATION: synthetic

<400> SEQUENCE: 425
gaggtgcagc tgttggagtc tgggggaggc ttggtacagc ctggggggtc cctgagactc        60
tcctgtgcag cctctggatt cacctttagg aagtatgcca tgagctgggt ccgccaggct       120
```
ccagggaagg ggctggagtg ggtctcagtt attagtgtta gtggtggtaa cacatactac    180
gcagactccg tgaagggccg gttcaccatc tccagagaca attccaagaa cacgctgtat    240
ctgcaactga acagcctgag agccgaggac acggccgtat attactgtgc gaaggatcta    300
acggatattg tacttatggt gtatgtcgac tactggggcc agggaaccct ggtcaccgtc    360
tcctca    366

<210> SEQ ID NO 426
<211> LENGTH: 122
<212> TYPE: PRT
<213> ORGANISM: Artificial Sequence
<220> FEATURE:
<223> OTHER INFORMATION: synthetic

<400> SEQUENCE: 426

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Ala Met Ser Trp Val Arg Gln Ala Pro Gly Lys Gly Leu Glu Trp Val
        35                  40                  45

Ser Val Ile Ser Val Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Asp Leu Thr Asp Ile Val Leu Met Val Tyr Val Asp Tyr Trp
            100                 105                 110

Gly Gln Gly Thr Leu Val Thr Val Ser Ser
        115                 120

<210> SEQ ID NO 427
<211> LENGTH: 321
<212> TYPE: DNA
<213> ORGANISM: Artificial Sequence
<220> FEATURE:
<223> OTHER INFORMATION: synthetic

<400> SEQUENCE: 427
gacatccaga tgacccagtc tccatcttcc gtgtctgcat ctgtaggaga cagagtcacc    60
atcacttgtc gggcgagtca ggatattgac aggtggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcac cctgcagcct    240
gaagattttg caacttacta ttgtcaacag gctaacagtt tgccgttcac tttcggcgga    300
gggaccaagg tggagatcaa a    321

<210> SEQ ID NO 428
<211> LENGTH: 107
<212> TYPE: PRT
<213> ORGANISM: Artificial Sequence
<220> FEATURE:
<223> OTHER INFORMATION: synthetic

<400> SEQUENCE: 428

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Asp Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Gly Gly Thr Lys Val Glu Ile Lys
            100                 105

<210> SEQ ID NO 429
<211> LENGTH: 366
<212> TYPE: DNA
<213> ORGANISM: Artificial Sequence
<220> FEATURE:
<223> OTHER INFORMATION: synthetic

<400> SEQUENCE: 429
gaggtgcagc tgttggagtc tgggggaggc ttggtacagc ctggggggtc cctgagactc     60
tcctgtgcag cctctggatt cacctttagg aagtatgcca tgagctgggt ccgccaggct    120
ccagggaagg ggctggagtg ggtctcagct attagtgtta gtggtggtaa cacatactac    180
gcagactccg tgaagggccg gttcaccatc tccagagaca attccaagaa cacgctgtat    240
ctgcaaatga acagcctgag agccgaggac acggccgtat attactgtgc gaaggatcta    300
acggatattg tacttatggt gtatgtcgac tactggggcc agggaaccct ggtcaccgtc    360
tcctca                                                               366

<210> SEQ ID NO 430
<211> LENGTH: 122
<212> TYPE: PRT
<213> ORGANISM: Artificial Sequence
<220> FEATURE:
<223> OTHER INFORMATION: synthetic

<400> SEQUENCE: 430

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Lys Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Thr Asp Ile Val Leu Met Val Tyr Val Asp Tyr Trp
            100                 105                 110

Gly Gln Gly Thr Leu Val Thr Val Ser Ser
        115                 120

<210> SEQ ID NO 431

<211> LENGTH: 322
<212> TYPE: DNA
<213> ORGANISM: Artificial Sequence
<220> FEATURE:
<223> OTHER INFORMATION: synthetic

<400> SEQUENCE: 431

```
gacatccaga tgacccagtc tccatcttct gtgtctgcat ctgtaggaga cagagtcacc      60
atcacttgtc gggcgagtca ggatattgac aggtggttag cctggtatca gcagaaacca     120
gggaaagccc ctaagctcct gatctatgct gcatccagtt tgcaaagtgg ggtcccatca     180
aggttcagcg gcagtggatc tgggacagat tcactctcac tatcagcagc ctgcagcct      240
gaagattttg caacttacta ttgtcaacag gctaacagtt tgccgttcac tttcggcgga     300
gggaccaagg tggagatcaa ac                                              322
```

<210> SEQ ID NO 432
<211> LENGTH: 107
<212> TYPE: PRT
<213> ORGANISM: Artificial Sequence
<220> FEATURE:
<223> OTHER INFORMATION: synthetic

<400> SEQUENCE: 432

```
Asp Ile Gln Met Thr Gln Ser Pro Ser Ser Val Ser Ala Ser Val Gly
 1               5                  10                  15
Asp Arg Val Thr Ile Thr Cys Arg Ala Ser Gln Asp Ile Asp Arg Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Leu Pro Phe
                85                  90                  95
Thr Phe Gly Gly Gly Thr Lys Val Glu Ile Lys
            100                 105
```

<210> SEQ ID NO 433
<211> LENGTH: 363
<212> TYPE: DNA
<213> ORGANISM: Artificial Sequence
<220> FEATURE:
<223> OTHER INFORMATION: synthetic

<400> SEQUENCE: 433

```
caggttcaat ggtacagtc tggagttgag gtgaagaagc ctggggcctc agtgaaggtc       60
tcctgcaaga cttctggtta cacttttagc aacaatggtt tcagctgggt gcggcaggcc     120
cctggacaag gcttgagtg gctgggatgg atcagcggtt acaatggaaa cacaaactat      180
gcacagaagt tccagggcag agtcaccatg accacagaca tccacgag tacagcctac       240
atggagttga ggactctgag atctgacgac acggccgtct attactgtgc gagagatcag     300
gactacagta acttccactg gctcgacccc tggggccagg gaaccctggt caccgtcgcc     360
tca                                                                  363
```

<210> SEQ ID NO 434
<211> LENGTH: 121
<212> TYPE: PRT

<213> ORGANISM: Artificial Sequence
<220> FEATURE:
<223> OTHER INFORMATION: synthetic

<400> SEQUENCE: 434

```
Gln Val Gln Leu Val Gln Ser Gly Val Glu Val Lys Lys Pro Gly Ala
1               5                   10                  15
Ser Val Lys Val Ser Cys Lys Thr Ser Gly Tyr Thr Phe Ser Asn Asn
            20                  25                  30
Gly Phe Ser Trp Val Arg Gln Ala Pro Gly Gln Gly Leu Glu Trp Leu
        35                  40                  45
Gly Trp Ile Ser Gly Tyr Asn Gly Asn Thr Asn Tyr Ala Gln Lys Phe
    50                  55                  60
Gln Gly Arg Val Thr Met Thr Thr Asp Thr Ser Thr Ser Thr Ala Tyr
65                  70                  75                  80
Met Glu Leu Arg Thr Leu Arg Ser Asp Asp Thr Ala Val Tyr Tyr Cys
                85                  90                  95
Ala Arg Asp Gln Asp Tyr Ser Asn Phe His Trp Leu Pro Trp Gly
            100                 105                 110
Gln Gly Thr Leu Val Thr Val Ala Ser
        115                 120
```

<210> SEQ ID NO 435
<211> LENGTH: 24
<212> TYPE: DNA
<213> ORGANISM: Artificial Sequence
<220> FEATURE:
<223> OTHER INFORMATION: synthetic

<400> SEQUENCE: 435
ggttacactt ttagcaacaa tggt                                            24

<210> SEQ ID NO 436
<211> LENGTH: 8
<212> TYPE: PRT
<213> ORGANISM: Artificial Sequence
<220> FEATURE:
<223> OTHER INFORMATION: synthetic

<400> SEQUENCE: 436

```
Gly Tyr Thr Phe Ser Asn Asn Gly
1               5
```

<210> SEQ ID NO 437
<211> LENGTH: 24
<212> TYPE: DNA
<213> ORGANISM: Artificial Sequence
<220> FEATURE:
<223> OTHER INFORMATION: synthetic

<400> SEQUENCE: 437
atcagcggtt acaatggaaa caca                                            24

<210> SEQ ID NO 438
<211> LENGTH: 8
<212> TYPE: PRT
<213> ORGANISM: Artificial Sequence
<220> FEATURE:
<223> OTHER INFORMATION: synthetic

<400> SEQUENCE: 438

```
Ile Ser Gly Tyr Asn Gly Asn Thr
1               5
```

<210> SEQ ID NO 439
<211> LENGTH: 42
<212> TYPE: DNA
<213> ORGANISM: Artificial Sequence
<220> FEATURE:
<223> OTHER INFORMATION: synthetic

<400> SEQUENCE: 439
gcgagagatc aggactacag taacttccac tggctcgacc cc         42

<210> SEQ ID NO 440
<211> LENGTH: 14
<212> TYPE: PRT
<213> ORGANISM: Artificial Sequence
<220> FEATURE:
<223> OTHER INFORMATION: synthetic

<400> SEQUENCE: 440

Ala Arg Asp Gln Asp Tyr Ser Asn Phe His Trp Leu Asp Pro
 1               5                  10

<210> SEQ ID NO 441
<211> LENGTH: 321
<212> TYPE: DNA
<213> ORGANISM: Artificial Sequence
<220> FEATURE:
<223> OTHER INFORMATION: synthetic

<400> SEQUENCE: 441
gacatccaga tgacccagtc tccatcctcc gtgtctgcat ctgtaggaga cagagtcatt    60
atcacttgtc gggcgagtca gggtcttagt agttggctag cctggtatca gcagaaacca   120
gggacagccc ctaagctcct gatccattct gcatccagtt tgcaaactgg ggtcccatca   180
agattcagcg gcagtggatc tgggacagaa ttcgctctca ccatcaacag cctgcagcct   240
gaagattttg gaacttacta ttgtcaacag gctaacagtt tcccgctcac tttcggcggg   300
gggaccaggg tggagatcaa a                                              321

<210> SEQ ID NO 442
<211> LENGTH: 107
<212> TYPE: PRT
<213> ORGANISM: Artificial Sequence
<220> FEATURE:
<223> OTHER INFORMATION: synthetic

<400> SEQUENCE: 442

Asp Ile Gln Met Thr Gln Ser Pro Ser Ser Val Ser Ala Ser Val Gly
 1               5                  10                  15

Asp Arg Val Ile Ile Thr Cys Arg Ala Ser Gln Gly Leu Ser Ser Trp
                20                  25                  30

Leu Ala Trp Tyr Gln Gln Lys Pro Gly Thr Ala Pro Lys Leu Leu Ile
            35                  40                  45

His Ser Ala Ser Ser Leu Gln Thr Gly Val Pro Ser Arg Phe Ser Gly
        50                  55                  60

Ser Gly Ser Gly Thr Glu Phe Ala Leu Thr Ile Asn Ser Leu Gln Pro
65                  70                  75                  80

Glu Asp Phe Gly Thr Tyr Tyr Cys Gln Gln Ala Asn Ser Phe Pro Leu
                85                  90                  95

Thr Phe Gly Gly Gly Thr Arg Val Glu Ile Lys
            100                 105

```
<210> SEQ ID NO 443
<211> LENGTH: 18
<212> TYPE: DNA
<213> ORGANISM: Artificial Sequence
<220> FEATURE:
<223> OTHER INFORMATION: synthetic

<400> SEQUENCE: 443
cagggtctta gtagttgg                                                 18

<210> SEQ ID NO 444
<211> LENGTH: 6
<212> TYPE: PRT
<213> ORGANISM: Artificial Sequence
<220> FEATURE:
<223> OTHER INFORMATION: synthetic

<400> SEQUENCE: 444

Gln Gly Leu Ser Ser Trp
 1               5

<210> SEQ ID NO 445
<211> LENGTH: 9
<212> TYPE: DNA
<213> ORGANISM: Artificial Sequence
<220> FEATURE:
<223> OTHER INFORMATION: synthetic

<400> SEQUENCE: 445 tctgcatcc                                                            9

<210> SEQ ID NO 446
<211> LENGTH: 3
<212> TYPE: PRT
<213> ORGANISM: Artificial Sequence
<220> FEATURE:
<223> OTHER INFORMATION: synthetic

<400> SEQUENCE: 446

Ser Ala Ser
 1

<210> SEQ ID NO 447
<211> LENGTH: 27
<212> TYPE: DNA
<213> ORGANISM: Artificial Sequence
<220> FEATURE:
<223> OTHER INFORMATION: synthetic

<400> SEQUENCE: 447
caacaggcta acagtttccc gctcact                                       27

<210> SEQ ID NO 448
<211> LENGTH: 9
<212> TYPE: PRT
<213> ORGANISM: Artificial Sequence
<220> FEATURE:
<223> OTHER INFORMATION: synthetic

<400> SEQUENCE: 448

Gln Gln Ala Asn Ser Phe Pro Leu Thr
 1               5

<210> SEQ ID NO 449
<211> LENGTH: 363
<212> TYPE: DNA
```

<213> ORGANISM: Artificial Sequence
<220> FEATURE:
<223> OTHER INFORMATION: synthetic

<400> SEQUENCE: 449

```
caggttcagc tggtgcagtc tggagttgag gtgaagaagc ctggggcctc agtgaaggtc    60
tcctgcaaga cttctggtta cacttttagc aacaatggtt tcagctgggt gcggcaggcc   120
cctggacaag gcttgagtg gctgggatgg atcagcggtt acaatggaaa cacaaactat    180
gcacagaagt tccagggcag agtcaccatg accacagaca catccacgag tacagcctac   240
atggagttga ggactctgag atctgacgac acggccgtct attactgtgc gagagatcag   300
gactacagta acttccactg gctcgacccc tggggccagg gaaccctggt caccgtctcc   360
tca                                                                 363
```

<210> SEQ ID NO 450
<211> LENGTH: 121
<212> TYPE: PRT
<213> ORGANISM: Artificial Sequence
<220> FEATURE:
<223> OTHER INFORMATION: synthetic

<400> SEQUENCE: 450

```
Gln Val Gln Leu Val Gln Ser Gly Val Glu Val Lys Lys Pro Gly Ala
 1               5                  10                  15
Ser Val Lys Val Ser Cys Lys Thr Ser Gly Tyr Thr Phe Ser Asn Asn
            20                  25                  30
Gly Phe Ser Trp Val Arg Gln Ala Pro Gly Gln Gly Leu Glu Trp Leu
        35                  40                  45
Gly Trp Ile Ser Gly Tyr Asn Gly Asn Thr Asn Tyr Ala Gln Lys Phe
    50                  55                  60
Gln Gly Arg Val Thr Met Thr Thr Asp Thr Ser Thr Ser Thr Ala Tyr
65                  70                  75                  80
Met Glu Leu Arg Thr Leu Arg Ser Asp Asp Thr Ala Val Tyr Tyr Cys
                85                  90                  95
Ala Arg Asp Gln Asp Tyr Ser Asn Phe His Trp Leu Asp Pro Trp Gly
            100                 105                 110
Gln Gly Thr Leu Val Thr Val Ser Ser
        115                 120
```

<210> SEQ ID NO 451
<211> LENGTH: 321
<212> TYPE: DNA
<213> ORGANISM: Artificial Sequence
<220> FEATURE:
<223> OTHER INFORMATION: synthetic

<400> SEQUENCE: 451

```
gacatccaga tgacccagtc tccatcctcc gtgtctgcat ctgtaggaga cagagtcatt    60
atcacttgtc gggcgagtca gggtcttagt agttggctag cctggtatca gcagaaacca   120
gggacagccc ctaagctcct gatccattct gcatccagtt tgcaaactgg ggtcccatca   180
agattcagcg gcagtggatc tgggacagaa ttcgctctca ccatcaacag cctgcagcct   240
gaagattttg gaacttacta ttgtcaacag gctaacagtt tcccgctcac tttcggcggg   300
gggaccaagg tggagatcaa a                                             321
```

<210> SEQ ID NO 452
<211> LENGTH: 107

<212> TYPE: PRT
<213> ORGANISM: Artificial Sequence
<220> FEATURE:
<223> OTHER INFORMATION: synthetic

<400> SEQUENCE: 452

Asp Ile Gln Met Thr Gln Ser Pro Ser Ser Val Ser Ala Ser Val Gly
1               5                   10                  15

Asp Arg Val Ile Ile Thr Cys Arg Ala Ser Gln Gly Leu Ser Ser Trp
            20                  25                  30

Leu Ala Trp Tyr Gln Gln Lys Pro Gly Thr Ala Pro Lys Leu Leu Ile
        35                  40                  45

His Ser Ala Ser Ser Leu Gln Thr Gly Val Pro Ser Arg Phe Ser Gly
    50                  55                  60

Ser Gly Ser Gly Thr Glu Phe Ala Leu Thr Ile Asn Ser Leu Gln Pro
65                  70                  75                  80

Glu Asp Phe Gly Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 453
<211> LENGTH: 363
<212> TYPE: DNA
<213> ORGANISM: Artificial Sequence
<220> FEATURE:
<223> OTHER INFORMATION: synthetic

<400> SEQUENCE: 453
caggttcagc tggtgcagtc tggagctgag gtgaagaagc ctggggcctc agtgaaggtc      60
tcctgcaagg cttctggtta cactttagc aacaatggta tcagctgggt gcgacaggcc     120
cctggacaag ggcttgagtg gatgggatgg atcagcggtt acaatggaaa cacaaactat     180
gcacagaagc tccagggcag agtcaccatg accacagaca catccacgag cacagcctac     240
atggagctga ggagcctgag atctgacgac acggccgtgt attactgtgc gagagatcag     300
gactacagta acttccactg gctcgacccc tggggccagg gaaccctggt caccgtctcc     360
tca                                                                    363

<210> SEQ ID NO 454
<211> LENGTH: 121
<212> TYPE: PRT
<213> ORGANISM: Artificial Sequence
<220> FEATURE:
<223> OTHER INFORMATION: synthetic

<400> SEQUENCE: 454

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Asn
            20                  25                  30

Gly Ile Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

```
Ala Arg Asp Gln Asp Tyr Ser Asn Phe His Trp Leu Asp Pro Trp Gly
            100                 105                 110

Gln Gly Thr Leu Val Thr Val Ser Ser
        115                 120

<210> SEQ ID NO 455
<211> LENGTH: 322
<212> TYPE: DNA
<213> ORGANISM: Artificial Sequence
<220> FEATURE:
<223> OTHER INFORMATION: synthetic

<400> SEQUENCE: 455
gacatccaga tgacccagtc tccatcttct gtgtctgcat ctgtaggaga cagagtcacc      60
atcacttgtc gggcgagtca ggtcttagt agttggttag cctggtatca gcagaaacca     120
gggaaagccc ctaagctcct gatctattct gcatccagtt tgcaaagtgg ggtcccatca    180
aggttcagcg gcagtggatc tgggacagat tcactctca ctatcagcag cctgcagcct     240
gaagattttg caacttacta ttgtcaacag gctaacagtt cccgctcac tttcggcgga    300 gggaccaagg tggagatcaa ac                                             322

<210> SEQ ID NO 456
<211> LENGTH: 107
<212> TYPE: PRT
<213> ORGANISM: Artificial Sequence
<220> FEATURE:
<223> OTHER INFORMATION: synthetic

<400> SEQUENCE: 456

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Leu Ser Ser Trp
            20                  25                  30

Leu Ala Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 457
<211> LENGTH: 360
<212> TYPE: DNA
<213> ORGANISM: Artificial Sequence
<220> FEATURE:
<223> OTHER INFORMATION: synthetic

<400> SEQUENCE: 457
caggtgaagt tggtggagtc tggggggaggc gtggtccagc ctggggaggtc cctgagagtc     60 tcctgtgcag cgtctggatt caccttcagt agctatggca tgcactgggt ccgccaggct    120
ccaggcaagg ggctggagtg gttggcaatt atatggtatg atggagataa taaatactat    180
tcagactccg tgaagggccg attcaccatc tccagagaca attccaagaa cacgctgtat    240
ctgcaaatga acagcctgag agccgaggac acggctgagt attactgtgt gagagatgcg    300
```
agtatagcat ctcgtttctt ggactattgg ggccaggaa ccttggtcac cgtctcctca   360

<210> SEQ ID NO 458
<211> LENGTH: 120
<212> TYPE: PRT
<213> ORGANISM: Artificial Sequence
<220> FEATURE:
<223> OTHER INFORMATION: synthetic

<400> SEQUENCE: 458

Gln Val Lys Leu Val Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Gly Met His Trp Val Arg Gln Ala Pro Gly Lys Gly Leu Glu Trp Leu
        35                  40                  45

Ala Ile Ile Trp Tyr Asp Gly Asp Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Glu Tyr Tyr Cys
                85                  90                  95

Val Arg Asp Ala Ser Ile Ala Ser Arg Phe Leu Asp Tyr Trp Gly Gln
            100                 105                 110

Gly Thr Leu Val Thr Val Ser Ser
        115                 120

<210> SEQ ID NO 459
<211> LENGTH: 24
<212> TYPE: DNA
<213> ORGANISM: Artificial Sequence
<220> FEATURE:
<223> OTHER INFORMATION: synthetic

<400> SEQUENCE: 459
ggattcacct tcagtagcta tggc                                          24

<210> SEQ ID NO 460
<211> LENGTH: 8
<212> TYPE: PRT
<213> ORGANISM: Artificial Sequence
<220> FEATURE:
<223> OTHER INFORMATION: synthetic

<400> SEQUENCE: 460

Gly Phe Thr Phe Ser Ser Tyr Gly
1               5

<210> SEQ ID NO 461
<211> LENGTH: 24
<212> TYPE: DNA
<213> ORGANISM: Artificial Sequence
<220> FEATURE:
<223> OTHER INFORMATION: synthetic

<400> SEQUENCE: 461
atatggtatg atggagataa taaa                                          24

<210> SEQ ID NO 462
<211> LENGTH: 8
<212> TYPE: PRT
<213> ORGANISM: Artificial Sequence
<220> FEATURE:
<223> OTHER INFORMATION: synthetic

<400> SEQUENCE: 462

Ile Trp Tyr Asp Gly Asp Asn Lys
1               5

<210> SEQ ID NO 463
<211> LENGTH: 39
<212> TYPE: DNA
<213> ORGANISM: Artificial Sequence
<220> FEATURE:
<223> OTHER INFORMATION: synthetic

<400> SEQUENCE: 463
gtgagagatg cgagtatagc atctcgtttc ttggactat                                39

<210> SEQ ID NO 464
<211> LENGTH: 13
<212> TYPE: PRT
<213> ORGANISM: Artificial Sequence
<220> FEATURE:
<223> OTHER INFORMATION: synthetic

<400> SEQUENCE: 464

Val Arg Asp Ala Ser Ile Ala Ser Arg Phe Leu Asp Tyr
1               5                   10

<210> SEQ ID NO 465
<211> LENGTH: 321
<212> TYPE: DNA
<213> ORGANISM: Artificial Sequence
<220> FEATURE:
<223> OTHER INFORMATION: synthetic

<400> SEQUENCE: 465
gacatccaga tgacccagtc tccatcctca ctgtctgcat ctataggaga cagagtcacc         60
atcacttgtc gggcgactca ggacattaac aattatttag cctggtttca gcagaaacca        120
gggaaagccc ctaagtccct gatctatgct acatccaatt tgcaaagtgg ggtcccatca        180
aagttcagcg gcagtggatc tgggacagat tacactctca ccatcagcag cctgcagcct        240
gaagattttt caacttatta ctgtcaacag tatcatagtt acccgctcac tttcggcgga        300
gggaccaagg tggagatcaa a                                                  321

<210> SEQ ID NO 466
<211> LENGTH: 107
<212> TYPE: PRT
<213> ORGANISM: Artificial Sequence
<220> FEATURE:
<223> OTHER INFORMATION: synthetic

<400> SEQUENCE: 466

Asp Ile Gln Met Thr Gln Ser Pro Ser Ser Leu Ser Ala Ser Ile Gly
1               5                   10                  15

Asp Arg Val Thr Ile Thr Cys Arg Ala Thr Gln Asp Ile Asn Asn Tyr
                20                  25                  30

Leu Ala Trp Phe Gln Gln Lys Pro Gly Lys Ala Pro Lys Ser Leu Ile
            35                  40                  45

Tyr Ala Thr Ser Asn Leu Gln Ser Gly Val Pro Ser Lys Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ser Thr Tyr Tyr Cys Gln Gln Tyr His Ser Tyr Pro Leu
            85                  90                  95

Thr Phe Gly Gly Gly Thr Lys Val Glu Ile Lys
            100                 105

<210> SEQ ID NO 467
<211> LENGTH: 18
<212> TYPE: DNA
<213> ORGANISM: Artificial Sequence
<220> FEATURE:
<223> OTHER INFORMATION: synthetic

<400> SEQUENCE: 467
caggacatta acaattat                                                 18

<210> SEQ ID NO 468
<211> LENGTH: 6
<212> TYPE: PRT
<213> ORGANISM: Artificial Sequence
<220> FEATURE:
<223> OTHER INFORMATION: synthetic

<400> SEQUENCE: 468

Gln Asp Ile Asn Asn Tyr
 1               5

<210> SEQ ID NO 469
<211> LENGTH: 9
<212> TYPE: DNA
<213> ORGANISM: Artificial Sequence
<220> FEATURE:
<223> OTHER INFORMATION: synthetic

<400> SEQUENCE: 469 gctacatcc                                                            9

<210> SEQ ID NO 470
<211> LENGTH: 3
<212> TYPE: PRT
<213> ORGANISM: Artificial Sequence
<220> FEATURE:
<223> OTHER INFORMATION: synthetic

<400> SEQUENCE: 470

Ala Thr Ser
 1

<210> SEQ ID NO 471
<211> LENGTH: 27
<212> TYPE: DNA
<213> ORGANISM: Artificial Sequence
<220> FEATURE:
<223> OTHER INFORMATION: synthetic

<400> SEQUENCE: 471
caacagtatc atagttaccc gctcact                                       27

<210> SEQ ID NO 472
<211> LENGTH: 9
<212> TYPE: PRT
<213> ORGANISM: Artificial Sequence
<220> FEATURE:
<223> OTHER INFORMATION: synthetic

<400> SEQUENCE: 472

Gln Gln Tyr His Ser Tyr Pro Leu Thr
  1               5

<210> SEQ ID NO 473
<211> LENGTH: 360
<212> TYPE: DNA
<213> ORGANISM: Artificial Sequence
<220> FEATURE:
<223> OTHER INFORMATION: synthetic

<400> SEQUENCE: 473

```
caggtgcagc tggtggagtc tgggggaggc gtggtccagc ctggagggtc cctgagagtc    60
tcctgtgcag cgtctggatt caccttcagt agctatggca tgcactgggt ccgccaggct   120
ccaggcaagg ggctggagtg gttggcaatt atatggtatg atggagataa taaatactat   180
tcagactccg tgaagggccg attcaccatc tccagagaca attccaagaa cacgctgtat   240
ctgcaaatga acagcctgag agccgaggac acggctgagt attactgtgt gagagatgcg   300
agtatagcat tcgtttctt ggactattgg ggccagggaa ccctggtcac cgtctcctca    360
```

<210> SEQ ID NO 474
<211> LENGTH: 120
<212> TYPE: PRT
<213> ORGANISM: Artificial Sequence
<220> FEATURE:
<223> OTHER INFORMATION: synthetic

<400> SEQUENCE: 474

Gln Val Gln Leu Val Glu Ser Gly Gly Gly Val Val Gln Pro Gly Arg
  1               5                  10                  15

Ser Leu Arg Val Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Leu
             35                  40                  45

Ala Ile Ile Trp Tyr Asp Gly Asp Asn Lys Tyr Tyr Ser Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Glu Tyr Tyr Cys
                 85                  90                  95

Val Arg Asp Ala Ser Ile Ala Ser Arg Phe Leu Asp Tyr Trp Gly Gln
                100                 105                 110

Gly Thr Leu Val Thr Val Ser Ser
            115                 120

<210> SEQ ID NO 475
<211> LENGTH: 321
<212> TYPE: DNA
<213> ORGANISM: Artificial Sequence
<220> FEATURE:
<223> OTHER INFORMATION: synthetic

<400> SEQUENCE: 475

```
gacatccaga tgacccagtc tccatcctca ctgtctgcat ctataggaga cagagtcacc    60
atcacttgtc gggcgactca ggacattaac aattatttag cctggtttca gcagaaacca   120
gggaaagccc ctaagtccct gatctatgct acatccaatt tgcaaagtgg ggtcccatca   180
aagttcagcg gcagtggatc tgggacagat tacactctca ccatcagcag cctgcagcct   240
gaagattttt caacttatta ctgtcaacag tatcatagtt acccgctcac tttcggcgga   300
```
gggaccaagg tggagatcaa a    321

<210> SEQ ID NO 476
<211> LENGTH: 107
<212> TYPE: PRT
<213> ORGANISM: Artificial Sequence
<220> FEATURE:
<223> OTHER INFORMATION: synthetic

<400> SEQUENCE: 476

Asp Ile Gln Met Thr Gln Ser Pro Ser Ser Leu Ser Ala Ser Ile Gly
1               5                   10                  15

Asp Arg Val Thr Ile Thr Cys Arg Ala Thr Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Ala Thr Ser Asn Leu Gln Ser Gly Val Pro Ser Lys Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ser Thr Tyr Tyr Cys Gln Gln Tyr His Ser Tyr Pro Leu
                85                  90                  95

Thr Phe Gly Gly Gly Thr Lys Val Glu Ile Lys
            100                 105

<210> SEQ ID NO 477
<211> LENGTH: 360
<212> TYPE: DNA
<213> ORGANISM: Artificial Sequence
<220> FEATURE:
<223> OTHER INFORMATION: synthetic

<400> SEQUENCE: 477
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggagataa taaatactat   180
gcagactccg tgaagggccg attcaccatc tccagagaca actccaagaa cacgctgtat   240
ctgcaaatga acagcctgag agccgaggac acggctgtgt attactgtgt gagagatgcg   300
agtatagcat ctcgtttctt ggactattgg ggccagggaa ccctggtcac cgtctcctca   360

<210> SEQ ID NO 478
<211> LENGTH: 120
<212> TYPE: PRT
<213> ORGANISM: Artificial Sequence
<220> FEATURE:
<223> OTHER INFORMATION: synthetic

<400> SEQUENCE: 478

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Val Arg Asp Ala Ser Ile Ala Ser Arg Phe Leu Asp Tyr Trp Gly Gln
            100                 105                 110

Gly Thr Leu Val Thr Val Ser Ser
        115                 120

<210> SEQ ID NO 479
<211> LENGTH: 322
<212> TYPE: DNA
<213> ORGANISM: Artificial Sequence
<220> FEATURE:
<223> OTHER INFORMATION: synthetic

<400> SEQUENCE: 479
gacatccaga tgacccagtc tccatcctca ctgtctgcat ctgtaggaga cagagtcacc      60
atcacttgtc gggcgagtca ggacattaac aattatttag cctggtttca gcagaaacca    120
gggaaagccc ctaagtccct gatctatgct acatccagtt tgcaaagtgg ggtcccatca    180
aggttcagcg gcagtggatc tgggacagat ttcactctca ccatcagcag cctgcagcct    240
gaagattttg caacttatta ctgccaacag tatcatagtt acccgctcac tttcggcgga    300
gggaccaagg tggagatcaa ac                                             322

<210> SEQ ID NO 480
<211> LENGTH: 107
<212> TYPE: PRT
<213> ORGANISM: Artificial Sequence
<220> FEATURE:
<223> OTHER INFORMATION: synthetic

<400> SEQUENCE: 480

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Leu
                85                  90                  95

Thr Phe Gly Gly Gly Thr Lys Val Glu Ile Lys
            100                 105

<210> SEQ ID NO 481
<211> LENGTH: 363
<212> TYPE: DNA
<213> ORGANISM: Artificial Sequence
<220> FEATURE:
<223> OTHER INFORMATION: synthetic

<400> SEQUENCE: 481
gaggtgcaac tgttggagtc tgggggagac ttggtacagc ctgggggtc cctgagactc      60 tcctgtgcag cctctgaatt caccttagc ggctatgcca tgagctgggt ccgccaggct    120
ccagggaagg ggctggagtg ggtctcagtg attcgtggta gtggtgataa acatactac    180
```

```
gcagactccg tgaagggccg gttcagcatc tccagagaca attccaagaa cacactgtat    240
ctgcaaatga acagcctgag agccgaggac acggccgtat attactgtgc gagagtgtat    300
tacgattttt gggaaggggc ttttgatatc tggggccaag gacaatggt caccgtctct    360 tca                                                                  363
```

```
<210> SEQ ID NO 482
<211> LENGTH: 121
<212> TYPE: PRT
<213> ORGANISM: Artificial Sequence
<220> FEATURE:
<223> OTHER INFORMATION: synthetic

<400> SEQUENCE: 482

Glu Val Gln Leu Leu Glu Ser Gly Gly Asp Leu Val Gln Pro Gly Gly
 1               5                  10                  15

Ser Leu Arg Leu Ser Cys Ala Ala Ser Glu Phe Thr Phe Ser Gly Tyr
            20                  25                  30

Ala Met Ser Trp Val Arg Gln Ala Pro Gly Lys Gly Leu Glu Trp Val
        35                  40                  45

Ser Val Ile Arg Gly Ser Gly Asp Asn Thr Tyr Tyr Ala Asp Ser Val
    50                  55                  60

Lys Gly Arg Phe Ser Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Val Tyr Tyr Asp Phe Trp Glu Gly Ala Phe Asp Ile Trp Gly
           100                 105                 110

Gln Gly Thr Met Val Thr Val Ser Ser
       115                 120
```

```
<210> SEQ ID NO 483
<211> LENGTH: 24
<212> TYPE: DNA
<213> ORGANISM: Artificial Sequence
<220> FEATURE:
<223> OTHER INFORMATION: synthetic

<400> SEQUENCE: 483
gaattcacct ttagcggcta tgcc                                            24
```

```
<210> SEQ ID NO 484
<211> LENGTH: 8
<212> TYPE: PRT
<213> ORGANISM: Artificial Sequence
<220> FEATURE:
<223> OTHER INFORMATION: synthetic

<400> SEQUENCE: 484

Glu Phe Thr Phe Ser Gly Tyr Ala
 1               5
```

```
<210> SEQ ID NO 485
<211> LENGTH: 24
<212> TYPE: DNA
<213> ORGANISM: Artificial Sequence
<220> FEATURE:
<223> OTHER INFORMATION: synthetic

<400> SEQUENCE: 485
attcgtggta gtggtgataa caca                                            24
```

<210> SEQ ID NO 486
<211> LENGTH: 8
<212> TYPE: PRT
<213> ORGANISM: Artificial Sequence
<220> FEATURE:
<223> OTHER INFORMATION: synthetic

<400> SEQUENCE: 486

Ile Arg Gly Ser Gly Asp Asn Thr
1               5

<210> SEQ ID NO 487
<211> LENGTH: 42
<212> TYPE: DNA
<213> ORGANISM: Artificial Sequence
<220> FEATURE:
<223> OTHER INFORMATION: synthetic

<400> SEQUENCE: 487
gcgagagtgt attacgattt tgggaaggg gcttttgata tc                        42

<210> SEQ ID NO 488
<211> LENGTH: 14
<212> TYPE: PRT
<213> ORGANISM: Artificial Sequence
<220> FEATURE:
<223> OTHER INFORMATION: synthetic

<400> SEQUENCE: 488

Ala Arg Val Tyr Tyr Asp Phe Trp Glu Gly Ala Phe Asp Ile
1               5                   10

<210> SEQ ID NO 489
<211> LENGTH: 321
<212> TYPE: DNA
<213> ORGANISM: Artificial Sequence
<220> FEATURE:
<223> OTHER INFORMATION: synthetic

<400> SEQUENCE: 489
gacatccaga tgacccagtc tccatcttcc gtgtctgcat ctgtaggaga cagagtcacc      60
atcacttgtc gggcgagtca gggtattagc acctggttag cctggtatca gcagaaacca    120
gggaaagccc ctaagctcct gatctatgct gcaaccagtt tgcaaagtgg ggtcccatca    180
aggttcagcg gcagtggatc tgggacagat ttcactctcg ccatcagcgg cctgcagcct    240
gaagattttg caacttacta ttgtcaacag gctaacaatt tcccgtacac ttttggccag    300
gggaccaagc tggagatcaa a                                               321

<210> SEQ ID NO 490
<211> LENGTH: 107
<212> TYPE: PRT
<213> ORGANISM: Artificial Sequence
<220> FEATURE:
<223> OTHER INFORMATION: synthetic

<400> SEQUENCE: 490

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

-continued

```
Tyr Ala Ala Thr Ser Leu Gln Ser Gly Val Pro Ser Arg Phe Ser Gly
 50                  55                  60

Ser Gly Ser Gly Thr Asp Phe Thr Leu Ala Ile Ser Gly Leu Gln Pro
 65                  70                  75                  80

Glu Asp Phe Ala Thr Tyr Tyr Cys Gln Gln Ala Asn Asn Phe Pro Tyr
                 85                  90                  95

Thr Phe Gly Gln Gly Thr Lys Leu Glu Ile Lys
            100                 105
```

<210> SEQ ID NO 491
<211> LENGTH: 18
<212> TYPE: DNA
<213> ORGANISM: Artificial Sequence
<220> FEATURE:
<223> OTHER INFORMATION: synthetic

<400> SEQUENCE: 491
cagggtatta gcacctgg                                             18

<210> SEQ ID NO 492
<211> LENGTH: 6
<212> TYPE: PRT
<213> ORGANISM: Artificial Sequence
<220> FEATURE:
<223> OTHER INFORMATION: synthetic

<400> SEQUENCE: 492

```
Gln Gly Ile Ser Thr Trp
 1               5
```

<210> SEQ ID NO 493
<211> LENGTH: 9
<212> TYPE: DNA
<213> ORGANISM: Artificial Sequence
<220> FEATURE:
<223> OTHER INFORMATION: synthetic

<400> SEQUENCE: 493 gctgcaacc                                                        9

<210> SEQ ID NO 494
<211> LENGTH: 3
<212> TYPE: PRT
<213> ORGANISM: Artificial Sequence
<220> FEATURE:
<223> OTHER INFORMATION: synthetic

<400> SEQUENCE: 494

```
Ala Ala Thr
 1
```

<210> SEQ ID NO 495
<211> LENGTH: 27
<212> TYPE: DNA
<213> ORGANISM: Artificial Sequence
<220> FEATURE:
<223> OTHER INFORMATION: synthetic

<400> SEQUENCE: 495
caacaggcta acaatttccc gtacact                                   27

<210> SEQ ID NO 496
<211> LENGTH: 9
<212> TYPE: PRT
<213> ORGANISM: Artificial Sequence
<220> FEATURE:
<223> OTHER INFORMATION: synthetic

<400> SEQUENCE: 496

Gln Gln Ala Asn Asn Phe Pro Tyr Thr
1               5

<210> SEQ ID NO 497
<211> LENGTH: 363
<212> TYPE: DNA
<213> ORGANISM: Artificial Sequence
<220> FEATURE:
<223> OTHER INFORMATION: synthetic

<400> SEQUENCE: 497

```
gaggtgcagc tgttggagtc tggggggagac ttggtacagc ctgggggggtc cctgagactc    60 tcctgtgcag cctctgaatt cacctttagc ggctatgcca tgagctgggt ccgccaggct   120
ccagggaagg gctggagtg gtctcagtg attcgtggta gtggtgataa cacatactac   180
gcagactccg tgaagggccg gttcagcatc tccagagaca attccaagaa cactctgtat   240
ctgcaaatga acagcctgag agccgaggac acggccgtat attactgtgc gagagtgtat   300
tacgattttt gggaaggggc ttttgatatc tggggccaag gacaatggt caccgtctct   360 tca                                                                  363
```

<210> SEQ ID NO 498
<211> LENGTH: 121
<212> TYPE: PRT
<213> ORGANISM: Artificial Sequence
<220> FEATURE:
<223> OTHER INFORMATION: synthetic

<400> SEQUENCE: 498

Glu Val Gln Leu Leu Glu Ser Gly Gly Asp Leu Val Gln Pro Gly Gly
1               5                   10                  15

Ser Leu Arg Leu Ser Cys Ala Ala Ser Glu Phe Thr Phe Ser Gly Tyr
            20                  25                  30

Ala Met Ser Trp Val Arg Gln Ala Pro Gly Lys Gly Leu Glu Trp Val
        35                  40                  45

Ser Val Ile Arg Gly Ser Gly Asp Asn Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Asp Phe Trp Glu Gly Ala Phe Asp Ile Trp Gly
            100                 105                 110

Gln Gly Thr Met Val Thr Val Ser Ser
        115                 120

<210> SEQ ID NO 499
<211> LENGTH: 321
<212> TYPE: DNA
<213> ORGANISM: Artificial Sequence
<220> FEATURE:
<223> OTHER INFORMATION: synthetic

<400> SEQUENCE: 499

```
gacatccaga tgacccagtc tccatcttcc gtgtctgcat ctgtaggaga cagagtcacc    60
atcacttgtc gggcgagtca gggtattagc acctggttag cctggtatca gcagaaacca   120
```

```
gggaaagccc ctaagctcct gatctatgct gcaaccagtt tgcaaagtgg ggtcccatca      180
aggttcagcg gcagtggatc tgggacagat ttcactctcg ccatcagcgg cctgcagcct      240
gaagattttg caacttacta ttgtcaacag gctaacaatt tcccgtacac ttttggccag      300
gggaccaagc tggagatcaa a                                                321
```

<210> SEQ ID NO 500
<211> LENGTH: 107
<212> TYPE: PRT
<213> ORGANISM: Artificial Sequence
<220> FEATURE:
<223> OTHER INFORMATION: synthetic

<400> SEQUENCE: 500

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Ala Ile Ser Gly Leu Gln Pro
65                  70                  75                  80

Glu Asp Phe Ala Thr Tyr Tyr Cys Gln Gln Ala Asn Asn Phe Pro Tyr
                85                  90                  95

Thr Phe Gly Gln Gly Thr Lys Leu Glu Ile Lys
            100                 105
```

<210> SEQ ID NO 501
<211> LENGTH: 363
<212> TYPE: DNA
<213> ORGANISM: Artificial Sequence
<220> FEATURE:
<223> OTHER INFORMATION: synthetic

<400> SEQUENCE: 501

```
gaggtgcagc tgttggagtc tgggggaggc ttggtacagc ctgggggggtc cctgagactc      60 tcctgtgcag cctctgaatt cacctttagc ggctatgcca tgagctgggt ccgccaggct     120
ccagggaagg ggctggagtg gtctcagct attcgtggta gtggtgataa cacatactac     180
gcagactccg tgaagggccg gttcaccatc tccagagaca attccaagaa cacgctgtat     240
ctgcaaatga acagcctgag agccgaggac acggccgtat attactgtgc gagagtgtat     300
tacgattttt gggaaggggc ttttgatatc tggggccaag ggacaatggt caccgtctct     360
tca                                                                    363
```

<210> SEQ ID NO 502
<211> LENGTH: 121
<212> TYPE: PRT
<213> ORGANISM: Artificial Sequence
<220> FEATURE:
<223> OTHER INFORMATION: synthetic

<400> SEQUENCE: 502

```
Glu Val Gln Leu Leu Glu Ser Gly Gly Gly Leu Val Gln Pro Gly Gly
 1               5                  10                  15

Ser Leu Arg Leu Ser Cys Ala Ala Ser Glu Phe Thr Phe Ser Gly Tyr
            20                  25                  30
```

Ala Met Ser Trp Val Arg Gln Ala Pro Gly Lys Gly Leu Glu Trp Val
            35                  40                  45

Ser Ala Ile Arg Gly Ser Gly Asp Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Asp Phe Trp Glu Gly Ala Phe Asp Ile Trp Gly
            100                 105                 110

Gln Gly Thr Met Val Thr Val Ser Ser
            115                 120

<210> SEQ ID NO 503
<211> LENGTH: 322
<212> TYPE: DNA
<213> ORGANISM: Artificial Sequence
<220> FEATURE:
<223> OTHER INFORMATION: synthetic

<400> SEQUENCE: 503
gacatccaga tgacccagtc tccatcttct gtgtctgcat ctgtaggaga cagagtcacc    60
atcacttgtc gggcgagtca gggtattagc acctggttag cctggtatca gcagaaacca   120
gggaaagccc ctaagctcct gatctatgct gcaaccagtt tgcaaagtgg ggtcccatca   180
aggttcagcg gcagtggatc tgggacagat ttcactctca ctatcagcag cctgcagcct   240
gaagattttg caacttacta ttgtcaacag gctaacaatt tcccgtacac ttttggccag   300
gggaccaagc tggagatcaa ac                                            322

<210> SEQ ID NO 504
<211> LENGTH: 107
<212> TYPE: PRT
<213> ORGANISM: Artificial Sequence
<220> FEATURE:
<223> OTHER INFORMATION: synthetic

<400> SEQUENCE: 504

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Tyr
                85                  90                  95

Thr Phe Gly Gln Gly Thr Lys Leu Glu Ile Lys
            100                 105

<210> SEQ ID NO 505
<211> LENGTH: 357
<212> TYPE: DNA
<213> ORGANISM: Artificial Sequence
<220> FEATURE:
<223> OTHER INFORMATION: synthetic

<400> SEQUENCE: 505

```
caggtgcagc tggtggagtc tgggggaggc gtggtccagc ctgggaggtc cctgagactc    60
tcctgtgcag cgtctggatt caccttcagt gcctatggca tgcactgggt ccgccaggct   120
ccaggcaagg gctggagtg gtggcaatt atatggtatg atggaagtaa taaatactac   180
gcagactccg tgaagggccg attcaccatc tccagagaca attccaagaa cacgctgtat   240
ctgcaaatga acagcctgag agccgaggac acggctgtgt attattgtgc gagagaggat   300
acctctatgg ttctctttga ctactggggc caggaaccc tggtcaccgt ctcctca      357
```

<210> SEQ ID NO 506
<211> LENGTH: 119
<212> TYPE: PRT
<213> ORGANISM: Artificial Sequence
<220> FEATURE:
<223> OTHER INFORMATION: synthetic

<400> SEQUENCE: 506

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ala Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Tyr Tyr Ala Asp Ser Val
    50                  55                  60
Lys Gly Arg Phe Thr Ile Ser Arg Asp Asn Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Asp Thr Ser Met Val Leu Phe Asp Tyr Trp Gly Gln Gly
            100                 105                 110
Thr Leu Val Thr Val Ser Ser
        115
```

<210> SEQ ID NO 507
<211> LENGTH: 24
<212> TYPE: DNA
<213> ORGANISM: Artificial Sequence
<220> FEATURE:
<223> OTHER INFORMATION: synthetic

<400> SEQUENCE: 507

```
ggattcacct tcagtgccta tggc                                           24
```

<210> SEQ ID NO 508
<211> LENGTH: 8
<212> TYPE: PRT
<213> ORGANISM: Artificial Sequence
<220> FEATURE:
<223> OTHER INFORMATION: synthetic

<400> SEQUENCE: 508

```
Gly Phe Thr Phe Ser Ala Tyr Gly
 1               5
```

<210> SEQ ID NO 509
<211> LENGTH: 24
<212> TYPE: DNA
<213> ORGANISM: Artificial Sequence

```
<220> FEATURE:
<223> OTHER INFORMATION: synthetic

<400> SEQUENCE: 509
atatggtatg atggaagtaa taaa                                          24

<210> SEQ ID NO 510
<211> LENGTH: 8
<212> TYPE: PRT
<213> ORGANISM: Artificial Sequence
<220> FEATURE:
<223> OTHER INFORMATION: synthetic

<400> SEQUENCE: 510

Ile Trp Tyr Asp Gly Ser Asn Lys
1               5

<210> SEQ ID NO 511
<211> LENGTH: 36
<212> TYPE: DNA
<213> ORGANISM: Artificial Sequence
<220> FEATURE:
<223> OTHER INFORMATION: synthetic

<400> SEQUENCE: 511
gcgagagagg atacctctat ggttctcttt gactac                             36

<210> SEQ ID NO 512
<211> LENGTH: 12
<212> TYPE: PRT
<213> ORGANISM: Artificial Sequence
<220> FEATURE:
<223> OTHER INFORMATION: synthetic

<400> SEQUENCE: 512

Ala Arg Glu Asp Thr Ser Met Val Leu Phe Asp Tyr
1               5                   10

<210> SEQ ID NO 513
<211> LENGTH: 357
<212> TYPE: DNA
<213> ORGANISM: Artificial Sequence
<220> FEATURE:
<223> OTHER INFORMATION: synthetic

<400> SEQUENCE: 513
caggtgcagc tggtggagtc tgggggaggc gtggtccagc ctggggaggtc cctgagactc    60 tcctgtgcag cgtctggatt caccttcagt gcctatggca tgcactgggt ccgccaggct   120
ccaggcaagg ggctggagtg ggtggcaatt atatggtatg atggaagtaa taaatactac   180
gcagactccg tgaagggccg attcaccatc tccagagaca attccaagaa cacgctgtat   240
ctgcaaatga acagcctgag agccgaggac acggctgtgt attattgtgc gagagaggat   300
acctctatgg ttctctttga ctactggggc cagggaaccc tggtcaccgt ctcctca     357

<210> SEQ ID NO 514
<211> LENGTH: 119
<212> TYPE: PRT
<213> ORGANISM: Artificial Sequence
<220> FEATURE:
<223> OTHER INFORMATION: synthetic

<400> SEQUENCE: 514

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ala Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Thr Ser Met Val Leu Phe Asp Tyr Trp Gly Gln Gly
            100                 105                 110

Thr Leu Val Thr Val Ser Ser
            115

<210> SEQ ID NO 515
<211> LENGTH: 357
<212> TYPE: DNA
<213> ORGANISM: Artificial Sequence
<220> FEATURE:
<223> OTHER INFORMATION: synthetic

<400> SEQUENCE: 515
caggtgcagc tggtggagtc tgggggaggc gtggtccagc ctggagagtc cctgagactc      60
tcctgtgcag cgtctggatt caccttcagt gcctatggca tgcactgggt ccgccaggct     120
ccaggcaagg ggctagagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagaggat     300
acctctatgg ttctctttga ctactgggc cagggaaccc tggtcaccgt ctcctca        357

<210> SEQ ID NO 516
<211> LENGTH: 119
<212> TYPE: PRT
<213> ORGANISM: Artificial Sequence
<220> FEATURE:
<223> OTHER INFORMATION: synthetic

<400> SEQUENCE: 516

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ala Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Thr Ser Met Val Leu Phe Asp Tyr Trp Gly Gln Gly
            100                 105                 110

Thr Leu Val Thr Val Ser Ser
            115

<210> SEQ ID NO 517
<211> LENGTH: 1488
<212> TYPE: DNA
<213> ORGANISM: Artificial Sequence
<220> FEATURE:
<223> OTHER INFORMATION: synthetic

<400> SEQUENCE: 517

```
atgtggcaga ttgttttctt tactctgagc tgtgatcttg tcttggccgc agcctataac      60
aactttcgga gagcatgga cagcatagga agaagcaat atcaggtcca gcatgggtcc       120
tgcagctaca ctttcctcct gccagagatg gacaactgcc gctcttcctc cagcccctac     180
gtgtccaatg ctgtgcagag ggacgcgccg ctcgaatacg atgactcggt gcagaggctg     240
caagtgctgg agaacatcat ggaaaacaac actcagtggc taatgaagct tgagaattat     300
atccaggaca catgaagaa agaaatggta gagatacagc agaatgcagt acagaaccag     360
acggctgtga tgatagaaat agggacaaac ctgttgaacc aaacagctga gcaaacgcgg     420
aagttaactg atgtggaagc ccaagtatta atcagacca cgagacttga acttcagctc     480
ttggaacact ccctctcgac aaacaaattg gaaaacaga ttttggacca gaccagtgaa     540
ataaacaaat tgcaagataa gaacagtttc ctagaaaaga aggtgctagc tatggaagac     600
aagcacatca tccaactaca gtcaataaaa gaagagaaag atcagctaca ggtgttagta     660
tccaagcaaa attccatcat tgaagaacta gaaaaaaaa tagtgactgc cacggtgaat     720
aattcagttc ttcaaaagca gcaacatgat ctcatggaga cagttaataa cttactgact     780
atgatgtcca catcaaactc agctaaggac cccactgttg ctaaagaaga acaaatcagc     840
ttcagagact gtgctgaagt attcaaatca ggacacacca caaatggcat ctacacgtta     900
acattcccta attctacaga agagatcaag gcctactgtg acatggaagc tggaggaggc     960
gggtggacaa ttattcagcg acgtgaggat ggcagcgttg attttcagag acttggaaaa    1020
gaatataaag tgggatttgg taaccccttca ggagaatatt ggctgggaaa tgagtttgtt    1080
tcgcaactga ctaatcagca acgctatgtg cttaaaatac accttaaaga ctgggaaggg    1140
aatgaggctt actcattgta tgaacatttc tatctctcaa gtgaagaact caattatagg    1200
attcacctta aaggacttac agggacagcc ggcaaataa gcagcatcag ccaaccagga    1260
aatgattttta gcacaaagga tggagacaac gacaaatgta tttgcaaatg ttcacaaatg    1320
ctaacaggag ctggtggtt tgatgcatgt ggtccttcca acttgaacgg aatgtactat    1380
ccacagaggc agaacacaa taagttcaac ggcattaaat ggtactactg gaaaggctca    1440
ggctattcgc tcaaggccac aaccatgatg atccgaccag cagatttc               1488
```

<210> SEQ ID NO 518
<211> LENGTH: 496
<212> TYPE: PRT
<213> ORGANISM: Artificial Sequence
<220> FEATURE:
<223> OTHER INFORMATION: synthetic

<400> SEQUENCE: 518

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
```

-continued

```
                50                  55                  60
Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
                115                 120                 125

Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
            210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480
```

```
Gly Tyr Ser Leu Lys Ala Thr Thr Met Met Ile Arg Pro Ala Asp Phe
            485                 490                 495
```

<210> SEQ ID NO 519
<211> LENGTH: 215
<212> TYPE: PRT
<213> ORGANISM: Artificial Sequence
<220> FEATURE:
<223> OTHER INFORMATION: synthetic

<400> SEQUENCE: 519

```
Arg Asp Cys Ala Glu Val Phe Lys Ser Gly His Thr Thr Asn Gly Ile
  1               5                  10                  15

Tyr Thr Leu Thr Phe Pro Asn Ser Thr Glu Glu Ile Lys Ala Tyr Cys
             20                  25                  30

Asp Met Glu Ala Gly Gly Gly Trp Thr Ile Ile Gln Arg Arg Glu
         35                  40                  45

Asp Gly Ser Val Asp Phe Gln Arg Thr Trp Lys Glu Tyr Lys Val Gly
     50                  55                  60

Phe Gly Asn Pro Ser Gly Glu Tyr Trp Leu Gly Asn Glu Phe Val Ser
 65                  70                  75                  80

Gln Leu Thr Asn Gln Gln Arg Tyr Val Leu Lys Ile His Leu Lys Asp
             85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
            115                 120                 125

Ala Gly Lys Ile Ser Ser Ile Ser Gln Pro Gly Asn Asp Phe Ser Thr
        130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe
    210                 215
```

<210> SEQ ID NO 520
<211> LENGTH: 215
<212> TYPE: PRT
<213> ORGANISM: Artificial Sequence
<220> FEATURE:
<223> OTHER INFORMATION: synthetic

<400> SEQUENCE: 520

```
Arg Asp Cys Ala Glu Ile Phe Lys Ser Gly Leu Thr Thr Ser Gly Ile
  1               5                  10                  15

Tyr Thr Leu Thr Phe Pro Asn Ser Thr Glu Glu Ile Lys Ala Tyr Cys
             20                  25                  30

Asp Met Asp Val Gly Gly Gly Trp Thr Val Ile Gln His Arg Glu
         35                  40                  45

Asp Gly Ser Val Asp Phe Gln Arg Thr Trp Lys Glu Tyr Lys Glu Gly
     50                  55                  60

Phe Gly Ser Pro Leu Gly Glu Tyr Trp Leu Gly Asn Glu Phe Val Ser
```

```
                65                  70                  75                  80
Gln Leu Thr Gly Gln His Arg Tyr Val Leu Lys Ile Gln Leu Lys Asp
                    85                  90                  95

Trp Glu Gly Asn Glu Ala His Ser Leu Tyr Asp His Phe Tyr Leu Ala
                100                 105                 110

Gly Glu Glu Ser Asn Tyr Arg Ile His Leu Thr Gly Leu Thr Gly Thr
                115                 120                 125

Ala Gly Lys Ile Ser Ser Ile Ser Gln Pro Gly Ser Asp Phe Ser Thr
            130                 135                 140

Lys Asp Ser Asp Asn Asp Lys Cys Ile Cys Lys Cys Ser Gln Met Leu
145                 150                 155                 160

Ser Gly Gly Trp Trp Phe Asp Ala Cys Gly Pro Ser Asn Leu Asn Gly
                    165                 170                 175

Gln Tyr Tyr Pro Gln Lys Gln Asn Thr Asn Lys Phe Asn Gly Ile Lys
                180                 185                 190

Trp Tyr Tyr Trp Lys Gly Ser Gly Tyr Ser Leu Lys Ala Thr Thr Met
                195                 200                 205

Met Ile Arg Pro Ala Asp Phe
            210                 215

<210> SEQ ID NO 521
<211> LENGTH: 215
<212> TYPE: PRT
<213> ORGANISM: Artificial Sequence
<220> FEATURE:
<223> OTHER INFORMATION: synthetic

<400> SEQUENCE: 521

Arg Asp Cys Ala Glu Val Phe Lys Ser Gly His Thr Thr Asn Gly Val
1               5                   10                  15

Tyr Thr Leu Thr Leu Pro Asn Ser Thr Glu Glu Val Lys Ala Tyr Cys
                20                  25                  30

Asp Met Glu Ala Gly Gly Gly Gly Trp Thr Ile Ile Gln Arg Arg Glu
            35                  40                  45

Asp Gly Ser Val Asp Phe Gln Arg Thr Trp Lys Glu Tyr Lys Val Gly
        50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                    85                  90                  95

Trp Glu Gly Asn Glu Ala Tyr Ser Leu Tyr Glu His Phe Tyr Leu Ser
                100                 105                 110

Ser Glu Glu Leu Asn Tyr Arg Ile His Leu Lys Gly Leu Thr Gly Thr
                115                 120                 125

Ala Gly Lys Ile Ser Ser Ile Ser Gln Pro Gly Asn Asp Phe Ser Thr
            130                 135                 140

Lys Asp Ala Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                    165                 170                 175

Met Tyr Tyr Pro Gln Arg Gln Asn Thr Asn Lys Phe Asn Gly Ile Lys
                180                 185                 190

Trp Tyr Tyr Trp Lys Gly Ser Gly Tyr Ser Leu Lys Gly Thr Thr Met
                195                 200                 205

Met Ile Arg Pro Ala Asp Phe
```

<210> SEQ ID NO 522
<211> LENGTH: 674
<212> TYPE: PRT
<213> ORGANISM: Artificial Sequence
<220> FEATURE:
<223> OTHER INFORMATION: synthetic

<400> SEQUENCE: 522

Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
            20                  25                  30

Asp Met Glu Ala Gly Gly Gly Gly Trp Thr Ile Ile Gln Arg Arg Glu
        35                  40                  45

Asp Gly Ser Val Asp Phe Gln Arg Thr Trp Lys Glu Tyr Lys Val Gly
    50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
        115                 120                 125

Ala Gly Lys Ile Ser Ser Ile Ser Gln Pro Gly Asn Asp Phe Ser Thr
    130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
            180                 185                 190

Trp Tyr Tyr Trp Lys Gly Ser Gly Tyr Ser Leu Lys Ala Thr Thr Met
        195                 200                 205

Met Ile Arg Pro Ala Asp Phe Gly Gly Pro Gly Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser

```
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys Gly Gly Gly Ser Gly Ala Pro Arg Asp Cys Ala Glu
            450                 455                 460
Val Phe Lys Ser Gly His Thr Thr Asn Gly Ile Tyr Thr Leu Thr Phe
465                 470                 475                 480
Pro Asn Ser Thr Glu Glu Ile Lys Ala Tyr Cys Asp Met Glu Ala Gly
                485                 490                 495
Gly Gly Gly Trp Thr Ile Ile Gln Arg Arg Glu Asp Gly Ser Val Asp
            500                 505                 510
Phe Gln Arg Thr Trp Lys Glu Tyr Lys Val Gly Phe Gly Asn Pro Ser
            515                 520                 525
Gly Glu Tyr Trp Leu Gly Asn Glu Phe Val Ser Gln Leu Thr Asn Gln
            530                 535                 540
Gln Arg Tyr Val Leu Lys Ile His Leu Lys Asp Trp Glu Gly Asn Glu
545                 550                 555                 560
Ala Tyr Ser Leu Tyr Glu His Phe Tyr Leu Ser Ser Glu Glu Leu Asn
                565                 570                 575
Tyr Arg Ile His Leu Lys Gly Leu Thr Gly Thr Ala Gly Lys Ile Ser
            580                 585                 590
Ser Ile Ser Gln Pro Gly Asn Asp Phe Ser Thr Lys Asp Gly Asp Asn
            595                 600                 605
Asp Lys Cys Ile Cys Lys Cys Ser Gln Met Leu Thr Gly Gly Trp Trp
            610                 615                 620
Phe Asp Ala Cys Gly Pro Ser Asn Leu Asn Gly Met Tyr Tyr Pro Gln
625                 630                 635                 640
Arg Gln Asn Thr Asn Lys Phe Asn Gly Ile Lys Trp Tyr Tyr Trp Lys
                645                 650                 655
Gly Ser Gly Tyr Ser Leu Lys Ala Thr Thr Met Met Ile Arg Pro Ala
            660                 665                 670
Asp Phe

<210> SEQ ID NO 523
<211> LENGTH: 663
<212> TYPE: PRT
<213> ORGANISM: Artificial Sequence
<220> FEATURE:
<223> OTHER INFORMATION: synthetic

<400> SEQUENCE: 523

Arg Asp Cys Ala Glu Val Phe Lys Ser Gly His Thr Thr Asn Gly Ile
1               5                   10                  15
Tyr Thr Leu Thr Phe Pro Asn Ser Thr Glu Glu Ile Lys Ala Tyr Cys
            20                  25                  30
Asp Met Glu Ala Gly Gly Gly Gly Trp Thr Ile Ile Gln Arg Arg Glu
        35                  40                  45
```

```
Asp Gly Ser Val Asp Phe Gln Arg Thr Trp Lys Glu Tyr Lys Val Gly
     50                  55                  60

Phe Gly Asn Pro Ser Gly Glu Tyr Trp Leu Gly Asn Glu Phe Val Ser
 65                  70                  75                  80

Gln Leu Thr Asn Gln Gln Arg Tyr Val Leu Lys Ile His Leu Lys Asp
                 85                  90                  95

Trp Glu Gly Asn Glu Ala Tyr Ser Leu Tyr Glu His Phe Tyr Leu Ser
                100                 105                 110

Ser Glu Glu Leu Asn Tyr Arg Ile His Leu Lys Gly Leu Thr Gly Thr
            115                 120                 125

Ala Gly Lys Ile Ser Ser Ile Ser Gln Pro Gly Asn Asp Phe Ser Thr
130                 135                 140

Lys Asp Gly Asp Asn Asp Lys Cys Ile Cys Lys Cys Ser Gln Met Leu
145                 150                 155                 160

Thr Gly Gly Trp Trp Phe Asp Ala Cys Gly Pro Ser Asn Leu Asn Gly
                165                 170                 175

Met Tyr Tyr Pro Gln Arg Gln Asn Thr Asn Lys Phe Asn Gly Ile Lys
                180                 185                 190

Trp Tyr Tyr Trp Lys Gly Ser Gly Tyr Ser Leu Lys Ala Thr Thr Met
            195                 200                 205

Met Ile Arg Pro Ala Asp Phe Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
                260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
                340                 345                 350

Pro Pro Pro Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
            370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
            435                 440                 445

Arg Asp Cys Ala Glu Val Phe Lys Ser Gly His Thr Thr Asn Gly Ile
450                 455                 460
```

```
Tyr Thr Leu Thr Phe Pro Asn Ser Thr Glu Glu Ile Lys Ala Tyr Cys
465                 470                 475                 480

Asp Met Glu Ala Gly Gly Gly Trp Thr Ile Ile Gln Arg Arg Glu
            485                 490                 495

Asp Gly Ser Val Asp Phe Gln Arg Thr Trp Lys Glu Tyr Lys Val Gly
            500                 505                 510

Phe Gly Asn Pro Ser Gly Glu Tyr Trp Leu Gly Asn Glu Phe Val Ser
            515                 520                 525

Gln Leu Thr Asn Gln Gln Arg Tyr Val Leu Lys Ile His Leu Lys Asp
            530                 535                 540

Trp Glu Gly Asn Glu Ala Tyr Ser Leu Tyr Glu His Phe Tyr Leu Ser
545                 550                 555                 560

Ser Glu Glu Leu Asn Tyr Arg Ile His Leu Lys Gly Leu Thr Gly Thr
                565                 570                 575

Ala Gly Lys Ile Ser Ser Ile Ser Gln Pro Gly Asn Asp Phe Ser Thr
            580                 585                 590

Lys Asp Gly Asp Asn Asp Lys Cys Ile Cys Lys Cys Ser Gln Met Leu
            595                 600                 605

Thr Gly Gly Trp Trp Phe Asp Ala Cys Gly Pro Ser Asn Leu Asn Gly
            610                 615                 620

Met Tyr Tyr Pro Gln Arg Gln Asn Thr Asn Lys Phe Asn Gly Ile Lys
625                 630                 635                 640

Trp Tyr Tyr Trp Lys Gly Ser Gly Tyr Ser Leu Lys Ala Thr Thr Met
                645                 650                 655

Met Ile Arg Pro Ala Asp Phe
            660

<210> SEQ ID NO 524
<211> LENGTH: 448
<212> TYPE: PRT
<213> ORGANISM: Artificial Sequence
<220> FEATURE:
<223> OTHER INFORMATION: synthetic

<400> SEQUENCE: 524

Arg Asp Cys Ala Glu Val Phe Lys Ser Gly His Thr Thr Asn Gly Ile
1               5                   10                  15

Tyr Thr Leu Thr Phe Pro Asn Ser Thr Glu Glu Ile Lys Ala Tyr Cys
                20                  25                  30

Asp Met Glu Ala Gly Gly Gly Trp Thr Ile Ile Gln Arg Arg Glu
            35                  40                  45

Asp Gly Ser Val Asp Phe Gln Arg Thr Trp Lys Glu Tyr Lys Val Gly
            50                  55                  60

Phe Gly Asn Pro Ser Gly Glu Tyr Trp Leu Gly Asn Glu Phe Val Ser
65                  70                  75                  80

Gln Leu Thr Asn Gln Gln Arg Tyr Val Leu Lys Ile His Leu Lys Asp
                85                  90                  95

Trp Glu Gly Asn Glu Ala Tyr Ser Leu Tyr Glu His Phe Tyr Leu Ser
            100                 105                 110

Ser Glu Glu Leu Asn Tyr Arg Ile His Leu Lys Gly Leu Thr Gly Thr
            115                 120                 125

Ala Gly Lys Ile Ser Ser Ile Ser Gln Pro Gly Asn Asp Phe Ser Thr
            130                 135                 140

Lys Asp Gly Asp Asn Asp Lys Cys Ile Cys Lys Cys Ser Gln Met Leu
145                 150                 155                 160
```

Thr Gly Gly Trp Trp Phe Asp Ala Cys Gly Pro Ser Asn Leu Asn Gly
            165                 170                 175

Met Tyr Tyr Pro Gln Arg Gln Asn Thr Asn Lys Phe Asn Gly Ile Lys
        180                 185                 190

Trp Tyr Tyr Trp Lys Gly Ser Gly Tyr Ser Leu Lys Ala Thr Thr Met
            195                 200                 205

Met Ile Arg Pro Ala Asp Phe Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
            245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
            275                 280                 285

Gln Thr Gln Thr His Arg Glu Asp Tyr Asn Ser Thr Leu Arg Val Val
            290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
            355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
            405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
            435                 440                 445

<210> SEQ ID NO 525
<211> LENGTH: 981
<212> TYPE: PRT
<213> ORGANISM: Artificial Sequence
<220> FEATURE:
<223> OTHER INFORMATION: synthetic

<400> SEQUENCE: 525

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

-continued

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu

```
              500                 505                   510
Tyr Glu Leu Cys Val Gln Leu Val Arg Arg Gly Glu Gly Gly Glu Gly
              515                 520                   525

His Pro Gly Pro Val Arg Arg Phe Thr Thr Ala Ser Ile Gly Leu Pro
              530                 535             540

Pro Pro Arg Gly Leu Asn Leu Leu Pro Lys Ser Gln Thr Thr Leu Asn
545                     550                 555                 560

Leu Thr Trp Gln Pro Ile Phe Pro Ser Ser Glu Asp Asp Phe Tyr Val
                    565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Ile Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Gly Pro Gly Glu Pro Arg Gly
            740                 745                 750

Pro Thr Ile Lys Pro Cys Pro Pro Cys Lys Cys Pro Ala Pro Asn Leu
        755                 760                 765

Leu Gly Gly Pro Ser Val Phe Ile Phe Pro Pro Lys Ile Lys Asp Val
    770                 775                 780

Leu Met Ile Ser Leu Ser Pro Ile Val Thr Cys Val Val Asp Val
785                 790                 795                 800

Ser Glu Asp Asp Pro Asp Val Gln Ile Ser Trp Phe Val Asn Asn Val
                805                 810                 815

Glu Val His Thr Ala Gln Thr Gln Thr His Arg Glu Asp Tyr Asn Ser
            820                 825                 830

Thr Leu Arg Val Val Ser Ala Leu Pro Ile Gln His Gln Asp Trp Met
        835                 840                 845

Ser Gly Lys Glu Phe Lys Cys Lys Val Asn Asn Lys Asp Leu Pro Ala
    850                 855                 860

Pro Ile Glu Arg Thr Ile Ser Lys Pro Lys Gly Ser Val Arg Ala Pro
865                 870                 875                 880

Gln Val Tyr Val Leu Pro Pro Glu Glu Glu Met Thr Lys Lys Gln
                885                 890                 895

Val Thr Leu Thr Cys Met Val Thr Asp Phe Met Pro Glu Asp Ile Tyr
        900                 905                 910

Val Glu Trp Thr Asn Asn Gly Lys Thr Glu Leu Asn Tyr Lys Asn Thr
    915                 920                 925
```

```
Glu Pro Val Leu Asp Ser Asp Gly Ser Tyr Phe Met Tyr Ser Lys Leu
    930                 935                 940

Arg Val Glu Lys Lys Asn Trp Val Glu Arg Asn Ser Tyr Ser Cys Ser
945                 950                 955                 960

Val Val His Glu Gly Leu His Asn His Thr Thr Lys Ser Phe Ser
                965                 970                 975

Arg Thr Pro Gly Lys
            980

<210> SEQ ID NO 526
<211> LENGTH: 753
<212> TYPE: PRT
<213> ORGANISM: Artificial Sequence
<220> FEATURE:
<223> OTHER INFORMATION: synthetic

<400> SEQUENCE: 526

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300
```

-continued

```
Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
            325                 330                 335

Gly Leu Gln Cys Glu Arg Glu Gly Ile Pro Arg Met Thr Pro Lys Ile
        340                 345                 350

Val Asp Leu Pro Asp His Ile Glu Val Asn Ser Gly Lys Phe Asn Pro
    355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Ile Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720
```

-continued

```
Ser Asn Pro Ala Phe Ser His Glu Leu Val Thr Leu Pro Glu Ser Gln
                725                 730                 735

Ala Pro Ala Asp Leu Gly Gly Gly Lys Ile Asp His His His His
            740                 745                 750

His

<210> SEQ ID NO 527
<211> LENGTH: 498
<212> TYPE: PRT
<213> ORGANISM: Artificial Sequence
<220> FEATURE:
<223> OTHER INFORMATION: synthetic

<400> SEQUENCE: 527

Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
                 20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
```

|  | | | | 325 | | | | 330 | | | | 335 | | |

Phe Gln Arg Gly Trp Lys Glu Tyr Lys Met Gly Phe Gly Asn Pro Ser
                340                 345                 350

Gly Glu Tyr Trp Leu Gly Asn Glu Phe Ile Phe Ala Ile Thr Ser Gln
                355                 360                 365

Arg Gln Tyr Met Leu Arg Ile Glu Leu Met Asp Trp Glu Gly Asn Arg
            370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 528
<211> LENGTH: 330
<212> TYPE: PRT
<213> ORGANISM: Artificial Sequence
<220> FEATURE:
<223> OTHER INFORMATION: synthetic

<400> SEQUENCE: 528

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 529
<211> LENGTH: 327
<212> TYPE: PRT
<213> ORGANISM: Artificial Sequence
<220> FEATURE:
<223> OTHER INFORMATION: synthetic

<400> SEQUENCE: 529

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 530
<211> LENGTH: 327
<212> TYPE: PRT
<213> ORGANISM: Artificial Sequence
<220> FEATURE:
<223> OTHER INFORMATION: synthetic

<400> SEQUENCE: 530

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 531
<211> LENGTH: 88
<212> TYPE: PRT
<213> ORGANISM: Homo sapiens

<400> SEQUENCE: 531

Thr Ala Gly Lys Gln Ser Ser Leu Ile Leu His Gly Ala Asp Phe Ser
1               5                   10                  15

Thr Lys Asp Ala Asp Asn Asp Asn Cys Met Cys Lys Cys Ala Leu Met
            20                  25                  30

Leu Thr Gly Gly Trp Trp Phe Asp Ala Cys Gly Pro Ser Asn Leu Asn
            35                  40                  45

Gly Met Phe Tyr Thr Ala Gly Gln Asn His Gly Lys Leu Asn Gly Ile
        50                  55                  60

Lys Trp His Tyr Phe Lys Gly Pro Ser Tyr Ser Leu Arg Ser Thr Thr
65                  70                  75                  80

Met Met Ile Arg Pro Leu Asp Phe
                85
```